United States Patent
Guo et al.

(10) Patent No.: US 9,266,904 B2
(45) Date of Patent: Feb. 23, 2016

(54) 6-BRIDGED HETEROARYLDIHYDROPYRIMIDINES FOR THE TREATMENT AND PROPHYLAXIS OF HEPATITIS B VIRUS INFECTION

(71) Applicant: Hoffmann-La Roche Inc., Nutley, NJ (US)

(72) Inventors: Lei Guo, Shanghai (CN); Taishan Hu, Shanghai (CN); Yimin Hu, Shanghai (CN); Buelent Kocer, Basel (CH); Buyu Kou, Shanghai (CN); Gangqin Li, Shanghai (CN); Xianfeng Lin, Shanghai (CN); Haixia Liu, Shanghai (CN); Hong Shen, Shanghai (CN); Houguang Shi, Shanghai (CN); Guolong Wu, Shanghai (CN); Zhisen Zhang, Shanghai (CN); Mingwei Zhou, Shanghai (CN); Wei Zhu, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 82 days.

(21) Appl. No.: 14/279,716

(22) Filed: May 16, 2014

(65) Prior Publication Data

US 2014/0343032 A1 Nov. 20, 2014

(30) Foreign Application Priority Data

May 17, 2013 (WO) ................ PCT/CN2013/075815
Apr. 15, 2014 (WO) ................ PCT/CN2014/075392

(51) Int. Cl.

| | |
|---|---|
| A61K 31/506 | (2006.01) |
| C07D 498/08 | (2006.01) |
| C07D 417/14 | (2006.01) |
| C07D 498/18 | (2006.01) |
| C07D 491/08 | (2006.01) |
| C07D 487/08 | (2006.01) |
| C07D 513/08 | (2006.01) |
| C07D 498/20 | (2006.01) |
| C07D 453/06 | (2006.01) |
| C07D 471/08 | (2006.01) |
| C07D 491/18 | (2006.01) |

(52) U.S. Cl.
CPC ............ *C07D 498/08* (2013.01); *C07D 417/14* (2013.01); *C07D 453/06* (2013.01); *C07D 471/08* (2013.01); *C07D 487/08* (2013.01); *C07D 491/08* (2013.01); *C07D 491/18* (2013.01); *C07D 498/18* (2013.01); *C07D 498/20* (2013.01); *C07D 513/08* (2013.01); *A61K 31/506* (2013.01)

(58) Field of Classification Search
CPC .. C07D 498/08; C07D 417/14; C07D 453/06; C07D 471/08; C07D 487/08; C07D 491/08; C07D 491/18; C07D 498/18; C07D 498/20; C07D 513/08; A61K 31/506

See application file for complete search history.

(56) References Cited

U.S. PATENT DOCUMENTS

| | | | | |
|---|---|---|---|---|
| 2013/0143863 | A1* | 6/2013 | Aebi ................... | C07D 401/04 514/210.18 |
| 2015/0031687 | A1* | 1/2015 | Guo ..................... | C07D 417/14 514/226.8 |
| 2015/0252057 | A1* | 9/2015 | Guo ..................... | C07D 498/04 514/230.5 |

FOREIGN PATENT DOCUMENTS

| | | | | |
|---|---|---|---|---|
| DE | WO 0168641 | A1 * | 9/2001 | ........... C07D 401/04 |
| WO | 01/68640 | A1 | 9/2001 | |
| WO | 01/68641 | A1 | 9/2001 | |
| WO | 2006/033995 | A2 | 3/2006 | |
| WO | 2006/033995 | A3 | 3/2006 | |

OTHER PUBLICATIONS

Brezillon et al., "Anitviral activity of Bay 41-4109 on hepatitis B virus in humanized Alb-uPA/SCID mice" PLoSONE 6(12 SUPPL 1-6):e25096 (Dec. 2011).
Deres et al., "Inhibition of hepatitis B virus replication by drug-induced depletion of nucleocapsids" Science 299(5608):893-6 (2003).
Feld et al., "The Phenylpropenamide derivative AT-130 blocks HBV replication at the level of viral RNA packaging" Antiviral Res 76:168-177 (2007).
International Search Report and Written Opinion for International Patent Application No. PCT/EP2014/060034.
Zlotnick et al., "A small molecule inhibits and misdirects assembly of hepatitis B virus capsids" J Virol 76(10):4848-4854 (May 2002).

* cited by examiner

*Primary Examiner* — Alexander R Pagano
(74) *Attorney, Agent, or Firm* — Genentech, Inc.

(57) ABSTRACT

The invention provides novel compounds having the general formula:

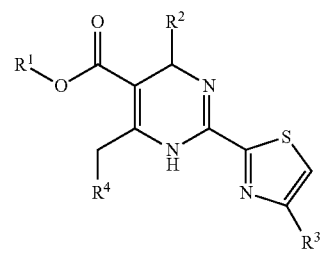

wherein $R^1$, $R^2$, $R^3$ and $R^4$ are as defined in the description and in the claims, as well as or pharmaceutically acceptable salts, or tautomerism isomers, or enantiomers, or diastereomers thereof. The invention also contains compositions including the compounds and methods of using the compounds.

23 Claims, 1 Drawing Sheet

X-ray crystal structure of compound B1
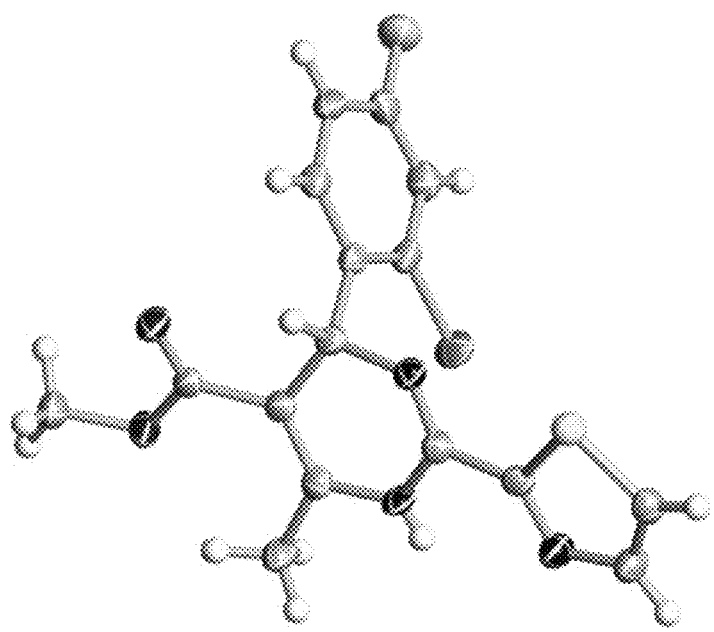

6-BRIDGED HETEROARYLDIHYDROPYRIMIDINES FOR THE TREATMENT AND PROPHYLAXIS OF HEPATITIS B VIRUS INFECTION

PRIORITY OF INVENTION

This application claims priority under 35 U.S.C. 119(a) and 35 U.S.C. 365(a) to International Application Nos. PCT/CN2014/075392 filed on Apr. 15, 2014 and to PCT/CN2013/075815 filed on May 17, 2013. The entire content of the applications referenced above are hereby incorporated by reference herein.

FIELD OF THE INVENTION

The present invention relates to organic compounds useful for therapy and/or prophylaxis in a human, and in particular to Hepatitis B virus (HBV) inhibitors by targeting on HBV capsid for the treatment of HBV infection.

HBV is a species of the hepadnaviridae family of viruses. HBV is a serious public health problem worldwide, with more than 400 million people especially in Asia-pacific regions chronically infected by this small enveloped DNA virus. Although most individuals seem to resolve the infection following acute symptoms, 15-40% of HBV patients will finally develop clinical diseases during their lifespan, most notably, hepatitis, liver cirrhosis, and hepatocellular carcinoma. Every year 500,000 to 1 million people die from the end stage of liver diseases caused by HBV infection.

HBV lifecycle begins with the binding of the "Dane" particle with an unidentified receptor on the surface of hepatocyte. Following entry, viral genome is delivered into nucleus where a covalently closed circular DNA (cccDNA) is formed through DNA repair of viral relaxed circular DNA. Unlike the mechanisms of most other DNA viruses, HBV cccDNA replicates through the retrotranscription of a 1.1-genome unit-length RNA copy (pregenomic RNA). Viral pregenomic RNA interacts with other two viral components, capsid protein and polymerase, as well as some host factors, to form capsid particles where viral DNA replication occurs. Most copies of the encapsidated genome then efficiently associate with the envelope proteins for virion assembly and secretion; a minority of these genomes is shunted to the nucleus, where they are converted to cccDNA.

Currently, there are two types of anti-HBV agents on the market, nucleoside (tide) analogs targeting viral polymerase (lamivudine, adefovir, tenofovir, telbivudine and entecavir) and interferon modulating host immune functions. Mutations in the primary sequence of the polymerase that confer resistance to lamivudine and adefovir have been identified clinically and underlie a rebound of serum virus titers that 70% of treated patients experience within 3 years of the start of lamivudine therapy. Although resistance to telbivudine, adefovir, and entecavir occurs more rarely, it has been recorded. Interferon alpha is the other major therapy available for hepatitis B, but it is limited by a poor long-term response and debilitating side effects. Some viral genotypes do not show good responses to interferon therapy. Now, the standard of clinic cure of HBV infection is the loss and/or seroconversion of HBsAg. The majority (around or more than 90%) of treated patients fail to achieve this goal. This drawback is mainly due to the presence of a stable pool of viral cccDNA in nucleus that doesn't replicate itself, therefore, shows no accessibility to nucleoside (tide) analogs.

Hence, there is certainly a medical need for treatments with improved characteristics and for a diversity of approaches in the development of therapies for HBV infection.

HBV capsid protein plays essential roles in HBV replication. HBV has an icosahedral core comprising of 240 copies of the capsid (or core) protein. The predominant biological function of capsid protein is to act as a structural protein to encapsidate pre-genomic RNA and form immature capsid particles in the cytoplasm. This step is prerequisite for viral DNA replication. The HBV capsid spontaneously self-assembles from many copies of core dimers present in the cytoplasm. It has been shown that the formation of a trimeric nucleus and the subsequent elongation reactions occur by adding one dimeric subunit at a time until it is complete. Besides this function, capsid protein regulates viral DNA synthesis through different phosphorylation status of its C-terminal phosphorylation sites. When a near full-length relaxed circular DNA is formed through reverse-transcription of viral pregenomic RNA, an immature capsid becomes a mature capsid. On one hand, capsid protein might facilitate the nuclear translocation of viral relaxed circular genome by means of the nuclear localization signals located in the Arginine-rich domain of the C-terminal region of capsid protein. In nucleus, as a component of viral cccDNA minichromosome, capsid protein could play a structural and regulatory role in the functionality of cccDNA minichromosomes. Capsid protein also interacts with viral large envelope protein in endoplasmic reticulum and triggers the release of intact viral particles from hepatocytes.

There has been a couple of capsid related anti-HBV inhibitors reported. For example, phenylpropenamide derivatives, including compounds named AT-61 and AT-130 (Feld J. et al. *Antiviral Research* 2007, 168-177), and a class of thiazolidin-4-ones from Valeant R&D (WO2006/033995), have been shown to inhibit pgRNA packaging. A recent study suggested that phenylpropenamides are, in fact, accelerators of HBV capsid assembly, and their actions result in the formation of empty capsids. These very interesting results illustrate the importance of the kinetic pathway in successful virus assembly.

Heteroaryldihydropyrimidines or HAP, including compounds named Bay 41-4109, Bay 38-7690 and Bay 39-5493, were discovered in a tissue culture-based screening (Deres K. et al. *Science* 2003, 893). These HAP analogs act as synthetic allosteric activators and are able to induce aberrant capsid formation that leads to degradation of the core protein. HAP analogs also reorganized core protein from preassembled capsids into noncapsid polymers, presumably by interaction of HAP with dimers freed during capsid 'breathing', the transitory breaking of individual intersubunit bonds. Bay 41-4109 was administered to HBV infected transgenic mouse or humanized mouse models and demonstrated in vivo efficacy with HBV DNA reduction (Deres K. et al. *Science* 2003, 893; Brezillon N. et al. *PLoS ONE* 2011, e25096). It was also shown that bis-ANS, a small molecule that acts as a molecular 'wedge' and interferes with normal capsid-protein geometry and capsid formation (Zlotnick A. et al. *J. Virol.* 2002, 4848-4854).

SUMMARY OF THE INVENTION

Objects of the present invention are novel compounds of formula I, their manufacture, medicaments based on a compound in accordance with the invention and their production as well as the use of compounds of formula I for the treatment or prophylaxis of HBV infection.

In one aspect the present invention provides for compounds of formula (I)

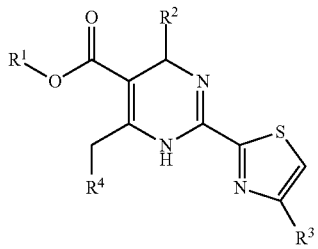

wherein, $R^1$ is $C_{1-6}$alkyl; $R^2$ is phenyl, which is once or twice or three times substituted by halogen or $C_{1-6}$alkyl; $R^3$ is hydrogen or $C_{1-6}$alkyl; $R^4$ is

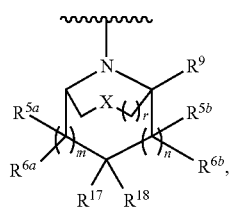

wherein one of $R^{5a}$ and $R^{6a}$ is hydrogen or halogen, and the other one is hydrogen, halogen or hydroxy; one of $R^{5b}$ and $R^{6b}$ is hydrogen or halogen, and the other one is hydrogen or halogen; $R^9$ is hydrogen or carboxy; one of $R^{17}$ and $R^{18}$ is hydrogen, halogen, hydroxy, amino, $C_{1-6}$alkylsulfonylamino or trifluoromethylcarbonylamino, the other one is hydrogen, halogen, hydroxy-$C_yH_{2y}$—, $C_{1-6}$alkylcarbonyl-O—, $C_{1-6}$alkoxycarbonyl-$C_yH_{2y}$—, carboxy-$C_yH_{2y}$—O—, carboxy-$C_yH_{2y}$—, $C_{1-6}$alkylcarbonyl-NH—, $C_{1-6}$alkylsulfonyl-NH—, aminocarbonyl-NH— or aminosulfonyl-NH—; wherein —$C_yH_{2y}$— is unsubstituted once or more times substituted by hydroxy; or $R^{6a}$ and $R^{17}$ together with the carbon atoms, to which they are attached, form a ring of isoxazolyl, pyrazolyl or oxo-dihydropyrazolyl, which ring is unsubstituted or once or more times substituted by $C_{1-6}$alkyl; or $R^{17}$ and $R^{18}$ together with the carbon atom, to which they are attached, form diazirinyl; X is oxygen; sulfur; —N(carbonyl$C_{1-6}$alkyl)-; or —C($R^{15}R^{16}$)—, wherein one of $R^{15}$ and $R^{16}$ is hydrogen or hydroxy, and the other one is hydrogen or carboxy-$C_yH_{2y}$—; r is 0 or 1; m is 0 or 1; n is 0 or 1; y is 0-6; or $R^4$ is

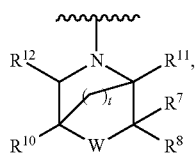

wherein $R^7$ is hydrogen or halogen; $R^8$ is hydrogen or halogen; $R^{10}$ is hydrogen, halogen, hydroxy-$C_yH_{2y}$— or $C_{1-6}$alkylcarbonylamino-$C_yH_{2y}$—; $R^{11}$ is hydrogen or carboxy; $R^{12}$ is hydrogen or carboxy; W is a bond, oxygen, —$CH_2$—, —$CF_2$— or —N(carbonyl$C_{1-6}$alkyl)-; t is 1 or 2; y is 0-6;

with the proviso that

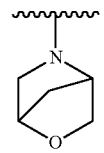 [SMILES: *N1CC2CC1CO2]

is excluded;
or $R^4$ is

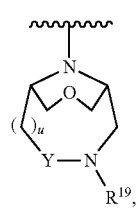

wherein $R^{19}$ is hydrogen; $C_{1-6}$alkyl, which is unsubstituted or once or more times substituted by halogen; $C_{1-6}$alkoxycarbonyl-$C_yH_{2y}$—; hydroxy-$C_yH_{2y}$-carbonyl; carboxy-$C_yH_{2y}$-carbonyl; $C_{1-6}$alkylaminosulfonyl; $C_{1-6}$alkylcarbonyl; $C_{1-6}$alkylsulfonyl; aminocarbonyl; or aminosulfonyl; Y is carbonyl or —$CH_2$—; u is 0 or 1; y is 0-6;
or $R^4$ is

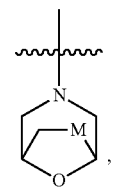

wherein M is a bond, —$CH_2$— or —N($R^{14}$)—$CH_2$—; K is $C_{1-6}$alkoxycarbonyl; or pharmaceutically acceptable salts, or tautomerism isomers, or enantiomers, or diastereomers thereof.

In another aspect, the present invention provides for methods of preparing compounds of Formula (I)

In another aspect the present invention provides for the use of compounds of formula (I) for the treatment or prophylaxis of HBV infection.

DETAILED DESCRIPTION OF THE INVENTION

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "cycloalkyl" groups are cyclopropyl, cyclopentyl and cyclohexyl.

The term "—$C_xH_{2x}$-" alone or in combination signifies a saturated, linear or branched chain alkyl group containing from 1 to 6 carbon atoms, particularly from 1 to 4 carbon atoms.

The term "—$C_yH_{2y}$-" alone or in combination signifies a chemical link or a saturated, linear or branched chain alkyl group containing from 1 to 6 carbon atoms, particularly, the term signifies a chemical link or a saturated, linear or branched chain alkyl group containing from 1 to 4 carbon atoms.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, isopropoxy, n-butoxy, i-butoxy, 2-butoxy, t-butoxy and the like. Particular $C_{1-6}$alkoxy groups are methoxy and ethoxy and more particularly methoxy.

The term "amino", alone or in combination, refers to primary (—$NH_2$), secondary (—NH—) or tertiary amino

The term "carboxy" alone or in combination refers to the group —COOH.

The term "cyano" alone or in combination refers to the group —CN.

The term "halogen" means fluorine, chlorine, bromine or iodine. Halogen is particularly fluorine, chlorine or bromine.

The term "hydroxy" alone or in combination refers to the group —OH.

The term "sulfonyl" alone or in combination refers to the group —$S(O)_2$—.

The term "carbonyl" alone or in combination refers to the group —C(O)—.

The term "carboxy-$C_yH_{2y}$-" refers to a group "—$C_yH_{2y}$—COOH", wherein the "—$C_yH_{2y}$-" is as defined above.

The term "hydroxy-$C_yH_{2y}$-" refers to a group "—$C_yH_{2y}$—OH", wherein the "—$C_yH_{2y}$-" is as defined above.

The term "$C_{1-6}$alkoxycarbonyl" refers to a group $C_{1-6}$alkoxy-C(O)—, wherein the "$C_{1-6}$alkoxy" is as defined above.

The term "$C_{1-6}$alkylcarbonyl" refers to a group $C_{1-6}$alkyl-C(O)—, wherein the "$C_{1-6}$alkyl" is as defined above.

The term "aminocarbonyl" refers to a group amino-C(O)—, wherein the "amino" is as defined above.

The term "$C_{1-6}$alkylsulfonyl" refers to a group $C_{1-6}$alkyl-$S(O)_2$—, wherein the "$C_{1-6}$alkyl" is as defined above.

The term "aminosulfonyl" refers to a group amino-$S(O)_2$—, wherein the "amino" is as defined above.

The term "tautomerism isomers" refers to constitutional isomers of organic compounds that readily interconvert by a chemical reaction called tautomerization. This reaction commonly results in the formal migration of a hydrogen atom or proton, accompanied by a switch of a single bond and adjacent double bond. For example, compounds of general formula (I)

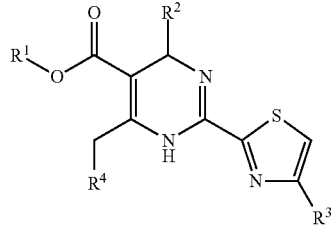

and its tautomerism isomer

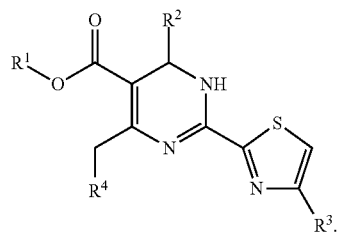

The term "enantiomer" denotes two stereoisomers of a compound which are non-superimposable mirror images of one another.

The term "diastereomer" denotes a stereoisomer with two or more centers of chirality and whose molecules are not mirror images of one another.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitors of HBV

The present invention provides (i) novel compounds having the general formula I:

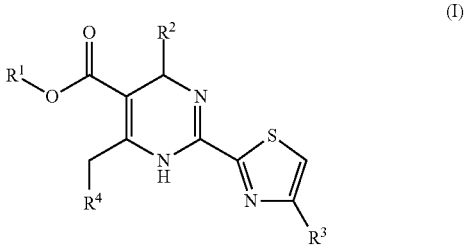

wherein
R¹ is $C_{1-6}$alkyl;
R² is phenyl, which is once or twice or three times substituted by halogen or $C_{1-6}$alkyl;
R³ is hydrogen or $C_{1-6}$alkyl;
R⁴ is

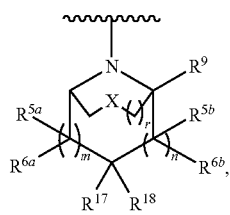

wherein one of $R^{5a}$ and $R^{6a}$ is hydrogen or halogen, and the other one is hydrogen, halogen or hydroxy;
one of $R^{5b}$ and $R^{6b}$ is hydrogen or halogen, and the other one is hydrogen or halogen;
R⁹ is hydrogen or carboxy;
one of $R^{17}$ and $R^{18}$ is hydrogen, halogen, hydroxy, amino, $C_{1-6}$alkylsulfonylamino or trifluoromethylcarbonylamino, the other one is hydrogen, halogen, hydroxy-$C_yH_{2y}$—, $C_{1-6}$alkylcarbonyl-O—, $C_{1-6}$alkoxycarbonyl-$C_yH_{2y}$—, carboxy-$C_yH_{2y}$—, carboxy-$C_yH_{2y}$—O—, $C_{1-6}$alkylcarbonyl-NH—, $C_{1-6}$alkylsulfonyl-NH—, aminocarbonyl-NH— or aminosulfonyl-NH—;
wherein —$C_yH_{2y}$— is unsubstituted once or more times substituted by hydroxy;
or $R^{6a}$ and $R^{17}$ together with the carbon atoms, to which they are attached, form a ring of isoxazolyl, pyrazolyl or oxo-dihydropyrazolyl, which ring is unsubstituted or once or more times substituted by $C_{1-6}$alkyl;
or $R^{17}$ and $R^{18}$ together with the carbon atom, to which they are attached, form diazirinyl;
X is oxygen; sulfur; —N(carbonyl$C_{1-6}$alkyl)-; or —C($R^{15}R^{16}$)—, wherein one of $R^{15}$ and $R^{16}$ is hydrogen or hydroxy, and the other one is hydrogen or carboxy-$C_yH_{2y}$—;
r is 0 or 1;
m is 0 or 1;
n is 0 or 1;
y is 0-6;
or R⁴ is

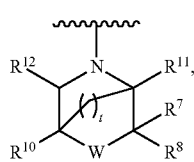

wherein R⁷ is hydrogen or halogen;
R⁸ is hydrogen or halogen;
R¹⁰ is hydrogen, halogen, hydroxy-$C_yH_{2y}$— or $C_{1-6}$alkylcarbonylamino-$C_yH_{2y}$—;
R¹¹ is hydrogen or carboxy;
R¹² is hydrogen or carboxy;
W is a bond, oxygen, —CH₂—, —CF₂— or —N(carbonyl$C_{1-6}$alkyl)-;
t is 1 or 2;
y is 0-6;
with the proviso that

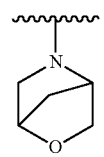

is excluded;
or R⁴ is

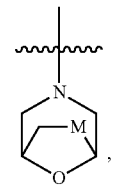

wherein R¹⁹ is hydrogen; $C_{1-6}$alkyl, which is unsubstituted or once or more times substituted by halogen; $C_{1-6}$alkoxycarbonyl-$C_yH_{2y}$—; hydroxy-$C_yH_{2y}$-carbonyl; carboxy-$C_yH_{2y}$-carbonyl; $C_{1-6}$alkylaminosulfonyl; $C_{1-6}$alkylcarbonyl; $C_{1-6}$alkylsulfonyl; aminocarbonyl; or aminosulfonyl;
Y is carbonyl or —CH₂—;
u is 0 or 1;
y is 0-6;
or R⁴ is

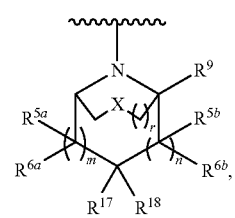

wherein M is a bond, —CH₂— or —N($R^{14}$)—CH₂—;
R¹⁴ is $C_{1-6}$alkoxycarbonyl;
or pharmaceutically acceptable salts, or tautomerism isomers, or enantiomers, or diastereomers thereof.

Another embodiment of present invention is (ii) a compound of formula I or a pharmaceutically acceptable salt or tautomerism isomers or enantiomers or diastereomers thereof, wherein
R¹ is methyl or ethyl;
R² is phenyl, which is once or twice or three times substituted by fluoro, chloro, bromo or methyl;
R³ is hydrogen or methyl;
R⁴ is wherein one of $R^{5a}$ and $R^{6a}$ is hydrogen or fluoro, and the other one is hydrogen, fluoro or hydroxy;

one of $R^{5b}$ and $R^{6b}$ is hydrogen or fluoro, and the other one is hydrogen or fluoro;

$R^9$ is hydrogen or carboxy;

one of $R^{17}$ and $R^{18}$ is hydrogen, fluoro, hydroxy, amino, methylsulfonylamino or trifluoromethylcarbonylamino, the other one is hydrogen, fluoro, hydroxy, hydroxymethyl, methylcarbonyl-O—, methoxycarbonyl, methoxycarbonylmethyl, ethoxycarbonylmethyl, methoxycarbonyl(hydroxy)methyl, ethoxycarbonyl(hydroxy)methyl, carboxymethyl-O—, carboxy, carboxymethyl, methylcarbonylamino, aminocarbonylamino, methylsulfonylamino or aminosulfonylamino;

or $R^{6a}$ and $R^{17}$ together with the carbon atoms, to which they are attached, form a ring of isoxazolyl, pyrazolyl or oxo-dihydropyrazolyl, which ring is unsubstituted or once or more times substituted by methyl;

or $R^{17}$ and $R^{18}$ together with the carbon atom, to which they are attached, form diazirinyl;

X is oxygen; sulfur; —N(carbonylmethyl)-; or —C($R^{15}R^{16}$)—, wherein one of $R^{15}$ and $R^{16}$ is hydrogen or hydroxy, and the other one is hydrogen, carboxy or carboxymethyl;

r is 0 or 1;
m is 0 or 1;
n is 0 or 1;
or $R^4$ is

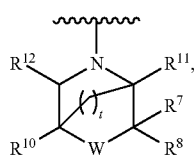

wherein $R^7$ is hydrogen or fluoro;
$R^8$ is hydrogen or fluoro;
$R^{10}$ is hydrogen, fluoro, hydroxymethyl or methylcarbonylaminomethyl;
$R^{11}$ is hydrogen or carboxy;
$R^{12}$ is hydrogen or carboxy;
W is a bond, oxygen, —CH$_2$—, —CF$_2$— or —N(carbonylmethyl)-;
t is 1 or 2;
with the proviso that

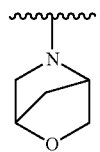

is excluded;
or $R^4$ is

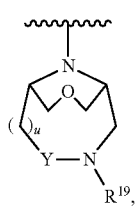

wherein $R^{19}$ is hydrogen, methyl, isopropyl, difluoromethylmethyl, methylcarbonyl, methoxycarbonyl, ethoxycarbonylisopropyl, hydroxymethylcarbonyl, carboxyisopropylcarbonyl, aminocarbonyl, methylsulfonyl, aminosulfonyl or methylaminosulfonyl;

Y is carbonyl or —CH$_2$—;
u is 0 or 1;
or $R^4$ is

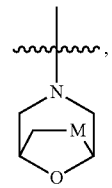

wherein M is a bond, —CH$_2$— or —N(carbonyltert-butoxy)-CH$_2$—; or pharmaceutically acceptable salts, or tautomerism isomers, or enantiomers, or diastereomers thereof.

Another embodiment of present invention is (iii) a compound of formula I or a pharmaceutically acceptable salt or tautomerism isomers or enantiomers or diastereomers thereof, wherein $R^1$ is $C_{1-6}$alkyl;
$R^2$ is phenyl, which is once or twice or three times substituted by halogen or $C_{1-6}$alkyl;
$R^3$ is hydrogen or $C_{1-6}$alkyl;
$R^4$ is

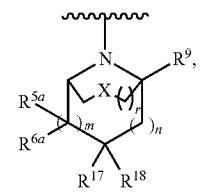

wherein one of $R^{5a}$ and $R^{6a}$ is hydrogen or halogen, and the other one is hydrogen or halogen;
$R^9$ is hydrogen or carboxy;
one of $R^{17}$ and $R^{18}$ is hydrogen or $C_{1-6}$alkylsulfonylamino, the other one is hydrogen, $C_{1-6}$alkoxycarbonyl-$C_yH_{2y}$—, carboxy-$C_yH_{2y}$—O—, carboxy-$C_yH_{2y}$—, $C_{1-6}$alkylcarbonyl-NH—, $C_{1-6}$alkylsulfonyl-NH— or aminosulfonyl-NH—;
or $R^{6a}$ and $R^{17}$ together with the carbon atoms, to which they are attached, form pyrazolyl;
X is oxygen; sulfur; or —C($R^{15}R^{16}$)—, wherein one of $R^{15}$ and $R^{16}$ is hydrogen or hydroxy, and the other one is hydrogen or carboxy-$C_yH_{2y}$—;
r is 0 or 1;
m is 0 or 1;
n is 0 or 1;
y is 0-6.

Further embodiment of present invention is (iv) a compound of formula I or a pharmaceutically acceptable salt or tautomerism isomers or enantiomers or diastereomers thereof, wherein $R^1$ is methyl or ethyl;
$R^2$ is phenyl, which is once or twice or three times substituted by fluoro, chloro, bromo or methyl;
$R^3$ is hydrogen or methyl;

R⁴ is

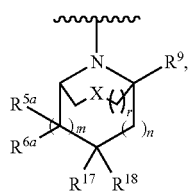

wherein one of $R^{5a}$ and $R^{6a}$ is hydrogen or fluoro, and the other one is hydrogen or fluoro;
$R^9$ is hydrogen or carboxy;
one of $R^{17}$ and $R^{18}$ is hydrogen or methylsulfonylamino, the other one is hydrogen, ethoxycarbonylmethyl, carboxymethyl-O—, carboxy, carboxymethyl, methylcarbonyl-NH—, methylsulfonyl-NH— or aminosulfonyl-NH—;
or $R^{6a}$ and $R^{17}$ together with the carbon atoms, to which they are attached, form pyrazolyl;
X is oxygen; sulfur; or —C($R^{15}R^{16}$)—, wherein one of $R^{15}$ and $R^{16}$ is hydrogen or hydroxy, and the other one is hydrogen, carboxy or carboxymethyl;
r is 0 or 1;
m is 0 or 1;
n is 0 or 1.

Another embodiment of present invention is (v) a compound of formula IA

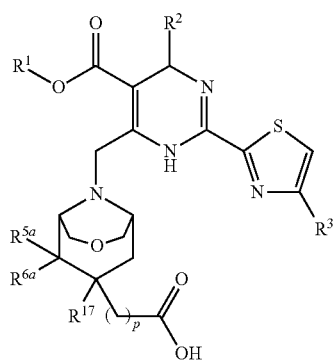

wherein
$R^1$ is $C_{1-6}$alkyl;
$R^2$ is phenyl, which is once or twice or three times substituted by halogen or $C_{1-6}$alkyl;
$R^3$ is hydrogen or $C_{1-6}$alkyl;
one of $R^{5a}$ and $R^{6a}$ is hydrogen or halogen, and the other one is hydrogen, halogen or hydroxy;
$R^{17}$ is hydrogen or amino;
p is 0 or 1;
or pharmaceutically acceptable salts, or tautomerism isomers, or enantiomers, or diastereomers thereof.

Further embodiment of present invention is (vi) a compound of formula IA or a pharmaceutically acceptable salt or tautomerism isomers or enantiomers or diastereomers thereof, wherein
$R^1$ is methyl or ethyl;
$R^2$ is phenyl, which is once or twice or three times substituted by fluoro, chloro, bromo or methyl;
$R^3$ is hydrogen or methyl;
one of $R^{5a}$ and $R^{6a}$ is hydrogen or fluoro, and the other one is hydrogen, fluoro or hydroxy;
$R^{17}$ is hydrogen or amino;
p is 0 or 1.

Another embodiment of present invention is (vii) a compound of formula IB

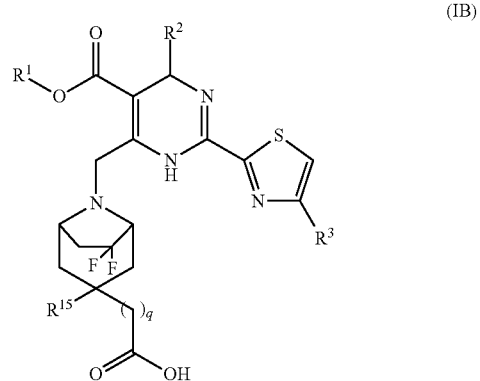

wherein
$R^1$ is $C_{1-6}$alkyl;
$R^2$ is phenyl, which is once or twice or three times substituted by halogen or $C_{1-6}$alkyl;
$R^3$ is hydrogen;
$R^{15}$ is hydrogen or hydroxy;
q is 0 or 1;
or pharmaceutically acceptable salts, or tautomerism isomers, or enantiomers, or diastereomers thereof.

Another embodiment of present invention is (viii) a compound of formula IB or a pharmaceutically acceptable salt or tautomerism isomers or enantiomers or diastereomers thereof, wherein
$R^1$ is methyl or ethyl;
$R^2$ is phenyl, which is once or twice or three times substituted by fluoro, chloro, bromo or methyl;
$R^3$ is hydrogen;
$R^{15}$ is hydrogen or hydroxy;
q is 0 or 1.

Another embodiment of present invention is (ix) a compound of formula I or a pharmaceutically acceptable salt or tautomerism isomers or enantiomers or diastereomers thereof, wherein
$R^1$ is $C_{1-6}$alkyl;
$R^2$ is phenyl, which is once or twice or three times substituted by halogen;
$R^3$ is hydrogen;
$R^4$ is

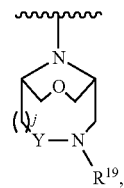

wherein $R^{19}$ is hydrogen, aminocarbonyl, aminosulfonyl or hydroxy-$C_yH_{2y}$-carbonyl;
Y is —CH₂— or carbonyl;
j is 0 or 1;
y is 0-6.

Further embodiment of present invention is (x) a compound of formula I or a pharmaceutically acceptable salt or tautomerism isomers or enantiomers or diastereomers thereof, wherein
$R^1$ is methyl;
$R^2$ is phenyl, which is once or twice or three times substituted by fluoro or chloro;
$R^3$ is hydrogen;
$R^4$ is

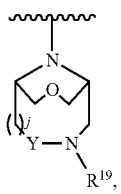

wherein $R^{19}$ is hydrogen, aminocarbonyl, aminosulfonyl or hydroxymethylcarbonyl;
Y is —CH$_2$— or carbonyl;
j is 0 or 1.

Another embodiment of present invention is (xi) a compound of formula I or a pharmaceutically acceptable salt or tautomerism isomers or enantiomers or diastereomers thereof, wherein
$R^1$ is $C_{1-6}$alkyl;
$R^2$ is phenyl, which is once or twice or three times substituted by halogen;
$R^3$ is hydrogen;
$R^4$ is

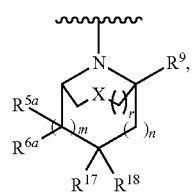

wherein one of $R^{5a}$ and $R^{6a}$ is hydrogen or halogen, and the other one is hydrogen or halogen;
$R^9$ is hydrogen or carboxy;
one of $R^{17}$ and $R^{18}$ is hydrogen, the other one is hydrogen or carboxy-$C_yH_{2y}$—;
X is oxygen; or —C($R^{15}R^{16}$)—, wherein one of $R^{15}$ and $R^{16}$ is hydrogen or hydroxy, and the other one is hydrogen or carboxy-$C_yH_{2y}$—;
r is 0 or 1;
m is 1;
n is 0 or 1;
y is 0-6.

Another embodiment of present invention is (xii) a compound of formula I or a pharmaceutically acceptable salt or tautomerism isomers or enantiomers or diastereomers thereof, wherein
$R^1$ is methyl or ethyl;
$R^2$ is phenyl, which is once or twice or three times substituted by fluoro or chloro;
$R^3$ is hydrogen;
$R^4$ is

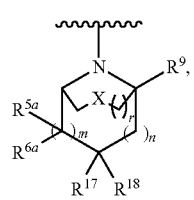

wherein one of $R^{5a}$ and $R^{6a}$ is hydrogen or fluoro, and the other one is hydrogen or fluoro;
$R^9$ is hydrogen or carboxy;
one of $R^{17}$ and $R^{18}$ is hydrogen, the other one is hydrogen or carboxymethyl;
X is oxygen; or —C($R^{15}R^{16}$)—, wherein one of $R^{15}$ and $R^{16}$ is hydrogen or hydroxy, and the other one is hydrogen or carboxymethyl;
r is 0 or 1;
m is 1;
n is 0 or 1.

Another embodiment of present invention is (xiii) a compound of formula I or a pharmaceutically acceptable salt or tautomerism isomers or enantiomers or diastereomers thereof, wherein
$R^1$ is $C_{1-6}$alkyl;
$R^2$ is phenyl, which is once or twice or three times substituted by halogen or $C_{1-6}$alkyl;
$R^3$ is hydrogen or $C_{1-6}$alkyl;
$R^4$ is

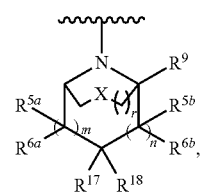

wherein one of $R^{5a}$ and $R^{6a}$ is hydrogen or halogen, and the other one is hydrogen, halogen or hydroxy;
one of $R^{5b}$ and $R^{6b}$ is hydrogen, and the other one is hydrogen or carboxy-$C_yH_{2y}$—;
$R^9$ is hydrogen or carboxy;
one of $R^{17}$ and $R^{18}$ is hydrogen or amino, the other one is hydrogen, carboxy-$C_yH_{2y}$—O—, carboxy-$C_yH_{2y}$—, $C_{1-6}$alkylcarbonyl-NH—, $C_{1-6}$alkylsulfonyl-NH—, aminocarbonyl-NH— or aminosulfonyl-NH—;
X is oxygen; —N(carbonyl$C_{1-6}$alkyl)- or —C($R^{15}R^{16}$)—, wherein one of $R^{15}$ and $R^{16}$ is hydrogen or hydroxy, and the other one is hydrogen or carboxy-$C_yH_{2y}$—;
r is 0 or 1;
m is 0 or 1;
n is 0 or 1;
y is 0-6;
or $R^4$ is

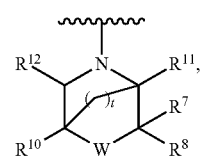

wherein $R^7$ is hydrogen;
$R^8$ is hydrogen;
$R^{10}$ is hydrogen, halogen or hydroxy-$C_yH_{2y}$—;
$R^{11}$ is hydrogen or carboxy;
$R^{12}$ is hydrogen or carboxy;
W is a bond, oxygen or —CH$_2$—;
t is 1 or 2;
y is 0-6;

with the proviso that

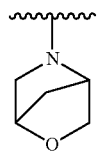

is excluded;
or $R^4$ is

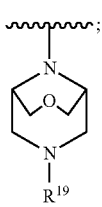

wherein $R^{19}$ is hydroxy-$C_yH_{2y}$-carbonyl, carboxy-$C_yH_{2y}$-carbonyl, $C_{1-6}$alkylsulfonyl, aminocarbonyl or aminosulfonyl;
y is 0-6.

Further embodiment of present invention is (xiv) a compound of formula I or a pharmaceutically acceptable salt or tautomerism isomers or enantiomers or diastereomers thereof, wherein $R^1$ is methyl or ethyl;
$R^2$ is phenyl, which is once or twice or three times substituted by fluoro, chloro, bromo or methyl;
$R^3$ is hydrogen or methyl;
$R^4$ is

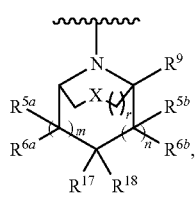

wherein one of $R^{5a}$ and $R^{6a}$ is hydrogen or fluoro, and the other one is hydrogen, fluoro or hydroxy;
one of $R^{5b}$ and $R^{6b}$ is hydrogen, and the other one is hydrogen or carboxymethyl;
$R^9$ is hydrogen or carboxy;
one of $R^{17}$ and $R^{18}$ is hydrogen or amino, the other one is hydrogen, carboxy, carboxymethyl, carboxymethyl-O—, methylcarbonylamino, aminocarbonylamino, methylsulfonylamino or aminosulfonylamino;
X is oxygen; —N(carbonylmethyl)-; or —C($R^{15}R^{16}$)—, wherein one of $R^{15}$ and $R^{16}$ is hydrogen or hydroxy, and the other one is hydrogen, carboxy, or carboxymethyl;
r is 0 or 1;
m is 0 or 1;
n is 0 or 1;

or $R^4$ is

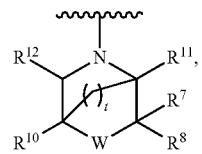

wherein $R^7$ is hydrogen;
$R^8$ is hydrogen;
$R^{10}$ is hydrogen, fluoro or hydroxymethyl;
$R^{11}$ is hydrogen or carboxy;
$R^{12}$ is hydrogen or carboxy;
W is a bond, oxygen or —$CF_2$—;
t is 1 or 2.
with the proviso that

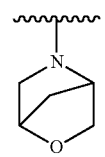 [SMILES: *N1CC2CC1CO2]

is excluded;
or $R^4$ is

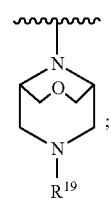

wherein $R^{19}$ is hydroxymethylcarbonyl, carboxyisopropylcarbonyl, aminocarbonyl, methylsulfonyl or aminosulfonyl.

Another embodiment of present invention is (xv) a compound of formula I or a pharmaceutically acceptable salt or tautomerism isomers or enantiomers or diastereomers thereof, wherein $R^1$ is $C_{1-6}$alkyl;
$R^2$ is phenyl, which is once or twice or three times substituted by halogen or $C_{1-6}$alkyl;
$R^3$ is hydrogen or $C_{1-6}$alkyl;
$R^4$ is

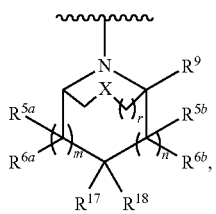

wherein one of $R^{5a}$ and $R^{6a}$ is hydrogen or halogen, and the other one is hydrogen, halogen or hydroxy;
one of $R^{5b}$ and $R^{6b}$ is hydrogen or halogen, and the other one is hydrogen or halogen;
$R^9$ is hydrogen or carboxy;

one of $R^{17}$ and $R^{18}$ is hydrogen, hydroxy or amino, the other one is hydroxy-$C_yH_{2y}$—, carboxy-$C_yH_{2y}$—O—, carboxy-$C_yH_{2y}$—, or $C_{1-6}$alkylcarbonyl-NH—;

or $R^{6a}$ and $R^{17}$ together with the carbon atoms, to which they are attached, form a ring of oxo-dihydropyrazolyl, which ring is unsubstituted or once or more times substituted by $C_{1-6}$alkyl;

X is oxygen; sulfur; or —$C(R^{15}R^{16})$—, wherein one of $R^{15}$ and $R^{16}$ is hydrogen, and the other one is hydrogen or carboxy-$C_yH_{2y}$—;

r is 0 or 1;
m is 0 or 1;
n is 0 or 1;
y is 0-6;
or $R^4$ is

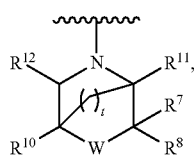

wherein $R^7$ is hydrogen;
$R^8$ is hydrogen;
$R^{10}$ is hydrogen, halogen, hydroxy-$C_yH_{2y}$— or $C_{1-6}$alkylcarbonylamino-$C_yH_{2y}$—;
$R^{11}$ is hydrogen or carboxy;
$R^{12}$ is hydrogen or carboxy;
W is a bond, oxygen, —$CF_2$—, or —N(carbonyl$C_{1-6}$alkyl)-;
t is 1 or 2;
y is 0-6;
with the proviso that

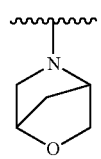

is excluded;
or $R^4$ is

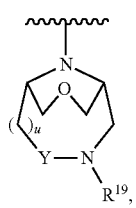

wherein $R^{19}$ is hydrogen, $C_{1-6}$alkyl, hydroxy-$C_yH_{2y}$-carbonyl, carboxy-$C_yH_{2y}$-carbonyl, $C_{1-6}$alkylcarbonyl or aminocarbonyl;
Y is carbonyl or —$CH_2$—;
u is 0 or 1;
y is 0-6.

Further embodiment of present invention is (xvi) a compound of formula I or a pharmaceutically acceptable salt or tautomerism isomers or enantiomers or diastereomers thereof, wherein $R^1$ is methyl or ethyl;
$R^2$ is phenyl, which is once or twice or three times substituted by fluoro, chloro, bromo or methyl;
$R^3$ is hydrogen or methyl;
$R^4$ is

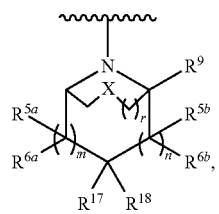

wherein one of $R^{5a}$ and $R^{6a}$ is hydrogen or fluoro, and the other one is hydrogen, fluoro or hydroxy;
one of $R^{5b}$ and $R^{6b}$ is hydrogen or fluoro, and the other one is hydrogen or fluoro;
$R^9$ is hydrogen or carboxy;
one of $R^{17}$ and $R^{18}$ is hydrogen, hydroxy or amino, the other one is hydroxy, carboxymethyl-O—, carboxy, carboxymethyl or methylcarbonylamino;
or $R^{6a}$ and $R^{17}$ together with the carbon atoms, to which they are attached, form a ring of oxo-dihydropyrazolyl, which ring is unsubstituted or once or more times substituted by methyl;
X is oxygen; sulfur; or —$C(R^{15}R^{16})$—, wherein one of $R^{15}$ and $R^{16}$ is hydrogen, and the other one is hydrogen carboxymethyl;
r is 0 or 1;
m is 0 or 1;
n is 0 or 1;
or $R^4$ is

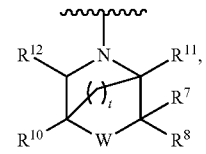

wherein $R^7$ is hydrogen;
$R^8$ is hydrogen;
$R^{10}$ is hydrogen, fluoro, hydroxymethyl or methylcarbonylaminomethyl;
$R^{11}$ is hydrogen or carboxy;
$R^{12}$ is hydrogen or carboxy;
W is a bond, oxygen, —$CF_2$—, or —N(carbonylmethyl)-;
t is 1 or 2;
with the proviso that

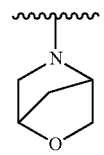 [SMILES: *N1CC2CC1CO2]

is excluded;

or R⁴ is

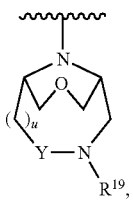

wherein R¹⁹ is hydrogen, methyl, isopropyl, methylcarbonyl, hydroxymethylcarbonyl, carboxyisopropylcarbonyl or aminocarbonyl;
Y is carbonyl or —CH₂—;
u is 0 or 1.

Another embodiment of present invention is (xvii) a compound of formula I or a pharmaceutically acceptable salt or tautomerism isomers or enantiomers or diastereomers thereof, wherein
R¹ is $C_{1-6}$alkyl;
R² is phenyl, which is once or twice or three times substituted by halogen or $C_{1-6}$alkyl;
R³ is hydrogen or $C_{1-6}$alkyl;
R⁴ is

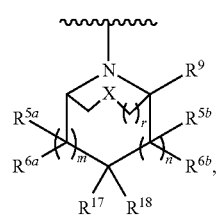

wherein one of R⁵ᵃ and R⁶ᵃ is hydrogen or halogen, and the other one is hydrogen or halogen;
one of R⁵ᵇ and R⁶ᵇ is hydrogen or halogen, and the other one is hydrogen or halogen;
R⁹ is hydrogen or carboxy; one of R¹⁷ and R¹⁸ is hydrogen, halogen, hydroxy, $C_{1-6}$alkylsulfonylamino or trifluoromethylcarbonylamino, the other one is hydrogen, halogen, hydroxy-$C_yH_{2y}$—, $C_{1-6}$alkoxycarbonyl-$C_yH_{2y}$—, carboxy-$C_yH_{2y}$—, $C_{1-6}$alkylcarbonyl-NH—, $C_{1-6}$alkylsulfonyl-NH—, aminocarbonyl-NH— or aminosulfonyl-NH—;
wherein —$C_yH_{2y}$— is unsubstituted once or more times substituted by hydroxy;
or R⁶ᵃ and R¹⁷ together with the carbon atoms, to which they are attached, form a ring of isoxazolyl, pyrazolyl or oxo-dihydropyrazolyl, which ring is unsubstituted or once or more times substituted by $C_{1-6}$alkyl;
or R¹⁷ and R¹⁸ together with the carbon atom, to which they are attached, form diazirinyl;
X is oxygen; or —C(R¹⁵R¹⁶)—, wherein one of R¹⁵ and R¹⁶ is hydrogen or hydroxy, and the other one is carboxy-$C_yH_{2y}$—;
r is 0 or 1;
m is 0 or 1;
n is 0 or 1;
y is 0-6;

or R⁴ is

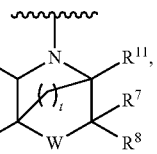

wherein R⁷ is hydrogen;
R⁸ is hydrogen;
R¹⁰ is hydroxy-$C_yH_{2y}$—;
R¹¹ is hydrogen;
R¹² is hydrogen;
W is oxygen;
t is 1;
y is 0-6;
with the proviso that

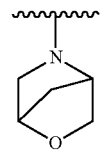 [SMILES: *N1CC2CC1CO2]

is excluded;
or R⁴ is

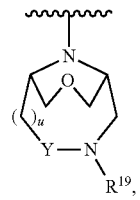

wherein R¹⁹ is $C_{1-6}$alkyl, which is unsubstituted or once or more times substituted by halogen; $C_{1-6}$alkoxycarbonyl-$C_yH_{2y}$—; $C_{1-6}$alkylsulfonyl; aminocarbonyl; or aminosulfonyl;
Y is —CH₂—;
u is 0;
y is 0-6;
or R⁴ is

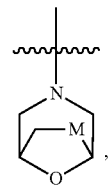

wherein M is a bond or —CH₂—.
Further embodiment of present invention is (xviii) a compound of formula I or a pharmaceutically acceptable salt or tautomerism isomers or enantiomers or diastereomers thereof, wherein
R¹ is methyl or ethyl;
R² is phenyl, which is once or twice or three times substituted by fluoro, chloro, bromo or methyl;
R³ is hydrogen or methyl;

$R^4$ is

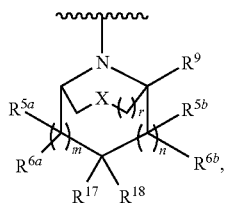

wherein one of $R^{5a}$ and $R^{6a}$ is hydrogen or fluoro, and the other one is hydrogen or fluoro;
one of $R^{5b}$ and $R^{6b}$ is hydrogen or fluoro, and the other one is hydrogen or fluoro;
$R^9$ is hydrogen or carboxy;
one of $R^{17}$ and $R^{18}$ is hydrogen, fluoro, hydroxy, methylsulfonylamino or trifluoromethylcarbonylamino, the other one is hydrogen, fluoro, hydroxy, hydroxymethyl, methoxycarbonylmethyl, ethoxycarbonylmethyl, ethoxycarbonyl(hydroxy)methyl, carboxy, carboxymethyl, methylcarbonylamino, aminocarbonylamino, methylsulfonylamino or aminosulfonylamino;
or $R^{6a}$ and $R^{17}$ together with the carbon atoms, to which they are attached, form a ring of isoxazolyl, pyrazolyl or oxo-dihydropyrazolyl, which ring is unsubstituted or once or more times substituted by methyl;
or $R^{17}$ and $R^{18}$ together with the carbon atom, to which they are attached, form diazirinyl;
X is oxygen; or —$C(R^{15}R^{16})$—, wherein one of $R^{15}$ and $R^{16}$ is hydrogen or hydroxy, and the other one is carboxy or carboxymethyl;
r is 0 or 1;
m is 0 or 1;
n is 0 or 1;
or $R^4$ is

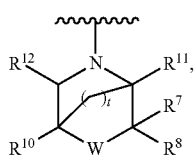

wherein $R^7$ is hydrogen;
$R^8$ is hydrogen;
$R^{10}$ is hydrogen, or hydroxymethyl;
$R^{11}$ is hydrogen;
$R^{12}$ is hydrogen;
W is oxygen;
t is 1;
with the proviso that

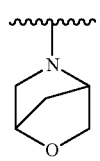

is excluded;

or $R^4$ is

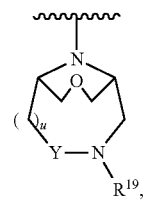

wherein $R^{19}$ is difluoromethylmethyl, methoxycarbonyl, aminocarbonyl, methylsulfonyl or aminosulfonyl;
Y is —$CH_2$—;
u is 0;
or $R^4$ is

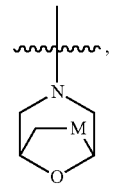

wherein M is a bond or —$CH_2$—.

Another embodiment of present invention is (xix) a compound of formula I or a pharmaceutically acceptable salt or tautomerism isomers or enantiomers or diastereomers thereof, wherein
$R^1$ is $C_{1-6}$alkyl;
$R^2$ is phenyl, which is once or twice or three times substituted by halogen;
$R^3$ is hydrogen;
$R^4$ is

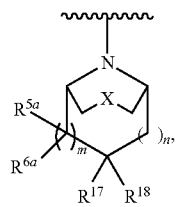

wherein one of $R^{5a}$ and $R^{6a}$ is hydrogen or halogen, and the other one is hydrogen or halogen;
one of $R^{17}$ and $R^{18}$ is hydrogen, the other one is hydrogen, carboxy-$C_yH_{2y}$—, $C_{1-6}$alkylcarbonyl-NH— or aminosulfonyl-NH—;
or $R^{6a}$ and $R^{17}$ together with the carbon atoms, to which they are attached, form pyrazolyl;
X is oxygen or —$C(\text{carboxy}C_{1-6}\text{alkyl})$-;
m is 0 or 1;
n is 0 or 1;
y is 0-6;

or $R^4$ is

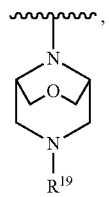, wherein $R^{19}$ is $C_{1-6}$alkyl;
or $R^4$ is

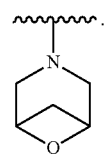.

Further embodiment of present invention is (xx) a compound of formula I or a pharmaceutically acceptable salt or tautomerism isomers or enantiomers or diastereomers thereof, wherein
$R^1$ is methyl or ethyl;
$R^2$ is phenyl, which is once or twice or three times substituted by fluoro, chloro or bromo;
$R^3$ is hydrogen;
$R^4$ is

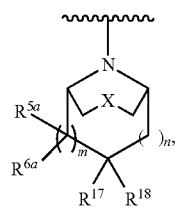, wherein one of $R^{5a}$ and $R^{6a}$ is hydrogen or fluoro, and the other one is hydrogen or fluoro;
one of $R^{17}$ and $R^{18}$ is hydrogen, the other one is hydrogen, carboxymethyl, methylcarbonylamino or aminosulfonylamino;
or $R^{6a}$ and $R^{17}$ together with the carbon atoms, to which they are attached, form pyrazolyl;
X is oxygen or —C(carboxymethyl)-;
m is 0 or 1;
n is 0 or 1;
or $R^4$ is

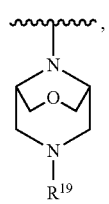, wherein $R^{19}$ is methyl;

or $R^4$ is

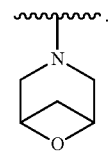.

Another embodiment of present invention is (xxi) a compound of formula IC, wherein

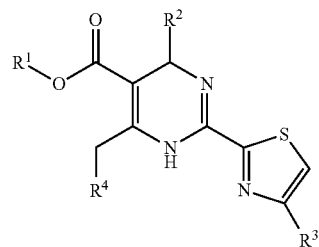

(IC)

$R^1$ is $C_{1-6}$alkyl;
$R^2$ is phenyl, which is once or twice or three times substituted by halogen;
$R^3$ is hydrogen or $C_{1-6}$alkyl;
$R^4$ is selected from

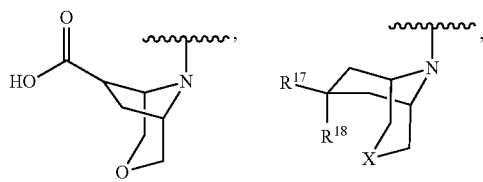

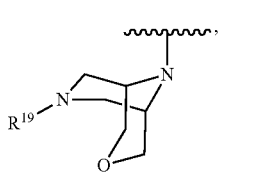, 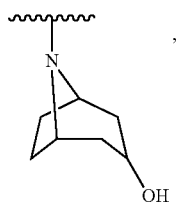

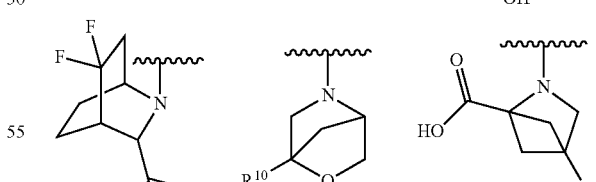

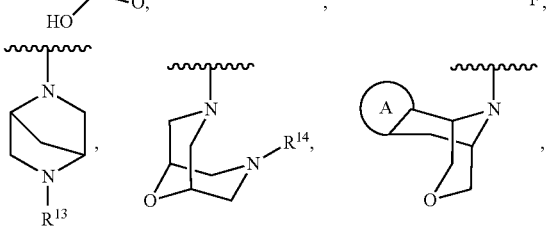

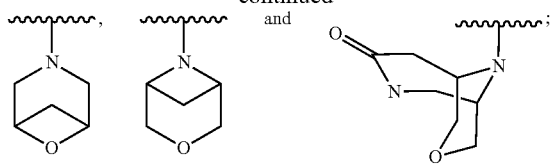

wherein $R^{10}$ is hydroxy-$C_yH_{2y}$—;
$R^{13}$ is $C_{1-6}$alkylcarbonyl;
$R^{14}$ is $C_{1-6}$alkoxycarbonyl;
X is —O— or —S—; provided that
when X is —O—, $R^{17}$ is hydrogen or hydroxy, $R^{18}$ is $C_{1-6}$alkoxycarbonyl-$C_yH_{2y}$—, carboxy-$C_yH_{2y}$—, hydroxy-$C_yH_{2y}$—, $C_{1-6}$alkylcarbonyl-O—, $C_{1-6}$alkylcarbonylamino, $C_{1-6}$alkylsulfonylamino or

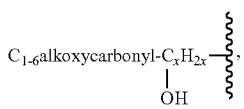

or $R^{17}$ and $R^{18}$, together with the carbon atom, to which they are attached, form

when X is —S—, $R^{17}$ is hydrogen, $R^{18}$ is carboxy-$C_yH_{2y}$—;
$R^{19}$ is selected from aminocarbonyl; aminosulfonyl; $C_{1-6}$alkoxycarbonyl-$C_yH_{2y}$—; $C_{1-6}$alkyl, which is unsubstituted or substituted by fluoro; $C_{1-6}$alkylaminosulfonyl; $C_{1-6}$alkylcarbonyl; $C_{1-6}$alkylsulfonyl and hydroxy-$C_xH_{2x}$-carbonyl;
A is pyrazolyl or oxopyrazolyl, which is unsubstituted or substituted by $C_{1-6}$alkyl;
x is 1-6;
y is 0-6;
or pharmaceutically acceptable salts, or tautomerism isomers, or enantiomers, or diastereomers thereof.

Further embodiment of present invention is (xxii) a compound of formula IC, wherein
$R^1$ is methyl or ethyl;
$R^2$ is phenyl, which is once or twice or three times substituted by fluoro, chloro or bromo;
$R^3$ is hydrogen or methyl;
$R^4$ is selected from

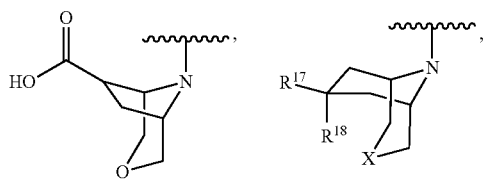

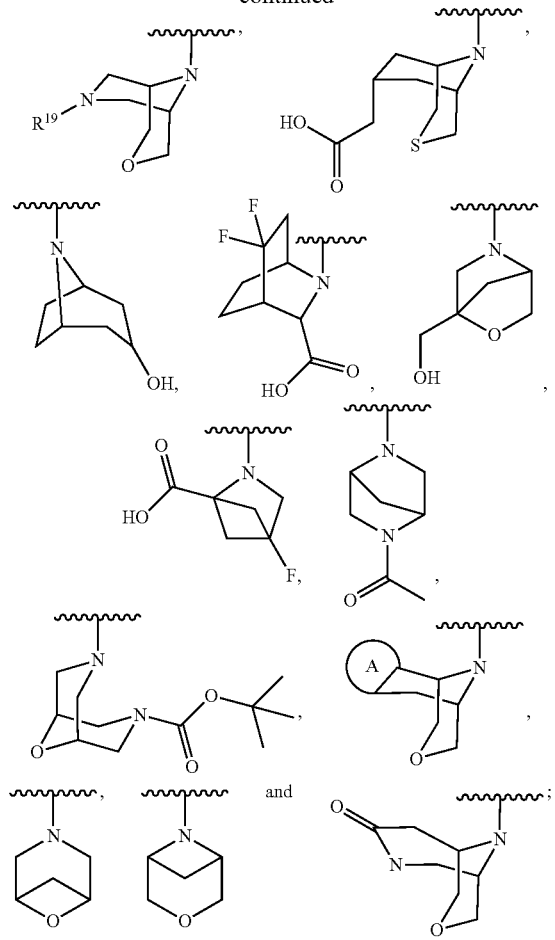

wherein $R^{17}$ is hydrogen or hydroxy;
$R^{18}$ is methoxycarbonyl, methoxycarbonylmethyl, methoxycarbonylmethyl(hydroxy), carboxy, carboxymethyl, hydroxy, hydroxymethyl, methylcarbonyl-O—, methylcarbonylamino or methylsulfonylamino;
or $R^{17}$ and $R^{18}$, together with the carbon atom, to which they are attached, form

$R^{19}$ is aminocarbonyl, aminosulfonyl, methoxycarbonyl, ethoxycarbonylisopropyl, methyl, isopropyl, difluoroethyl, methylaminosulfonyl, methylcarbonyl, methylsulfonyl or hydroxymethylcarbonyl;
A is pyrazolyl or oxopyrazolyl, which is unsubstituted or substituted by methyl; or pharmaceutically acceptable salts, or tautomerism isomers, or enantiomers, or diastereomers thereof.

Another embodiment of present invention is (xxiii) a compound of formula IC, wherein
$R^1$ is $C_{1-6}$alkyl;
$R^2$ is phenyl, which is once or twice or three times substituted by halogen;
$R^3$ is hydrogen;

$R^4$ is selected from

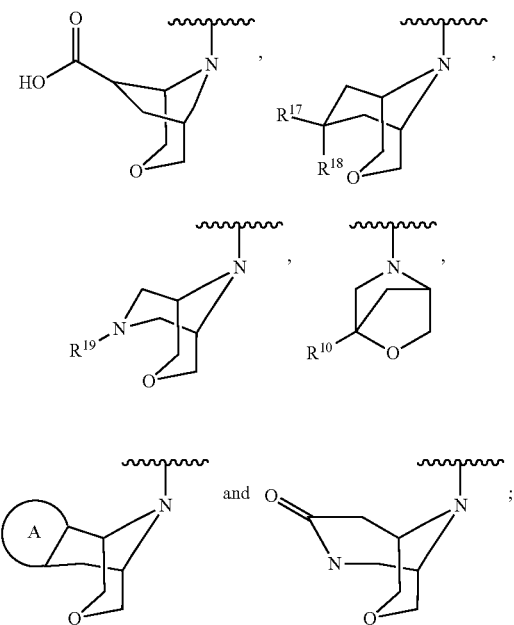

wherein $R^{10}$ is hydroxy-$C_xH_{2x}$—;

$R^{17}$ is hydrogen, $R^{18}$ is $C_{1-6}$alkoxycarbonyl, carboxy-$C_xH_{2x}$—, hydroxy, $C_{1-6}$alkylcarbonylamino, $C_{1-6}$alkylsulfonylamino or

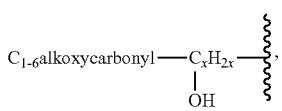

or $R^{17}$ and $R^{18}$, together with the carbon atom, to which they are attached, form

$R^{19}$ is selected from aminocarbonyl; aminosulfonyl; $C_{1-6}$alkoxycarbonyl-$C_yH_{2y}$—; $C_{1-6}$alkyl, which is unsubstituted or substituted by fluoro; $C_{1-6}$alkylaminosulfonyl; $C_{1-6}$alkylcarbonyl; and hydroxy-$C_xH_{2x}$-carbonyl;

A is $C_{1-6}$alkylpyrazolyl;

x is 1-6;

y is 0-6;

or pharmaceutically acceptable salts, or tautomerism isomers, or enantiomers, or diastereomers thereof.

Further embodiment of present invention is (xxiv) a compound of formula IC, wherein $R^1$ is methyl or ethyl;

$R^2$ is phenyl, which is once or twice or three times substituted by fluoro, chloro or bromo;

$R^3$ is hydrogen;

$R^4$ is selected from

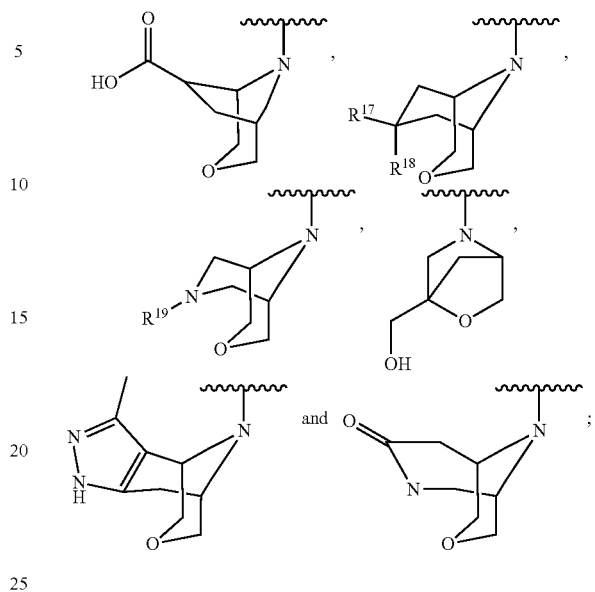

wherein $R^{17}$ is hydrogen;

$R^{18}$ is methoxycarbonyl, methoxycarbonylmethyl(hydroxy), carboxymethyl, hydroxy, methylcarbonylamino or methylsulfonylamino;

or $R^{17}$ and $R^{18}$, together with the carbon atom, to which they are attached, form

$R^{19}$ is aminocarbonyl, aminosulfonyl, methoxycarbonyl, ethoxycarbonylisopropyl, methyl, difluoroethyl, methylaminosulfonyl, methylcarbonyl, or hydroxymethylcarbonyl; or pharmaceutically acceptable salts, or tautomerism isomers, or enantiomers, or diastereomers thereof.

Another embodiment of present invention is (xxv) a compound of formula IC or a pharmaceutically acceptable salt or tautomerism isomers or enantiomers or diastereomers thereof, wherein $R^1$ is $C_{1-6}$alkyl;

$R^2$ is phenyl, which is once or twice or three times substituted by halogen;

$R^3$ is hydrogen or $C_{1-6}$alkyl;

$R^4$ is selected from

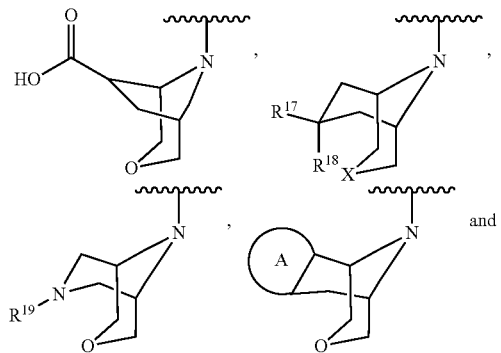

-continued

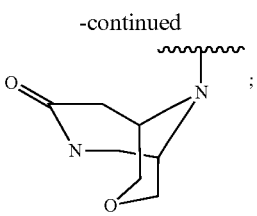

X is —O— or —S—; provided that
when X is —O—, $R^{17}$ is hydrogen or hydroxy, $R^{18}$ is $C_{1-6}$alkoxycarbonyl-$C_yH_{2y}$—, carboxy-$C_yH_{2y}$—, hydroxy-$C_yH_{2y}$—, $C_{1-6}$alkylcarbonyl-O—, $C_{1-6}$alkylcarbonylamino, $C_{1-6}$alkylsulfonylamino or

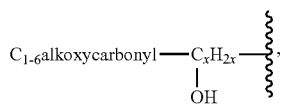

or $R^{17}$ and $R^{18}$, together with the carbon atom, to which they are attached, form

when X is —S—, $R^{17}$ is hydrogen, $R^{18}$ is carboxy-$C_yH_{2y}$—;
$R^{19}$ is selected from aminocarbonyl; aminosulfonyl; $C_{1-6}$alkoxycarbonyl-$C_yH_{2y}$—; $C_{1-6}$alkyl, which is unsubstituted or substituted by fluoro; $C_{1-6}$alkylaminosulfonyl; $C_{1-6}$alkylcarbonyl; $C_{1-6}$alkylsulfonyl and hydroxy-$C_xH_{2x}$-carbonyl;
A is pyrazolyl or oxopyrazolyl, which is unsubstituted or substituted by $C_{1-6}$alkyl;
x is 1-6;
y is 0-6.

Further embodiment of present invention is (xxvi) a compound of formula IC or a pharmaceutically acceptable salt or tautomerism isomers or enantiomers or diastereomers thereof, wherein
$R^1$ is methyl or ethyl;
$R^2$ is phenyl, which is once or twice or three times substituted by fluoro, chloro or bromo;
$R^3$ is hydrogen or methyl;
$R^4$ is selected from

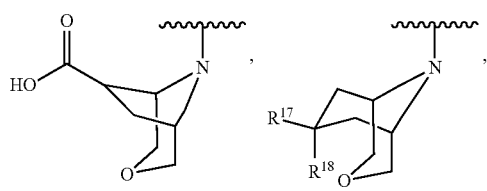

-continued

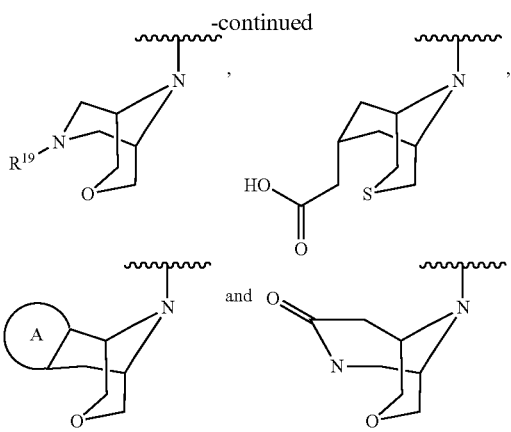

$R^{17}$ is hydrogen or hydroxy;
$R^{18}$ is methoxycarbonyl, methoxycarbonylmethyl, methoxycarbonylmethyl(hydroxy), carboxy, carboxymethyl, hydroxy, hydroxymethyl, methylcarbonyl-O—, methylcarbonylamino or methylsulfonylamino;
or $R^{17}$ and $R^{18}$, together with the carbon atom, to which they are attached, form

$R^{19}$ is aminocarbonyl, aminosulfonyl, methoxycarbonyl, ethoxycarbonylisopropyl, methyl, isopropyl, difluoroethyl, methylaminosulfonyl, methylcarbonyl, methylsulfonyl or hydroxymethylcarbonyl;
A is pyrazolyl or oxopyrazolyl, which is unsubstituted or substituted by methyl.

Another embodiment of present invention is (xxvii) a compound of formula IC or a pharmaceutically acceptable salt or tautomerism isomers or enantiomers or diastereomers thereof, wherein
$R^1$ is $C_{1-6}$alkyl;
$R^2$ is phenyl, which is once or twice or three times substituted by halogen;
$R^3$ is hydrogen;
$R^4$ is

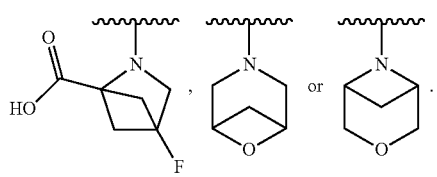

Further embodiment of present invention is (xxviii) a compound of formula IC or a pharmaceutically acceptable salt or tautomerism isomers or enantiomers or diastereomers thereof, wherein
$R^1$ is methyl;
$R^2$ is phenyl, which is once or twice or three times substituted by fluoro, chloro or bromo;
$R^3$ is hydrogen;

$R^4$ is

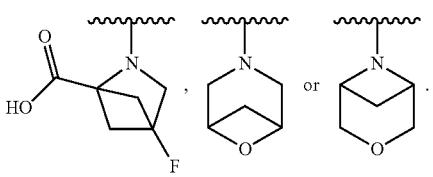

Particular compounds of formula I, including their activity data, NMR data and MS data are summarized in the following Table 1 and 2.

Particular compounds of formula I include the following:
- 9-[[(4R)-4-(2-chloro-4-fluoro-phenyl)-5-methoxycarbonyl-2-thiazol-2-yl-1,4-dihydropyrimidin-6-yl]methyl]-3-oxa-9-azabicyclo[3.3.1]nonane-7-carboxylic acid;
- 9-[(R)-6-(2-Chloro-4-fluoro-phenyl)-5-methoxycarbonyl-2-(4-methyl-thiazol-2-yl)-3,6-dihydro-pyrimidin-4-ylmethyl]-3-oxa-9-aza-bicyclo[3.3.1]nonane-7-carboxylic acid;
- 9-[6-(3,4-Difluoro-phenyl)-5-methoxycarbonyl-2-thiazol-2-yl-3,6-dihydro-pyrimidin-4-ylmethyl]-3-oxa-9-aza-bicyclo[3.3.1]nonane-7-carboxylic acid;
- 9-[(R)-6-(2-Bromo-4-fluoro-phenyl)-5-methoxycarbonyl-2-thiazol-2-yl-3,6-dihydro-pyrimidin-4-ylmethyl]-3-oxa-9-aza-bicyclo[3.3.1]nonane-7-carboxylic acid methyl ester;
- 9-[(R)-6-(2-Bromo-4-fluoro-phenyl)-5-methoxycarbonyl-2-thiazol-2-yl-3,6-dihydro-pyrimidin-4-ylmethyl]-3-oxa-9-aza-bicyclo[3.3.1]nonane-7-carboxylic acid;
- 8-[(R)-6-(2-Chloro-4-fluoro-phenyl)-5-methoxycarbonyl-2-thiazol-2-yl-3,6-dihydro-pyrimidin-4-ylmethyl]-3-oxa-8-aza-bicyclo[3.2.1]octane-6-carboxylic acid;
- (R)-4-(2-Chloro-4-fluoro-phenyl)-6-(7-hydroxy-3-oxa-9-aza-bicyclo[3.3.1]non-9-ylmethyl)-2-thiazol-2-yl-1,4-dihydro-pyrimidine-5-carboxylic acid methyl ester;
- (R)-6-(7-Acetoxy-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;
- (R)-4-(2-Chloro-4-fluoro-phenyl)-6-(7-hydroxy-3-oxa-9-aza-bicyclo[3.3.1]non-9-ylmethyl)-2-thiazol-2-yl-1,4-dihydro-pyrimidine-5-carboxylic acid methyl ester;
- (R)-4-(2-Chloro-4-fluoro-phenyl)-6-(7-hydroxy-7-hydroxymethyl-3-oxa-9-aza-bicyclo[3.3.1]non-9-ylmethyl)-2-thiazol-2-yl-1,4-dihydro-pyrimidine-5-carboxylic acid methyl ester;
- (R)-4-(2-Chloro-4-fluoro-phenyl)-6-(7-methanesulfonyl-3-oxa-7,9-diaza-bicyclo[3.3.1]non-9-ylmethyl)-2-thiazol-2-yl-1,4-dihydro-pyrimidine-5-carboxylic acid methyl ester;
- (R)-4-(2-Chloro-4-fluoro-phenyl)-6-(7-methyl-3-oxa-7,9-diaza-bicyclo[3.3.1]non-9-ylmethyl)-2-thiazol-2-yl-1,4-dihydro-pyrimidine-5-carboxylic acid methyl ester;
- (R)-4-(2-Chloro-4-fluoro-phenyl)-6-(7-isopropyl-3-oxa-7,9-diaza-bicyclo[3.3.1]non-9-ylmethyl)-2-thiazol-2-yl-1,4-dihydro-pyrimidine-5-carboxylic acid methyl ester;
- (R)-4-(2-Chloro-4-fluoro-phenyl)-6-[7-(2,2-difluoro-ethyl)-3-oxa-7,9-diaza-bicyclo[3.3.1]non-9-ylmethyl]-2-thiazol-2-yl-1,4-dihydro-pyrimidine-5-carboxylic acid methyl ester;
- (R)-6-(7-Acetyl-3-oxa-7,9-diaza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;
- (R)-4-(2-Chloro-4-fluoro-phenyl)-6-(7-methylsulfamoyl-3-oxa-7,9-diaza-bicyclo[3.3.1]non-9-ylmethyl)-2-thiazol-2-yl-1,4-dihydro-pyrimidine-5-carboxylic acid methyl ester;
- 9-[(R)-6-(2-Chloro-4-fluoro-phenyl)-5-methoxycarbonyl-2-thiazol-2-yl-3,6-dihydro-pyrimidin-4-ylmethyl]-3-oxa-7,9-diaza-bicyclo[3.3.1]nonane-7-carboxylic acid methyl ester;
- (R)-6-(7-Carbamoyl-3-oxa-7,9-diaza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;
- (R)-4-(2-Chloro-4-fluoro-phenyl)-6-(7-sulfamoyl-3-oxa-7,9-diaza-bicyclo[3.3.1]non-9-ylmethyl)-2-thiazol-2-yl-1,4-dihydro-pyrimidine-5-carboxylic acid methyl ester;
- (R)-4-(2-Chloro-4-fluoro-phenyl)-6-[7-(1-ethoxycarbonyl-1-methyl-ethyl)-3-oxa-7,9-diaza-bicyclo[3.3.1]non-9-ylmethyl]-2-thiazol-2-yl-1,4-dihydro-pyrimidine-5-carboxylic acid methyl ester;
- (R)-4-(2-Chloro-4-fluoro-phenyl)-6-[7-(2-hydroxy-acetyl)-3-oxa-7,9-diaza-bicyclo[3.3.1]non-9-ylmethyl]-2-thiazol-2-yl-1,4-dihydro-pyrimidine-5-carboxylic acid methyl ester;
- 7-[(R)-6-(2-Chloro-4-fluoro-phenyl)-5-methoxycarbonyl-2-thiazol-2-yl-3,6-dihydro-pyrimidin-4-ylmethyl]-9-oxa-3,7-diaza-bicyclo[3.3.1]nonane-3-carboxylic acid tert-butyl ester;
- (S)-2-[(R)-6-(2-Chloro-4-fluoro-phenyl)-5-methoxycarbonyl-2-thiazol-2-yl-3,6-dihydro-pyrimidin-4-ylmethyl]-5,5-difluoro-2-aza-bicyclo[2.2.2]octane-3-carboxylic acid;
- (R)-6-(7-Carboxymethyl-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;
- (R)-4-(2-Chloro-4-fluoro-phenyl)-6-(7-methoxycarbonylmethyl-3-oxa-9-aza-bicyclo[3.3.1]non-9-ylmethyl)-2-thiazol-2-yl-1,4-dihydro-pyrimidine-5-carboxylic acid methyl ester;
- (R)-6-(7-Carboxymethyl-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid ethyl ester;
- 6-(7-Carboxymethyl-3-oxa-9-aza-bicyclo[3.3.1]non-9-ylmethyl)-4-(3,4-difluoro-phenyl)-2-thiazol-2-yl-1,4-dihydro-pyrimidine-5-carboxylic acid methyl ester;
- (R)-4-(2-Bromo-4-fluoro-phenyl)-6-(7-carboxymethyl-3-oxa-9-aza-bicyclo[3.3.1]non-9-ylmethyl)-2-thiazol-2-yl-1,4-dihydro-pyrimidine-5-carboxylic acid methyl ester;
- (S)-6-(7-Carboxymethyl-3-oxa-9-aza-bicyclo[3.3.1]non-9-ylmethyl)-4-(3,4-difluoro-phenyl)-2-thiazol-2-yl-1,4-dihydro-pyrimidine-5-carboxylic acid ethyl ester;
- (R)-4-(2-Chloro-4-fluoro-phenyl)-6-[7-(hydroxy-methoxycarbonyl-methyl)-3-oxa-9-aza-bicyclo[3.3.1]non-9-ylmethyl]-2-thiazol-2-yl-1,4-dihydro-pyrimidine-5-carboxylic acid methyl ester;
- (R)-4-(2-Chloro-4-fluoro-phenyl)-6-(10-oxa-4,5,12-triaza-tricyclo[6.3.1.0*2,6*]dodeca-2(6),3-dien-12-ylmethyl)-2-thiazol-2-yl-1,4-dihydro-pyrimidine-5-carboxylic acid methyl ester;
- (R)-4-(2-Chloro-4-fluoro-phenyl)-6-(3-methyl-10-oxa-4,5,12-triaza-tricyclo[6.3.1.0*2,6*]dodeca-2(6),3-dien-12-ylmethyl)-2-thiazol-2-yl-1,4-dihydro-pyrimidine-5-carboxylic acid methyl ester;
- (R)-4-(2-Chloro-4-fluoro-phenyl)-6-(5-methyl-3-oxo-10-oxa-4,5,12-triaza-tricyclo[6.3.1.0*2,6*]dodec-2(6)-en-12-ylmethyl)-2-thiazol-2-yl-1,4-dihydro-pyrimidine-5-carboxylic acid methyl ester;
- (R)-4-(2-Chloro-4-fluoro-phenyl)-6-(4-oxo-8-oxa-3,10-diaza-bicyclo[4.3.1]dec-10-ylmethyl)-2-thiazol-2-yl-1,4-dihydro-pyrimidine-5-carboxylic acid methyl ester;
- (R)-6-(7-Acetylamino-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;
- (R)-4-(2-Chloro-4-fluoro-phenyl)-6-(7-methanesulfonylamino-3-oxa-9-aza-bicyclo[3.3.1]non-9-ylmethyl)-2-thiazol-2-yl-1,4-dihydro-pyrimidine-5-carboxylic acid methyl ester;

(R)-4-(2-Chloro-4-fluoro-phenyl)-6-(2-methoxymethyl-azetidin-1-ylmethyl)-2-thiazol-2-yl-1,4-dihydro-pyrimidine-5-carboxylic acid methyl ester;

(R)-4-(2-Chloro-4-fluoro-phenyl)-6-(6-oxa-3-aza-bicyclo[3.1.1]hept-3-ylmethyl)-2-thiazol-2-yl-1,4-dihydro-pyrimidine-5-carboxylic acid methyl ester;

(S)-3-[(R)-6-(2-Chloro-4-fluoro-phenyl)-5-methoxycarbonyl-2-thiazol-2-yl-3,6-dihydro-pyrimidin-4-ylmethyl]-3,6-diaza-bicyclo[3.2.1]octane-7-carboxylic acid;

2-[(R)-6-(2-Chloro-4-fluoro-phenyl)-5-methoxycarbonyl-2-thiazol-2-yl-3,6-dihydro-pyrimidin-4-ylmethyl]-4-fluoro-2-aza-bicyclo[2.1.1]hexane-1-carboxylic acid;

(R)-6-(5-Acetyl-2,5-diaza-bicyclo[2.2.1]hept-2-ylmethyl)-4-(2-chloro-4-fluoro-phenyl)-2-thiazol-2-yl-1,4-dihydro-pyrimidine-5-carboxylic acid methyl ester;

6-(7-Carboxymethyl-3-thia-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-6-(7-Diazirine-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-4-(2-Chloro-4-fluoro-phenyl)-6-((1R,3R,5S)-3-hydroxy-8-aza-bicyclo[3.2.1]oct-8-ylmethyl)-2-thiazol-2-yl-1,4-dihydro-pyrimidine-5-carboxylic acid methyl ester;

(R)-4-(2-Chloro-4-fluoro-phenyl)-6-(9-oxa-3,4,11-triazatricyclo[5.3.1.0*2,6*]undeca-2(6),4-dien-11-ylmethyl)-2-thiazol-2-yl-1,4-dihydro-pyrimidine-5-carboxylic acid methyl ester;

2-[[(1R,5S)-9-[[(4R)-4-(2-chloro-4-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]oxy]acetic acid;

2-[[(1R,5S)-9-[[(4S)-4-(3,4-difluorophenyl)-5-methoxycarbonyl-2-thiazol-2-yl-1,4-dihydropyrimidin-6-yl]methyl]-3-oxa-9-azabicyclo[3.3.1]nonan-7-yl]oxy]acetic acid;

Methyl (4R)-6-[(6-acetamido-3-oxa-8-azabicyclo[3.2.1]octan-8-yl)methyl]-4-(2-chloro-4-fluoro-phenyl)-2-thiazol-2-yl-1,4-dihydropyrimidine-5-carboxylate;

Methyl (4R)-4-(2-chloro-4-fluoro-phenyl)-6-[(6-hydroxy-3-oxa-8-azabicyclo[3.2.1]octan-8-yl)methyl]-2-thiazol-2-yl-1,4-dihydropyrimidine-5-carboxylate;

2-[[8-[[(4R)-4-(2-bromo-4-fluoro-phenyl)-5-ethoxycarbonyl-2-thiazol-2-yl-1,4-dihydropyrimidin-6-yl]methyl]-3-oxa-8-azabicyclo[3.2.1]octan-6-yl]oxy]acetic acid;

Methyl (4R)-4-(2-chloro-4-fluoro-phenyl)-6-[(6-fluoro-3-oxa-8-azabicyclo[3.2.1]octan-8-yl)methyl]-2-thiazol-2-yl-1,4-dihydropyrimidine-5-carboxylate;

8-[[(4R)-4-(2-bromo-4-fluoro-phenyl)-5-ethoxycarbonyl-2-thiazol-2-yl-1,4-dihydropyrimidin-6-yl]methyl]-3-oxa-8-azabicyclo[3.2.1]octane-6-carboxylic acid;

Methyl (4R)-4-(2-bromo-4-fluoro-phenyl)-6-[[7-(2-hydroxyacetyl)-3-oxa-7,9-diazabicyclo[3.3.1]nonan-9-yl]methyl]-2-thiazol-2-yl-1,4-dihydropyrimidine-5-carboxylate;

Methyl (4R)-4-(2-bromo-4-fluoro-phenyl)-6-[(7-carbamoyl-3-oxa-7,9-diazabicyclo[3.3.1]nonan-9-yl)methyl]-2-thiazol-2-yl-1,4-dihydropyrimidine-5-carboxylate;

2-[(1R,5S)-9-[[(4R)-4-(2-chloro-3-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Methyl (4R)-4-(2-chloro-4-fluoro-phenyl)-6-[[(1R,5S)-7-endo-(sulfamoylamino)-3-oxa-9-azabicyclo[3.3.1]nonan-9-yl]methyl]-2-thiazol-2-yl-1,4-dihydropyrimidine-5-carboxylate;

Methyl (4R)-4-(2-chloro-4-fluoro-phenyl)-2-thiazol-2-yl-6-[[(1S,5R)-7-endo-ureido-3-oxa-9-azabicyclo[3.3.1]nonan-9-yl]methyl]-1,4-dihydropyrimidine-5-carboxylate;

2-[(1S,5R)-9-[[(4R)-4-(2-bromo-4-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-chloro-3-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Methyl (4R)-4-(2-chloro-4-fluoro-phenyl)-6-[[(1R,5S)-7-exo-(methanesulfonamido)-3-oxa-9-azabicyclo[3.3.1]nonan-9-yl]methyl]-2-thiazol-2-yl-1,4-dihydropyrimidine-5-carboxylate;

Methyl (4R)-6-[[(1S,5R)-7-exo-acetamido-3-oxa-9-azabicyclo[3.3.1]nonan-9-yl]methyl]-4-(2-chloro-4-fluoro-phenyl)-2-thiazol-2-yl-1,4-dihydropyrimidine-5-carboxylate;

Methyl (4R)-4-(2-chloro-4-fluoro-phenyl)-2-thiazol-2-yl-6-[[(1S,5R)-7-exo-ureido-3-oxa-9-azabicyclo[3.3.1]nonan-9-yl]methyl]-1,4-dihydropyrimidine-5-carboxylate;

Methyl (4R)-4-(2-chloro-4-fluoro-phenyl)-6-[[(1R,5S)-7-exo-(sulfamoylamino)-3-oxa-9-azabicyclo[3.3.1]nonan-9-yl]methyl]-2-thiazol-2-yl-1,4-dihydropyrimidine-5-carboxylate;

2-[(1R,5S,6S)-8-[[(4R)-4-(2-bromo-4-fluoro-phenyl)-5-methoxycarbonyl-2-thiazol-2-yl-1,4-dihydropyrimidin-6-yl]methyl]-3-oxa-8-azabicyclo[3.2.1]octan-6-yl]acetic acid;

Endo-2-[(1S,5R)-9-[[(4R)-4-(2-chloro-3-fluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-chloro-3-fluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-bromo-4-fluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-bromo-3-fluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-chloro-3,4-difluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Ethyl (4R)-6-[[(1S,5R)-7-endo-acetamido-3-oxa-9-azabicyclo[3.3.1]nonan-9-yl]methyl]-4-(2-bromo-4-fluoro-phenyl)-2-thiazol-2-yl-1,4-dihydropyrimidine-5-carboxylate;

Ethyl (4R)-6-[[(1S,5R)-7-exo-acetamido-3-oxa-9-azabicyclo[3.3.1]nonan-9-yl]methyl]-4-(2-bromo-4-fluoro-phenyl)-2-thiazol-2-yl-1,4-dihydropyrimidine-5-carboxylate;

Exo-2-[(1S,5R)-9-[[(4R)-4-(2-chlorophenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-chloro-3,4-difluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-bromo-3-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2,3-difluorophenyl)-5-ethoxy-carbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-bromophenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-bromophenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4S)-4-(3,4-difluoro-2-methyl-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

3-[(1S,5R)-9-[[(4R)-4-(2-chloro-4-fluoro-phenyl)-5-methoxycarbonyl-2-thiazol-2-yl-1,4-dihydropyrimidin-6-yl]methyl]-3-oxa-7,9-diazabicyclo[3.3.1]nonan-7-yl]-2,2-dimethyl-3-oxo-propanoic acid;

Exo-2-[(1S,5R)-9-[[(4R)-4-(2-bromo-3,4-difluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

(1S,5R)-8-[[(4R)-4-(2-chloro-4-fluoro-phenyl)-5-methoxycarbonyl-2-thiazol-2-yl-1,4-dihydropyrimidin-6-yl]methyl]-3-oxa-8-azabicyclo[3.2.1]octane-5-carboxylic acid;

(1R,5S)-8-[[(4R)-4-(2-chloro-4-fluoro-phenyl)-5-methoxycarbonyl-2-thiazol-2-yl-1,4-dihydropyrimidin-6-yl]methyl]-3-oxa-8-azabicyclo[3.2.1]octane-5-carboxylic acid;

8-[[(4R)-4-(2-chloro-3-fluoro-phenyl)-5-ethoxycarbonyl-2-thiazol-2-yl-1,4-dihydropyrimidin-6-yl]methyl]-3-oxa-8-azabicyclo[3.2.1]octane-5-carboxylic acid;

(1S,5R)-8-[[(4S)-4-(3,4-difluoro-2-methyl-phenyl)-5-methoxycarbonyl-2-thiazol-2-yl-1,4-dihydropyrimidin-6-yl]methyl]-3-oxa-8-azabicyclo[3.2.1]octane-5-carboxylic acid;

(1R,5S)-8-[[(4S)-4-(3,4-difluoro-2-methyl-phenyl)-5-methoxycarbonyl-2-thiazol-2-yl-1,4-dihydropyrimidin-6-yl]methyl]-3-oxa-8-azabicyclo[3.2.1]octane-5-carboxylic acid;

2-[(1R,3S,5S)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4R)-4-(2-chlorophenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-chlorophenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4R)-4-(2-bromophenyl)-5-ethoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-bromophenyl)-5-ethoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4R)-4-(2-bromo-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-bromo-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4S)-4-(4-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4S)-4-(4-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4R)-4-(2-chloro-3-fluoro-phenyl)-5-ethoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-chloro-3-fluoro-phenyl)-5-ethoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,5S,6R,7R)-9-[[(4R)-4-(2-chloro-3-fluoro-phenyl)-5-methoxycarbonyl-2-thiazol-2-yl-1,4-dihydropyrimidin-6-yl]methyl]-6-fluoro-3-oxa-9-azabicyclo[3.3.1]nonan-7-yl]acetic acid;

2-[(1R,5R,6S,7S)-9-[[(4R)-4-(2-chloro-3-fluoro-phenyl)-5-methoxycarbonyl-2-thiazol-2-yl-1,4-dihydropyrimidin-6-yl]methyl]-6-fluoro-3-oxa-9-azabicyclo[3.3.1]nonan-7-yl]acetic acid;

2-[(1S,5S,6R,7R)-9-[[(4R)-4-(2-chlorophenyl)-5-ethoxycarbonyl-2-thiazol-2-yl-1,4-dihydropyrimidin-6-yl]methyl]-6-fluoro-3-oxa-9-azabicyclo[3.3.1]nonan-7-yl]acetic acid;

2-[(1R,5R,6S,7S)-9-[[(4R)-4-(2-chlorophenyl)-5-ethoxycarbonyl-2-thiazol-2-yl-1,4-dihydropyrimidin-6-yl]methyl]-6-fluoro-3-oxa-9-azabicyclo[3.3.1]nonan-7-yl]acetic acid;

(4R)-4-(2-Chloro-4-fluoro-phenyl)-6-(4,10-dioxa-5,12-diaza-tricyclo[6.3.1.0*2,6*]dodeca-2,5-dien-12-ylmethyl)-2-thiazol-2-yl-1,4-dihydro-pyrimidine-5-carboxylic acid methyl ester;

(4R)-4-(2-Chloro-4-fluoro-phenyl)-6-(5,10-dioxa-4,12-diaza-tricyclo[6.3.1.0*2,6*]dodeca-2(6),3-dien-12-ylmethyl)-2-thiazol-2-yl-1,4-dihydro-pyrimidine-5-carboxylic acid methyl ester;

(4R)-4-(2-Chloro-4-fluoro-phenyl)-6-(7-fluoro-5,10-dioxa-4,12-diaza-tricyclo[6.3.1.0*2,6*]dodeca-2(6),3-dien-12-ylmethyl)-2-thiazol-2-yl-1,4-dihydropyrimidine-5-carrboxylic acid methyl ester;

(R)-4-(2-Chloro-4-fluoro-phenyl)-6-(7,7-difluoro-10-oxa-4,5,12-triaza-tricyclo[6.3.1.0*2,6*]dodeca-2(6),3-dien-12-ylmethyl)-2-thiazol-2-yl-1,4-dihydro-pyrimidine-5-arboxylic acid methyl ester;

Methyl (4R)-4-(2-chloro-4-fluorophenyl)-6-[(6,6-difluoro-3-oxa-8-azabicyclo[3.2.1]octan-8-yl)methyl]-2-(1,3-thiazol-2-yl)-1,4-dihydropyrimidine-5-carboxylate;

2-[(1R,3R,5S)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3S,5R)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3R,5S)-8-[[(4S)-4-(3,4-difluoro-2-methyl-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3S,5R)-8-[[(4S)-4-(3,4-difluoro-2-methyl-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3R,5S)-8-[[(4S)-4-(4-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid or 2-[(1 S,3 S,5R)-8-[[(4S)-4-(4-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4S)-4-(3,4-difluorophenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4S)-4-(3,4-difluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(3R)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3S)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3R)-8-[[(4R)-4-(3,4-difluoro-2-methyl-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3S)-8-[[(4S)-4-(3,4-difluoro-2-methyl-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

Methyl (4R)-6-[(3-acetyl-3,8-diazabicyclo[3.2.1]octan-8-yl)methyl]-4-(2-chloro-4-fluoro-phenyl)-2-thiazol-2-yl-1,4-dihydropyrimidine-5-carboxylate;

2-[(7S)-9-[[(4R)-4-(2-chloro-4-fluoro-phenyl)-5-methoxycarbonyl-2-thiazol-2-yl-1,4-dihydropyrimidin-6-yl]methyl]-6-hydroxy-3-oxa-9-azabicyclo[3.3.1]nonan-7-yl]acetic acid;

2-[(7R)-9-[[(4R)-4-(2-chloro-4-fluoro-phenyl)-5-methoxycarbonyl-2-thiazol-2-yl-1,4-dihydropyrimidin-6-yl]methyl]-6-hydroxy-3-oxa-9-azabicyclo[3.3.1]nonan-7-yl]acetic acid;

2-[(7R)-9-[[(4R)-4-(2-chloro-4-fluoro-phenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

2-[(7S)-9-[[(4R)-4-(2-chloro-4-fluoro-phenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

2-[(7R)-9-[[(4S)-4-(3,4-difluoro-2-methyl-phenyl)-5-ethoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

2-[(7S)-9-[[(4S)-4-(3,4-difluoro-2-methyl-phenyl)-5-ethoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

2-[(7R)-9-[[(4R)-4-(2-chloro-3-fluoro-phenyl)-5-ethoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

2-[(7S)-9-[[(4R)-4-(2-chloro-3-fluoro-phenyl)-5-ethoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

2-[(1R,5R,7S)-9-[[(4R)-4-(2-chloro-3,4-difluoro-phenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid or 2-[(1S,5S,7R)-9-[[(4R)-4-(2-chloro-3,4-difluoro-phenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

2-[(1R,5R,7S)-9-[[(4S)-4-(3,4-difluoro-2-methyl-phenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid or 2-[(1S,5S,7R)-9-[[(4S)-4-(3,4-difluoro-2-methyl-phenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

Methyl (4R)-4-(2-chloro-4-fluoro-phenyl)-6-[(6-oxo-3-oxa-7,9-diazabicyclo[3.3.1]nonan-9-yl)methyl]-2-thiazol-2-yl-1,4-dihydropyrimidine-5-carboxylate;

Endo-2-[9-[[(4R)-4-(2-bromophenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Endo-2-[9-[[(4R)-4-(2-chloro-3,4-difluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Endo-2-[9-[[(4S)-4-(4-chloro-3-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Methyl (4R)-4-(2-chloro-4-fluoro-phenyl)-6-[[7-(2-ethoxy-1-hydroxy-2-oxo-ethyl)-7-hydroxy-3-oxa-9-azabicyclo[3.3.1]nonan-9-yl]methyl]-2-thiazol-2-yl-1,4-dihydropyrimidine-5-carboxylate;

Methyl (4R)-4-(2-chloro-4-fluoro-phenyl)-6-[[7-(2-ethoxy-2-oxo-ethyl)-6,7-dihydroxy-3-oxa-9-azabicyclo[3.3.1]nonan-9-yl]methyl]-2-thiazol-2-yl-1,4-dihydropyrimidine-5-carboxylate;

7-amino-9-[[(4R)-4-(2-chloro-4-fluoro-phenyl)-5-methoxycarbonyl-2-thiazol-2-yl-1,4-dihydropyrimidin-6-yl]methyl]-3-oxa-9-azabicyclo[3.3.1]nonane-7-carboxylic acid;

7-amino-9-[[(4R)-4-(2,3-difluorophenyl)-5-ethoxycarbonyl-2-thiazol-2-yl-1,4-dihydropyrimidin-6-yl]methyl]-3-oxa-9-azabicyclo[3.3.1]nonane-7-carboxylic acid;

7-amino-9-[[(4R)-4-(2-bromo-4-fluoro-phenyl)-5-ethoxycarbonyl-2-thiazol-2-yl-1,4-dihydropyrimidin-6-yl]methyl]-3-oxa-9-azabicyclo[3.3.1]nonane-7-carboxylic acid;

Methyl (4R)-4-(2-chloro-4-fluoro-phenyl)-6-(8-oxa-3-azabicyclo[3.2.1]octan-3-ylmethyl)-2-thiazol-2-yl-1,4-dihydropyrimidine-5-carboxylate;

Methyl (4R)-4-(2-chloro-4-fluoro-phenyl)-6-[(5,5-difluoro-2-azabicyclo[2.2.1]heptan-2-yl)methyl]-2-thiazol-2-yl-1,4-dihydropyrimidine-5-carboxylate;

Methyl (4R)-4-(2-chloro-4-fluoro-phenyl)-6-[(5,5-difluoro-3-azabicyclo[2.2.1]heptan-3-yl)methyl]-2-thiazol-2-yl-1,4-dihydropyrimidine-5-carboxylate;

Methyl (4R)-6-[[4-(acetamidomethyl)-5-oxa-2-azabicyclo[2.2.1]heptan-2-yl]methyl]-4-(2-chloro-4-fluoro-phenyl)-2-thiazol-2-yl-1,4-dihydropyrimidine-5-carboxylate;

Methyl (4R)-4-(2-chloro-4-fluoro-phenyl)-6-[[7-(2-ethoxy-2-oxo-ethyl)-7-(methanesulfonamido)-3-oxa-9-azabicyclo[3.3.1]nonan-9-yl]methyl]-2-thiazol-2-yl-1,4-dihydropyrimidine-5-carboxylate;

Methyl (4R)-4-(2-chloro-4-fluoro-phenyl)-6-[[7-(2-ethoxy-2-oxo-ethyl)-7-[(2,2,2-trifluoroacetyl)amino]-3-oxa-9-azabicyclo[3.3.1]nonan-9-yl]methyl]-2-thiazol-2-yl-1,4-dihydropyrimidine-5-carboxylate;

(1S,4R)-7-[[(4R)-4-(2-chloro-4-fluoro-phenyl)-5-methoxycarbonyl-2-thiazol-2-yl-1,4-dihydropyrimidin-6-yl]methyl]-2,2-difluoro-7-azabicyclo[2.2.1]heptane-4-carboxylic acid;

(1R,4S)-7-[[(4R)-4-(2-chloro-4-fluoro-phenyl)-5-methoxycarbonyl-2-thiazol-2-yl-1,4-dihydropyrimidin-6-yl]methyl]-2,2-difluoro-7-azabicyclo[2.2.1]heptane-4-carboxylic acid;

8-[[(4R)-4-(2-chloro-3-fluoro-phenyl)-5-ethoxycarbonyl-2-thiazol-2-yl-1,4-dihydropyrimidin-6-yl]methyl]-6,6-difluoro-8-azabicyclo[3.2.1]octane-3-carboxylic acid;

(5S)-7-[[(4R)-4-(2-chloro-4-fluoro-phenyl)-5-methoxycarbonyl-2-thiazol-2-yl-1,4-dihydropyrimidin-6-yl]methyl]-2,2-difluoro-7-azabicyclo[2.2.1]heptane-5-carboxylic acid; and (5R)-7-[[(4R)-4-(2-chloro-4-fluoro-phenyl)-5-methoxycarbonyl-2-thiazol-2-yl-1,4-dihydropyrimidin-6-yl]methyl]-2,2-difluoro-7-azabicyclo[2.2.1]heptane-5-carboxylic acid.

TABLE 1

NMR and MS data of particular compounds

| Example No. | $^1$H NMR data | MW data |
|---|---|---|
| 1 | $^1$H NMR (CDCl$_3$, 400 MHz): 10.0 (br s, 1H), 7.88 (d, J = 3.0 Hz, 1H), 7.48 (d, J = 2.3 Hz, 1H), 7.27 (m, 1H), 7.15 (dd, J = 2.4, 8.5 Hz, 1H), 6.94 (m, 1H), 6.22 (s, 1H), 4.50 (m, 2H), 4.23 (s, 2H), 3.95 (m, 2H), 3.85 (m, 1H), 3.63 ( s, 3H), 2.83 (m, 2H), 2.33 (m, 2H), 2.05 (m, 2 H). | LC/MS: calc'd 535 (MH$^+$), exp 535 (MH$^+$) |
| 2 | $^1$H NMR (METHANOL-d4, 400 MHz): 7.41 (dd, J = 8.7, 6.1 Hz, 1H), 7.32 (d, J = 1 Hz, 1H), 7.24 (dd, J = 8.8, 2.8 Hz, 1H), 7.04 (m, 1H), 6.16 (s, 1H), 4.62 (d, J = 17.8 Hz, 1H), 4.08-4.23 (m, 3H), 3.92 (m, 2H), 3.71 (m, 1H), 3.63 (s, 3H), 2.88 (m, 1H), 2.83 (m, 1H), 2.49 (d, J = 0.8 Hz, 3H), 2.30 (m, 2H), 2.04 (m, 2 H). | LC/MS: calc'd 549 (MH$^+$), exp 549 (MH$^+$) |
| 3 | $^1$H NMR (METHANOL-d4, 400 MHz): 8.01 (d, J = 3.3 Hz, 1H), 7.80 (d, J = 3.3 Hz, 1H), 7.13-7.27 (m, 3H), 5.73 (s, 1H), 4.54 (d, J = 17.8 Hz, 1H), 4.14 (m, 2H), 4.01 (d, J = 17.8 Hz, 1H), 3.81-3.96 (m, 2H), 3.72 (s, 3H), 3.64 (m, 1H), 2.78 (m, 1H), 2.68 (m, 1H), 2.22 (m, 2H), 1.93 (m, 2 H). | LC/MS: calc'd 519 (MH$^+$), exp 519 (MH$^+$) |
| 4 | $^1$H NMR (DMSO-d6, 400 MHz): 9.84-10.20 (m, 1H), 7.99-8.07 (m, 1H), 7.95 (d, J = 3.3 Hz, 1H), 7.57 (dd, J = 8.7, 2.64 Hz, 1H), 7.39 (dd, J = 8.7, 6.15 Hz, 1H), 7.20 (td, J = 8.5, 2.64 Hz, 1H), 6.02 (s, 1H) 4.35 (d, J = 17.6 Hz, 1H), 4.02-4.13 (m, 1H), 3.79-3.98 (m, 4H), 3.68 (s, 3H), 3.59 (t, J = 5.8 Hz, 1H), 3.53 (s, 3H), 2.82 (m, 1H), 2.64-2.72 (m, 1H), 1.95-2.13 (m, 2H), 1.83 (td, J = 13.2, 5.1 Hz, 2 H). | LC/MS: calc'd 593&595 (MH$^+$), exp 593&595 (MH$^+$) |
| 5 | $^1$H NMR (METHANOL-d4, 400 MHz): 7.96 (d, J = 3.3 Hz, 1H), 7.75 (d, J = 3.0 Hz, 1H), 7.35-7.47 (m, 2H), 7.09 (td, J = 8.4, 2.8 Hz, 1H), 6.16 (s, 1H), 4.56 (d, J = 17.6 Hz, 1H), 4.04-4.21 (m, 3H), 3.86-3.97 (m, 2H), 3.65-3.74 (m, 1H), 3.60 (s, 3H), 2.84 (m, 1H), 2.73 (m, 1H), 2.25 (d, J = 12.3 Hz, 2H), 1.89-2.03 (m, 2 H). | LC/MS: calc'd 579&581 (MH$^+$), exp 579&581 (MH$^+$) |
| 6 | $^1$H NMR (METHANOL-d4, 400 MHz): 7.98 (d, J = 3.1 Hz, 0.5H), 7.97 (d, J = 3.1 Hz, 0.5H), 7.77 (d, J = 3.0 Hz, 1H), 7.44 (m, 1H), 7.24 (dd, J = 8.8, 2.8 Hz, 1H), 7.06 (td, J = 8.4, 2.8 Hz, 1H), 6.18 (s, 0.5H), 6.18 (s, 0.5H), 4.20 (m, 1H), 3.88-4.07 (m, 4H), 3.68 (m, 1H), 3.61 (s, 3H), 3.47 (m, 2H), 3.31 (m, 1H), 2.48 (m, 1H), 2.36 (m, 1H). | LC/MS: calc'd 521 (MH$^+$), exp 521 (MH$^+$) |
| 7 | $^1$H NMR (METHANOL-d4, 400 MHz): 7.98 (d, J = 3.3 Hz, 1H), 7.76 (d, J = 3.0 Hz, 1H), 7.41 (dd, J = 8.7, 6.1 Hz, 1H), 7.24 (dd, J = 8.8, 2.8 Hz, 1H), 7.04 (td, J = 8.4, 2.8 Hz, 1H), 6.17 (s, 1H), 4.52 (d, J = 17.8 Hz, 1H), 4.04-4.16 (m, 4H), 3.86 (m, 2H), 3.62 (s, 3H), 2.86 (m, 1H), 2.77 (m, 1H), 2.49 (m, 2H), 1.73 (m, 2 H). | LC/MS: calc'd 507 (MH$^+$), exp 507 (MH$^+$) |
| 8 | $^1$H NMR (METHANOL-d4, 400 MHz): 7.98 (d, J = 3.0 Hz, 1H), 7.76 (d, J = 3.0 Hz, 1H), 7.41 (dd, J = 8.7, 6.1 Hz, 1H), 7.24 (dd, J = 8.8, 2.5 Hz, 1H), 7.04 (td, J = 8.4, 2.5 Hz, 1H), 6.18 (s, 1H), 5.86 (m, 1H), 4.53 (d, J = 17.8 Hz, 1H), 4.08 (d, J = 17.8 Hz, 1H), 4.04 (m, 2H), 3.86 (dd, J = 18.3, 11.0 Hz, 2H), 3.63 (s, 3H), 2.96 (m, 1H), 2.83 (m, 1H), 2.07 (s, 3H), 2.05 (m, 4H). | LC/MS: calc'd 549 (MH$^+$), exp 549 (MH$^+$) |
| 9 | $^1$H NMR (METHANOL-d4, 400 MHz): 7.97 (d, J = 3.0 Hz, 1H), 7.75 (d, J = 3.3 Hz, 1H), 7.41 (dd, J = 8.7, 6.1 Hz, 1H), 7.23 (dd, J = 8.7, 2.6 Hz, 1H), 7.04 (td, J = 8.4, 2.8 Hz, 1H), 6.17 (s, 1H), 4.73 (m, 1H), 4.49 (d, J = 17.8 Hz, 1H), 3.97-4.14 | LC/MS: calc'd 507 (MH$^+$), exp 507 (MH$^+$) |

TABLE 1-continued

NMR and MS data of particular compounds

| Example No. | ¹H NMR data | MW data |
|---|---|---|
| | (m, 3H), 3.82 (dd, J = 17.8, 11.0 Hz, 2H), 3.63 (s, 3H), 2.91 (m, 1H), 2.79 (m, 1H), 1.84-2.09 (m, 4 H). | |
| 10 | ¹H NMR (METHANOL-d4, 400 MHz): 7.87 (d, J = 3.2 Hz, 1H), 7.75 (d, J = 3.1 Hz, 1H), 7.42 (m, 1H), 7.24 (m, 1H), 7.06 (m, 1H), 6.18 (s, 1H), 4.54 (d, J = 14.6, 1H), 4.12 (d, J = 13.0, 1H), 4.04 (m, 1H), 3.88 (s, 2H), 3.70 (m, 2H), 3.63 (s, 3H), 2.84 (m, 2H), 2.14 (m, 2H), 1.98 (m, 2H). | LC/MS: calc'd 537 (MH⁺), exp 537 (MH⁺) |
| 11 | ¹H NMR (METHANOL-d4, 400 MHz): 7.97 (d, J = 3.0 Hz, 1H), 7.77 (d, J = 3.3 Hz, 1H), 7.43 (dd, J = 8.8, 6.0 Hz, 1H), 7.24 (dd, J = 8.8, 2.8 Hz, 1H), 7.05 (td, J = 8.4, 2.8 Hz, 1H), 6.18 (s, 1H), 4.68 (d, J = 17.3 Hz, 1H), 4.16-4.22 (m, 3H), 3.95 (m, 2H), 3.73 (m, 2H), 3.63 (s, 3H), 3.54 (m, 2H), 2.94 (s, 3H), 2.86 (m, 2 H). | LC/MS: calc'd 570 (MH⁺), exp 570 (MH⁺) |
| 12 | ¹H NMR (METHANOL-d4, 400 MHz): 8.18 (d, J = 3.3 Hz, 1H), 8.10 (d, J = 3.0 Hz, 1H), 7.56 (dd, J = 8.8, 6.0 Hz, 1H), 7.34 (dd, J = 8.7, 2.6 Hz, 1H), 7.15 (td, J = 8.3, 2.6 Hz, 1H), 6.28 (s, 1H), 4.56 (d, J = 16.1 Hz, 1H), 4.20 (m, 3H), 4.10 (m, 2H), 3.72 (m, 1H), 3.68 (m, 1H), 3.67 (s, 3H), 3.54-3.61 (m, 2H), 3.16 (m, 2H), 2.95 (s, 3 H). | LC/MS: calc'd 506 (MH⁺), exp 506 (MH⁺) |
| 13 | ¹H NMR (METHANOL-d4, 400 MHz): 7.96 (d, J = 3.0 Hz, 1H), 7.77 (d, J = 3.3 Hz, 1H), 7.41 (dd, J = 8.7, 6.1 Hz, 1H), 7.24 (dd, J = 8.8, 2.8 Hz, 1H), 7.05 (td, J = 8.5, 2.6 Hz, 1H), 6.18 (s, 1H), 4.62 (d, J = 18.1 Hz, 1H), 4.09-4.21 (m, 3H), 3.91 (m, 2H), 3.63 (s, 3H), 3.02 (m, 4H), 2.79 (m, 2H), 2.70 (m, 1H), 1.20 (d, J = 5.8 Hz, 6H). | LC/MS: calc'd 534 (MH⁺), exp 534 (MH⁺) |
| 14 | ¹H NMR (METHANOL-d4, 400 MHz): 8.09 (d, J = 3.0 Hz, 1H), 7.97 (d, J = 3.0 Hz, 1H), 7.52 (dd, J = 8.8, 6.0 Hz, 2H), 7.31 (dd, J = 8.5, 2.5 Hz, 1H), 7.11 (td, J = 8.3, 2.6 Hz, 1H), 6.47 (m, 1H), 6.24 (s, 1H), 4.65 (d, J = 16.3 Hz, 1H), 4.30 (d, J = 16.3 Hz, 1H), 4.23 (m, 2H), 4.15 (m, 2H), 3.72 (m, 4H), 3.66 (s, 3H), 3.64 (m, 2H), 3.30 (m, 2H). | LC/MS: calc'd 556 (MH⁺), exp 556 (MH⁺) |
| 15 | ¹H NMR (METHANOL-d4, 400 MHz): 8.02-8.09 (m, 1H), 7.97 (d, J = 3.0 Hz, 1H), 7.57 (dd, J = 8.7, 5.9 Hz, 1H), 7.31 (dd, J = 8.7, 2.6 Hz, 1H), 7.13 (td, J = 8.4, 2.5 Hz, 1H), 6.24 (s, 1H), 5.03 (dd, J = 16.9, 2.1 Hz, 1H), 4.91 (m, 1H), 4.68 (d, J = 16.8 Hz, 1H), 4.19-4.37 (m, 4H), 4.03-4.14 (m, 2H), 3.67 (s, 3H), 3.45-3.59 (m, 3H), 2.20 (d, J = 0.7 Hz, 3 H). | LC/MS: calc'd 534 (MH⁺), exp 534 (MH⁺) |
| 16 | ¹H NMR (METHANOL-d4, 400 MHz): 8.07 (d, J = 3.3 Hz, 1H), 7.97 (d, J = 3.3 Hz, 1H), 7.56 (dd, J = 8.7, 5.9 Hz, 1H), 7.31 (dd, J = 8.7, 2.6 Hz, 1H), 7.13 (td, J = 8.4, 2.5 Hz, 1H), 6.24 (s, 1H), 4.98 (d, J = 17.1 Hz, 1H), 4.59 (d, J = 15.1 Hz, 1H), 4.31 (d, J = 12.8 Hz, 2H), 4.11 (d, J = 12.8 Hz, 2H), 3.84 (dd, J = 13.4, 6.40 Hz, 2H), 3.62-3.75 (m, 5H), 3.50 (d, J = 1.8 Hz, 2H), 2.72 (s, 3 H). | LC/MS: calc'd 585 (MH⁺), exp 585 (MH⁺) |
| 17 | ¹H NMR (METHANOL-d4, 400 MHz): 7.98 (d, J = 3.3 Hz, 1H), 7.79 (d, J = 3.3 Hz, 1H), 7.44 (dd, J = 8.8, 6.0 Hz, 1H), 7.25 (dd, J = 8.7, 2.6 Hz, 1H), 7.06 (td, J = 8.4, 2.5 Hz, 1H), 6.19 (s, 1H), 4.72 (d, J = 17.3 Hz, 1H), 4.11-4.32 (m, 5H), 3.89-4.01 (m, 2H), 3.75 (s, 3H), 3.53-3.71 (m, 5H), 2.72-2.89 (m, 2 H). | LC/MS: calc'd 550 (MH⁺), exp 550 (MH⁺) |
| 18 | ¹H NMR (METHANOL-d4, 400 MHz): 7.98 (d, J = 3.3 Hz, 1H), 7.76 (d, J = 3.0 Hz, 1H), 7.43 (dd, J = 8.8, 6.0 Hz, 1H), 7.24 (dd, J = 8.8, 2.51 Hz, 1H), 7.05 (td, J = 8.4, 2.8 Hz, 1H), 6.18 (s, 1H), 4.67 (d, J = 17.6 Hz, 1H), 4.10-4.26 (m, 3H), 3.98-4.07 (m, 2H), 3.87-3.96 (m, 2H), 3.63 (s, 3H), 3.57 (m, 2H), 2.75 (d, J = 19.3 Hz, 2 H). | LC/MS: calc'd 535 (MH⁺), exp 535 (MH⁺) |
| 19 | ¹H NMR (METHANOL-d4, 400 MHz): 7.92-8.03 (m, 1H), 7.76 (d, J = 3.0 Hz, 1H), 7.43 (dd, J = 8.7, 6.1 Hz, 1H), 7.24 (dd, J = 8.8, 2.5 Hz, 1H), 7.05 (td, J = 8.4, 2.8 Hz, 1H), 6.18 (s, 1H), 4.58-4.72 (m, 1H), 4.10-4.26 (m, 3H), 3.89-4.01 (m, 2H), 3.62 (s, 3H), 3.53-3.61 (m, 2H), 3.39-3.48 (m, 2H), 2.92 (m, 1H), 2.80-2.89 (m, 1 H). | LC/MS: calc'd 571 (MH⁺), exp 571 (MH⁺) |
| 20 | ¹H NMR (METHANOL-d4, 400 MHz): 7.97 (d, J = 3.0 Hz, 1H), 7.76 (d, J = 3.0 Hz, 1H), 7.41 (dd, J = 8.8, 6.0 Hz, 1H), 7.23 (dd, J = 8.8, 2.5 Hz, 1H), 7.04 (td, J = 8.4, 2.5 Hz, 1H), 6.15-6.20 (m, 1H), 4.62 (d, J = 17.8 Hz, 1H), 4.25 (q, J = 7.0 Hz, 2H), 4.11-4.20 (m, 3H), 3.87 (t, J = 10.9 Hz, 2H), 3.62 (s, 3H), 3.09-3.17 (m, 2H), 2.98 (d, J = 11.5 Hz, 2H), 2.71-2.81 (m, 2H), 1.40 (s, 6H), 1.35 (t, J = 7.1 Hz, 3 H). | LC/MS: calc'd 606 (MH⁺), exp 606 (MH⁺) |
| 21 | ¹H NMR (METHANOL-d4, 400 MHz): 7.97 (dd, J = 3.0, 1.8 Hz, 1H), 7.76 (d, J = 3.0 Hz, 1H), 7.43 (dd, J = 8.8, 6.0 Hz, 1H), 7.24 (dd, J = 8.7, 2.6 Hz, 1H), 7.01-7.09 (m, 1H), 6.18 (s, 1H), 4.69 (d, J = 17.6 Hz, 1H), 4.54 (d, J = 13.8 Hz, 1H), 4.18-4.36 (m, 3H), 4.15 (dt, J = 11.3, 2.5 Hz, 2H), 3.86-4.02 (m, | LC/MS: calc'd 550 (MH⁺), exp 550 (MH⁺) |

TABLE 1-continued

NMR and MS data of particular compounds

| Example No. | $^1$H NMR data | MW data |
|---|---|---|
| | 2H), 3.79 (d, J = 6.8 Hz, 2H), 3.63 (s, 3H), 3.44 (t, J = 11.2 Hz, 1H), 2.78 (t, J = 16.6 Hz, 2 H). | |
| 22 | $^1$H NMR (METHANOL-d4, 400 MHz): 8.00 (m, 1H), 7.72 (m, 1H), 7.45 (m, 1H), 7.25 (m, 1H), 7.10 (m, 1H), 6.17 (s, 1H), 4.60 (m, 1H), 3.75-4.16 (m, 6H), 3.45 (m, 1H), 3.62 (s, 3H), 3.06 (m, 2H), 2.77 (m, 2H), 1.37 (s, 9 H). | LC/MS: calc'd 592 (MH$^+$), exp 592 (MH$^+$) |
| 23 | $^1$H NMR (METHANOL-d4, 400 MHz): 7.97 (d, J = 3.0 Hz, 1H), 7.87 (d, J = 2.8 Hz, 1H), 7.54 (dd, J = 8.7, 6.1 Hz, 1H), 7.27 (dd, J = 8.7, 2.6 Hz, 1H), 7.15 (td, J = 8.4, 2.5 Hz, 1H), 6.19 (s, 1H), 4.10 (m, 2H), 3.85 (m, 1H), 3.65 (s, 3H), 2.85 (m, 2H), 2.40 (m, 1H), 2.20 (m, 1H), 1.79-2.04 (m, 4 H). | LC/MS: calc'd 555 (MH$^+$), exp 555 (MH$^+$) |
| 24 | $^1$H NMR (DMSO-d6, DMSO-d6): 12.05 (brs., 1H), 10.04 (s, 1H), 8.00 (d, J = 3.3 Hz, 1H), 7.94 (d, J = 3.0 Hz, 1H), 7.34-7.48 (m, 2H), 7.16 (td, J = 8.5, 2.6 Hz, 1H), 6.04 (s, 1H), 4.34 (d, J = 18.1, 1H), 4.14 (d, J = 17.8 Hz, 1H), 3.80 (m, 2H), 3.53 (s, 3H), 3.44 (dd, J = 10.8, 3.5 Hz, 2H), 2.84 (m, 2H), 2.43 (m, 1H), 2.35 (m, 2H), 2.23 (m, 2H), 1.29 (m, 2 H). | LC/MS: calc'd 549 (MH$^+$), exp 549 (MH$^+$) |
| 25 | $^1$H NMR (METHANOL-d4, 400 MHz): 7.96-8.02 (m, 1H), 7.75 (d, J = 3.3 Hz, 1H), 7.41 (dd, J = 8.7, 6.1 Hz, 1H), 7.23 (dd, J = 8.8, 2.5 Hz, 1H), 7.04 (td, J = 8.4, 2.8 Hz, 1H), 6.17 (s, 1H), 4.47-4.59 (m, 1H), 4.14 (d, J = 17.8 Hz, 1H), 4.01 (ddd, J = 11.2, 7.4, 2.0 Hz, 2H), 3.69 (s, 3H), 3.61 (s, 3H), 3.45-3.55 (m, 2H), 2.84 (t, J = 8.5 Hz, 2H), 2.60-2.73 (m, 1H), 2.50-2.59 (m, 2H), 2.37 (dq, J = 14.3, 7.0 Hz, 2H), 1.38-1.51 (m, 2 H). | LC/MS: calc'd 563 (MH$^+$), exp 563 (MH$^+$) |
| 26 | $^1$H NMR (METHANOL-d4, 400 MHz): 7.89-8.03 (m, 1H), 7.73-7.83 (m, 1H), 7.49 (dd, J = 8.8, 6.0 Hz, 1H), 7.24 (dd, J = 8.7, 2.6 Hz, 1H), 7.07 (td, J = 8.4, 2.5 Hz, 1H), 6.11-6.24 (m, 1H), 4.72 (d, J = 17.6 Hz, 1H), 4.30-4.46 (m, 1H), 3.95-4.18 (m, 4H), 3.65 (dd, J = 11.8, 4.3 Hz, 2H), 3.11-3.27 (m, 2H), 2.60-2.73 (m, 1H), 2.42-2.60 (m, 4H), 1.52-1.70 (m, 2H), 1.03-1.26 (m, 3 H). | LC/MS: calc'd 563 (MH$^+$), exp 563 (MH$^+$) |
| 27 | $^1$H NMR (METHANOL-d4, 400 MHz): 8.07 (d, J = 3.0 Hz, 1H), 7.78 (d, J = 3.1 Hz, 1H), 7.12-7.26 (m, 3H), 5.72 (s, 1H), 4.52 (d, J = 18.1 Hz, 1H), 4.05 (d, J = 18.1 Hz, 1H), 3.99 (m, 2H), 3.72 (s, 3H), 3.52 (m, 2H), 2.82 (m, 2H), 2.56 (m, 1H), 2.28-2.43 (m, 4H), 1.43 (m, 2 H). | LC/MS: calc'd 533 (MH$^+$), exp 533 (MH$^+$) |
| 28 | $^1$H NMR (METHANOL-d4, 400 MHz): 7.99 (d, J = 3.0 Hz, 1H), 7.74 (d, J = 3.0 Hz, 1H), 7.33-7.49 (m, 2H), 7.09 (td, J = 8.4, 2.5 Hz, 1H), 6.11-6.19 (m, 1H), 4.56 (d, J = 17.8 Hz, 1H), 4.16 (d, J = 18.3 Hz, 1H), 3.96-4.08 (m, 2H), 3.65 (s, 3H), 3.53 (d, J = 11.5 Hz, 2H), 2.86 (m, 2H), 2.59-2.69 (m, 1H), 2.47 (d, J = 7.0 Hz, 2H), 2.42 (m, 2H), 1.39-1.54 (m, 2 H). | LC/MS: calc'd 593&595 (MH$^+$), exp 593&595 (MH$^+$) |
| 29 | $^1$H NMR (METHANOL-d4, 400 MHz): 8.03 (d, J = 3.1 Hz, 1H), 7.79 (d, J = 2.9 Hz, 1H), 7.12-7.28 (m, 3H), 5.73 (s, 1H), 4.57 (d, J = 19.4 Hz, 1H), 4.07-4.23 (m, 3H), 3.95-4.03 (m, 2H), 3.52 (d, J = 11.9 Hz, 2H), 2.76-2.88 (m, 2H), 2.59-2.68 (m, 1H), 2.46 (d, J = 7.1 Hz, 2H), 2.38 (m, 2H), 1.39-1.51 (m, 2H), 1.27 (t, J = 7.1 Hz, 3 H). | LC/MS: calc'd 547 (MH$^+$), exp 547 (MH$^+$) |
| 30 | $^1$H NMR (METHANOL-d4, 400 MHz): 8.01 (d, J = 3.0 Hz, 1H), 7.75 (d, J = 3.0 Hz, 1H), 7.40 (dd, J = 8.5, 6.3 Hz, 1H), 7.23 (dd, J = 8.7, 2.6 Hz, 1H), 7.04 (td, J = 8.4, 2.0 Hz, 1H), 6.17 (d, J = 3.0 Hz, 1H), 4.44-4.63 (m, 1H), 4.32-4.40 (m, 1H), 4.07-4.23 (m, 1H), 3.94-4.05 (m, 2H), 3.76 (m, 3H), 3.63 (s, 3H), 3.47-3.59 (m, 2H), 2.77-2.95 (m, 2H), 2.48-2.65 (m, 1H), 2.11-2.27 (m, 2H), 1.83 (d, J = 2.5 Hz, 1H), 1.70 (m, 1 H). | LC/MS: calc'd 579 (MH$^+$), exp 579 (MH$^+$) |
| 31 | $^1$H NMR (METHANOL-d4, 400 MHz): 8.04 (d, J = 3.1 Hz, 0.5H), 8.03 (d, J = 3.1 Hz, 0.5H), 7.95 (d, J = 3.0 Hz, 0.5H), 7.94 (d, J = 3.0 Hz, 0.5H), 7.71 (s, 0.5H), 7.66 (s, 0.5H), 7.53 (m, 1H), 7.29 (m, 1H), 7.12 (m, 1H), 6.18 (s, 1H), 5.08 (s, 0.5H), 4.95 (s, 0.5H) 4.71 (m, 1H), 4.46 (m, 0.5H), 4.42 (m, 0.5H), 4.19-4.34 (m, 3H), 4.12 (m, 1H), 3.90 (m, 1H), 3.57 (s, 1.5H), 3.55 (s, 1.5H), 3.53 (m, 1H), 3.26 (m, 1H). | LC/MS: calc'd 529 (MH$^+$), exp 529 (MH$^+$) |
| 32 | $^1$H NMR (METHANOL-d4, 400 MHz): 8.00 (m, 1H), 7.77 (m, 1H), 7.44 (m, 1H), 7.25 (m, 1H), 7.07 (m, 1H), 6.17 (s, 0.5H), 6.15 (s, 0.5H), 4.11 (m, 3H), 3.85 (m, 3H), 3.79 (m, 2H), 3.52 (s, 1.5H), 3.50 (s, 1.5H), 3.20 (m, 1H), 2.71 (m, 1H), 2.24 (s, 1.5H), 2.18 (s, 1.5H). | LC/MS: calc'd 543 (MH$^+$), exp 543 (MH$^+$) |
| 33 | $^1$H NMR (METHANOL-d4, 400 MHz): 8.00 (m, 1H), 7.77 (m, 1H), 7.44 (m, 1H), 7.25 (m, 1H), 7.07 (m, 1H), 6.18 (s, 0.5H), 6.15 (s, 0.5H), 4.11 (m, 3H), 3.90 (m, 2H), 3.61 (m, 7H), 3.28 (m, 1H), 3.05 (m, 2H), 2.60 (m, 1H). | LC/MS: calc'd 559 (MH$^+$), exp 559 (MH$^+$) |
| 34 | $^1$H NMR (METHANOL-d4, 400 MHz): 7.98 (d, J = 3.0 Hz, 0.5H), 7.97 (d, J = 3.0 Hz, 0.5H), 7.76 (d, J = 3.3 Hz, 1H), 7.42 | LC/MS: calc'd 520 (MH$^+$), exp |

TABLE 1-continued

NMR and MS data of particular compounds

| Example No. | $^1$H NMR data | MW data |
|---|---|---|
| | (dd, J = 8.7, 6.1 Hz, 0.5H), 7.41 (dd, J = 8.7, 6.1 Hz, 0.5H), 7.24 (dd, J = 8.8, 2.8 Hz, 1H), 7.04 (m, 1H), 6.19 (s, 0.5H), 6.18 (s, 0.5H), 4.71 (d, J = 17.6 Hz, 0.5H), 4.64 (d, J = 17.6 Hz, 0.5H), 4.23 (d, J = 17.6 Hz, 0.5H), 4.21 (d, J = 17.6 Hz, 0.5H), 4.08 (m, 2H), 3.85-4.0 (m, 3H), 3.63 (s, 3H), 3.26 (m, 2H), 2.70-3.00 (m, 2H), 2.49 (m, 1H). | 520 (MH$^+$) |
| 35 | $^1$H NMR (METHANOL-d4, 400 MHz): 7.99 (d, J = 3.0 Hz, 1H), 7.76 (d, J = 3.3 Hz, 1H), 7.40 (dd, J = 8.7, 6.1 Hz, 1H), 7.24 (dd, J = 8.8, 2.6 Hz, 1H), 6.99-7.10 (m, 1H), 6.17 (s, 1H), 4.55 (d, J = 17.8 Hz, 1H), 4.46 (m, 1H), 4.04-4.19 (m, 3H), 3.86 (m, 2H), 3.63 (s, 3H), 2.80 (m, 1H), 2.74 (m, 1H), 2.52 (m, 2H), 1.59 (m, 2 H). | LC/MS: calc'd 538 (MH$^+$), exp 538 (MH$^+$) |
| 36 | $^1$H NMR (METHANOL-d4, 400 MHz): 7.99 (d, J = 3.0 Hz, 1H), 7.76 (d, J = 3.3 Hz, 1H), 7.41 (dd, J = 8.7, 6.1 Hz, 1H), 7.23 (dd, J = 8.8, 2.5 Hz, 1H), 7.04 (td, J = 8.4, 2.8 Hz, 1H), 6.17 (s, 1H), 4.53 (d, J = 17.6 Hz, 1H), 4.14 (m, 2H), 4.08 (d, J = 17.6 Hz, 1H), 3.72-3.96 (m, 3H), 3.63 (s, 3H), 3.02 (s, 3H), 2.82 (m, 1H), 2.75 (m, 1H), 2.58 (m, 2H), 1.78 (m, 2 H). | LC/MS: calc'd 584 (MH$^+$), exp 584 (MH$^+$) |
| 37 | $^1$H NMR (METHANOL-d4, 400 MHz): 7.96 (d, J = 3.0 Hz, 1H), 7.75 (d, J = 3.3 Hz, 1H), 7.34-7.44 (m, 1H), 7.23 (dd, J = 8.8, 2.3 Hz, 1H), 6.97-7.09 (m, 1H), 6.16 (s, 1H), 4.13-4.46 (m, 4H), 3.79-3.93 (m, 2H), 3.63 (s, 3H), 3.57 (m, 1H), 3.34-3.39 (m, 1H), 2.91 (m, 1H), 1.96 (d, J = 8.5 Hz, 1 H). | LC/MS: calc'd 463 (MH$^+$), exp 463 (MH$^+$) |
| 38 | $^1$H NMR (METHANOL-d4, 400 MHz): 8.01 (d, J = 3.0 Hz, 1H), 7.90 (d, J = 3.0 Hz, 1H), 7.55 (dd, J = 8.5, 6.0 Hz, 1H), 7.30 (dd, J = 8.7, 2.4 Hz, 1H), 7.13 (td, J = 8.3, 2.5 Hz, 1H), 6.21 (s, 1H), 4.89-4.83 (m, 1H), 4.81-4.69 (m, 3H), 4.10 (d, J = 12.8 Hz, 1H), 4.01 (d, J = 12.8 Hz, 1H), 3.94-3.78 (m, 2H), 3.68 (s, 3H), 3.55-3.43 (m, 1H), 2.36(d, J = 10.3 Hz, 1 H). | LC/MS: calc'd (MH$^+$) 463 exp (MH$^+$) 463. |
| 39 | $^1$H NMR (METHANOL-d4, 400 MHz): 7.98 (s, 1H), 7.75 (s, 1H), 7.51 (m, 1H), 7.28 (m, 1H), 7.12 (m, 1H), 6.19 (s, 1H), 4.35~4.15 (m, 3H), 3.8~3.92 (m, 3H), 3.60 (s, 3H), 3.59 (1H, m), 3.10 (m, 1H), 2.80 (m, 1H), 2.05 (m, 1H), 1.85 (m, 1H). | LC/MS: calc'd 493 (MH$^+$), exp 493 (MH$^+$) |
| 40 | $^1$H NMR (METHANOL-d4, 400 MHz): 8.00 (d, J = 3.0 Hz, 1H), 7.90 (d, J = 3.3 Hz, 1H), 7.56 (dd, J = 8.5, 6.0 Hz, 1H), 7.29 (dd, J = 8.5, 2.5 Hz, 1H), 7.12 (td, J = 8.3, 2.6 Hz, 1H), 6.20 (s, 1H), 4.99 (m, 1H), 3.88 (m, 3H), 3.63 (s, 3H), 3.37 (s, 2H), 2.74 (d, J = 7.8 Hz, 4 H). | LC/MS: calc'd 509 (MH$^+$), exp 509 (MH$^+$) |
| 41 | $^1$H NMR (METHANOL-d4, 400 MHz): 7.99 (m, 1H), 7.76-7.90 (m, 1H), 7.41-7.53 (m, 1H), 7.20-7.31 (m, 1H), 7.01-7.15 (m, 1H), 6.16 (s, 1H), 4.17-4.82 (m, 3H), 3.74-4.11 (m, 3H), 3.37-3.72 (m, 5H), 1.85-2.52 (m, 5 H). | LC/MS: calc'd 504 (MH$^+$), exp 504 (MH$^+$) |
| 42 | $^1$H NMR (METHANOL-d4, 400 MHz): 7.95-8.03 (m, 1H), 7.76 (d, J = 3.3 Hz, 1H), 7.41 (dd, J = 8.8, 6.3 Hz, 1H), 7.24 (dd, J = 8.8, 2.5 Hz, 1H), 7.05 (td, J = 8.4, 2.5 Hz, 1H), 6.17 (s, 1H), 4.56 (d, J = 17.8 Hz, 1H), 3.96-4.13 (m, 2H), 3.64 (s, 3H), 3.46-3.60 (m, 2H), 3.05-3.18 (m, 2H), 2.37-2.50 (m, 2H), 2.22 (d, J = 7.0 Hz, 2H), 1.95-2.05 (m, 2H), 1.80-1.95 (m, 2 H). | LC/MS: calc'd 565 (MH$^+$), exp 565 (MH$^+$) |
| 43 | $^1$H NMR (METHANOL-d4, 400 MHz): 8.00 (d, J = 3.2 Hz, 1H), 7.77 (d, J = 3.2 Hz, 1H), 7.43 (dd, J = 8.8, 6.0 Hz, 1H), 7.25 (dd, J = 8.8, 2.8 Hz, 1H), 7.05 (td, J = 8.4, 2.8 Hz, 1H), 6.19 (s, 1H), 4.63 (d, J = 17.2 Hz, 1H), 4.15 (m, 3H), 3.89 (m, 2H), 3.65 (s, 3H), 2.89 (m, 2H), 2.44 (td, J = 14.0, 5.0 Hz, 2H), 0.60 (m, 2H). | LC/MS: calc'd 517 (MH$^+$), exp 517 (MH$^+$) |
| 44 | $^1$H NMR (METHANOL-d4, 400 MHz): 8.01 (d, J = 3.2 Hz, 1H), 7.90 (d, J = 3.2 Hz, 1H), 7.55 (dd, J = 8.8, 6 Hz, 1H), 7.31 (d, J = 8.8, 2.4 Hz, 1H), 7.12 (td, J = 8.3, 2.6 Hz, 1H), 6.20 (s, 1H), 4.65 (d, J = 16.6 Hz, 1H), 4.43 (d, J = 16.6 Hz, 1H), 4.19 (m, 2H), 4.08 (m, 1H), 3.64 (s, 3H), 2.67 (m, 2H), 2.53 (m, 2H), 2.32 (m, 2H), 2.21 (m, 2 H). | LC/MS: calc'd 491 (MH$^+$), exp 491 (MH$^+$) |
| 45 | $^1$H NMR (METHANOL-d4, 400 MHz): 8.01 (d, J = 3.0 Hz, 1H), 7.78 (d, J = 3.3 Hz, 1H), 7.39-7.49 (m, 2H), 7.23 (dd, J = 8.7, 2.6 Hz, 1H), 7.06 (td, J = 8.4, 2.8 Hz, 1H), 6.17 (s, 1H), 3.85-4.24 (m, 5H), 3.58-3.85 (m, 3H), 3.51 (s, 3H). | LC/MS: calc'd 515 (MH$^+$), exp 515 (MH$^+$) |
| 46 | $^1$H NMR (METHANOL-d4, 400 MHz): 8.02 (d, J = 3.0 Hz, 1H), 7.81 (d, J = 3.0 Hz, 1H), 7.08-7.34 (m, 3H), 5.72 (s, 1H), 4.54 (d, J = 17.6 Hz, 1H), 4.17 (s, 2H), 3.94-4.12 (m, 4H), 3.71 (s, 3H), 3.70 (2H, m), 2.76-2.93 (m, 2H), 2.47 (m, 2H), 1.86(m, 2H). | LC/MS: calc'd 549 (MH$^+$), exp 549 (MH$^+$) |
| 47 | $^1$H NMR (METHANOL-d4, 400 MHz): 8.02 (d, J = 3.0 Hz, 1H), 7.81 (d, J = 3.0 Hz, 1H), 7.08-7.34 (m, 3H), 5.72 (s, 1H), 4.54 (d, J = 17.6 Hz, 1H), 4.17 (s, 2H), 3.94-4.12 (m, 4H), 3.71 (s, 3H), 3.70 (2H, m), 2.76-2.93 (m, 2H), 2.47 (m, 2H), 1.86(m, 2H). | LC/MS: calc'd 549 (MH$^+$), exp 549 (MH$^+$) |

TABLE 1-continued

NMR and MS data of particular compounds

| Example No. | $^1$H NMR data | MW data |
|---|---|---|
| 48 | $^1$H NMR (METHANOL-d4, 400 MHz): 7.97 (d, J = 3.3 Hz, 1H), 7.76 (d, J = 3.3 Hz, 1H), 7.43 (m, 1H), 7.23 (dd, J = 8.7, 2.6 Hz, 1H), 7.06 (td, J = 8.4, 2.4 Hz, 0.5H), 7.05 (td, J = 8.4, 2.4 Hz, 0.5H), 6.17 (s, 1H), 4.68 (m, 1H), 4.17 (m, 1H), 3.63-4.09 (m, 5H), 3.61 (s, 3H), 3.30 (m, 0.5H), 3.20 (m, 1H), 3.08 (m, 0.5H), 2.63 (m, 1H), 2.03 (s, 1.5H), 2.02 (s, 1.5H), 1.85 (m, 1H). | LC/MS: calc'd 534 (MH$^+$), exp 534 (MH$^+$) |
| 49 | $^1$H NMR (METHANOL-d4, 400 MHz): 7.98 (d, J = 3.1 Hz, 0.5H), 7.97 (d, J = 3.1 Hz, 0.5H), 7.77 (d, J = 3.1 Hz, 1H), 7.44 (dd, J = 8.7, 6.1 Hz, 0.5H), 7.43 (dd, J = 8.7, 6.1 Hz, 0.5H), 7.24 (dd, J = 8.8, 2.8 Hz, 1H), 7.06 (tt, J = 8.4, 2.8 Hz, 1H), 6.18 (s, 1H), 4.66 (m, 1H), 4.51 (m, 1H), 4.20 (m, 1H), 3.71-3.98 (m, 3H), 3.61 (s, 1.5H), 3.60 (s, 1.5H) 3.48-3.59 (m, 1H), 3.19 (m, 1H), 3.09 (m, 1H), 2.40 (m, 1H), 2.12 (m, 1H). | LC/MS: calc'd 493 (MH$^+$), exp 493 (MH$^+$) |
| 50 | $^1$H NMR (METHANOL-d4, 400 MHz): 7.98 (d, J = 3.1 Hz, 0.5H) 7.97 (d, J = 3.1 Hz, 0.5H), 7.79 (d, J = 3.3 Hz, 1H), 7.48 (m, 1H), 7.43 (m, 1H), 7.08-7.22 (m, 1H), 6.18 (s, 0.5H), 6.16 (s, 0.5H), 4.21-4.71 (m, 3H), 4.01-4.20 (m, 4H), 3.82-3.99 (m, 3H), 3.43-3.78 (m, 3H), 2.38-2.56 (m, 1H), 2.32 (d, J = 11.5 Hz, 1H), 1.16 ppm (t, J = 7.1 Hz, 1.5H), 1.15 (t, J = 7.1 Hz, 1.5H). | LC/MS: calc'd 609, 611 (MH$^+$), exp 609, 611 (MH$^+$) |
| 51 | $^1$H NMR (METHANOL-d4, 400 MHz): 8.02 (d, J = 3.3 Hz, 1H), 7.92 (d, J = 3.0 Hz, 1H), 7.55 (m, 1H), 7.30 (dd, J = 8.7, 2.6 Hz, 1H), 7.12 (td, J = 8.3, 2.6 Hz, 0.5H), 7.11 (dt, J = 8.3, 2.6 Hz, 0.5H), 6.21 (s, 0.5H), 6.20 (s, 0.5H), 5.75 (m, 0.5H), 5.61 (m, 0.5H), 4.92 (m, 1H), 4.71 (m, 1H), 4.29-4.54 (m, 2H), 4.18 (m, 3H), 3.89 (m, 1H), 3.65 (s, 1.5H), 3.64 (s, 1.5H), 2.58-2.97 (m, 2H). | LC/MS: calc'd 495 (MH$^+$), exp 495 (MH$^+$) |
| 52 | $^1$H NMR (METHANOL-d4, 400 MHz): 7.97 (d, J = 3.3 Hz, 1H), 7.76 (d, J = 3.0 Hz, 1H), 7.45 (m, 1H), 7.42 (dd, J = 8.4, 2.6 Hz, 1H), 7.12 (td, J = 8.4, 2.5 Hz, 1H), 6.18 (s, 1H), 4.17 (m, 1H), 4.06 (q, J = 7.0 Hz, 2H), 3.97 (m, 2H), 3.90 (m, 2H), 3.69 (m, 1H), 3.45(m, 2H), 3.24 (m, 0.5H), 3.07 (m, 0.5H), 2.45 (m, 1H), 2.33 (m, 1H), 1.15 (t, J = 7.2 Hz, 3H). | LC/MS: calc'd 579, 581 (MH$^+$), exp 579, 581 (MH$^+$) |
| 53 | $^1$H NMR (METHANOL-d4, 400 MHz): 7.97 (dd, J = 3.01, 1.76 Hz, 1 H) 7.76 (d, J = 3.01 Hz, 1 H) 7.35-7.46 (m, 2 H) 7.09 (d, J = 2.51 Hz, 1 H) 6.17 (s, 1 H) 4.70 (d, J = 17.57 Hz, 1 H) 4.54 (dd, J = 13.55, 2.51 Hz, 1 H) 4.11-4.36 (m, 5 H) 3.84-4.01 (m, 2 H) 3.73-3.84 (m, 2 H) 3.63 (s, 3 H) 3.40-3.52 (m, 1 H) 2.78 (t, J = 17.19 Hz, 2 H). | MS: calc'd (MH$^+$) 594, exp (MH$^+$) 594 |
| 54 | $^1$H NMR (METHANOL-d4, 400 MHz): 7.97 (d, J = 3.26 Hz, 1 H) 7.76 (d, J = 3.01 Hz, 1 H) 7.35-7.49 (m, 2 H) 7.09 (td, J = 8.41, 2.51 Hz, 1 H) 6.17 (s, 1 H) 4.68 (d, J = 17.57 Hz, 1 H) 4.11-4.25 (m, 3 H) 3.99 (d, J = 5.77 Hz, 2 H) 3.89-3.97 (m, 2 H) 3.63 (s, 3 H) 3.57 (br. s., 2 H) 2.78 (br. s., 1 H) 2.73 (br. s., 1 H). | MS: calc'd (MH$^+$) 579, exp (MH$^+$) 579 |
| 55 | $^1$H NMR (METHANOL-d4, 400 MHz): 8.02 (d, J = 3.26 Hz, 1 H) 7.92 (d, J = 3.26 Hz, 1 H) 7.31-7.42 (m, 2 H) 7.25 (ddd, J = 9.10, 7.09, 2.38 Hz, 1 H) 6.22-6.30 (m, 1 H) 5.05 (d, J = 16.81 Hz, 1 H) 4.71 (d, J = 17.07 Hz, 1 H) 4.16-4.27 (m, 2 H) 3.85 (br. s., 2 H) 3.68-3.80 (m, 2 H) 3.60-3.68 (m, 3 H) 2.56-2.80 (m, 5 H) 1.90 (d, J = 6.53 Hz, 2 H). | LC/MS: calc'd 550 (MH$^+$), exp 550 (MH$^+$) |
| 56 | $^1$H NMR (METHANOL-d4, 400 MHz): 8.02 (d, J = 3.26 Hz, 1 H) 7.92 (d, J = 3.26 Hz, 1 H) 7.56 (dd, J = 8.78, 6.02 Hz, 1 H) 7.30 (dd, J = 8.66, 2.64 Hz, 1 H) 7.12 (td, J = 8.34, 2.64 Hz, 1 H) 6.16-6.25 (m, 1 H) 5.03 (d, J = 16.81 Hz, 1 H) 4.73 (d, J = 17.07 Hz, 1 H) 4.64 (dt, J = 11.98, 5.93 Hz, 1 H) 4.26-4.35 (m, 2 H) 4.12-4.24 (m, 2 H) 3.79 (br. s., 2 H) 3.67 (s, 3 H) 2.58 (br. s., 2 H) 2.20-2.38 (m, 2 H). | LC/MS: calc'd 586 (MH$^+$), exp 586 (MH$^+$) |
| 57 | $^1$H NMR (METHANOL-d4, 400 MHz): 8.02 (d, J = 3.26 Hz, 1 H) 7.93 (d, J = 3.26 Hz, 1 H) 7.56 (dd, J = 8.78, 6.02 Hz, 1 H) 7.30 (dd, J = 8.78, 2.51 Hz, 1 H) 7.13 (td, J = 8.41, 2.76 Hz, 1 H) 6.21 (s, 1 H) 5.06 (d, J = 16.56 Hz, 1 H) 4.89-4.94 (m, 1 H) 4.76 (d, J = 16.56 Hz, 1 H) 4.09-4.35 (m, 4 H) 3.78 (br. s., 2 H) 3.67 (s, 3 H) 2.43 (br. s., 2 H) 2.10-2.28 (m, 2 H). | LC/MS: calc'd 550 (MH$^+$), exp 550 (MH$^+$) |
| 58 | $^1$H NMR ((METHANOL-d4, 400 MHz): 8.01 (d, J = 3.01 Hz, 1 H) 7.88-7.94 (m, 1 H) 7.52-7.65 (m, 1 H) 7.46 (d, J = 2.76 Hz, 1 H) 7.17 (td, J = 8.34, 2.64 Hz, 1 H) 6.20 (s, 1 H) 5.08 (d, J = 15.56 Hz, 1 H) 4.73 (dd, J = 16.06, 8.28 Hz, 1 H) 4.04-4.41 (m, 4 H) 3.61-3.86 (m, 5 H) 3.15-3.29 (m, 1 H) 2.21-2.55 (m, 4 H) 2.14 (t, J = 11.04 Hz, 2 H). | LC/MS: calc'd 594(MH$^+$), exp 594 (MH$^+$) |
| 59 | $^1$H NMR (METHANOL-d4, 400 MHz): 7.97-8.06 (m, 1 H) 7.92 (d, J = 3.26 Hz, 1 H) 7.32-7.45 (m, 2 H) 7.15-7.28 (m, 1 H) 6.26 (s, 1 H) 4.98-5.15 (m, 1 H) 4.63-4.77 (m, 1 H) 4.30 (br. s., 4 H) 3.59-3.83 (m, 5 H) 3.15-3.29 (m, 1 H) 2.62-2.77 (m, 1 H) 2.38 (d, J = 6.78 Hz, 3 H) 2.14 (br. s., 2 H). | LC/MS: calc'd 550 (MH$^+$), exp 550 (MH$^+$) |

TABLE 1-continued

NMR and MS data of particular compounds

| Example No. | $^1$H NMR data | MW data |
|---|---|---|
| 60 | $^1$H NMR (METHANOL-d4, 400 MHz): 7.90-8.03 (m, 1 H) 7.76 (d, J = 3.26 Hz, 1 H) 7.41 (dd, J = 8.78, 6.02 Hz, 1 H) 7.23 (dd, J = 8.78, 2.51 Hz, 1 H) 7.04 (td, J = 8.41, 2.76 Hz, 1 H) 6.17 (s, 1 H) 4.53 (d, J = 17.57 Hz, 1 H) 4.01-4.23 (m, 3 H) 3.79-3.96 (m, 3 H) 3.63 (s, 3 H) 2.95-3.11 (m, 3 H) 2.82 (br. s., 1 H) 2.75 (br. s., 1 H) 2.51-2.65 (m, 2 H) 1.78 (dd, J = 13.55, 9.79 Hz, 2 H). | LC/MS: calc'd 585 (MH$^+$), exp 585 (MH$^+$) |
| 61 | $^1$H NMR (METHANOL-d4, 400 MHz): 7.99 (d, J = 3.01, 1 H) 7.76 (d, J = 3.26 Hz, 1 H) 7.41 (dd, J = 8.66, 6.15 Hz, 1 H) 7.24 (dd, J = 8.78, 2.76 Hz, 1 H) 7.04 (td, J = 8.41, 2.76 Hz, 1 H) 6.17 (s, 1 H) 4.55 (d, J = 17.82 Hz, 1 H) 4.45 (t, J = 6.65 Hz, 1 H) 4.02-4.19 (m, 3 H) 3.76-3.92 (m, 2 H) 3.63 (s, 3 H) 2.80 (br. s., 1 H) 2.73 (br. s., 1 H) 2.43-2.58 (m, 2 H) 1.93-2.05 (m, 3 H) 1.51-1.66 (m, 2 H). | LC/MS: calc'd 549 (MH$^+$), exp 549 (MH$^+$) |
| 62 | $^1$H NMR (METHANOL-d4, 400 MHz): 7.97 (d, J = 3.26 Hz, 1 H) 7.75 (d, J = 3.01 Hz, 1 H) 7.40 (dd, J = 8.66, 6.15 Hz, 1 H) 7.23 (dd, J = 8.78, 2.51 Hz, 1 H) 7.04 (d, J = 2.51 Hz, 1 H) 6.17 (s, 1 H) 4.53 (d, J = 17.82 Hz, 1 H) 4.18-4.32 (m, 1 H) 4.01-4.18 (m, 3 H) 3.77-3.91 (m, 2 H) 3.63 (s, 3 H) 2.70-2.79 (m, 2 H) 2.53 (dq, J = 14.40, 7.08 Hz, 2 H) 1.59 (dd, J = 14.43, 9.91 Hz, 2 H). | LC/MS: calc'd 550 (MH$^+$), exp 550 (MH$^+$) |
| 63 | $^1$H NMR (METHANOL-d4, 400 MHz): 7.99 (d, J = 3.01 Hz, 1 H) 7.78 (d, J = 2.76 Hz, 1 H) 7.39-7.47 (m, 1 H) 7.25 (dd, J = 8.78, 2.51 Hz, 1 H) 7.05 (td, J = 8.34, 2.64 Hz, 1 H) 6.18 (s, 1 H) 4.58 (d, J = 17.82 Hz, 1 H) 4.16 (d, J = 10.04 Hz, 3 H) 3.77-3.98 (m, 3 H) 3.63 (s, 3 H) 2.83 (br. s., 2 H) 2.55 (br. s., 2 H) 1.95 (br. s., 2 H). | LC/MS: calc'd 586 (MH$^+$), exp 586 (MH$^+$) |
| 64 | $^1$H NMR (METHANOL-d4, 400 MHz): 7.92-8.03 (m, 1 H) 7.71-7.84 (m, 1 H) 7.36-7.52 (m, 2 H) 7.11 (td, J = 8.41, 2.51 Hz, 1 H) 6.16 (s, 1 H) 4.32 (d, J = 16.81 Hz, 1 H) 4.12 (d, J = 17.32 Hz, 1 H) 3.84-4.04 (m, 3 H) 3.70 (d, J = 10.79 Hz, 1 H) 3.62 (s, 3 H) 3.44 (d, J = 9.29 Hz, 1 H) 3.27 (br. s., 1 H) 2.84-2.98 (m, 1 H) 2.64-2.81 (m, 2 H) 2.56 (td, J = 12.05, 7.28 Hz, 1 H) 1.70 (dd, J = 12.92, 5.14 Hz, 1 H). | LC/MS: calc'd 579 (MH$^+$), exp 579 (MH$^+$) |
| 65 | $^1$H NMR (METHANOL-d4, 400 MHz): 8.02 (d, J = 3.01 Hz, 1 H) 7.86-7.94 (m, 1 H) 7.30-7.47 (m, 2 H) 7.25 (ddd, J = 9.16, 7.40, 2.01 Hz, 1 H) 6.28 (s, 1 H) 5.04 (d, J = 17.07 Hz, 1 H) 4.71 (d, J = 16.81 Hz, 1 H) 4.04-4.28 (m, 4 H) 3.86 (br. s., 2 H) 3.63-3.78 (m, 2 H) 2.69 (d, J = 4.77 Hz, 5 H) 1.90 (d, J = 6.53 Hz, 2H) 1.14 (t, J = 7.15 Hz, 3 H). | LC/MS: calc'd 564 (MH$^+$), exp 564 (MH$^+$) |
| 66 | $^1$H NMR (METHANOL-d4, 400 MHz): 7.98 (d, J = 3.01 Hz, 1 H) 7.77 (d, J = 3.01 Hz, 1 H) 7.21-7.34 (m, 2 H) 7.15 (td, J = 8.47, 1.88 Hz, 1 H) 6.24 (s, 1 H) 4.54 (d, J = 17.57 Hz, 1 H) 4.07 (dd, J = 7.15, 0.88 Hz, 5 H) 3.84-3.96 (m, 2 H) 3.07-3.21 (m, 1 H) 2.65-2.85 (m, 2 H) 2.23 (d, J = 7.03 Hz, 2 H) 1.70-1.94 (m, 4 H) 1.16 (t, J = 7.15 Hz, 3 H). | LC/MS: calc'd 564 (MH$^+$), exp 564 (MH$^+$) |
| 67 | $^1$H NMR (METHANOL-d4, 400 MHz): 7.88-8.04 (m, 1 H) 7.66-7.81 (m, 1 H) 7.35-7.48 (m, 2 H) 7.10 (td, J = 8.41, 2.51 Hz, 1 H) 6.11-6.22 (m, 1 H) 4.58 (d, J = 17.57 Hz, 1 H) 4.01-4.27 (m, 5 H) 3.92 (t, J = 11.17 Hz, 2 H) 3.15 (tt, J = 12.30, 6.02 Hz, 1 H) 2.76-2.94 (m, 2 H) 2.17-2.31 (m, 2 H) 1.73-1.99 (m, 4 H) 1.09-1.24 (m, 3 H). | LC/MS: calc'd 608 (MH$^+$), exp 608 (MH$^+$) |
| 68 | $^1$H NMR (METHANOL-d4, 400 MHz): 7.92-8.02 (m, 1 H) 7.77 (d, J = 3.26 Hz, 1 H) 7.29-7.39 (m, 1 H) 7.24 (d, J = 7.78 Hz, 1 H) 7.13 (td, J = 8.28, 1.25 Hz, 1 H) 6.25 (s, 1 H) 4.60 (d, J = 17.07 Hz, 1 H) 4.10-4.27 (m, 3 H) 4.01-4.10 (m, 2 H) 3.85-3.98 (m, 2 H) 3.15 (tt, J = 12.23, 6.21 Hz, 1 H) 2.74-2.98 (m, 2 H) 2.25 (d, J = 7.28 Hz, 2 H) 1.77-2.00 (m, 4 H) 1.15 (t, J = 7.15 Hz, 3 H). | LC/MS: calc'd 608 (MH$^+$), exp 608 (MH$^+$) |
| 69 | $^1$H NMR (METHANOL-d4, 400 MHz): 7.93-8.01 (m, 1 H) 7.77 (d, J = 3.01 Hz, 1 H) 7.13-7.28 (m, 2 H) 6.18 (s, 1 H) 4.54 (d, J = 17.82 Hz, 1 H) 4.01-4.19 (m, 5 H) 3.91 (t, J = 11.54 Hz, 2 H) 3.04-3.20 (m, 1 H) 2.69-2.88 (m, 2 H) 2.23 (d, J = 7.03 Hz, 2 H) 1.73-1.96 (m, 4 H) 1.17 (t, J = 7.03 Hz, 3 H). | LC/MS: calc'd 582 (MH$^+$), exp 582 (MH$^+$) |
| 70 | $^1$H NMR (METHANOL-d4, 400 MHz): 7.98-8.07 (m, 1 H) 7.92 (d, J = 3.01 Hz, 1 H) 7.54-7.65 (m, 1 H) 7.48 (dd, J = 8.41, 2.64 Hz, 1 H) 7.18 (td, J = 8.34, 2.64 Hz, 1 H) 6.22 (s, 1 H) 5.00-5.17 (m, 2 H) 4.78 (d, J = 16.81 Hz, 1 H) 4.26-4.38 (m, 2 H) 4.03-4.24 (m, 4 H) 3.81 (br. s., 2 H) 2.41 (br. s., 2 H) 2.18-2.32 (m, 2 H) 1.93-2.09 (m, 3 H) 1.16 (t, J = 7.03 Hz, 3 H). | LC/MS: calc'd 606 (MH$^+$), exp 606 (MH$^+$) |
| 71 | $^1$H NMR (METHANOL-d4, 400 MHz): 8.02 (d, J = 3.01 Hz, 1 H) 7.93 (d, J = 3.01 Hz, 1 H) 7.57 (dd, J = 8.78, 6.02 Hz, 1 H) 7.48 (dd, J = 8.41, 2.64 Hz, 1 H) 7.18 (td, J = 8.34, 2.64 Hz, 1 H) 6.22 (s, 1 H) 5.03 (d, J = 16.81 Hz, 1 H) 4.73 (d, J = 16.56 | LC/MS: calc'd 606 (MH$^+$), exp 606 (MH$^+$) |

TABLE 1-continued

NMR and MS data of particular compounds

| Example No. | ¹H NMR data | MW data |
|---|---|---|
|  | Hz, 1 H) 4.51 (t, J = 7.03 Hz, 1 H) 4.25-4.37 (m, 2 H) 4.04-4.22 (m, 4 H) 3.75 (d, J = 4.27 Hz, 2 H) 2.73-2.88 (m, 2 H) 2.03-2.16 (m, 2 H) 1.95-2.03 (m, 3 H) 1.16 (t, J = 7.15 Hz, 3 H). |  |
| 72 | ¹H NMR (DMSO-d6, 400 MHz): 12.04 (br. s., 1 H) 9.98 (s, 1 H) 8.01-8.09 (m, 1 H) 7.95 (d, J = 3.01 Hz, 1 H) 7.44 (dd, J = 7.53, 1.76 Hz, 1 H) 7.38 (dd, J = 7.53, 2.01 Hz, 1 H) 7.21-7.32 (m, 2 H) 6.09 (s, 1 H) 4.33 (d, J = 17.82 Hz, 1 H) 3.85-4.09 (m, 5 H) 3.71-3.83 (m, 2 H) 2.94 (dt, J = 12.36, 6.24 Hz, 1 H) 2.75 (br. s., 1 H) 2.64 (br. s., 1 H) 2.09 (d, J = 7.03 Hz, 2 H) 1.73 (td, J = 12.05, 5.02 Hz, 2 H) 1.60 (d, J = 13.05 Hz, 2 H) 1.08 (t, J = 7.03 Hz, 3 H). | LC/MS: calc'd 546 (MH⁺), exp 546 (MH⁺) |
| 73 | ¹H NMR (METHANOL-d4, 400 MHz): 7.98 (d, J = 3.01 Hz, 1 H) 7.77 (d, J = 3.01 Hz, 1 H) 7.14-7.29 (m, 2 H) 6.17 (s, 1 H) 4.53 (d, J = 17.32 Hz, 1 H) 4.01-4.21 (m, 3 H) 3.90 (t, J = 11.67 Hz, 2 H) 3.63 (s, 3 H) 3.08-3.22 (m, 1 H) 2.64-2.84 (m, 2 H) 2.24 (d, J = 6.78 Hz, 2 H) 1.70-1.98 (m, 4 H). | LC/MS: calc'd 568 (MH⁺), exp 568 (MH⁺) |
| 74 | ¹H NMR (METHANOL-d4, 400 MHz): 7.98 (d, J = 3.01 Hz, 1 H) 7.76 (d, J = 3.01 Hz, 1 H) 7.33 (td, J = 7.97, 5.40 Hz, 1 H) 7.21 (d, J = 7.78 Hz, 1 H) 7.11 (td, J = 8.28, 1.51 Hz, 1 H) 6.23 (s, 1 H) 4.54 (d, J = 18.07 Hz, 1 H) 4.01-4.20 (m, 3 H) 3.90 (t, J = 11.92 Hz, 2 H) 3.62 (s, 3 H) 3.13 (dd, J = 12.92, 5.90 Hz, 1 H) 2.65-2.85 (m, 2 H) 2.24 (d, J = 7.03 Hz, 2 H) 1.86 (d, J = 8.53 Hz, 4 H). | LC/MS: calc'd 594 (MH⁺), exp 594 (MH⁺) |
| 75 | ¹H NMR (METHANOL-d4, 400 MHz): 8.00 (d, J = 3.01 Hz, 1 H) 7.80 (d, J = 3.01 Hz, 1 H) 7.03-7.26 (m, 3 H) 6.07 (s, 1 H) 4.51 (br. s., 1 H) 4.04-4.24 (m, 5 H) 3.94 (d, J = 11.80 Hz, 2 H) 3.05-3.19 (m, 1 H) 2.82 (br. s., 2 H) 2.24 (d, J = 7.03 Hz, 2 H) 1.84 (br. s., 4 H) 1.21 (t, J = 7.15 Hz, 3 H). | LC/MS: calc'd 547 (MH⁺), exp 547 (MH⁺) |
| 76 | ¹H NMR (METHANOL-d4, 400 MHz): 7.97 (d, J = 3.26 Hz, 1 H) 7.76 (d, J = 3.01 Hz, 1 H) 7.61 (dd, J = 8.03, 1.25 Hz, 1 H) 7.35-7.43 (m, 1 H) 7.31 (td, J = 7.47, 1.13 Hz, 1 H) 7.15 (td, J = 7.65, 1.76 Hz, 1 H) 6.19 (s, 1 H) 4.55 (d, J = 18.07 Hz, 1 H) 4.02-4.25 (m, 3 H) 3.84-3.96 (m, 2 H) 3.63 (s, 3 H) 3.08-3.19 (m, 1 H) 2.66-2.87 (m, 2 H) 2.24 (d, J = 7.03 Hz, 2 H) 1.73-1.99 (m, 4 H). | LC/MS: calc'd 576 (MH⁺), exp 576 (MH⁺) |
| 77 | ¹H NMR (METHANOL-d4, 400 MHz): 7.98 (d, J = 3.26 Hz, 1 H) 7.75 (d, J = 3.26 Hz, 1 H) 7.61 (dd, J = 8.03, 1.25 Hz, 1 H) 7.35-7.45 (m, 1 H) 7.27-7.34 (m, 1 H) 7.16 (td, J = 7.65, 1.76 Hz, 1 H) 6.16-6.22 (m, 1 H) 4.54 (d, J = 17.57 Hz, 1 H) 3.99-4.21 (m, 5 H) 3.90 (t, J = 12.17 Hz, 2 H) 3.13 (dd, J = 12.05, 6.02 Hz, 1 H) 2.62-2.84 (m, 2 H) 2.22 (d, J = 7.03 Hz, 2 H) 1.74-1.95 (m, 4 H) 1.16 (t, J = 7.15 Hz, 3 H) 1H NMR (METHANOL-d4, 400 MHz): 7.98 (d, J = 3.26 Hz, 1 H) 7.75 (d, J = 3.26 Hz, 1 H) 7.61 (dd, J = 8.03, 1.25 Hz, 1 H) 7.35-7.45 (m, 1 H) 7.27-7.34 (m, 1 H) 7.16 (td, J = 7.65, 1.76 Hz, 1 H) 6.16-6.22 (m, 1 H) 4.54 (d, J = 17.57 Hz, 1 H) 3.99-4.21 (m, 5H) 3.90 (t, J = 12.17 Hz, 2 H) 3.13 (dd, J = 12.05, 6.02 Hz, 1 H) 2.62-2.84 (m, 2 H) 2.22 (d, J = 7.03 Hz, 2 H) 1.74-1.95 (m, 4 H) 1.16 (t, J = 7.15 Hz, 3 H). | LC/MS: calc'd 590 (MH⁺), exp 590 (MH⁺) |
| 78 | ¹H NMR (METHANOL-d4, 400 MHz): 7.97 (d, J = 3.26 Hz, 1 H) 7.75 (d, J = 3.26 Hz, 1 H) 6.95-7.12 (m, 2 H) 5.93 (s, 1 H) 4.57 (d, J = 17.57 Hz, 1 H) 4.03-4.22 (m, 5 H) 3.91 (t, J = 12.17 Hz, 2 H) 3.07-3.21 (m, 1 H) 2.68-2.88 (m, 2 H) 2.23 (d, J = 7.03 Hz, 2 H) 1.72-1.98 (m, 4 H) 1.19 (t, J = 7.15 Hz, 3 H). | LC/MS: calc'd 561 (MH⁺), exp 561 (MH⁺) |
| 79 | ¹H NMR (METHANOL-d4, 400 MHz4): 8.00 (d, J = 3.01 Hz, 1 H) 7.83 (d, J = 3.26 Hz, 1 H) 7.47 (dd, J = 8.66, 6.15 Hz, 1 H) 7.22-7.31 (m, 1 H) 7.07 (td, J = 8.41, 2.76 Hz, 1 H) 6.20 (s, 1 H) 4.77 (d, J = 16.81 Hz, 1 H) 4.65 (br. s., 1 H) 4.33 (d, J = 17.57 Hz, 1 H) 4.18 (d, J = 11.80 Hz, 2 H) 4.00 (d, J = 17.07 Hz, 2 H) 3.84 (br. s., 2 H) 3.64 (s, 3 H) 3.48 (d, J = 18.82 Hz, 1 H) 3.02 (br. s., 2 H) 1.36-1.58 (m, 6 H). | LC/MS: calc'd 607 (MH⁺), exp 607 (MH⁺) |
| 80 | ¹H NMR (METHANOL-d4, 400 MHz): 7.91-8.04 (m, 1 H) 7.76 (d, J = 3.01 Hz, 1 H) 7.17-7.31 (m, 2 H) 6.19 (s, 1 H) 4.55 (d, J = 17.82 Hz, 1 H) 3.99-4.22 (m, 5 H) 3.91 (t, J = 11.67 Hz, 2 H) 3.13 (td, J = 11.92, 6.02 Hz, 1 H) 2.67-2.87 (m, 2 H) 2.23 (d, J = 7.03 Hz, 2 H) 1.71-1.96 (m, 4 H) 1.17 (t, J = 7.15 Hz, 3 H). | LC/MS: calc'd 626 (MH⁺), exp 626 (MH⁺) |
| 81 | ¹H NMR (METHANOL-d4, 400 MHz): 7.95-8.02 (m, 1 H) 7.80-7.88 (m, 1 H) 7.50-7.60 (m, 1 H) 7.21-7.30 (m, 1 H) 7.01-7.12 (m, 1 H) 6.13-6.22 (m, 1 H) 4.67-4.79 (m, 1 H) 4.36-4.49 (m, 1 H) 4.07-4.22 (m, 2 H) 3.94-4.04 (m, 1 H) 3.70-3.85 (m, 2 H) 3.62 (s, 3 H) 2.26-2.50 (m, 3 H) 2.14-2.26 (m, 1 H). | LC/MS: calc'd 521 (MH⁺), exp 521 (MH⁺) |

TABLE 1-continued

NMR and MS data of particular compounds

| Example No. | $^1$H NMR data | MW data |
|---|---|---|
| 82 | $^1$H NMR (METHANOL-d4, 400 MHz): 7.98 (d, J = 3.14 Hz, 1 H) 7.84 (s, 1 H) 7.49-7.57 (m, 1 H) 7.21-7.30 (m, 1 H) 7.04-7.15 (m, 1 H) 6.19 (s, 1 H) 4.80-4.89 (m, 1 H) 4.28-4.39 (m, 1 H) 4.08-4.20 (m, 2 H) 3.91-4.02 (m, 1 H) 3.80-3.90 (m, 1 H) 3.70-3.79 (m, 1 H) 3.62 (s, 3 H) 2.31-2.50 (m, 3 H) 2.15-2.27 (m, 1 H). | LC/MS: calc'd 521 (MH$^+$), exp 521 (MH$^+$) |
| 83 | $^1$H NMR (METHANOL-d4, 400 MHz): 7.96-8.02 (m, 1 H) 7.78-7.86 (m, 1 H) 7.30-7.44 (m, 2 H) 7.16-7.23 (m, 1 H) 6.25 (s, 1 H) 4.17-4.46 (m, 2 H) 4.00-4.16 (m, 4 H) 3.88-3.96 (m, 1 H) 3.66-3.81 (m, 2 H) 2.27-2.48 (m, 3 H) 2.13-2.22 (m, 1H) 1.13 (td, J = 7.12, 1.94 Hz, 3 H). | LC/MS: calc'd 535 (MH$^+$), exp 535(MH$^+$) |
| 84 | $^1$H NMR (METHANOL-d4, 400 MHz): 7.97 (d, J = 3.14 Hz, 1 H) 7.79 (m, 1 H) 7.22 (m, 1 H) 7.00-7.12 (m, 1 H) 5.92 (s, 1 H) 4.75-4.86 (m, 1 H) 4.09 (m, 3 H) 3.92 (m, 2 H) 3.68-3.76 (m, 1 H) 3.62 (s, 3 H) 2.54 (d, J = 2.26 Hz, 3 H) 2.35 (m, 3 H) 2.04-2.16 (m, 1 H). | LC/MS: calc'd 519(MH$^+$), exp 519(MH$^+$) |
| 85 | $^1$H NMR (METHANOL-d4, 400 MHz): 7.96 (d, J = 3.14 Hz, 1 H) 7.72-7.84 (m, 1 H) 7.13-7.27 (m, 1 H) 7.05 (d, J = 9.29 Hz, 1 H) 5.93 (s, 1 H) 4.65-4.78 (m, 1 H) 4.15-4.26 (m, 1 H) 4.01-4.14 (m, 3 H) 3.86-3.97 (m, 1 H) 3.66-3.75 (m, 1 H) 3.63 (s, 3 H) 2.54 (d, J = 2.13 Hz, 3 H) 2.25-2.44 (m, 3 H) 2.09-2.22 (m, 1 H). | LC/MS: calc'd 519 (MH$^+$), exp 519(MH$^+$) |
| 86 | $^1$H NMR (400 MHz, METHANOL-d4) 8.06-7.93 (m, 1H), 7.79-7.72 (m, 1H), 7.47-7.37 (m, 1H), 7.32-7.18 (m, 1H), 7.13-6.98 (m, 1H), 6.22-6.12 (m, 1H), 4.30-4.20 (m, 2H), 3.62 (s, 2H), 3.53-3.44 (m, 1H), 3.31-3.24 (m, 1H), 2.88-2.65 (m, 2H), 2.50-2.21 (m, 4H), 2.05-1.93 (m, 1H), 1.84-1.58 (m, 3H). | LC/MS: calc'd 569 (MH$^+$), exp 569(MH$^+$) |
| 87 | $^1$H NMR (400 MHz, METHANOL-d4) 8.04-7.88 (m, 1H), 7.83-7.69 (m, 1H), 7.29-7.20 (m, 1H), 7.11-7.00 (m, 1H), 6.18 (s, 1H), 4.59-4.46 (m, 1H), 4.03-3.92 (m, 1H), 3.61 (s, 3H), 3.38 (br. s., 2H), 2.85-2.60 (m, 2H), 2.35 (s, 4H), 2.11-2.01 (m, 1H), 1.90-1.62 (m, 3H). | LC/MS: calc'd 569 (MH$^+$), exp 569(MH$^+$) |
| 88 | $^1$H NMR (400 MHz, METHANOL-d4) 7.97 (d, J = 3.0 Hz, 1H), 7.76 (d, J = 3.0 Hz, 1H), 7.39-7.21 (m, 2H), 7.19-7.10 (m, 1H), 6.23 (s, 1H), 4.26 (s, 2H), 3.61 (s, 3H), 3.50 (br. s., 1H), 2.91-2.61 (m, 2H), 2.51-2.19 (m, 4H), 1.98 (d, J = 12.0 Hz, 1H), 1.87-1.60 (m, 3H). | LC/MS: calc'd 569 (MH$^+$), exp 569(MH$^+$) |
| 89 | $^1$H NMR (400 MHz, METHANOL-d4) 8.02-7.90 (m, 1H), 7.79-7.71 (m, 1H), 7.37-7.21 (m, 2H), 7.19-7.10 (m, 1H), 6.23 (s, 1H), 4.56-4.44 (m, 1H), 4.06-3.89 (m, 2H), 3.61 (s, 3H), 3.39 (br. s., 1H), 2.86-2.61 (m, 2H), 2.50-2.19 (m, 4H), 2.04 (d, J = 14.1 Hz, 1H), 1.90-1.63 (m, 3H). | LC/MS: calc'd 569 (MH$^+$), exp 569(MH$^+$) |
| 90 | $^1$H NMR (400 MHz, METHANOL-d4) 8.04-7.94 (m, 1H), 7.78-7.70 (m, 1H), 7.45-7.36 (m, 2H), 7.30-7.19 (m, 2H), 6.20 (s, 1H), 4.24 (s, 2H), 3.60 (s, 3H), 3.53-3.43 (m, 1H), 3.30-3.25 (m, 1H), 2.86-2.66 (m, 1H), 2.50-2.22 (m, 4H), 2.03-1.92 (m, 1H), 1.86-1.61 (m, 3H). | LC/MS: calc'd 551 (MH$^+$), exp 551(MH$^+$) |
| 91 | $^1$H NMR (400 MHz, METHANOL-d4) 7.96 (d, J = 3.3 Hz, 1H), 7.74 (d, J = 3.3 Hz, 1H), 7.48-7.33 (m, 2H), 7.25 (ddd, J = 1.6, 7.3, 9.1 Hz, 2H), 6.22 (s, 1H), 4.46 (d, J = 1.8 Hz, 1H), 3.96 (d, J = 17.8 Hz, 1H), 3.60 (s, 3H), 3.42-3.38 (m, 1H), 3.37 (br. s., 2H), 2.82-2.63 (m, 1H), 2.48-2.21 (m, 4H), 2.09-1.98 (m, 1H), 1.89-1.59 (m, 3H). | LC/MS: calc'd 551 (MH$^+$), exp 551(MH$^+$) |
| 92 | $^1$H NMR (400 MHz, METHANOL-d4) 8.01-7.90 (m, 1H), 7.78-7.70 (m, 1H), 7.60 (d, J = 8.0 Hz, 1H), 7.45-7.37 (m, 1H), 7.32 (s, 1H), 7.21-7.07 (m, 1H), 6.19 (s, 1H), 4.25 (s, 2H), 4.04 (q, J = 7.0 Hz, 2H), 3.55-3.47 (m, 1H), 3.30 (br. s., 1H), 2.71 (d, J = 5.0 Hz, 1H), 2.48-2.22 (m, 4H), 1.96 (br. s., 1H), 1.86-1.61 (m, 3H), 1.15 (t, J = 7.0 Hz, 3H). | LC/MS: calc'd 609 (MH$^+$), exp 609 (MH$^+$) |
| 93 | $^1$H NMR (400 MHz, METHANOL-d4) 7.96 (d, J = 3.3 Hz, 1H), 7.73 (d, J = 3.0 Hz, 1H), 7.60 (dd, J = 1.1, 7.9 Hz, 1H), 7.41 (dd, J = 1.8, 7.8 Hz, 1H), 7.32 (dt, J = 1.0, 7.5 Hz, 1H), 7.15 (dt, J = 1.8, 7.7 Hz, 1H), 6.20 (s, 1H), 4.49 (dd, J = 1.6, 17.7 Hz, 1H), 4.11-3.90 (m, 3H), 3.39 (d, J = 8.3 Hz, 2H), 2.71 (s, 1H), 2.48-2.17 (m, 4H), 2.04 (d, J = 13.6 Hz, 1H), 1.89-1.73 (m, 2H), 1.66 (t, J = 12.7 Hz, 1H), 1.15 (t, J = 7.2 Hz, 3H). | LC/MS: calc'd 609 (MH$^+$), exp 609 (MH$^+$) |
| 94 | $^1$H NMR (400 MHz, METHANOL-d4) 8.02-7.93 (m, 1H), 7.79-7.69 (m, 1H), 7.41-7.28 (m, 1H), 7.27-7.18 (m, 1H), 7.15-7.03 (m, 1H), 6.22 (s, 1H), 4.25 (s, 2H), 3.60 (s, 3H), 3.51-3.42 (m, 1H), 3.31-3.22 (m, 1H), 2.85-2.66 (m, 1H), 2.49-2.18 (m, 4H), 2.05-1.91 (m, 1H), 1.85-1.61 (m, 3H). | LC/MS: calc'd 613 (MH$^+$), exp 613 (MH$^+$) |
| 95 | $^1$H NMR (400 MHz, METHANOL-d4) 8.02-7.90 (m, 1H), 7.81-7.64 (m, 1H), 7.39-7.27 (m, 1H), 7.26-7.18 (m, 1H), 7.15-7.04 (m, 1H), 6.28-6.16 (m, 1H), 4.57-4.41 (m, 1H), 4.04- | LC/MS: calc'd 613 (MH$^+$), exp 613 (MH$^+$) |

TABLE 1-continued

NMR and MS data of particular compounds

| Example No. | ¹H NMR data | MW data |
|---|---|---|
| | 3.90 (m, 1H), 3.60 (s, 3H), 3.44-3.34 (m, 2H), 2.79-2.63 (m, 1H), 2.28 (s, 4H), 2.08-1.96 (m, 1H), 1.87-1.58 (m, 3H). | |
| 96 | ¹H NMR (400 MHz, METHANOL-d4) 8.07-7.98 (m, 1H), 7.83-7.74 (m, 1H), 7.52-7.37 (m, 1H), 7.26-7.13 (m, 2H), 5.74 (s, 1H), 4.33-4.06 (m, 2H), 3.70 (s, 3H), 3.46-3.37 (m, 1H), 3.29-3.20 (m, 1H), 2.82-2.62 (m, 1H), 2.46-2.15 (m, 4H), 2.02-1.89 (m, 1H), 1.85-1.57 (m, 3H). | LC/MS: calc'd 569 (MH⁺), exp 569 (MH⁺) |
| 97 | ¹H NMR (400 MHz, METHANOL-d4) 8.13-7.94 (m, 1H), 7.85-7.74 (m, 1H), 7.48-7.35 (m, 1H), 7.30-7.08 (m, 2H), 5.79-5.67 (m, 1H), 4.57-4.41 (m, 1H), 3.99-3.84 (m, 1H), 3.70 (s, 3H), 3.39-3.34 (m, 1H), 3.32-3.26 (m, 1H), 2.80-2.60 (m, 1H), 2.48-2.16 (m, 4H), 2.07-1.94 (m, 1H), 1.88-1.54 (m, 3H). | LC/MS: calc'd 569 (MH⁺), exp 569 (MH⁺) |
| 98 | ¹H NMR (400 MHz, METHANOL-d4) 7.98 (d, J = 3.3 Hz, 1H), 7.75 (d, J = 3.3 Hz, 1H), 7.36-7.21 (m, 2H), 7.19-7.10 (m, 1H), 6.27-6.16 (m, 1H), 4.24 (d, J = 4.3 Hz, 2H), 4.12-3.99 (m, 2H), 3.47 (d, J = 6.5 Hz, 1H), 3.30 (d, J = 12.8 Hz, 1H), 2.84-2.62 (m, 1H), 2.48-2.16 (m, 4H), 2.03-1.91 (m, 1H), 1.86-1.60 (m, 3H), 1.15 (t, J = 7.0 Hz, 3H). | LC/MS: calc'd 583 (MH⁺), exp 583 (MH⁺) |
| 99 | ¹H NMR (400 MHz, METHANOL-d4) 8.06-7.89 (m, 1H), 7.80-7.67 (m, 1H), 7.35-7.20 (m, 2H), 7.19-7.05 (m, 1H), 6.29-6.13 (m, 1H), 4.56-4.38 (m, 1H), 4.13-4.00 (m, 2H), 4.00-3.89 (m, 1H), 3.34 (s, 2H), 2.79-2.61 (m, 1H), 2.51-2.17 (m, 4H), 2.11-1.98 (m, 1H), 1.88-1.57 (m, 3H), 1.15 (t, J = 7.2 Hz, 3H). | LC/MS: calc'd 583 (MH⁺), exp 583 (MH⁺) |
| 100 | ¹H NMR (400 MHz, METHANOL-d4) 7.97-7.89 (m, 1H), 7.81-7.75 (m, 1H), 7.27-7.19 (m, 2H), 7.16-7.05 (m, 1H), 6.19-6.12 (m, 1H), 4.98-4.91 (m, 1H), 4.89-4.83 (m, 1H), 4.50 (s, 1H), 4.14-4.02 (m, 2H), 3.93-3.85 (m, 1H), 3.70-3.62 (m, 1H), 3.60-3.56 (m, 1H), 3.44-3.38 (m, 1H), 2.85-2.75 (m, 2H), 2.75-2.62 (m, 2H), 2.60-2.49 (m, 1H), 1.71-1.58 (m, 1H). | LC/MS: calc'd 567 (MH⁺), exp 567 (MH⁺) |
| 101 | ¹H NMR (400 MHz, METHANOL-d4) 7.92 (s, 1H), 7.79 (d, J = 3.0 Hz, 1H), 7.23 (s, 2H), 7.16-7.03 (m, 1H), 6.16 (s, 1H), 4.93-4.85 (m, 1H), 4.64-4.52 (m, 1H), 4.15-3.99 (m, 2H), 3.95-3.83 (m, 1H), 3.66-3.59 (m, 1H), 3.54 (s, 3H), 3.42-3.32 (m, 1H), 2.87-2.69 (m, 2H), 2.69-2.59 (m, 1H), 2.59-2.45 (m, 1H), 1.73-1.56 (m, 1H), 1.35-1.05 (m, 1H). | LC/MS: calc'd 567 (MH⁺), exp 567 (MH⁺) |
| 102 | ¹H NMR (400 MHz, METHANOL-d4) 8.07-7.96 (m, 1H), 7.79-7.66 (m, 1H), 7.48-7.34 (m, 2H), 7.32-7.14 (m, 2H), 6.30-6.14 (m, 1H), 4.78-4.70 (m, 1H), 4.64-4.54 (m, 1H), 4.40-4.24 (m, 1H), 4.15-3.81 (m, 4H), 3.81-3.70 (m, 1H), 3.51-3.42 (m, 1H), 3.12-2.98 (m, 1H), 2.96-2.73 (m, 3H), 2.64-2.50 (m, 1H), 2.49-2.39 (m, 1H), 1.52-1.37 (m, 1H), 1.17 (t, J = 7.2 Hz, 3H). | LC/MS: calc'd 563(MH⁺), exp 563(MH⁺) |
| 103 | ¹H NMR (400 MHz, METHANOL-d4) 8.02-7.90 (m, 1H), 7.73 (d, J = 3.3 Hz, 1H), 7.42 (ddd, J = 1.6, 5.1, 7.3 Hz, 2H), 7.33-7.14 (m, 2H), 6.22 (s, 1H), 4.75-4.67 (m, 1H), 4.65 (s, 1H), 4.59 (s, 2H), 4.57 (s, 1H), 4.23 (d, J = 17.6 Hz, 1H), 4.13-3.93 (m, 4H), 3.78 (d, J = 11.3 Hz, 1H), 3.49 (d, J = 11.0 Hz, 1H), 3.11-2.96 (m, 1H), 2.91 (d, J = 8.8 Hz, 1H), 2.87-2.73 (m, 2H), 2.62-2.39 (m, 2H), 1.49-1.35 (m, 1H), 1.16 (t, J = 7.2 Hz, 3H). | LC/MS: calc'd 563(MH⁺), exp 563(MH⁺) |
| 104 | ¹H NMR (CD₃OD, 400 MHz): ppm 8.51 (s, 0.5H), 8.45 (s, 0.5H), 7.99 (t, J = 3.2 Hz, 1H), 7.78 (m, 1H), 7.42 (m, 1 H), 7.25 (dd, J = 8.8, 2.4 Hz, 1 H), 7.05 (m, 1H), 6.17 (s, 0.5H), 6.16 (s, 0.5H), 4.15 (m, 3H), 3.95 (m, 3H), 3.70 (m, 1H), 3.54 (s, 1.5H), 3.52 (s, 1.5H), 3.32 (m, 1H), 3.27 (m, 1H), 2.90 (m, 1H). | LC/MS: calc'd 530 (MH⁺), exp 530 (MH⁺) |
| 105 | ¹H NMR (400 MHz, METHANOL-d4) 8.35 (s, 0.5H), 8.29 (s, 0.5H), 8.00 (t, J = 3.2 Hz, 1H), 7.78 (dd, J = 2.4, 3.0 Hz, 1H), 7.45-7.41 (m, 1H), 7.24 (dd, J = 2.4, 8.7 Hz, 1H), 7.09-7.02 (m, 1H), 6.17 (s, 0.5H), 6.16 (s, 0.5H), 4.20-3.75 (m, 6H), 3.71-3.58 (m, 1H), 3.54 (s, 1.5H), 3.52 (s, 1.5H), 3.32-3.18 (m, 2H), 2.93-2.76 (m, 1H). | LC/MS: calc'd 530 (MH⁺), exp 530 (MH⁺) |
| 106 | ¹H NMR (400 MHz, METHANOL-d4) 8.50 (s, 0.6H), 8.44 (s, 0.4H), 8.06-7.91 (m, 1H), 7.78 (dd, J = 1.8, 3.0 Hz, 1H), 7.52-7.35 (m, 1H), 7.24 (dd, J = 2.5, 8.8 Hz, 1H), 7.13-6.97 (m, 1H), 6.18 (br, 1H), 5.86-5.59 (m, 1H), 4.51-4.20 (m, 1H), 4.16-3.85 (m, 5H), 3.75-3.41 (m, 5H). | LC/MS: calc'd 548 (MH⁺), exp 548 (MH⁺) |
| 107 | ¹H NMR (400 MHz, METHANOL-d4): 8.15 (dd, J = 1.5, 3.0 Hz, 1H), 8.03 (dd, J = 3.0, 6.8 Hz, 1H), 7.63 (d, J = 18.6 Hz, 1H), 7.55-7.52 (m, 1H), 7.35-7.26 (m, 1H), 7.20-7.07 (m, 1H), 6.26 (s, 0.5H), 6.25 (s, 0.5H), 4.46 (dd, J = 2.1, 17.4 Hz, 1H), 4.35-4.00 (m, 4H), 3.99-3.91 (m, 1H), 3.73-3.59 (m, 1H), 3.55 (s, 1.5H), 3.52 (s, 1.5H), 3.49-3.37 (m, 1H). | LC/MS: calc'd 565 (MH⁺), exp 565 (MH⁺) |

TABLE 1-continued

NMR and MS data of particular compounds

| Example No. | $^1$H NMR data | MW data |
|---|---|---|
| 108 | $^1$H NMR (400 MHz, METHANOL-d4): 8.11 (dd, J = 1.1, 3.1 Hz, 1H), 8.02-7.94 (m, 1H), 7.56-7.53 (m, 1H), 7.31 (dd, J = 2.6, 8.7 Hz, 1H), 7.21-7.07 (m, 1H), 6.25 (s, 1H), 4.47-4.26 (m, 2H), 4.18-3.91 (m, 3H), 3.80-3.61 (m, 5H), 3.59-3.43 (m, 1H), 2.91-2.73 (m, 1H), 2.60-2.41 (m, 1H). | LC/MS: calc'd 513 (MH$^+$), exp 513 (MH$^+$) |
| 109 | $^1$H NMR (400 MHz, DMSO-d6): 9.87 (s, 1H), 7.96 (dd, J = 3.0, 16.8 Hz, 2H), 7.51-7.34 (m, 2H), 7.18 (dt, J = 2.6, 8.5 Hz, 1H), 6.04 (s, 1H), 4.23 (d, J = 17.3 Hz, 1H), 4.13 (d, J = 17.4 Hz, 1H), 3.51 (s, 3H), 3.50 (br, 1H), 2.79-2.60 (m, 1H), 2.45-2.11 (m, 7H), 1.54 (d, J = 13.8 Hz, 1H), 1.29 (dd, J = 3.5, 14.1 Hz, 1H). | LC/MS: calc'd 569 (MH$^+$), exp 569 (MH$^+$) |
| 110 | $^1$H NMR (400 MHz, METHANOL-d4): 8.03 (d, J = 3.0 Hz, 1H), 7.92 (d, J = 3.0 Hz, 1H), 7.54 (dd, J = 6.0, 8.8 Hz, 1H), 7.30 (dd, J = 2.6, 8.7 Hz, 1H), 7.12 (dt, J = 2.5, 8.4 Hz, 1H), 6.22 (s, 1H), 4.85 (d, J = 17.3 Hz, 1H), 4.50 (d, J = 17.3 Hz, 1H), 4.15 (d, J = 4.8 Hz, 2H), 3.65 (s, 3H), 3.10-2.94 (m, 1H), 2.84-2.56 (m, 6H), 2.07 (d, J = 14.1 Hz, 1H), 1.81 (d, J = 14.6 Hz, 1H). | LC/MS: calc'd 569 (MH$^+$), exp 569 (MH$^+$) |
| 111 | $^1$H NMR (400 MHz, METHANOL-d4): 7.95 (d, J = 3.3 Hz, 1H), 7.74 (d, J = 3.0 Hz, 1H), 7.11-6.95 (m, 2H), 5.93 (s, 1H), 4.28 (d, J = 3.3 Hz, 1H), 3.62 (s, 2H), 3.56-3.48 (m, 1H), 2.86-2.63 (m, 2H), 2.61-2.33 (m, 8H), 2.32-2.20 (m, 2H), 1.76-1.66 (m, 1H), 1.40 (dd, J = 3.5, 14.3 Hz, 1H). | LC/MS: calc'd 567 (MH$^+$), exp 567 (MH$^+$) |
| 112 | $^1$H NMR (400 MHz, METHANOL-d4): 7.95 (d, J = 3.0 Hz, 1H), 7.73 (d, J = 3.3 Hz, 1H), 7.12-6.95 (m, 2H), 5.94 (s, 1H), 4.52 (dd, J = 2.0, 17.8 Hz, 1H), 3.98 (d, J = 17.8 Hz, 1H), 3.62 (s, 3H), 3.41-3.36 (m, 1H), 2.81-2.62 (m, 2H), 2.60-2.29 (m, 7H), 2.28-2.12 (m, 2H), 1.74 (d, J = 10.8 Hz, 1H), 1.34 (dd, J = 3.8, 14.1 Hz, 1H). | LC/MS: calc'd 567 (MH$^+$), exp 567 (MH$^+$) |
| 113 | $^1$H NMR (400 MHz, METHANOL-d4): 8.00 (d, J = 3.3 Hz, 1H), 7.80 (d, J = 3.0 Hz, 1H), 7.44 (t, J = 7.9 Hz, 1H), 7.28-7.14 (m, 2H), 5.74 (s, 1H), 4.35-4.10 (m, 2H), 3.70 (s, 3H), 3.44 (br, 1H), 3.24 (d, J = 11.8 Hz, 1H), 2.84-2.65 (m, 2H), 2.55-2.30 (m, 4H), 2.29-2.16 (m, 1H), 1.69 (d, J = 13.8 Hz, 1H), 1.38 (dd, J = 4.8, 13.8 Hz, 1H). | LC/MS: calc'd 569 (MH$^+$), exp 569 (MH$^+$) |
| 114 | $^1$H NMR (400 MHz, METHANOL-d4): 8.00 (d, J = 3.0 Hz, 1H), 7.81 (d, J = 3.0 Hz, 1H), 7.29-7.08 (m, 3H), 5.73 (s, 1H), 4.31-4.10 (m, 2H), 3.70 (s, 3H), 3.43 (d, J = 6.0 Hz, 1H), 3.28 (d, J = 11.8 Hz, 1H), 2.82-2.64 (m, 1H), 2.48-2.19 (m, 4H), 2.00-1.91 (m, 1H), 1.85-1.61 (m, 3H). | LC/MS: calc'd 553 (MH$^+$), exp 553 (MH$^+$) |
| 115 | $^1$H NMR (400 MHz, METHANOL-d4): 8.02 (d, J = 3.3 Hz, 1H), 7.80 (d, J = 3.0 Hz, 1H), 7.32-7.04 (m, 3H), 5.73 (s, 1H), 4.46 (dd, J = 1.4, 17.7 Hz, 1H), 3.88 (d, J = 17.8 Hz, 1H), 3.70 (s, 3H), 3.29 (br, 2H), 2.76-2.61 (m, 1H), 2.45-2.18 (m, 4H), 2.02 (d, J = 12.8 Hz, 1H), 1.88-1.57 (m, 3H). | LC/MS: calc'd 553 (MH$^+$), exp 553 (MH$^+$) |
| 116 | $^1$H NMR (400 MHz, METHANOL-d4) Shift = 7.98 (d, J = 3.3 Hz, 1H), 7.76 (d, J = 3.0 Hz, 1H), 7.42 (dd, J = 6.1, 8.7 Hz, 1H), 7.24 (dd, J = 2.5, 8.8 Hz, 1H), 7.06 (dt, J = 2.8, 8.4 Hz, 1H), 6.17 (s, 1H), 4.26 (s, 2H), 3.62 (s, 3H), 3.50 (br. s., 1H), 3.27 (d, J = 12.8 Hz, 1H), 2.96-2.85 (m, 1H), 2.69-2.49 (m, 3H), 2.33-2.15 (m, 3H), 1.94 (d, J = 13.3 Hz, 1H). | LC/MS: calc'd 585 (MH$^+$), exp 585 (MH$^+$) |
| 117 | $^1$H NMR (400 MHz, METHANOL-d4) Shift = 7.99 (d, J = 3.3 Hz, 1H), 7.75 (d, J = 3.3 Hz, 1H), 7.42 (dd, J = 6.3, 8.8 Hz, 1H), 7.24 (dd, J = 2.8, 8.8 Hz, 1H), 7.05 (dt, J = 2.8, 8.4 Hz, 1H), 6.18 (s, 1H), 4.53 (dd, J = 2.0, 18.1 Hz, 1H), 3.95 (d, J = 17.8 Hz, 1H), 3.62 (s, 3H), 3.40-3.35 (m, 1H), 3.31-3.23 (m, 1H), 2.95-2.80 (m, 1H), 2.53 (s, 3H), 2.44-2.33 (m, 1H), 2.24 (d, J = 11.0 Hz, 2H), 1.90 (d, J = 13.8 Hz, 1H). | LC/MS: calc'd 585 (MH$^+$), exp 585 (MH$^+$) |
| 118 | $^1$H NMR (400 MHz, METHANOL-d4) 7.95 (d, J = 3.0 Hz, 1H), 7.74 (d, J = 3.3 Hz, 1H), 7.11-6.94 (m, 2H), 5.93 (s, 1H), 4.38-4.16 (m, 2H), 3.63 (s, 3H), 3.50 (br. s., 1H), 3.26 (br. s., 1H), 2.96-2.83 (m, 1H), 2.70-2.52 (m, 6H), 2.37-2.14 (m, 3H), 1.93 (d, J = 14.6 Hz, 1H). | LC/MS: calc'd 583 (MH$^+$), exp 583 (MH$^+$) |
| 119 | $^1$H NMR (400 MHz, METHANOL-d4) ppm 7.95 (d, J = 3.3 Hz, 1H), 7.74 (d, J = 3.3 Hz, 1H), 7.09-6.94 (m, 2H), 5.94 (s, 1H), 4.55 (dd, J = 2.4, 17.9 Hz, 1H), 3.97 (d, J = 18.1 Hz, 1H), 3.63 (s, 3H), 3.41-3.36 (m, 1H), 3.31-3.27 (m, 1H), 2.94-2.79 (m, 1H), 2.57 (d, J = 2.5 Hz, 6H), 2.41 (d, J = 14.8 Hz, 1H), 2.25 (br. s., 2H), 1.89 (d, J = 14.6 Hz, 1H). | LC/MS: calc'd 583 (MH$^+$), exp 583 (MH$^+$) |
| 120 | $^1$H NMR (400 MHz, METHANOL-d4) 7.96 (d, J = 3.0 Hz, 1H), 7.76 (d, J = 3.0 Hz, 1H), 7.36-7.10 (m, 3H), 6.23 (s, 1H), 4.28 (s, 2H), 3.62 (s, 3H), 3.50 (br. s., 1H), 3.27 (br. s., 1H), 2.99-2.83 (m, 1H), 2.65-2.57 (m, 3H), 2.36-2.14 (m, 3H), 1.94 (d, J = 14.1 Hz, 1H). | LC/MS: calc'd 585 (MH$^+$), exp 585 (MH$^+$) |
| 121 | $^1$H NMR (400 MHz, METHANOL-d4) 7.96 (d, J = 3.3 Hz, 1H), 7.75 (d, J = 3.0 Hz, 1H), 7.34-7.11 (m, 3H), 6.24 (s, 1H), 4.54 | LC/MS: calc'd 585 (MH$^+$), exp |

TABLE 1-continued

NMR and MS data of particular compounds

| Example No. | ¹H NMR data | MW data |
|---|---|---|
| | (dd, J = 2.1, 17.9 Hz, 1H), 3.97 (d, J = 17.8 Hz, 1H), 3.61 (s, 3H), 3.43-3.35 (m, 2H), 2.94-2.80 (m, 1H), 2.67-2.46 (m, 3H), 2.40 (dd, J = 2.9, 14.2 Hz, 1H), 2.26 (br. s., 2H), 1.97-1.85 (m, 1H). | 585 (MH$^+$) |
| 122 | ¹H NMR (400 MHz, METHANOL-d4): 7.95 (dd, J = 3.1, 6.1 Hz, 1H), 7.76 (d, J = 2.5 Hz, 1H), 7.48-7.39 (m, 1H), 7.24 (dd, J = 2.3, 8.8 Hz, 1H), 7.06 (t, J = 8.4 Hz, 1H), 6.18 (s, 1H), 4.31-4.18 (m, 1H), 4.12 (d, J = 4.0, 17.6 Hz, 1H), 3.87 (dd, J = 4.5, 17.6 Hz, 1H), 3.77-3.66 (m, 1H), 3.62-3.54 (m, 4H), 3.40 (br. s., 1H), 3.27 (br. s., 1H), 3.08 (t, J = 14.1 Hz, 1H), 2.17-2.03 (m, 5H), 1.83-1.62 (m, 2H). | LC/MS: calc'd 518 (MH$^+$), exp 518 (MH$^+$) |
| 123 | ¹H NMR (400 MHz, METHANOL-d4) 8.03-7.94 (m, 1H), 7.79 (d, J = 2.8 Hz, 1H), 7.49-7.40 (m, 1H), 7.31-7.20 (m, 1H), 7.13-7.01 (m, 1H), 6.17 (s, 1H), 4.85-4.67 (m, 1H), 4.46-4.33 (m, 1H), 4.28-4.11 (m, 2H), 4.05 (br. s., 1H), 3.84 (d, J = 11.0 Hz, 2H), 3.68-3.60 (m, 3H), 3.24-3.11 (m, 1H), 2.98-2.68 (m, 2H), 2.61-2.50 (m, 1H), 2.42-2.26 (m, 1H), 2.25-2.06 (m, 1H), 1.78 (br. s., 1H). | LC/MS: calc'd 565 (MH$^+$), exp 565 (MH$^+$) |
| 124 | ¹H NMR (400 MHz, METHANOL-d4) 7.99 (dd, J = 3.1, 9.2 Hz, 1H), 7.74 (dd, J = 3.3, 5.0 Hz, 1H), 7.43 (ddd, J = 2.8, 6.0, 8.8 Hz, 1H), 7.23 (dd, J = 2.5, 8.8 Hz, 1H), 7.11-6.98 (m, 1H), 6.17 (d, J = 3.5 Hz, 1H), 4.74-4.49 (m, 1H), 4.40-4.17 (m, 1H), 4.05-3.92 (m, 2H), 3.73-3.65 (m, 2H), 3.63 (d, J = 1.5 Hz, 3H), 3.46-3.35 (m, 1H), 2.99-2.83 (m, 2H), 2.76 (br. s., 1H), 2.67-2.43 (m, 1H), 2.36-2.23 (m, 1H), 1.49-1.36 (m, 1H). | LC/MS: calc'd 565 (MH$^+$), exp 565 (MH$^+$) |
| 125 | ¹H NMR (400 MHz, DMSO-d6) 9.77 (br. s., 1H), 8.04 (d, J = 3.1 Hz, 1H), 7.95 (d, J = 3.1 Hz, 1H), 7.48-7.36 (m, 2H), 7.16 (dt, J = 2.6, 8.5 Hz, 1H), 6.04 (s, 1H), 4.55 (dd, J = 2.3, 17.6 Hz, 1H), 4.08 (d, J = 17.4 Hz, 1H), 3.99-3.84 (m, 3H), 3.79 (d, J = 11.2 Hz, 1H), 3.52 (s, 3H), 3.19 (d, J = 10.4 Hz, 2H), 2.71-2.61 (m, 2H), 2.15 (dd, J = 9.4, 15.8 Hz, 1H), 1.99-1.82 (m, 2H). | LC/MS: calc'd 585 (MH$^+$), exp 585 (MH$^+$) |
| 126 | ¹H NMR (400 MHz, CDCl$_3$) 9.80-9.66 (m, 1H), 7.88 (d, J = 3.0 Hz, 1H), 7.48 (d, J = 3.1 Hz, 1H), 7.28-7.23 (m, 1H), 7.15 (dd, J = 2.6, 8.6 Hz, 1H), 6.92 (dt, J = 2.6, 8.3 Hz, 1H), 6.21 (s, 1H), 4.52-4.39 (m, 1H), 4.35-4.26 (m, 1H), 4.16 (d, J = 10.3 Hz, 1H), 4.10-3.97 (m, 2H), 3.93-3.87 (m, 1H), 3.63 (s, 3H), 3.53-3.36 (m, 1H), 3.04-2.83 (m, 2H), 2.71 (br. s., 1H), 2.42 (dd, J = 9.9, 16.3 Hz, 1H), 2.15 (d, J = 7.7 Hz, 2H). | LC/MS: calc'd 585 (MH$^+$), exp 585 (MH$^+$) |
| 127 | ¹H NMR (400 MHz, METHANOL-d4) 7.97 (d, J = 3.3 Hz, 1H), 7.75 (d, J = 3.0 Hz, 1H), 7.12-6.96 (m, 2H), 5.93 (s, 1H), 4.86-4.76 (m, 1H), 4.19-3.99 (m, 6H), 3.87 (d, J = 11.0 Hz, 1H), 3.52-3.37 (m, 1H), 3.07 (d, J = 10.0 Hz, 1H), 2.82 (dd, J = 3.8, 15.8 Hz, 1H), 2.67 (br. s., 1H), 2.57 (d, J = 2.3 Hz, 3H), 2.26 (dd, J = 9.9, 15.9 Hz, 1H), 2.06 (d, J = 7.5 Hz, 2H), 1.18 (t, J = 7.2 Hz, 3H). | LC/MS: calc'd 596 (MH$^+$), exp 596 (MH$^+$) |
| 128 | ¹H NMR (400 MHz, METHANOL-d4) 7.97 (d, J = 3.3 Hz, 1H), 7.75 (d, J = 3.0 Hz, 1H), 7.09-6.98 (m, 2H), 5.93 (s, 1H), 4.54-4.32 (m, 2H), 4.17-4.04 (m, 4H), 4.01-3.81 (m, 2H), 3.51-3.37 (m, 1H), 3.01 (d, J = 10.8 Hz, 1H), 2.88-2.73 (m, 2H), 2.57 (d, J = 2.5 Hz, 3H), 2.30 (dd, J = 9.8, 15.8 Hz, 1H), 2.13 (d, J = 7.5 Hz, 2H), 1.18 (t, J = 7.2 Hz, 3H). | LC/MS: calc'd 596 (MH$^+$), exp 596 (MH$^+$) |
| 129 | ¹H NMR (400 MHz, METHANOL-d4) 7.98 (d, J = 3.0 Hz, 1H), 7.76 (d, J = 3.3 Hz, 1H), 7.27 (d, J = 1.8 Hz, 2H), 7.21-7.10 (m, 1H), 6.24 (s, 1H), 4.86-4.73 (m, 1H), 4.20-4.12 (m, 1H), 4.11-3.99 (m, 5H), 3.88 (d, J = 11.0 Hz, 1H), 3.51-3.37 (m, 1H), 3.12-3.02 (m, 1H), 2.80 (d, J = 3.8 Hz, 1H), 2.70 (br. s., 1H), 2.33-2.20 (m, 1H), 2.06 (d, J = 9.3 Hz, 2H), 1.16 (t, J = 7.0 Hz, 3H). | LC/MS: calc'd 599 (MH$^+$), exp 599 (MH$^+$) |
| 130 | ¹H NMR (400 MHz, METHANOL-d4) 7.98 (d, J = 3.3 Hz, 1H), 7.76 (d, J = 3.3 Hz, 1H), 7.33-7.21 (m, 2H), 7.16 (dd, J = 1.6, 9.2 Hz, 1H), 6.24 (s, 1H), 4.43 (d, J = 8.0 Hz, 2H), 4.16-4.00 (m, 4H), 3.98-3.82 (m, 2H), 3.53-3.36 (m, 1H), 3.02 (d, J = 10.5 Hz, 1H), 2.90-2.75 (m, 2H), 2.31 (dd, J = 9.8, 15.8 Hz, 1H), 2.13 (d, J = 7.0 Hz, 2H), 1.16 (t, J = 7.2 Hz, 3H). | LC/MS: calc'd 599 (MH$^+$), exp 599 (MH$^+$) |
| 131 | ¹H NMR (400 MHz, METHANOL-d4) 7.98 (d, J = 3.0 Hz, 1H), 7.76 (d, J = 3.0 Hz, 1H), 7.27-7.16 (m, 2H), 6.17 (s, 1H), 4.82-4.72 (m, 1H), 4.43 (d, J = 18.6 Hz, 1H), 4.19-3.86 (m, 4H), 3.62 (s, 3H), 3.51-3.37 (m, 1H), 3.10-2.96 (m, 1H), 2.90-2.65 (m, 2H), 2.35-2.20 (m, 1H), 2.17-2.02 (m, 2H). | LC/MS: calc'd 603 (MH$^+$), exp 603 (MH$^+$) |
| 132 | ¹H NMR (400 MHz, METHANOL-d4) 7.96 (d, J = 3.3 Hz, 1H), 7.74 (d, J = 3.3 Hz, 1H), 7.03 (d, J = 6.3 Hz, 2H), 5.93 (s, 1H), 4.55-4.44 (m, 1H), 4.42-4.33 (m, 1H), 4.16-4.01 (m, 2H), 3.89 (s, 2H), 3.63 (s, 3H), 3.51-3.36 (m, 1H), 3.00 (d, J = 10.8 | LC/MS: calc'd 582 (MH$^+$), exp 582 (MH$^+$) |

TABLE 1-continued

NMR and MS data of particular compounds

| Example No. | ¹H NMR data | MW data |
|---|---|---|
| | Hz, 1H), 2.88-2.74 (m, 2H), 2.57 (d, J = 2.3 Hz, 3H), 2.31 (dd, J = 9.8, 15.8 Hz, 1H), 2.13 (d, J = 8.5 Hz, 2H). | |
| 133 | ¹H NMR (METHANOL-d4, 400 MHz): 7.98 (d, 1H), 7.77 (d, 1H), 7.40-7.48 (m, 1H), 7.24 (m, 1H), 7.06 (m, 1H), 6.18 (d, 1H), 4.42-4.53 (m, 1H), 4.10-4.18 (m, 1H), 4.00-4.10 (m, 2H), 3.87-4.00 (m, 3H), 3.65 (d, 3H), 3.41-3.52 (m, 2H), 2.18-2.25 (m, 1H). | LC/MS: exp 506 [M + H]⁺) |
| 134 | ¹H NMR (METHANOL-d4, 400 MHz): 7.93-8.01 (m, 1H), 7.75 (d, 1H), 7.61 (m, 1H), 7.37-7.45 (m, 1H), 7.32 (m, 1H), 7.16 (m, 1H), 6.19 (s, 1H), 4.62 (d, 1H), 4.23 (d, 1H), 3.96-4.09 (m, 2H), 3.62 (s, 3H), 3.56 (d, 2H), 2.90-3.02 (m, 2H), 2.62-2.71 (m, 1H), 2.49-2.54 (m, 2H), 2.38-2.49 (m, 2H), 1.44-1.57 (m, 2H). | LC/MS: calc'd 576 (MH⁺), exp 576(MH⁺) |
| 135 | ¹H NMR (METHANOL-d4, 400 MHz): 8.02 (d, 1H), 7.92 (d, 1H), 7.35-7.44 (m, 1H), 7.30 (m, 1H), 6.21 (s, 1H), 5.03 (d, 1H), 4.71 (d, 1H), 4.14-4.26 (m, 2H), 3.85 (br. s., 1H), 3.76 (d, 1H), 3.71 (br. s., 1H), 3.67 (s, 3H), 2.68 (m, 6H), 1.90 (d, 2H). | LC/MS: calc'd 567 (MH⁺), exp 567(MH⁺) |
| 136 | ¹H NMR (METHANOL-d4, 400 MHz): 8.04 (d, 1H), 7.93 (d, 1H), 7.44-7.54 (m, 1H), 7.16-7.35 (m, 2H), 5.72 (s, 1H), 5.05 (d, 1H), 4.64 (d, 1H), 4.11-4.26 (m, 2H), 3.77-3.92 (m, 1H), 3.67-3.76 (m, 4H), 3.64 (d, 1H), 2.50-2.76 (m, 5H), 1.88 (d, 2H). | LC/MS: calc'd 549 (MH⁺), exp 549(MH⁺) |
| 137 | ¹H NMR (METHANOL-d4, 400 MHz): 7.94-8.03 (m, 1H), 7.76 (d, 1H), 7.38-7.47 (m, 1H), 7.38-7.47 (m, 1H), 7.24 (m, 1H), 7.06 (m, 1H), 6.17 (s, 1H), 4.49-4.63 (m, 1H), 4.22-4.33 (m, 2H), 4.05-4.18 (m, 1H), 3.66-3.80 (m, 2H), 3.63 (s, 3H), 2.91 (br. s., 1H), 2.39 (br. s., 1H), 1.98-2.31 (m, 5H), 1.63 (br. s., 1H), 1.33-1.36 (m, 3H). | LC/MS: calc'd 609 (MH⁺), exp 609 (MH⁺) |
| 138 | ¹H NMR (METHANOL-d4, 400 MHz): 7.93-8.03 (m, 1H), 7.83 (br. s., 1H), 7.44-7.56 (m, 1H), 7.26 (m, 1H), 7.09 (m, 1H), 6.18 (s, 1H), 5.00 (br. s., 1H), 4.61 (br. s., 2H), 4.20 (m, 5H), 3.71-3.86 (m, 1H), 3.65 (s, 3H), 3.52 (m, 1H), 2.83-2.97 (m, 1H), 2.72-2.83 (m, 1H), 2.60-2.72 (m, 1H), 2.00-2.20 (m, 1H), 1.33-1.51 (m, 1H), 1.30 (m, 3H). | LC/MS: calc'd 609 (MH⁺), exp 609(MH⁺) |
| 139 | ¹H NMR (METHANOL-d4, 400 MHz): 7.98 (d, 1H), 7.78 (d, 1H), 7.44 (m, 1H), 7.25 (m, 1H), 7.05 (m, 1H), 6.18 (s, 1H), 4.69 (d, 1H), 4.08-4.26 (m, 3H), 3.87-3.98 (m, 2H), 3.65 (s, 3H), 3.09 (br. s., 1H), 2.94-3.07 (m, 3H), 2.25-2.25 (m, 1H), 2.14-2.25 (m, 1H), 2.00-2.11 (m, 1H). | LC/MS: calc'd 550 (MH⁺), exp 550 (MH⁺) |
| 140 | 1H NMR (METHANOL-d4, 400 MHz): 7.98-8.08 (m, 1H), 7.90 (d, 1H), 7.07-7.27 (m, 3H), 6.10 (s, 1H), 4.69 (d, 1H), 4.19-4.29 (m, 2H), 4.06-4.19 (m, 3H), 3.95 (m, 2H), 3.19 (d, 1H), 3.09-3.17 (m, 1H), 2.99 (m, 2H), 1.92-2.06 (m, 2H), 1.14-1.26 (m, 3H). | LC/MS: calc'd 548 (MH⁺), exp 548(MH⁺) |
| 141 | ¹H NMR (METHANOL-d4, 400 MHz): 8.04 (d, 1H), 7.91 (d, 1H), 7.42-7.56 (m, 2H), 7.14 (m, 1H), 6.23 (s, 1H), 4.71 (d, 1H), 4.18-4.30 (m, 3H), 4.05-4.17 (m, 2H), 3.96 (m, 2H), 3.19-3.26 (m, 1H), 3.15 (d, 1H), 2.94-3.05 (m, 2H), 1.92-2.08 (m, 2H), 1.19 (m, 3H). | LC/MS: calc'd 609 (MH⁺), exp 609(MH⁺) |
| 142 | 1H NMR (METHANOL-d4, 400 MHz): 7.95(d, J = 4.0 Hz, 1 H), 7.77 (d, J = 4.0 Hz, 1H), 7.42 (m, 1 H), 7.25 (m, 1H), 7.08 (m, 1 H), 6.16 (s, 1 H), 4.32~4.39 (m, 2H), 4.03-3.98 (d, J = 3H, 1H), 3.84-3.80 (d, J = 16 Hz, 1H), 3.60 (s, 3H), 2.80-2.28 (m, 6 H), 2.00(m, 2H). | LC/MS: calc'd 477 (MH⁺), exp 477 (MH⁺) |
| 143 | ¹H NMR (METHANOL-d4, 400 MHz): 7.93(d, J = 4.0 Hz, 1 H, 7.74 (d, J = 4.0 Hz, 1H), 7.43 (m, 1 H), 7.25 (m, 1H), 7.08 (m, 1 H), 6.17 (s, 1 H), 4.47~4.36 (m, 1H), 4.18~4.11 (m, 1H), 3.61 (s, 3H), 3.37 (m, 1H), 3.0 (m, 1 H), 2.74-2.61 (m, 2H), 2.10 (m, 1H), 1.92~1.80(m, 3H). | LC/MS: calc'd 497 (MH⁺), exp 497 (MH⁺) |
| 144 | ¹H NMR (METHANOL-d4, 400 MHz): 7.94(d, J = 4.0 Hz, 1 H), 7.76 (d, J = 4.0 Hz, 1H), 7.42 (m, 1 H), 7.25 (m, 1H), 7.08 (m, 1 H), 6.15 (s, 1 H), 4.37-3.94 (m, 2H), 3.61 (s, 3H), 3.34 (m, 1H), 3.09~2.75 (m, 3 H), 2.36 (m, 1H), 2.04~1.92(m, 3H). | LC/MS: calc'd 497 (MH⁺), exp 497 (MH⁺) |
| 145 | ¹H NMR (METHANOL-d4, 400 MHz): 7.94(d, J = 4.0 Hz, 1 H), 7.75 (d, J = 4.0 Hz, 1H), 7.42 (m, 1 H), 7.25 (m, 1H), 7.08 (m, 1 H), 6.15 (s, 1 H), 4.30-4.14 (m, 3H), 3.87-3.85 (m, 3H), 3.65-3.55 (m, 6H), 3.06-3.04 (d, J = 8 Hz, 1H), 2.75-2.72 (d, J = 12 Hz, 1 H), 2.05-2.03(d, J = 8 Hz, 1H), 1.99 (s, 3H), 1.79-1.76(d, J = 12 Hz, 1H), 1.29 (m, 1H). | LC/MS: calc'd 534 (MH⁺), exp 534 (MH⁺) |
| 146 | ¹H NMR (METHANOL-d4, 400 MHz): 7.99 (d, J = 4.0 Hz, 1 H), 7.77 (d, J = 4.0 Hz, 1H), 7.42 (m, 1 H), 7.24 (m, 1H), 7.04 (m, 1 H), 6.17 (s, 1 H), 4.53~4.49 (d, J = 16 Hz, 1H), 4.25~4.20 (m, 2H), 4.17~4.14 (m, 2H), 4.06~4.02 (d, J = 16 Hz, 1H), 4.00~3.93 (m, 2H), 3.65 (s, 3 H), 3.12 (s, 2H), 3.08 (s, 3H), 2.90 (m, 2H), 2.50 (m, 2H), 2.18~2.15 (t, J1 = 16 Hz, J2 = 28 Hz, 2H), 1.31 (t, J1 = 8 Hz, J2 = 16 Hz, 3H). | LC/MS: calc'd 670 (MH⁺), exp 670 (MH⁺) |

TABLE 1-continued

NMR and MS data of particular compounds

| Example No. | $^1$H NMR data | MW data |
|---|---|---|
| 147 | $^1$H NMR (METHANOL-d4, 400 MHz): 7.99 (d, J = 4.0 Hz, 1 H), 7.77 (d, J = 4.0 Hz, 1H), 7.42 (m, 1 H), 7.24 (m, 1H), 7.04 (m, 1 H), 6.17 (s, 1 H), 4.52~4.57 (d, J = 16 Hz, 1H), 4.19~4.10 (m, 2H), 4.08~4.03 (m, 2H), 3.85~3.80 (m, 2H), 3.83 (s, 3 H), 3.16 (s, 2H), 3.08 (s, 3H), 2.80 (m, 2H), 2.46 (m, 2H), 2.32 (m, 2H), 1.28 (t, J1 = 4 Hz, J2 = 12 Hz, 3H). | LC/MS: calc'd 688 (MH$^+$), exp 688 (MH$^+$) |
| 148 | $^1$H NMR (METHANOL-d4, 400 MHz): 8.09(d, J = 4.0 Hz, 1 H), 8.06 (d, J = 4.0 Hz, 1H), 7.66 (m, 1 H), 7.30 (m, 1H), 7.10 (m, 1 H), 6.24 (s, 1 H), 4.22 (m, 2H), 3.74 (m, 1H), 3.64 (s, 3H), 2.69-2.60 (m, 1H), 2.33-2.20(m, 2 H), 2.08-2.01(m, 3H). | LC/MS: calc'd 541 (MH$^+$), exp 541 (MH$^+$) |
| 149 | $^1$H NMR (METHANOL-d4, 400 MHz): 8.03(d, J = 4.0 Hz, 1 H), 7.90 (d, J = 4.0 Hz, 1H), 7.55 (m, 1 H), 7.28 (m, 1H), 7.10 (m, 1 H), 6.22 (s, 1 H), 4.29~4.15 (m, 2H), 3.75 (m, 1H), 3.63 (s, 3H), 2.62-2.71 (m, 1H), 2.33-2.15(m, 3 H), 2.07-2.02(m, 2H). | LC/MS: calc'd 541 (MH$^+$), exp 541 (MH$^+$) |
| 150 | $^1$H NMR (400 MHz, METHANOL-d4) d ppm 8.04 (d, J = 3.26 Hz, 1 H), 7.95 (d, J = 3.26 Hz, 1 H), 7.15-7.38 (m, 3 H), 6.29 (s, 1 H), 4.51-4.71 (m, 2 H), 3.92-4.23 (m, 4 H), 3.12 (m, 2 H), 2.21-2.75(m, 4 H), 1.13(m, 3H). | LC/MS: calc'd 569 (MH$^+$), exp 569 (MH$^+$) |
| 151 | $^1$H NMR (METHANOL-d4, 400 MHz): 7.99(d, J = 4.0 Hz, 1 H), 7.82 (d, J = 4.0 Hz, 1H), 7.51 (m, 1 H), 7.27 (m, 1H), 7.11 (m, 1 H), 6.17 (s, 1 H), 4.29~4.33 (m, 1H), 4.04~4.10 (m, 2H), 3.75 (m, 1H), 3.63 (s, 3 H), 2.91(m, 1H), 2.54~2.01 (m, 4H). | LC/MS: calc'd 541 (MH$^+$), exp 541 (MH$^+$) |
| 152 | $^1$H NMR (METHANOL-d4, 400 MHz): 7.95(d, J = 4.0 Hz, 1 H), 7.78 (d, J = 4.0 Hz, 1H), 7.49 (m, 1 H), 7.27 (m, 1H), 7.08 (m, 1 H), 6.18 (s, 1 H), 4.35~4.01 (m, 2H), 4.04~4.10 (m, 2H), 3.86 (m, 1H), 3.61 (s, 3 H), 3.40(m, 1H), 2.40~2.01 (m, 5H). | LC/MS: calc'd 541 (MH$^+$), exp 541 (MH$^+$) |

TABLE 2

Anti-HBV activity data of particular compounds in HepG2.2.15 cells

| Example No. | EC$_{50}$ (μM) | Example No. | EC$_{50}$ (μM) | Example No. | EC$_{50}$ (μM) |
|---|---|---|---|---|---|
| 1 | 0.059 | 2 | 0.1143 | 3 | 0.4002 |
| 4 | 0.039 | 5 | 0.021 | 6 | 0.032 |
| 7 | 0.012 | 9 | 0.014 | 10 | 0.0088 |
| 11 | 0.0066 | 12 | 0.566 | 13 | 0.27 |
| 14 | 0.013 | 15 | 0.043 | 16 | 0.015 |
| 17 | 0.004 | 18 | 0.020 | 19 | 0.004 |
| 20 | 0.035 | 21 | 0.020 | 23 | 0.3675 |
| 24 | 0.013 | 25 | 0.0145 | 26 | 0.013 |
| 27 | 0.2541 | 28 | 0.015 | 29 | 0.0343 |
| 30 | 0.011 | 31 | 0.035 | 32 | 0.032 |
| 33 | 0.011 | 34 | 0.042 | 35 | 0.006 |
| 36 | 0.003 | 38 | 0.1145 | 39 | 0.032 |
| 40 | 0.032 | 41 | 0.1326 | 42 | 0.0545 |
| 43 | 0.003 | 45 | 0.0005 | 46 | 0.0866 |
| 47 | 0.2952 | 48 | 0.0194 | 49 | 0.0172 |
| 50 | 0.0241 | 51 | 0.0149 | 52 | 0.0179 |
| 53 | 0.0168 | 54 | 0.0082 | 55 | 0.0223 |
| 56 | 0.0044 | 57 | 0.0219 | 58 | 0.0114 |
| 59 | 0.0156 | 60 | 0.0016 | 61 | 0.0048 |
| 62 | 0.007 | 63 | 0.0015 | 64 | 0.0166 |
| 65 | 0.0118 | 66 | 0.0036 | 67 | 0.004 |
| 68 | 0.0038 | 69 | 0.0031 | 70 | 0.0082 |
| 71 | 0.003 | 72 | 0.0132 | 73 | 0.003 |
| 74 | 0.0109 | 75 | 0.0291 | 76 | 0.031 |
| 77 | 0.014 | 78 | 0.002 | 79 | 0.2933 |
| 80 | 0.0017 | 81 | 0.0405 | 82 | 0.0131 |
| 83 | 0.0086 | 84 | 0.0376 | 85 | 0.0066 |
| 86 | 0.002 | 87 | 0.0394 | 88 | 0.0013 |
| 89 | 0.0305 | 90 | 0.0035 | 91 | 0.0907 |
| 92 | 0.0015 | 93 | 0.0289 | 94 | 0.0217 |
| 95 | 0.0311 | 96 | 0.0068 | 97 | 0.1558 |
| 98 | 0.0007 | 99 | 0.0126 | 100 | 0.2829 |
| 101 | 0.024 | 102 | 0.066 | 103 | 0.2738 |
| 104 | 0.0048 | 105 | 0.0027 | 106 | 0.0085 |
| 107 | 0.0021 | 108 | 0.0074 | 109 | 0.0017 |
| 110 | 0.0443 | 111 | 0.0012 | 112 | 0.0358 |
| 113 | 0.0091 | 114 | 0.0063 | 115 | 0.1627 |
| 116 | 0.0073 | 117 | 0.0402 | 118 | 0.005 |
| 119 | 0.0213 | 120 | 0.0096 | 121 | 0.033 |
| 122 | 0.0774 | 123 | 0.0357 | 124 | 0.2956 |
| 125 | 0.0261 | 126 | 0.0103 | 127 | 0.0161 |
| 128 | 0.0025 | 129 | 0.021 | 130 | 0.0064 |
| 131 | 0.0057 | 132 | 0.0103 | 133 | 0.034 |
| 134 | 0.021 | 135 | 0.0065 | 136 | 0.102 |
| 137 | 0.0032 | 138 | 0.0582 | 139 | 0.172 |
| 140 | 0.103 | 141 | 0.271 | 142 | 0.13 |
| 143 | 0.041 | 144 | 0.094 | 145 | 0.017 |
| 146 | 0.0005 | 147 | 0.0009 | 148 | 0.0592 |
| 149 | 0.004 | 150 | 0.0077 | 151 | 0.0295 |
| 152 | 0.0177 | | | | |

More particular compounds of formula I include the following:

9-[[(4R)-4-(2-chloro-4-fluoro-phenyl)-5-methoxycarbonyl-2-thiazol-2-yl-1,4-dihydropyrimidin-6-yl]methyl]-3-oxa-9-azabicyclo[3.3.1]nonane-7-carboxylic acid;

8-[(R)-6-(2-Chloro-4-fluoro-phenyl)-5-methoxycarbonyl-2-thiazol-2-yl-3,6-dihydro-pyrimidin-4-ylmethyl]-3-oxa-8-aza-bicyclo[3.2.1]octane-6-carboxylic acid;

(R)-6-(7-Carbamoyl-3-oxa-7,9-diaza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-4-(2-Chloro-4-fluoro-phenyl)-6-(7-sulfamoyl-3-oxa-7,9-diaza-bicyclo[3.3.1]non-9-ylmethyl)-2-thiazol-2-yl-1,4-dihydro-pyrimidine-5-carboxylic acid methyl ester;

(R)-4-(2-Chloro-4-fluoro-phenyl)-6-[7-(2-hydroxy-acetyl)-3-oxa-7,9-diaza-bicyclo[3.3.1]non-9-ylmethyl]-2-thiazol-2-yl-1,4-dihydro-pyrimidine-5-carboxylic acid methyl ester;

(R)-6-(7-Carboxymethyl-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-6-(7-Carboxymethyl-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid ethyl ester;

(R)-4-(2-Bromo-4-fluoro-phenyl)-6-(7-carboxymethyl-3-oxa-9-aza-bicyclo[3.3.1]non-9-ylmethyl)-2-thiazol-2-yl-1,4-dihydro-pyrimidine-5-carboxylic acid methyl ester;

(R)-4-(2-Chloro-4-fluoro-phenyl)-6-(10-oxa-4,5,12-triazatricyclo[6.3.1.0*2,6*]dodeca-2(6),3-dien-12-ylmethyl)-2-thiazol-2-yl-1,4-dihydro-pyrimidine-5-carboxylic acid methyl ester;

(R)-4-(2-Chloro-4-fluoro-phenyl)-6-(4-oxo-8-oxa-3,10-diaza-bicyclo[4.3.1]dec-10-ylmethyl)-2-thiazol-2-yl-1,4-dihydro-pyrimidine-5-carboxylic acid methyl ester;

(R)-6-(7-Acetylamino-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-4-(2-Chloro-4-fluoro-phenyl)-6-(7-methanesulfonylamino-3-oxa-9-aza-bicyclo[3.3.1]non-9-ylmethyl)-2-thiazol-2-yl-1,4-dihydro-pyrimidine-5-carboxylic acid methyl ester;

2-[(R)-6-(2-Chloro-4-fluoro-phenyl)-5-methoxycarbonyl-2-thiazol-2-yl-3,6-dihydro-pyrimidin-4-ylmethyl]-4-fluoro-2-aza-bicyclo[2.1.1]hexane-1-carboxylic acid;

6-(7-Carboxymethyl-3-thia-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-4-(2-Chloro-4-fluoro-phenyl)-6-(9-oxa-3,4,11-triazatricyclo[5.3.1.0*2,6*]undeca-2(6),4-dien-11-ylmethyl)-2-thiazol-2-yl-1,4-dihydro-pyrimidine-5-carboxylic acid methyl ester;

2-[[(1R,5S)-9-[[(4R)-4-(2-chloro-4-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]oxy]acetic acid;

2-[[8-[[(4R)-4-(2-bromo-4-fluoro-phenyl)-5-ethoxycarbonyl-2-thiazol-2-yl-1,4-dihydropyrimidin-6-yl]methyl]-3-oxa-8-azabicyclo[3.2.1]octan-6-yl]oxy]acetic acid;

8-[[(4R)-4-(2-bromo-4-fluoro-phenyl)-5-ethoxycarbonyl-2-thiazol-2-yl-1,4-dihydropyrimidin-6-yl]methyl]-3-oxa-8-azabicyclo[3.2.1]octane-6-carboxylic acid;

Methyl (4R)-4-(2-bromo-4-fluoro-phenyl)-6-[(7-carbamoyl-3-oxa-7,9-diazabicyclo[3.3.1]nonan-9-yl)methyl]-2-thiazol-2-yl-1,4-dihydropyrimidine-5-carboxylate;

Methyl (4R)-4-(2-chloro-4-fluoro-phenyl)-6-[[(1R,5S)-7-endo-(sulfamoylamino)-3-oxa-9-azabicyclo[3.3.1]nonan-9-yl]methyl]-2-thiazol-2-yl-1,4-dihydropyrimidine-5-carboxylate;

Methyl (4R)-4-(2-chloro-4-fluoro-phenyl)-6-[[(1R,5S)-7-exo-(methanesulfonamido)-3-oxa-9-azabicyclo[3.3.1]nonan-9-yl]methyl]-2-thiazol-2-yl-1,4-dihydropyrimidine-5-carboxylate;

2-[(1R,5S,6S)-8-[[(4R)-4-(2-bromo-4-fluoro-phenyl)-5-methoxycarbonyl-2-thiazol-2-yl-1,4-dihydropyrimidin-6-yl]methyl]-3-oxa-8-azabicyclo[3.2.1]octan-6-yl]acetic acid;

Exo-2-[(1S,5R)-9-[[(4R)-4-(2-chloro-3-fluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4S)-4-(3,4-difluoro-2-methyl-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

(1S,5R)-8-[[(4R)-4-(2-chloro-4-fluoro-phenyl)-5-methoxycarbonyl-2-thiazol-2-yl-1,4-dihydropyrimidin-6-yl]methyl]-3-oxa-8-azabicyclo[3.2.1]octane-5-carboxylic acid;

(1R,5S)-8-[[(4R)-4-(2-chloro-4-fluoro-phenyl)-5-methoxycarbonyl-2-thiazol-2-yl-1,4-dihydropyrimidin-6-yl]methyl]-3-oxa-8-azabicyclo[3.2.1]octane-5-carboxylic acid;

2-[(1R,3S,5S)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4R)-4-(2-chloro-3-fluoro-phenyl)-5-ethoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-chloro-3-fluoro-phenyl)-5-ethoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3R,5S)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3S,5R)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4S)-4-(3,4-difluorophenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4S)-4-(3,4-difluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(3R)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3S)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3R)-8-[[(4R)-4-(3,4-difluoro-2-methyl-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3S)-8-[[(4S)-4-(3,4-difluoro-2-methyl-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(7R)-9-[[(4R)-4-(2-chloro-4-fluoro-phenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

2-[(7S)-9-[[(4R)-4-(2-chloro-4-fluoro-phenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

Methyl (4R)-4-(2-chloro-4-fluoro-phenyl)-6-[[7-(2-ethoxy-2-oxo-ethyl)-7-(methanesulfonamido)-3-oxa-9-azabicyclo[3.3.1]nonan-9-yl]methyl]-2-thiazol-2-yl-1,4-dihydropyrimidine-5-carboxylate;

(1S,4R)-7-[[(4R)-4-(2-chloro-4-fluoro-phenyl)-5-methoxycarbonyl-2-thiazol-2-yl-1,4-dihydropyrimidin-6-yl]methyl]-2,2-difluoro-7-azabicyclo[2.2.1]heptane-4-carboxylic acid;

(1R,4S)-7-[[(4R)-4-(2-chloro-4-fluoro-phenyl)-5-methoxycarbonyl-2-thiazol-2-yl-1,4-dihydropyrimidin-6-yl]methyl]-2,2-difluoro-7-azabicyclo[2.2.1]heptane-4-carboxylic acid;

8-[[(4R)-4-(2-chloro-3-fluoro-phenyl)-5-ethoxycarbonyl-2-thiazol-2-yl-1,4-dihydropyrimidin-6-yl]methyl]-6,6-difluoro-8-azabicyclo[3.2.1]octane-3-carboxylic acid;

2-[(7R)-9-[[(4R)-4-(2-chloro-3-fluoro-phenyl)-5-ethoxycarbonyl-2-thiazol-2-yl-1,4-dihydropyrimidin-6-yl]methyl]-6,6-difluoro-3-oxa-9-azabicyclo[3.3.1]nonan-7-yl]acetic acid; and 2-[(7S)-9-[[(4R)-4-(2-chloro-3-fluoro-phenyl)-5-ethoxycarbonyl-2-thiazol-2-yl-1,4-dihydropyrimidin-6-yl]methyl]-6,6-difluoro-3-oxa-9-azabicyclo[3.3.1]nonan-7-yl]acetic acid.

Compound with favorable pharmacokinetics is more likely to be efficacious and safe. It is very important for a drug to have a moderate or low clearance and a reasonable half-life, as this often leads to a good oral bioavailability and high systemic exposure. Reducing the clearance of a compound or drug could reduce the daily dose required for efficacy and therefore give a better efficacy and safety profile. As shown in Table 3, compounds of the present invention show low human microsomal clearance.

Results of human microsomal clearance data of particular compounds are given in Table 3.

TABLE 3

Human microsomal clearance data of particular compounds

| Example No. | CLh (mL/min/Kg) | Example No. | CLh (mL/min/Kg) | Example No. | CLh (mL/min/Kg) |
|---|---|---|---|---|---|
| 1 | 3.0 | 2 | 3.2 | 3 | 0 |
| 5 | 0 | 6 | 0.5 | 8 | 0 |
| 11 | 9.0 | 18 | 1.3 | 19 | 4.6 |
| 21 | 4.3 | 23 | 7.1 | 24 | 2.6 |
| 26 | 3.5 | 28 | 0.6 | 29 | 1.7 |
| 35 | 6.4 | 36 | 7.8 | 39 | 7.4 |
| 40 | 1.4 | 44 | 7.1 | 46 | 4.0 |
| 48 | 4.8 | 50 | 1.4 | 52 | 2.7 |
| 53 | 7.0 | 54 | 6.5 | 55 | 0 |
| 56 | 6.1 | 57 | 5.0 | 58 | 2.1 |
| 59 | 2.1 | 60 | 6.4 | 61 | 6.3 |
| 62 | 4.6 | 63 | 4.1 | 64 | 2.6 |
| 65 | 2.8 | 66 | 3.2 | 67 | 2.9 |
| 68 | 3.5 | 69 | 2.4 | 72 | 2.8 |
| 73 | 3.6 | 74 | 0.5 | 75 | 1.0 |
| 76 | 3.3 | 77 | 1.3 | 78 | 1.9 |
| 79 | 3.5 | 80 | 4.6 | 81 | 0 |
| 82 | 0 | 83 | 1.6 | 84 | 0 |
| 85 | 1.3 | 86 | 0 | 87 | 0 |
| 88 | 0.2 | 89 | 0 | 90 | 1.5 |
| 91 | 5.1 | 92 | 1.7 | 93 | 0.2 |
| 94 | 0 | 95 | 0 | 96 | 1.8 |
| 97 | 0 | 98 | 4.5 | 99 | 3 |
| 100 | 0 | 101 | 0 | 102 | 3.0 |
| 103 | 0 | 109 | 7.2 | 110 | 4.1 |
| 111 | 4.8 | 113 | 6.2 | 114 | 1.2 |
| 115 | 4.6 | 116 | 2.6 | 117 | 1.8 |
| 118 | 3.1 | 120 | 0 | 122 | 7.0 |
| 123 | 3.0 | 124 | 4.2 | 125 | 0 |
| 126 | 0 | 127 | 2.9 | 128 | 3.8 |
| 129 | 2.0 | 130 | 5.0 | 131 | 0 |
| 132 | 2.6 | 134 | 1.7 | 135 | 4.2 |
| 136 | 5.5 | 139 | 5.1 | 148 | 2.3 |
| 149 | 3.4 | 150 | 3.1 | | |

The aqueous solubility is an important physico-chemical property that plays a significant role in various physical and biological processes. It is desirable to have good solubility which enables good permeability and gastric and intestinal absorption, linear dose proportionality, less PK variability, and easy formulation for PD/PK studies. At different stages of the drug discovery/development process solubility has to be determined and especially in the early phases (lead generation to lead optimization) high throughput methods are needed. Lyophilisation solubility assay (Lysa) is a well adopted high throughput assay to measure compound solubility in industry.

Results of Lysa are given in Table 4.

TABLE 4

Solubility data of particular compounds

| Example No. | Lysa (µg/mL) | Example No. | Lysa (µg/mL) | Example No. | Lysa (µg/mL) |
|---|---|---|---|---|---|
| 1 | 540 | 2 | 450 | 3 | >678 |
| 5 | >660 | 6 | >665 | 10 | 435 |
| 12 | >597 | 13 | 313 | 15 | 233 |
| 23 | 573 | 24 | >621 | 26 | 470 |
| 28 | >655 | 29 | >600 | 33 | 100 |
| 34 | 263 | 39 | >610 | 40 | >634 |
| 41 | >552 | 42 | 188 | 44 | >623 |
| 46 | >685 | 48 | 100 | 50 | >724 |
| 52 | >630 | 53 | 163 | 54 | 119 |
| 55 | 505 | 58 | >701 | 59 | >732 |
| 64 | 660 | 65 | 375 | 66 | 390 |
| 67 | 319 | 68 | 320 | 69 | 203 |
| 72 | 640 | 73 | >654 | 74 | >621 |
| 75 | >656 | 76 | >706 | 77 | 491 |
| 78 | 111 | 79 | >745 | 80 | 221 |
| 81 | >673 | 82 | >628 | 83 | 564 |
| 84 | >643 | 85 | >639 | 86 | 149 |
| 88 | 120 | 90 | 230 | 101 | 580 |
| 102 | 410 | 103 | 345 | 109 | 107 |
| 114 | 224 | 115 | 128 | 116 | 495 |
| 118 | 112 | 120 | 317 | 123 | >753 |
| 124 | >753 | 125 | 170 | 126 | >605 |
| 130 | 219 | 131 | 261 | 132 | 330 |
| 134 | >695 | 135 | 533 | 136 | 485 |
| 139 | >610 | 145 | 585 | 148 | >655 |
| 149 | >665 | | | | |

Based on FDA guidance, in order to support clinical testing in humans, the assessment of acceptable risk-benefit has to be achieved by providing clear evidence of in vitro antiviral activity ($EC_{50}$) and cytotoxicity ($CC_{50}$). It is important to establish that an investigational product has antiviral activity at concentrations that can be achieved in vivo without inducing toxic effects to cells. Furthermore, in a cell culture model, apparent antiviral activity of an investigational product can be the result of host cell death after exposure to the product. The relative effectiveness of the compound in inhibiting viral replication compared to inducing cell death is defined as the selectivity index ($CC_{50}$ value/$EC_{50}$ value). It is desirable to have a high selectivity index giving maximum antiviral activity with minimal cell toxicity.

Results of $CC_{50}$ and the corresponding selectivity index are given in Table 5.

TABLE 5

$CC_{50}$ and selectivity index of particular compounds

| Example No. | $CC_{50}$ (μM) | Selectivity index ($CC_{50}/EC_{50}$) | Example No. | $CC_{50}$ (μM) | Selectivity index ($CC_{50}/EC_{50}$) |
|---|---|---|---|---|---|
| 7 | >100 | >8333 | 10 | >100 | >11364 |
| 11 | >100 | >15152 | 14 | >100 | >7692 |
| 17 | 50 | 11628 | 19 | 58 | 16571 |
| 24 | >100 | >7692 | 25 | >100 | >6897 |
| 26 | 68 | 5231 | 28 | >100 | >9804 |
| 33 | >100 | >9091 | 35 | 50 | 7813 |
| 36 | 38 | 11875 | 39 | >100 | >5848 |
| 43 | 43 | 14845 | 45 | 43 | 85280 |
| 52 | >100 | >5587 | 54 | 60 | 7300 |
| 56 | 43 | 9766 | 58 | >100 | >8772 |
| 59 | >100 | >6410 | 60 | 34 | 21169 |
| 61 | 53 | 10942 | 62 | 46 | 6571 |
| 63 | 34 | 22367 | 64 | >100 | >6024 |
| 65 | 71 | 5980 | 67 | >100 | >25000 |
| 69 | >100 | >32258 | 70 | 60 | 7268 |
| 71 | 44 | 14690 | 72 | >100 | >7576 |
| 73 | 72 | 24083 | 74 | >100 | >9174 |
| 77 | >100 | >7143 | 78 | 73 | 36515 |
| 80 | 38 | 22394 | 82 | >100 | >7634 |
| 83 | 65 | 7558 | 85 | >100 | >15152 |
| 88 | 52 | 39662 | 104 | 44 | 9079 |
| 105 | 33 | 12041 | 107 | 26 | 12495 |
| 108 | 74 | 9953 | 109 | >100 | >58824 |
| 111 | 79 | 65983 | 113 | 58 | 6404 |
| 116 | >100 | >13699 | 118 | 45 | 8960 |
| 120 | 87 | 9083 | 126 | >100 | >9709 |
| 128 | 35 | 14056 | 130 | 69 | 10830 |
| 131 | 53 | 9346 | 135 | >100 | >15385 |
| 137 | 55 | 17031 | 145 | >100 | >5882 |
| 146 | >100 | >200000 | 147 | >100 | >111111 |
| 152 | >100 | >5650 | | | |

TABLE 6

Relative induction values of particular compounds to 10 μM rifampicin

| Example No. | % of Positive control (10 μM Rifampicin) |
|---|---|
| 12 | 21 |
| 24 | 29 |
| 26 | 36 |
| 31 | 25 |
| 35 | 20 |
| 38 | 35 |
| 48 | 17 |
| 56 | 23 |
| 66 | 6.2 |
| 68 | 7.7 |
| 69 | 21 |
| 73 | 21 |
| 80 | 35 |
| 88 | 39 |
| 90 | 37 |
| 126 | 17 |
| 135 | 27 |

Synthesis

The compounds of the present invention can be prepared by any conventional means. Suitable processes for synthesizing these compounds as well as their starting materials are provided in the schemes below and in the examples. All substituents, in particular, $R^1$ to $R^4$ are as defined above unless otherwise indicated. Furthermore, and unless explicitly otherwise stated, all reactions, reaction conditions, abbreviations and symbols have the meanings well known to a person of ordinary skill in organic chemistry.

General Synthetic Route for Compound Ia (Scheme 1)

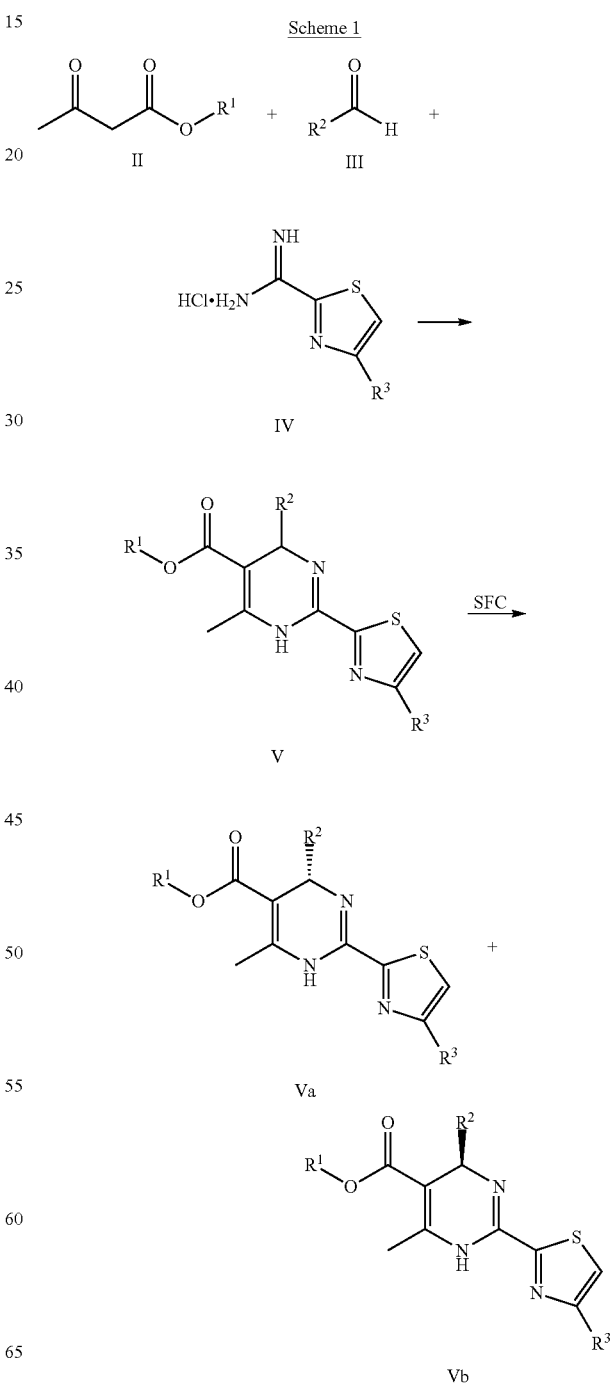

-continued

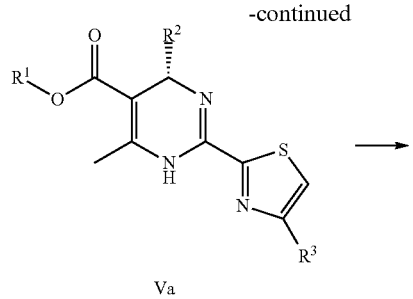

Va

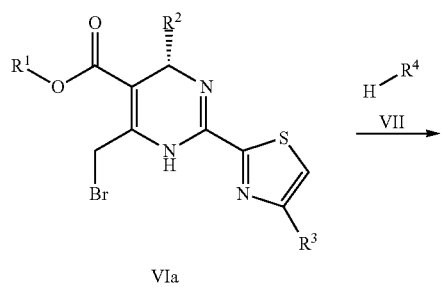

VIa

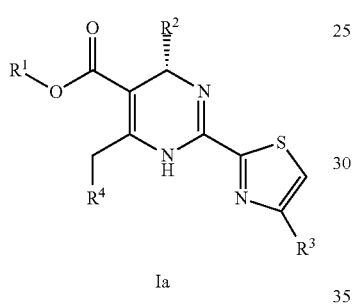

Ia

Compound of interest Ia can be prepared according to Scheme 1. A one-pot reaction between acetyl acetate II, aldehyde III and thiazole amidine IV gives dihydropyrimidine V. (−)-Enantiomer Va is then obtained by SFC chiral separation of V. The absolute stereochemistry of one specific compound B1 is determined by X-ray diffraction study (FIG. 1) and others are assigned based on comparison of SFC retention time. Bromination of Va affords VIa. Coupling VIa with a suitable bridged amine VII gives the compound of interest Ia.

Dihydropyrimidine V can be prepared from condensation and cyclization sequence of acetyl acetate II, aldehyde III and thiazole amidine IV. The reaction can be carried out in a suitable alcoholic solvent such as trifluoroethanol in the presence of a base such as potassium acetate under a heating condition over several hours.

(−)-Enantiomer Va is obtained by SFC chiral separation of V.

Bromide VIa can be prepared by reaction of Va with a bromination reagent such as N-bromosuccinimide, in a suitable inert solvent such as carbon tetrachloride at 80-100 degrees Celsius for about 1 hour.

Compound of interest Ia can be obtained by coupling bromide VIa with bridged amine VII. The reaction is typically performed in a suitable solvent such as 1,2-dichloroethane at room temperature over several hours in the presence of an organic base such as N,N-diisopropylethylamine.

An alternative general synthetic route for compounds I, Ia and Ib (Scheme 2)

Scheme 2

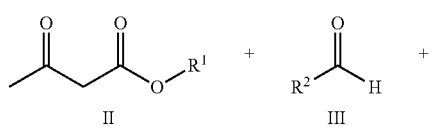

II      III

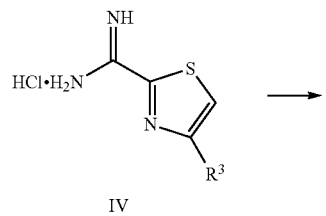

IV

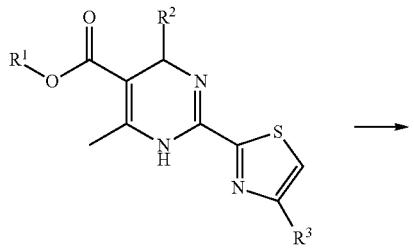

V

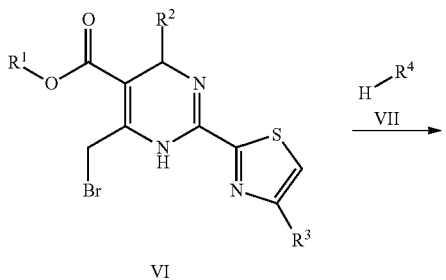

VI

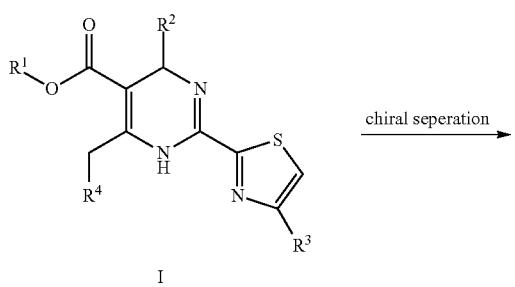

I chiral seperation →

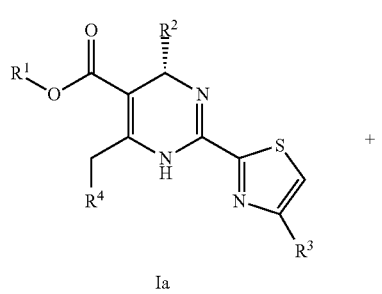

Ia

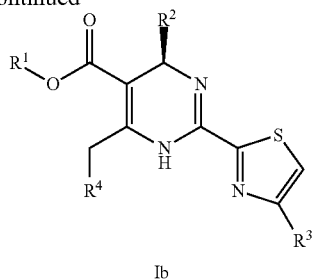

Ib

Compounds of interest I, Ia and Ib can be prepared according to Scheme 2. Starting with acetyl acetate II, aldehyde III and thiazole amidine IV, dihydropyrimidine V can be synthesized through a one-pot condensation reaction. Bromination of Compound V affords bromide VI. Coupling bromide VI with bridged amine VII generates compound of interest I. Further chiral separation of I affords two enantiomerically pure compounds of interest Ia and Ib.

Dihydropyrimidine V can be prepared from condensation and cyclization sequence of acetyl acetate II, aldehyde III and thiazole amidine IV. The reaction can be carried out in a suitable alcoholic solvent such as trifluoroethanol in the presence of a base such as potassium acetate under a heating condition over several hours.

Bromide VI can be prepared by reaction of V with a bromination reagent such as N-bromosuccinimide in a suitable inert solvent such as carbon tetrachloride at 80-100 degrees Celsius for about 1 hour.

Compound of interest I can be obtained by coupling bromide VI with bridged amine VII.

The reaction is typically performed in a suitable solvent such as 1,2-dichloroethane at room temperature over several hours in the presence of an organic base such as N,N-diisopropylethylamine.

Compounds of further interest Ia and Ib are obtained by preparative HPLC separation of diastereomeric mixture I. The stereochemistry of Ia is assigned based on the comparison of its analytical data with the compound made by synthetic route A.

This invention also relates to a process for the preparation of a compound of formula I comprising the reaction of
(a) a compound of formula (A)

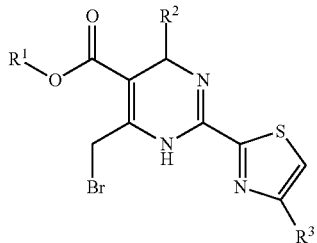

(A)

with bridged amine in the presence of a base;
(b) a compound of formula (B)

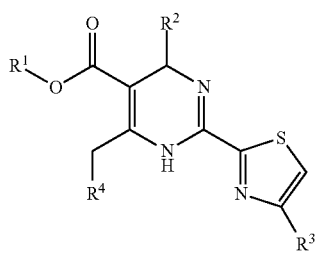

(B)

under chiral separation condition;

wherein $R^1$ to $R^4$ are defined above unless otherwise indicated.

In step (a), the base can be for example N,N-diisopropylethylamine.

A compound of formula I when manufactured according to the above process is also an object of the invention.

Pharmaceutical Compositions and Administration

The invention also relates to a compound of formula I for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular human being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to the suppression of serum HBV DNA levels, or HBeAg seroconversion to HBeAb, or HBsAg loss, or normalization of alanine aminotransferase levels and improvement in liver histology. For example, such amount may be below the amount that is toxic to normal cells, or the human as a whole.

In one example, the pharmaceutically effective amount of the compound of the invention administered parenterally per dose will be in the range of about 0.01 to 100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 mg to 1000 mg of the compound of the invention compounded with about 90 mg to 30 mg anhydrous lactose, about 5 mg to 40 mg sodium croscarmellose, about 5 mg to 30 mg polyvinylpyrrolidone (PVP) K30, and about 1 mg to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 mg to 400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

Indications and Methods of Treatment

The compounds of the invention can inhibit HBV's de novo DNA synthesis and reduce HBV DNA levels. Accordingly, the compounds of the invention are useful for the treatment or prophylaxis of HBV infection.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method for the treatment or prophylaxis of HBV infection in a human in need of such treatment, wherein the method comprises administering to said human a therapeutically effective amount of a compound of Formula I, a stereoisomer, tautomer or pharmaceutically acceptable salt thereof.

Combination Therapy

The compounds of the invention can be used together with interferon, pegylated interferons, Lamivudine, Adefovir dipivoxil, Entecavir, Telbivudine, and Tenofovir disoproxil for the treatment or prophylaxis of HBV.

BRIEF DESCRIPTION OF THE FIGURE

FIG. 1. X-ray crystal structure of compound B1

EXAMPLES

The invention will be more fully understood by reference to the following examples. They should not, however, be construed as limiting the scope of the invention.

Abbreviations used herein are as follows:
$[\alpha]_D^{20}$: specific optical rotation at 20 degrees Celsius
ACN acetonitrile
n-BuLi: n-butyl lithium
t-BuOH: tert-butyl alcohol
calc'd: calculated
CbzCl: benzyl chloroformate
$CC_{50}$: concentration results in the death of 50 percent of the cells
CCK-8: cell counting kit-8
$CCl_4$: carbon tetrachloride
$CDCl_3$: deuterated chloroform
conc. concentrated
m-CPBA m-chloroperbenzoic acid
CLh: hepatic clearance
CMV: cytomegalovirus
DBB: di-tert-butylbiphenyl
DIAD: diisopropyl azodicarboxylate
DIG: digoxigenin
DIPEA: N,N-diisopropylethylamine
DCM: dichloromethylene
DAST N,N'-diethylaminosulfur trifluoride
DBU 1,8-diazabicyclo[5.4.0]undec-7-ene
DMF N,N-dimethylformamide
DMF-DMA N,N-dimethylformamide dimethyl acetal
DMP Dess-Martin periodinane
eq equivalent
FDA: Food and Drug Administration
PE: petroleum ether
DMSO: dimethylsulfoxide
DMSO-d6: deuterated dimethylsulfoxide
DNA: deoxyribonucleic acid
EDTA: ethylenediaminetetraacetic acid
EtOH: ethanol
EA or EtOAc: ethyl acetate
g: gram
$EC_{50}$: half maximal effective concentration
HAP: heteroaryldihydropyrimidine
HATU 1-[bis(dimethylamino)methylene]-1H-1,2,3-triazolo[4,5-b]pyridinium 3-oxid hexafluorophosphate
HBeAb: hepatitis B e antibody
HBeAg: hepatitis B e antigen
HBsAg: hepatitis B surface antigen
HCl: hydrogen chloride
HPLC: high performance liquid chromatography
HPLC-UV: high performance liquid chromatography with ultraviolet detector
Hz: hertz
IPA: isopropanol
LiHMDS: lithium hexamethyldisilazide
LCMS liquid chromatography—mass spectrometry
ESI electrospray ionization
obsd. observed
TBSCl tert-butyldimethylsilyl chloride
NFTh 1-fluoro-4-hydroxy-1,4-diazoniabicyclo[2.2.2]octane bis(tetrafluoroborate)
TosMIC (p-tolylsulfonyl)methyl isocyanide
$PhI(OAc)_2$ (diacetoxyiodo)benzene METHANOL-d4: deuterated methanol
MeOH: methanol
mg: milligram
MHz: megahertz
min: minute
mins: minutes
mL: milliliter
mm: millimeter
mM: millimolar
mmol: millimole
MS: mass spectrometry
MsCl: methanesulfonyl chloride
MW: molecular weight
NaCl: sodium chloride
NADP: nicotinamide adenine dinucleotide phosphate (oxidized form)
NADPH: nicotinamide adenine dinucleotide phosphate (reduced form)
$Na_2SO_4$: sodium sulfate
NaOH: sodium hydroxide
NBS: N-bromosuccinimide
NMR: nuclear magnetic resonance
PBS: phosphate buffered saline
PD: pharmacodynamics
PK: pharmacokinetics
prep-HPLC: preparative high performance liquid chromatography
Prep-TLC: preparative thin layer chromatography
rpm: round per minute
sat. saturated
SFC: supercritical fluid chromatography
SSC: saline-sodium citrate buffer
TBAF: tetrabutylammonium fluoride
TBAI: tetrabutylammonium iodide
TEA: triethylamine
Tet: tetracycline
TFA: trifluoroacetic acid
THF: tetrahydrofuran
Tris: tris(hydroxymethyl)aminomethane
p-TsCl: p-toluenesulfonyl chloride
μg: microgram
μL: microliter
μM: micromolar
UV: ultraviolet detector
OD: optical density
pgRNA: pre-genomic RNA
qPCR: quantitative polymerase chain reaction General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C18 (5 μm, OBD™ 30×100 mm) column or SunFire™ Prep-C18 (5 μm, OBD™ 30×100 mm) column. Waters AutoP purification System (Column: XBridge™ Prep-C18, 30×100 mm, Sample Manager 2767, Pump 2525, Detector: Micromass ZQ and UV 2487, solvent system: acetonitrile and 0.1% ammonium hydroxide in water). For SFC chiral separation, intermediates were separated by chiral column (Daicel chiralpak IC, 5 μm, 30×250 mm) column using Mettler Toledo SFC-Multigram III system, solvent system: 95% $CO_2$ and 5% IPA (0.5% TEA in IPA), back pressure 100 bar, detection UV@ 254 nm.

LC/MS spectra of compounds were obtained using a LC/MS (Waters™ Alliance 2795-Micromass ZQ), LC/MS conditions were as follows (running time 6 mins):

Acidic condition: A: 0.1% formic acid in $H_2O$; B: 0.1% formic acid in acetonitrile;

Basic condition: A: 0.1% $NH_3.H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(MH)^+$.

NMR Spectra were obtained using Bruker Avance 400 MHz.

The microwave assisted reactions were carried out in a Biotage Initiator Sixty microwave synthesizer.

A single crystal was mounted in a loop and cooled to 160 K in a nitrogen stream. Data were collected on a Gemini R Ultra diffractometer (Oxford Diffraction, UK) with Cu—K-alpha-radiation (1.54178 Å) and processed with the Crysalis-package. Structure solution and refinement was performed using the ShelXTL software (Bruker AXS, Karlsruhe).

All reactions involving air-sensitive reagents were performed under an argon atmosphere. Reagents were used as received from commercial suppliers without further purification unless otherwise noted.

The following examples are intended to illustrate the meaning of the present invention but should by no means represent a limitation within the meaning of the present invention:

PREPARATIVE EXAMPLES

Example 1

9-[[(4R)-4-(2-chloro-4-fluoro-phenyl)-5-methoxy-carbonyl-2-thiazol-2-yl-1,4-dihydropyrimidin-6-yl]methyl]-3-oxa-9-azabicyclo[3.3.1]nonane-7-carboxylic acid

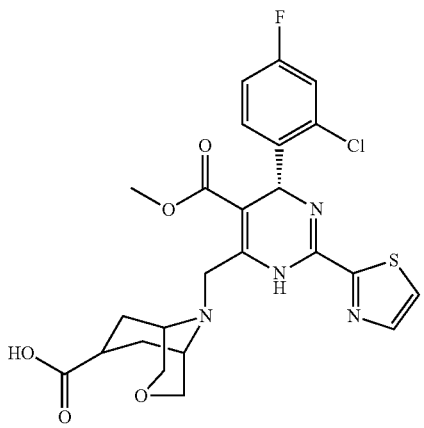

The title compound was prepared according to the general synthetic route shown in Scheme 1. A detailed synthetic route is provided in Scheme 3.

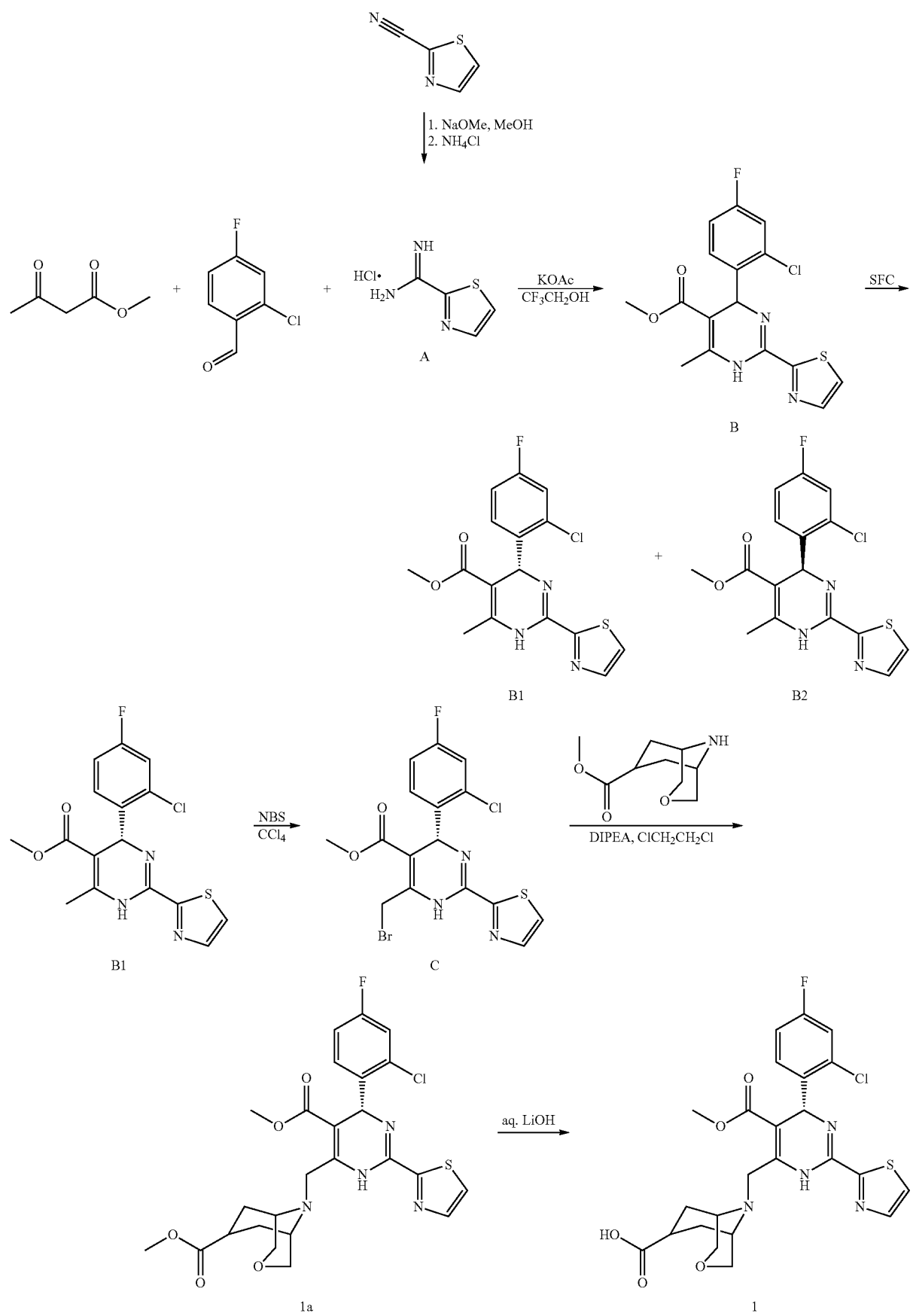
Scheme 3

Preparation of Compound A

To a stirred solution of thiazole-2-carbonitrile (1.5 g, 14 mmol) in 5 mL of dry MeOH was added dropwise a solution of sodium methoxide (0.74 g, 14 mmol) in 10 mL of dry methanol. The reaction mixture was stirred at room temperature until the disappearance of starting material monitored by LC/MS. After that, ammonium chloride (1.5 g, 28 mmol) was added in one portion and the reaction mixture was stirred overnight. The undissolved material was removed by filtration and the filtrate was concentrated to afford thiazole-2-carboxamidine hydrochloride (Compound A) as a grey solid which was used directly in the next step without further purification. MS: calc'd 128 ($MH^+$), measured 128 ($MH^+$).

Preparation of Compound B

To a stirred solution of thiazole-2-carboxamidine hydrochloride (0.13 g, 1.0 mmol), methyl acetoacetate (0.12 g, 1.0 mmol) and 2-chloro-5-fluorobenzaldehyde (0.16 g, 1.0 mmol) in $CF_3CH_2OH$ (8 mL) was added potassium acetate (0.20 g, 2.0 mmol). The reaction mixture was refluxed for 16 hours. After it was cooled to room temperature, the reaction mixture was concentrated and the residue was dissolved in ethyl acetate and then washed with brine. The organic layer was dried over sodium sulfate. The solvent was concentrated, and the residue was purified by column chromatography (ethyl acetate/petroleum ether is from ¼ to ½) to afford 4-(2-chloro-4-fluoro-phenyl)-6-methyl-2-thiazol-2-yl-1,4-dihydro-pyrimidine-5-carboxylic acid methyl ester (Compound B) as a yellow solid. MS: calc'd ($MH^+$) 366, measured ($MH^+$) 366. $^1$H NMR (DMSO-$d_6$, 400 MHz): δ ppm 9.98 (s, 1H), 7.97 (d, J=4.0 Hz, 1H), 7.90 (d, J=4.0 Hz, 1H), 7.41 (dd, J=8.0, 4.0 Hz, 1H), 7.35 (dd, J=8.0, 8.0 Hz, 1H), 7.18 (td, J=8.0, 4.0 Hz, 1H), 5.98 (s, 1H), 3.53 (s, 3H), 2.47 (s, 3H).

Preparation of Compound B1

The enantiopure (R)-4-(2-chloro-4-fluoro-phenyl)-6-methyl-2-thiazol-2-yl-1,4-dihydro-pyrimidine-5-carboxylic acid methyl ester (Compound B1) was obtained through SFC (SFC-Multigram; IC: 5×250 mm, 5μ) chiral separation of the stereomixture of 4-(2-chloro-4-fluoro-phenyl)-6-methyl-2-oxazol-2-yl-1,4-dihydro-pyrimidine-5-carboxylic acid methyl ester (Compound B) eluting with a mixed solvent of 85% supercritical $CO_2$/15% EtOH at 100 mL/min rate. The desired (−)-enantiomer B1 has a relatively short retention time. The absolute stereochemistry of (−)-enantiomer B1 was determined by X-ray diffraction study (FIG. 1).

Compound B1: $[α]_D^{20}$ −55.0 (c 0.845, MeOH).

Compound B2: $[α]_D^{20}$ +44.6 (c 0.175, MeOH).

Preparation of Compound C

To a stirred solution of (R)-4-(2-chloro-4-fluoro-phenyl)-6-methyl-2-thiazol-2-yl-1,4-dihydro-pyrimidine-5-carboxylic acid methyl ester (0.37 g, 1.0 mmol) in $CCl_4$ (5 mL) was added NBS (0.20 g, 1.1 mmol) in portions. After the reaction mixture was stirred at room temperature for 1 hour, the solvent was removed in vacuo and the residue was purified by column chromatography to give (R)-6-bromomethyl-4-(2-chloro-4-fluoro-phenyl)-2-thiazol-2-yl-1,4-dihydro-pyrimidine-5-carboxylic acid methyl ester (Compound C) as a yellow solid. MS: calc'd 445 ($MH^+$), measured 445 ($MH^+$).

Preparation of Example 1a

To a stirred solution 3-oxa-9-azabicyclo[3.3.1]nonane-7-carboxylic acid methyl ester (90 mg, 0.48 mmol) (PharmaBlock (Nanjing) R&D Co. Ltd, CAS: 1363382-76-6) and (R)-6-bromomethyl-4-(2-chloro-4-fluoro-phenyl)-2-thiazol-2-yl-1,4-dihydro-pyrimidine-5-carboxylic acid methyl ester (104 mg, 0.24 mmol) in $ClCH_2CH_2Cl$ (5 mL) was added DIPEA (0.15 mL, 0.48 mmol) at room temperature. The reaction mixture was stirred overnight at room temperature, then diluted with EtOAc (60 mL), washed with sat. $NH_4Cl$, sat. $NaHCO_3$ and brine (20 mL) respectively. The organic layer was dried over $Na_2SO_4$, concentrated under reduced pressure to give methyl 9-[[(4R)-4-(2-chloro-4-fluoro-phenyl)-5-methoxycarbonyl-2-thiazol-2-yl-1,4-dihydropyrimidin-6-yl]methyl]-3-oxa-9-azabicyclo[3.3.1]nonane-7-carboxylate as a crude product which was used directly in next step.

Preparation of Example 1

To a stirred solution of methyl 9-[[(4R)-4-(2-chloro-4-fluoro-phenyl)-5-methoxycarbonyl-2-thiazol-2-yl-1,4-dihydropyrimidin-6-yl]methyl]-3-oxa-9-azabicyclo[3.3.1]nonane-7-carboxylate in THF (3 mL) was added 0.3 M aq. LiOH (3 mL) at 0° C. After the reaction mixture was stirred at room temperature for 8 hours, it was neutralized with 1N HCl to pH around 7, then extracted with EtOAc (60 mL). The organic layer was washed with brine (20 mL), dried over $Na_2SO_4$, concentrated under reduced pressure to give the crude product which was further purified by reverse phase HPLC to give Example 1 as a light yellow solid.

Example 2

9-[(R)-6-(2-Chloro-4-fluoro-phenyl)-5-methoxycarbonyl-2-(4-methyl-thiazol-2-yl)-3,6-dihydro-pyrimidin-4-ylmethyl]-3-oxa-9-aza-bicyclo[3.3.1]nonane-7-carboxylic acid

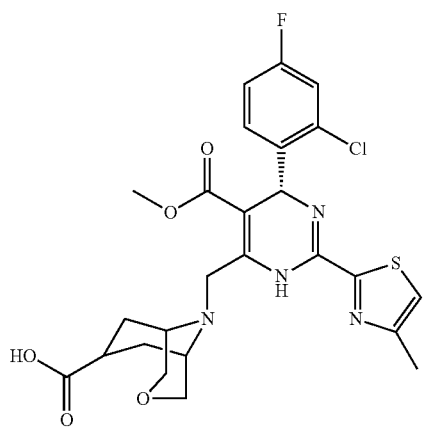 [SMILES: COC(=O)C1=C(CN2C3COCC2CC(C(=O)O)C3)NC(c2nc(C)cs2)=N[C@H]1c1ccc(F)cc1Cl]

The title compound was prepared in analogy to Example 1 with the procedure shown in Scheme 3 by using 4-methyl-thiazole-2-carbonitrile instead of thiazole-2-carbonitrile.

Example 3

9-[6-(3,4-Difluoro-phenyl)-5-methoxycarbonyl-2-thiazol-2-yl-3,6-dihydro-pyrimidin-4-ylmethyl]-3-oxa-9-aza-bicyclo[3.3.1]nonane-7-carboxylic acid

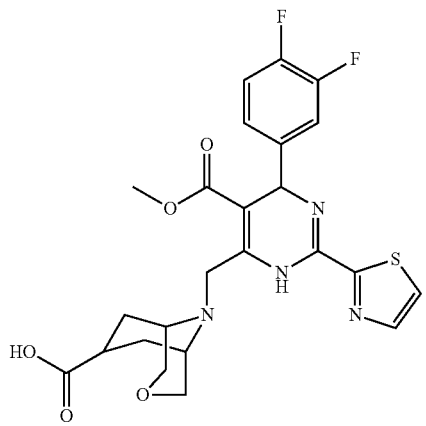 [SMILES: COC(=O)C1=C(CN2C3COCC2CC(C(=O)O)C3)NC(c2nccs2)=NC1c1ccc(F)c(F)c1]

The title compounds were prepared according to the general synthetic routes shown in Scheme 2. A detailed synthetic route is provided in Scheme 4.

Scheme 4

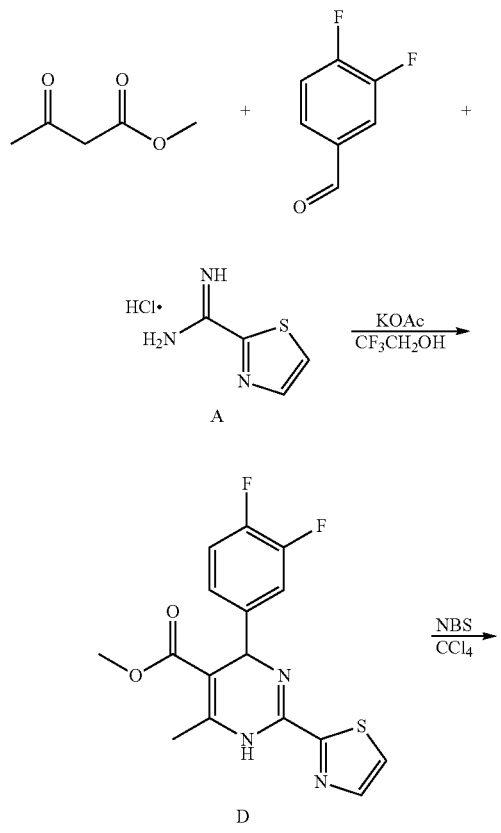

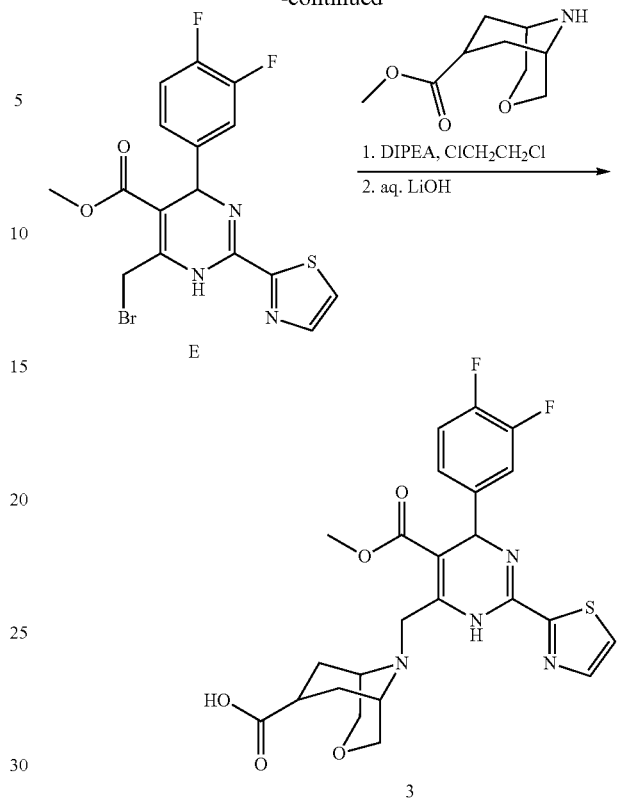

Example 3 was prepared in analogy to Example 1 with the procedure shown in Scheme 3 by using 4-(3,4-difluoro-phenyl)-6-methyl-2-thiazol-2-yl-1,4-dihydro-pyrimidine-5-carboxylic acid methyl ester (Compound D) instead of (R)-4-(2-chloro-4-fluoro-phenyl)-6-methyl-2-thiazol-2-yl-1,4-dihydro-pyrimidine-5-carboxylic acid methyl ester (Compound B).

Preparation of 4-(3,4-difluoro-phenyl)-6-methyl-2-thiazol-2-yl-1,4-dihydro-pyrimidine-5-carboxylic acid methyl ester (Compound D)

Compound D was prepared in analogy to Compound B with the procedure shown in Scheme 3 by using 3,4-difluoro-benzaldehye instead of 2-chloro-5-fluorobenzaldehyde.

Example 4

9-[(R)-6-(2-Bromo-4-fluoro-phenyl)-5-methoxycarbonyl-2-thiazol-2-yl-3,6-dihydro-pyrimidin-4-ylmethyl]-3-oxa-9-aza-bicyclo[3.3.1]nonane-7-carboxylic acid methyl ester

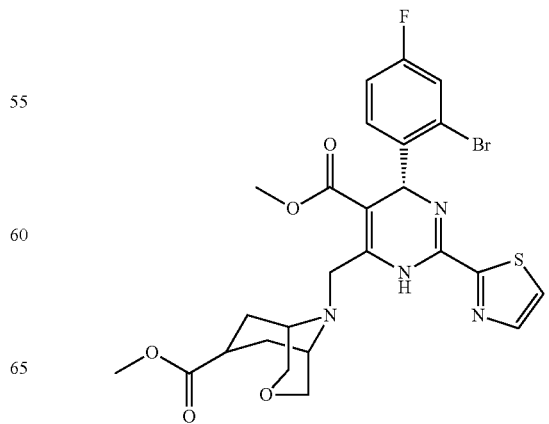

The title compound was prepared in analogy to Example 1a with the procedure shown in Scheme 3 by using 2-bromo-5-fluorobenzaldehyde instead of 2-chloro-5-fluorobenzaldehyde.

Example 5

9-[(R)-6-(2-Bromo-4-fluoro-phenyl)-5-methoxycarbonyl-2-thiazol-2-yl-3,6-dihydro-pyrimidin-4-ylmethyl]-3-oxa-9-aza-bicyclo[3.3.1]nonane-7-carboxylic acid

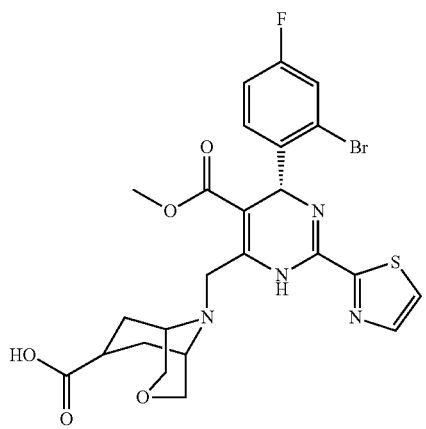 [SMILES: COC(=O)C1=C(CN2C3COCC2CC(C(=O)O)C3)NC(c2nccs2)=N[C@H]1c1ccc(F)cc1Br]

The title compound was prepared in analogy to Example 1 with the procedure shown in Scheme 3 by using 2-bromo-5-fluorobenzaldehyde instead of 2-chloro-5-fluorobenzaldehyde.

Example 6

8-[(R)-6-(2-Chloro-4-fluoro-phenyl)-5-methoxycarbonyl-2-thiazol-2-yl-3,6-dihydro-pyrimidin-4-ylmethyl]-3-oxa-8-aza-bicyclo[3.2.1]octane-6-carboxylic acid

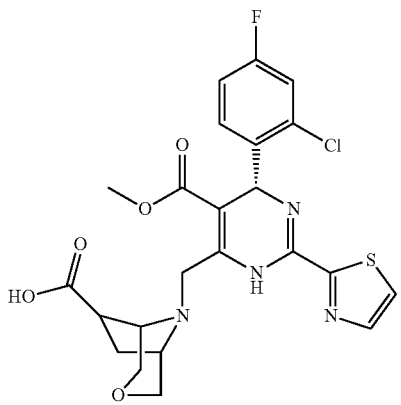 [SMILES: COC(=O)C1=C(CN2C3COCC2C(C(=O)O)C3)NC(c2nccs2)=N[C@H]1c1ccc(F)cc1Cl]

The title compound was prepared in analogy to Example 1a with the procedure shown in Scheme 3 by using 3-oxa-8-aza-bicyclo[3.2.1]octane-6-carboxylic acid (Compound F) instead of 3-oxa-9-aza-bicyclo[3.3.1]nonane-7-carboxylic acid methyl ester.

Preparation 3-oxa-8-aza-bicyclo[3.2.1]octane-6-carboxylic acid (Compound F)

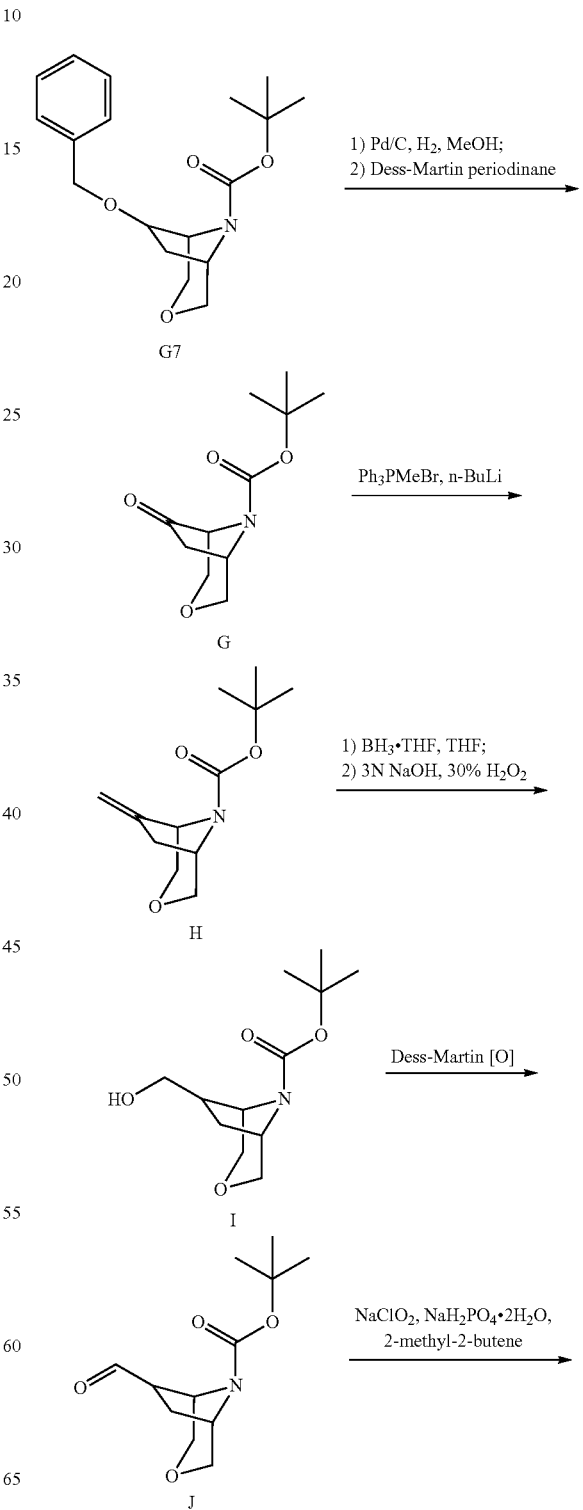

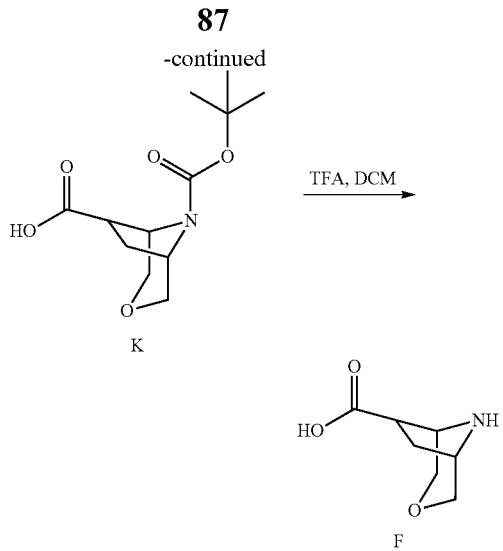

K

F

Step I: To a solution of 6-benzyloxy-3-oxa-8-aza-bicyclo[3.2.1]octane-8-carboxylic acid tert-butyl ester (G7) (160 mg, 0.50 mmol) in MeOH (20 mL) was added Pd on carbon (32 mg). The mixture was stirred at room temperature under $H_2$ for 8 hours, and then filtered. The solvent was removed under reduced pressure. The residue was dissolved in $CH_2Cl_2$ (10 mL). To the solution was added Dess-Martin periodinane (318 mg, 0.75 mmol) at room temperature. The reaction mixture was stirred for 4 hours, and then quenched with sat. $NaHCO_3$, then extracted with EtOAc (30 mL) three times. The combined organic layer was washed successively with sat. $Na_2CO_3$ (15 mL) three times, sat. $NH_4Cl$ and brine. The organic layer was dried over $Na_2SO_4$. The solvent was removed. The residue was purified by column chromatography to give Compound G (100 mg, 88%) as a white solid. MS: calc'd (MH$^+$) 228, measured (MH$^+$) 228.

Step II: To a solution of methyltriphenylphonium bromide (314 mg, 0.88 mmol) in anhydrous THF (5 mL) was added n-BuLi (1.6 M in hexane, 0.58 mL) at −10° C. under argon atmosphere. The reaction mixture was warmed to room temperature and then stirred for 2 hours. A solution of Compound G (100 mg, 0.44 mmol) in anhydrous THF (2 mL) was added to the above mixture at room temperature. The mixture was stirred for additional 3 hours at room temperature, and then quenched with sat. $NH_4Cl$. The mixture was extracted with EtOAc (30 mL) three times. The combined organic layer was washed with sat. $NH_4Cl$ and brine (20 mL) respectively. The organic layer was dried over $Na_2SO_4$. The solvent was removed under reduced pressure. The residue was purified by column chromatography to give Compound H (80 mg, 81%) as yellowish oil. MS: calc'd (MH$^+$) 226, measured (MH$^+$) 226.

Step III: To a solution of Compound H (75 mg, 0.33 mmol) in anhydrous THF was added $BH_3$/THF (1.0 M solution in THF, 0.43 mL) at 0° C. under argon atmosphere. The reaction mixture was stirred for 1.5 hours at 0° C. To this reaction mixture was added 3N NaOH (0.33 mL, 1.33 mmol) and 30% $H_2O_2$ (0.33 mL) at 0° C. and the mixture was stirred for 1.5 hours at 0° C. The reaction mixture was poured into water, and then extracted with EtOAc (30 mL) three times. The combined organic layer was washed with sat. $NH_4Cl$ and brine, and then dried over $Na_2SO_4$. The solvent was removed under reduced pressure to give Compound I (80 mg, 98%) as colorless oil. $^1$H NMR (CDCl$_3$, 400 MHz): 4.15 (m, 1H), 4.04 (m, 1H), 3.86-3.96 (m, 3H), 3.76 (m, 2H), 3.57 (d, J=9.8 Hz, 1H), 2.55 (m, 1H), 2.20 (m, 1H), 1.50 (s, 9H).

Step IV: To a solution of Compound I (80 mg, 0.33 mmol) in $CH_2Cl_2$ (10 mL) was added Dess-Martin periodinane (210 mg, 0.50 mmol) at room temperature. The reaction mixture was stirred at room temperature for 2 hours, and then diluted with EtOAc (60 mL). The reaction mixture was washed successively with sat. $Na_2CO_3$ (10 mL) three times, sat. $NH_4Cl$ (20 mL) and brine (20 mL). The organic layer was dried over $Na_2SO_4$. The solvent was removed under reduced pressure to give Compound J (80 mg, 99%) as colorless oil. $^1$H NMR (CDCl$_3$, 400 MHz): 9.93 (d, J=1.8 Hz, 1H), 4.38 (m, 1H), 4.24 (m, 1H), 3.76 (m, 2H), 3.66 (m, 2H), 3.01 (m, 1H), 2.33 (m, 1H), 2.26 (m, 1H), 1.48 (s, 9H).

Step V: To a solution of Compound J (80 mg, 0.33 mmol) in t-BuOH (3 mL) was added a-methyl-2-butene (0.75 mL) and a solution of NaClO$_2$ (278 mg, 3.07 mmol) and NaH$_2$PO$_4$/2H$_2$O (373 mg, 2.39 mmol) in H$_2$O (3 mL) at room temperature. The reaction mixture was stirred for 2 hours at room temperature. t-BuOH was removed under reduced pressure and aqueous residue was poured into 10% aqueous solution of citric acid. The mixture was extracted with EtOAc (30 mL) three times. The combined organic layer was washed with sat. $NH_4Cl$ and brine, and then dried over $Na_2SO_4$. The solvent was removed under reduced pressure. The residue was further dried under reduced pressure to give Compound K (80 mg, 94%) as colorless oil. $^1$H NMR (CDCl$_3$, 400 MHz): 9.63 (brs, 1H), 4.32 (m, 1H), 4.18 (m, 1H), 4.05 (d, J=10.8 Hz, 1H), 3.68 (m, 2H), 3.64 (d, J=10.8 Hz, 1H), 3.26 (m, 1H), 2.43 (dd, J=12.8, 5.5 Hz, 1H), 2.27 (m, 1H), 1.50 (s, 9H).

Step VI: To a solution of Compound K (80 mg, 0.31 mmol) in $CH_2Cl_2$ (5 mL) was added trifluoroacetic acid (2 mL) at 0° C. The mixture was stirred at room temperature for 2 hours. The solvent was removed under reduced pressure. The residue was further dried under high-vacuum to give 3-oxa-8-aza-bicyclo[3.2.1]octane-6-carboxylic acid (Compound F) (85 mg, 100%) as brown oil. MS (ESI, [M+H]$^+$): Calc'd. for $C_7H_{12}NO_3$: 158. Found: 158.

Preparation of Literature Known Intermediate G7 (*J. Org. Chem.* 2010, 75, 1643)

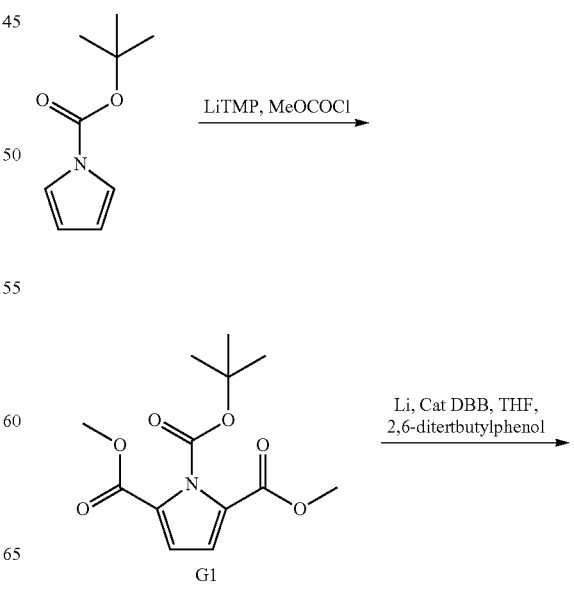

G1

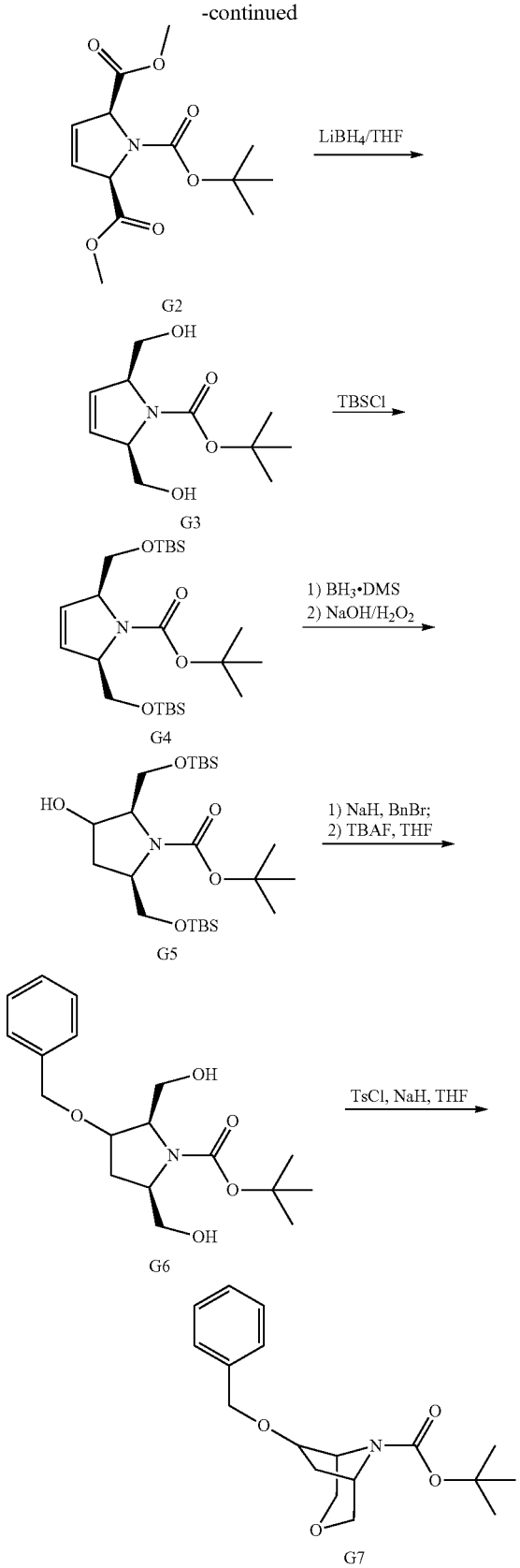

ylpiperidine (12.6 mL, 75 mmol) in THF (100 mL) at −78° C. under argon. N-Boc-pyrrole (5 g, 30 mmol) in THF (25 mL) was then added to the mixture. The mixture was stirred for 3 hours, then transferred into methyl chloroformate (3 equivalents, 6.95 mL) via cannula and stirred for a further 30 minutes. Sat. NH$_4$Cl (20 mL) was added and the mixture was allowed to warm to room temperature. The mixture was then diluted with ether (50 mL), washed with 1 M HCl solution (100 mL) and sat. brine (100 mL). The organic layers were dried over Na$_2$SO$_4$, filtered and concentrated to give the crude product which was purified by flash column chromatography to give 1-tert-butyl, 2,5-dimethyl pyrrole-1,2,5-tricarboxylate (6.60 g, 78%) as a white solid.

Step II: To a Schlenk tube containing DBB (15 mg, 0.10 mmol) and antibumping granules under argon was added freshly cut lithium wire (98 mg, 14 mmol). The contents of the tube were then stirred until the lithium had been completely reduced to a powder. The tube was then cooled to −78° C. and THF (25 mL) was added resulting in a turquoise solution. 1-tert-butyl, 2,5-dimethyl pyrrole-1,2,5-tricarboxylate (1.0 g, 3.5 mmol) was then added in THF (10 mL) and the resulting red solution was stirred at −78° C. until the solution appeared turquoise again. 1,2-Dibromoethane (0.2 mL, 7.0 mmol) was then added, followed by 2,6-ditertbutylphenol (1.5 g, 7.0 mmol) in THF (10 mL). The mixture was then stirred for a further 2.5 hours before the addition of Sat. NH$_4$Cl solution (10 mL) and the mixture was warmed to room temperature. The mixture was extracted with ether (2×20 mL) and the organic layers were combined, then dried over Na$_2$SO$_4$, filtered and concentrated to give the crude product which was purified by flash chromatography to give 1-tert-butyl, 2,5-dimethyl (2S,5R)-2,5-dihydropyrrole-1,2,5-tricarboxylate (800 mg, 80%) as yellow oil.

Step III: To a solution of 1-tert-butyl, 2,5-dimethyl (2S, 5R)-2,5-dihydropyrrole-1,2,5-tricarboxylate (6.6 g, 23.1 mmol) in THF (100 mL) was added slowly a LiBH$_4$ solution (2 M in THF, 34.7 mL, 69.4 mmol) at 0° C. The resulting mixture was stirred at room temperature for 3 hours and then cooled to 0° C. HCl solution (1 M, 30 mL) was added to the reaction mixture and the reaction was stirred for 10 minutes before being diluted with EtOAc. The organic layer was separated, and the aqueous phase was extracted with EtOAc. Combined organic phases were washed with water and brine and dried over Na$_2$SO$_4$. The organic solvent was removed to give the crude product, which was purified by flash chromatography on silica gel to give tert-butyl (2R,5S)-2,5-bis(hydroxymethyl)-2,5-dihydropyrrole-1-carboxylate (3.8 g, 72%). $^1$H NMR (CDCl$_3$, 300 MHz): 5.77 (d, 2H, J=3.0 Hz), 4.70 (s, 1H), 4.59 (s, 1H), 4.06 (d, 1H, J=11.3 Hz), 3.97 (d, 1H, J=11.3 Hz), 3.66 (m, 2H), 1.49 (s, 9H).

Step IV: To a solution of tert-butyl (2R,5S)-2,5-bis(hydroxymethyl)-2,5-dihydropyrrole-1-carboxylate (3.57 g, 15.6 mmol) in DMF (15 mL) were added TBSCl (5.16 g, 34.3 mmol) and imidazole (3.18 g, 46.7 mmol). The mixture was heated at 80° C. for 30 minutes, then cooled to room temperature. The mixture was taken up in water (50 mL) and EtOAc (50 mL). The organic layer was separated, and the aqueous phase was extracted with EtOAc. The combined organic phases were washed with water and brine and dried over Na$_2$SO$_4$. The organic solvent was removed to give the crude product, which was purified by flash chromatography on silica gel to give the tert-butyl (2R,5S)-2,5-diethyl-2,5-dihydropyrrole-1-carboxylate (7.12 g, 98%). $^1$H NMR (CDCl$_3$, 300 MHz): 5.85 (d, 2H, J=3.0 Hz), 4.50 (s, 1H), 4.36 (s, 1H), 3.85 (m, 2H), 3.47 (t, 1H, J=8.0 Hz), 3.35 (t, 1H, J=8.7 Hz), 1.43 (s, 9H), 0.85 (s, 9H), 0.84 (s, 9H), 0.00 (s, 12H).

Step I: A 1.6 M solution of n-butyllithium in hexanes (46.5 ml, 75 mmol) was added to a solution of 2,2,6,6-tetrameth- Step V: To a solution of tert-butyl (2R,5S)-2,5-diethyl-2,5-dihydropyrrole-1-carboxylate (4.8 g, 10.5 mmol) in THF (50 mL) was added slowly BH$_3$.DMS solution (2M in THF, 6.97 mL, 13.9 mmol) at 0° C. The resulting mixture was stirred at room temperature for 3 hours and then cooled to 0° C. NaOH solution (5 M, 12.6 mL, 63.2 mmol) was added to the reaction mixture, followed by addition of H$_2$O$_2$ (30%, 6.33 mL, 62.0 mmol). The resulting mixture was stirred for 5 hours before diluted with EtOAc. The organic layer was separated, and the aqueous phase was extracted with EtOAc. The combined organic phases were washed with water and brine and dried over Na$_2$SO$_4$. The organic solvent was removed to give the crude product, which was purified by flash chromatography on silica gel to give the tert-butyl (2R,5S)-2,5-diethyl-3-hydroxy-pyrrolidine-1-carboxylate (3.8 g, 77%). $^1$HNMR (CDCl$_3$, 300 MHz): 4.35 (s, 1H), 4.0-3.46 (m, 5H), 3.33 (m, 1H), 2.22-2.10 (m, 1H), 1.89-1.73 (m, 1H), 1.39 (s, 9H), 0.82 (s, 18H), −0.01 (s, 6H), −0.03 (s, 6H).

Step VI: To a solution of tert-butyl (2R,5S)-2,5-diethyl-3-hydroxy-pyrrolidine-1-carboxylate (2.51 g, 5.3 mmol) in THF (50 mL) was added NaH (60%, 0.423 g, 10.6 mmol). The mixture was stirred at room temperature for 30 minutes, and benzyl bromide (1.085 g, 6.3 mmol) and TBAI (0.195 g, 0.5 mmol) were added. The mixture was stirred at room temperature for 12 hours and quenched by addition of sat. NH$_4$Cl (20 mL). The mixture was concentrated and the residue was taken up in water and EtOAc. The organic layer was separated, and the aqueous phase was extracted with EtOAc. The combined organic phases were washed with water and brine and dried over Na$_2$SO$_4$. The organic solvent was removed to give the crude product, which was purified by flash chromatography on silica gel with give the 3-OBn intermediate (2.9 g, 95%) as colorless oil. To a solution of the 3-OBn intermediate (2.9 g, 5.2 mmol) in THF (50 mL) was added slowly of TBAF solution (1M in THF, 21.8 mL, 21.8 mmol) at 0° C. The resulting mixture was stirred at room temperature for 6 hours and quenched by addition of sat. NH$_4$Cl (10 mL). The mixture was concentrated in vacuo, and the residue was treated with water and EtOAc. The organic layer was separated, and the aqueous phase was extracted with EtOAc. The combined organic phases were washed with water and brine and dried over Na$_2$SO$_4$. The organic solvent was removed in vacuo to give the crude product, which was purified by flash chromatography on silica gel to give tert-butyl (2R,5R)-3-benzyloxy-2,5-bis(hydroxymethyl)pyrrolidine-1-carboxylate (1.15 g, 63%). $^1$H NMR (DMSO-d$^6$, 300 MHz): 7.31 (m, 5H), 4.82 (t, 1H, J=5.5 Hz), 4.71 (s, 1H), 4.47 (m, 2H), 4.02 (s, 1H), 3.89-3.73 (m, 2H), 3.54-3.40 (m, 3H), 3.22 (m, 1H), 2.04 (m, 2H), 1.39 (s, 9H).

Step VII: To a solution of tert-butyl (2R,5R)-3-benzyloxy-2,5-bis(hydroxymethyl)pyrrolidine-1-carboxylate (1.15 g, 3.4 mmol) in THF (50 mL) was added NaH (60%, 0.409 g, 10.2 mmol). The mixture was stirred at room temperature for 30 minutes and cooled to 0° C. A solution of p-TsCl (0.65 g, 3.4 mmol) in THF (5 mL) was slowly added to the mixture. The reaction mixture was then stirred at room temperature for 12 hours and quenched by sat. NH$_4$Cl solution (20 mL). The mixture was concentrated in vacuo, and the residue was taken up with water and EtOAc. The organic layer was separated, and the aqueous phase was extracted with EtOAc. The combined organic phases were washed with water and brine and dried over Na$_2$SO$_4$. The organic solvent was removed in vacuo to give the crude product, which was purified by flash chromatography on silica gel to give 6-benzyloxy-3-oxa-8-aza-bicyclo[3.2.1]octane-8-carboxylic acid tert-butyl ester (716 mg, 66%) as an off-white solid. $^1$H NMR (CDCl$_3$, 300 MHz): 7.35-7.27 (m, 5H), 4.59-4.43 (m, 2H), 4.38-4.07 (m, 3H), 3.73-3.56 (m, 3H), 3.47 (t, 1H, J=9.8 Hz), 2.27 (m, 1H), 1.96 (m, 1H), 1.48 (s, 4.5H), 1.44 (s, 4.5H).

Example 7

(R)-4-(2-Chloro-4-fluoro-phenyl)-6-(7-hydroxy-3-oxa-9-aza-bicyclo[3.3.1]non-9-ylmethyl)-2-thiazol-2-yl-1,4-dihydro-pyrimidine-5-carboxylic acid methyl ester

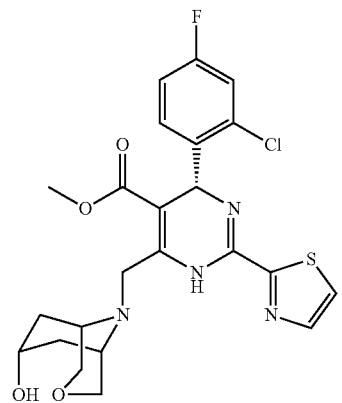 [SMILES: COC(=O)C1=C(CN2C3COCC2CC(O)C3)NC(c2nccs2)=N[C@H]1c1ccc(F)cc1Cl]

The title compound was prepared in analogy to Example 1a with the procedure shown in Scheme 3 by using 3-oxa-9-aza-bicyclo[3.3.1]nonan-7-ol (Compound L) instead of 3-oxa-9-aza-bicyclo[3.3.1]nonane-7-carboxylic acid methyl ester.

Preparation of 3-oxa-9-aza-bicyclo[3.3.1]nonan-7-ol (Compound L)

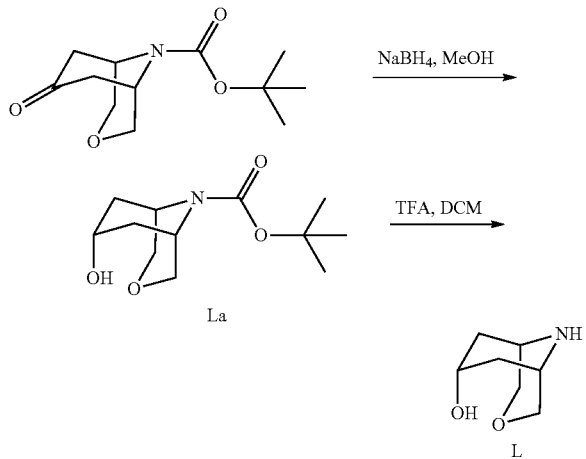

To a stirred solution of 7-oxo-3-oxa-9-aza-bicyclo[3.3.1]nonane-9-carboxylic acid tert-butyl ester (100 mg, 0.41 mmol) in MeOH (5 mL) was added NaBH$_4$ (47 mg, 1.24 mmol) in one portion at room temperature. The mixture was stirred at room temperature overnight, and then quenched with sat. NaHCO$_3$. The mixture was extracted with EtOAc (20 mL) three times. The organic layer was washed with sat. NaHCO$_3$ and brine (20 mL) respectively. The organic layer was dried over Na$_2$SO$_4$, and then filtered. The solvent was concentrated under reduced pressure to give a crude product La, which was dissolved in $CH_2Cl_2$ (5 mL). Trifluoroacetic acid (2 mL) was added to the solution dropwise at 0° C. After being stirred at room temperature for 2 hours, the mixture was concentrated under reduced pressure. The residue was further dried on high-vacuum to give 3-oxa-9-aza-bicyclo[3.3.1]nonan-7-ol (Compound L) which was directly used for next step. MS: calc'd $(MH^+)$ 144, measured $(MH^+)$ 144.

Example 8

(R)-6-(7-Acetoxy-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester

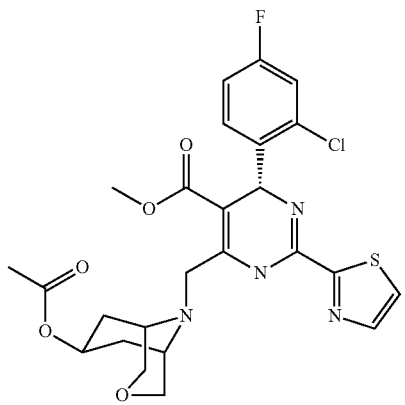 [SMILES: COC(=O)C1=C(CN2C3COCC2CC(OC(C)=O)C3)NC(c2nccs2)=N[C@H]1c1ccc(F)cc1Cl]

The title compound was prepared in analogy to Example 1a with the procedure shown in Scheme 3 by using acetic acid 3-oxa-9-aza-bicyclo[3.3.1]non-7-yl ester (Compound M) instead of 3-oxa-9-aza-bicyclo[3.3.1]nonane-7-carboxylic acid methyl ester.

Preparation of acetic acid 3-oxa-9-aza-bicyclo[3.3.1]non-7-yl ester (Compound M)

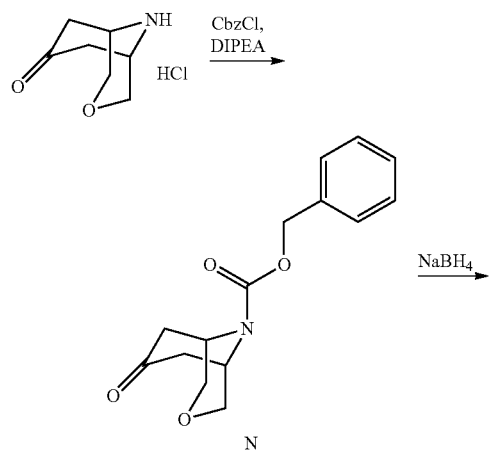

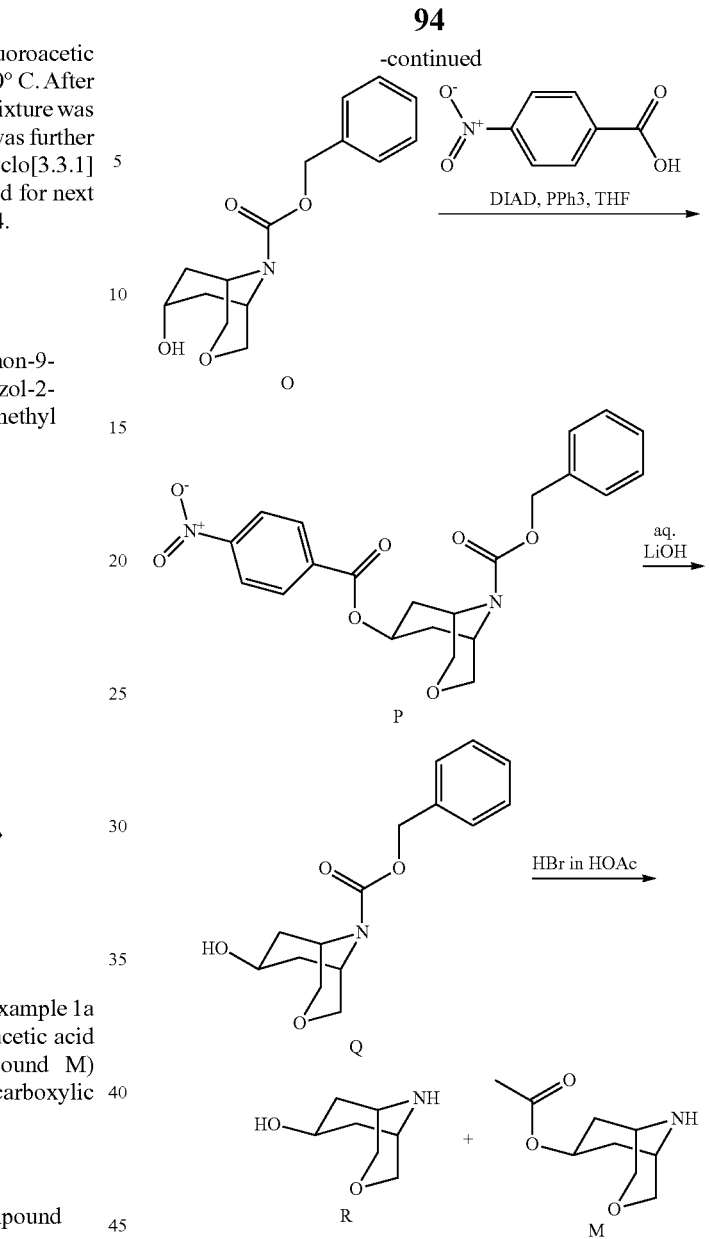

Step I: To a solution of 3-oxa-9-aza-bicyclo[3.3.1]nonan-7-one (PharmaBlock (Nanjing) R&D Co. Ltd, CAS: 1126795-00-3) (1.0 g, 5.6 mmol) and DIPEA (2.9 mL, 17.7 mmol) in $CH_2Cl_2$ (30 mL) was added CbzCl (0.76 mL, 5.3 mmol) at 0° C. under argon atmosphere. The mixture was stirred at room temperature for 2 hours, and then quenched with sat. $NH_4Cl$, then extracted with EtOAc (50 mL) three times. The combined organic layer was washed with 1N aq. HCl, sat. $NaHCO_3$ and brine respectively. The organic layer was dried over $Na_2SO_4$. The solvent was removed under reduced pressure to give Compound N (1.4 g, 91%).

Step II: To a solution of Compound N (810 mg, 2.9 mmol) in THF (20 mL) was added $NaBH_4$ (220 mg, 5.8 mmol). The reaction mixture was stirred at room temperature for 3 hours, and then quenched with sat. $NH_4Cl$. THF was removed under reduced pressure and the residue was extracted with EtOAc (30 mL) three times. The combined organic layer was washed with sat. $NH_4Cl$, sat. $NaHCO_3$ and brine respectively, and then dried over $Na_2SO_4$. The solvent was concentrated to give Compound O (700 mg, 87%) as a white solid. $^1H$ NMR (CDCl$_3$, 400 MHz): 7.39-7.32 (m, 5H), 5.45 (d, 1H), 5.15 (s, 2H), 4.21-4.11 (m, 2H), 3.89-3.72 (m, 4H), 2.23-2.12 (m, 2H), 1.87-1.82 (m, 2H).

Step III: To a solution of Compound O (300 mg, 1.1 mmol), 4-nitrobenzoic acid (181 mg, 1.1 mmol) and PPh$_3$ (578 mg, 2.2 mmol) in anhydrous THF (5.0 mL) was added DIAD (445 mg, 2.2 mmol) under argon. The reaction mixture was stirred at room temperature for 16 hours. The solvent was removed and the residue was purified by Prep-TLC (DCM/MeOH=30/1) to give Compound P (230 mg, 50%) as a white solid. $^1$H NMR (CDCl$_3$, 400 MHz): 8.28 (d, 2H), 8.17 (d, 2H), 7.38-7.31 (m, 5H), 6.22-6.17 (m, 1H), 5.19 (s, 2H), 4.33 (s, 1H), 4.25 (s, 1H), 3.93-3.85 (m, 2H), 3.74-3.70 (m, 2H), 2.34-2.29 (m, 2H), 1.98-1.88 (m, 2H).

Step IV: To a solution of Compound P (230 mg, 0.54 mmol) in THF (3 mL) was added aq. LiOH (1.0 M, 3.0 mL). The reaction mixture was stirred at room temperature for 2 hours, and then diluted with EtOAc (80 mL). The organic layer was washed successively with sat. Na$_2$CO$_3$ (10 mL) three times sat. NH$_4$Cl (20 mL) and brine (20 mL). The organic layer was dried over Na$_2$SO$_4$, and then concentrated to give Compound Q (89 mg, 60%) as a white solid. $^1$H NMR (CDCl$_3$, 400 MHz): 7.40-7.31 (m, 5H), 5.16 (s, 2H), 4.91-4.86 (m, 1H), 4.23 (s, 1H), 4.16 (s, 1H), 3.83-3.65 (m, 4H), 2.15-2.09 (m, 2H), 1.74-1.69 (m, 2H).

Step V: The crude Compound Q was dissolved in HBr/HOAc (33 wt. %, 3 mL). The mixture was stirred at room temperature for 2 hours. The solvent was removed under reduced pressure and further dried on high-vacuum to give 3-oxa-9-aza-bicyclo[3.3.1]nonan-7-ol (Compound R) and 3-oxa-9-aza-bicyclo[3.3.1]non-7-yl ester (Compound M) which were directly used for next step.

Compound R: MS: calc'd (MH$^+$) 144, measured (MH$^+$) 144.

Compound M: MS: calc'd (MH$^+$) 186, measured (MH$^+$) 186.

Example 9

(R)-4-(2-Chloro-4-fluoro-phenyl)-6-(7-hydroxy-3-oxa-9-aza-bicyclo[3.3.1]non-9-ylmethyl)-2-thiazol-2-yl-1,4-dihydro-pyrimidine-5-carboxylic acid methyl ester

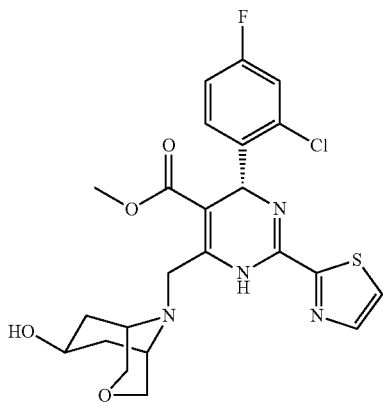 [SMILES: COC(=O)C1=C(CN2C3COCC2CC(O)C3)NC(c2nccs2)=N[C@H]1c1ccc(F)cc1Cl]

The title compound was prepared in analogy to Example 1a with the procedure shown in Scheme 3 by using 3-oxa-9-aza-bicyclo[3.3.1]nonan-7-ol (Compound R) instead of 3-oxa-9-aza-bicyclo[3.3.1]nonane-7-carboxylic acid methyl ester.

Example 10

(R)-4-(2-Chloro-4-fluoro-phenyl)-6-(7-hydroxy-7-hydroxymethyl-3-oxa-9-aza-bicyclo[3.3.1]non-9-ylmethyl)-2-thiazol-2-yl-1,4-dihydro-pyrimidine-5-carboxylic acid methyl ester

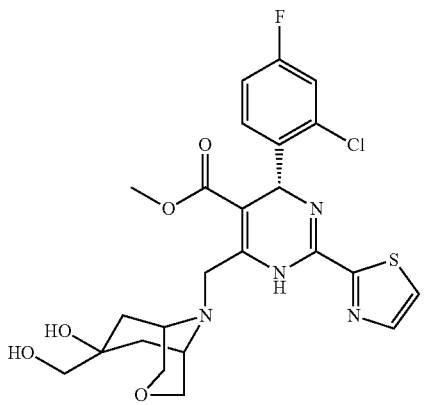 [SMILES: COC(=O)C1=C(CN2C3COCC2CC(O)(CO)C3)NC(c2nccs2)=N[C@H]1c1ccc(F)cc1Cl]

The title compound was prepared in analogy to Example 1a with the procedure shown in Scheme 3 by using 7-hydroxymethyl-3-oxa-9-aza-bicyclo[3.3.1]nonan-7-ol (Compound S) instead of 3-oxa-9-aza-bicyclo[3.3.1]nonane-7-carboxylic acid methyl ester.

Preparation of 7-hydroxymethyl-3-oxa-9-aza-bicyclo[3.3.1]nonan-7-ol (Compound S)

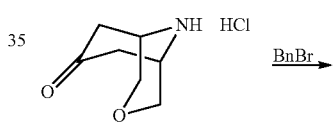

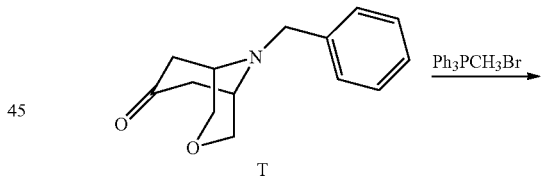

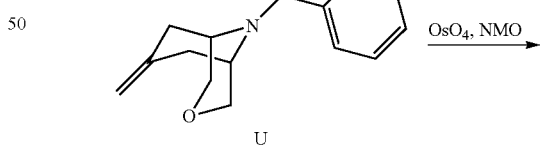

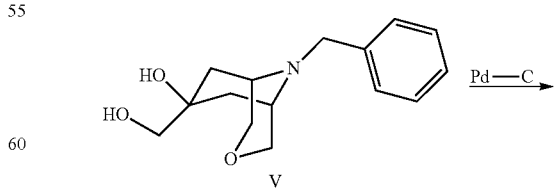

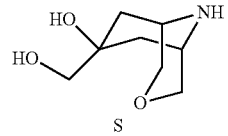

Step I: To a stirred solution of 3-oxa-9-azabicyclo[3.3.1]nonan-7-one hydrochloride (1.26 g, 7.08 mmol, cas: 1126795-00-3, purchased from PharmaBlock (Nanjing) R&D Co. Ltd) and potassium carbonate (2.94 g, 14.16 mmol) in DMF (10 mL) was added benzyl bromide (1.33 g, 7.78 mmol) dropwise at room temperature. The resulting mixture was stirred at room temperature overnight, then concentrated and the residue was partitioned between $H_2O$ (5 mL) and EtOAc (20 mL). The organic layer was dried, and then concentrated. The residue was purified to give Compound T (1.38 g, 84.2%). $^1H$ NMR ($CDCl_3$, 400 MHz): 7.36 (m, 5H), 3.93 (s, 2H), 3.86 (d, J=11.0, 2H), 3.73 (d, J=10.8, 2H), 3.18 (d, J=5.6, 2H), 2.76 (dd, J=15.9, 5.6 Hz, 2H), 2.35 (d, J=15.6, 2H) ppm. LC/MS: calc'd 232 ($MH^+$), exp 232 ($MH^+$).

Step II: A mixture of potassium tert-butoxide (0.292 g, 2.60 mmol) and methyltriphenyl phosphonium bromide (0.927 g, 2.60 mmol) in dry THF (5 mL) was stirred at 0° C. for 30 mins. Then a solution of 9-benzyl-3-oxa-9-aza-bicyclo [3.3.1]nonan-7-one (Compound T) (0.231 g, 1.00 mmol) in dry THF (2 mL) was added to the reaction mixture. The resulting mixture was allowed to warm to room temperature and then heated at 50° C. overnight. The mixture was concentrated and the residue was partitioned between $H_2O$ (2 mL) and EtOAc (10 mL). The organic phase was dried, and then concentrated. The residue was purified to give Compound U (0.098 g, 42.8%). $^1H$ NMR ($CDCl_3$, 400 MHz): 7.37 (m, 5H), 4.73 (s, 2H), 3.98 (m, 4H), 3.79 (d, J=10.8, 2H), 2.83 (m, 4H), 2.29 (m, 2H). LC/MS: calc'd 230 ($MH^+$), exp 230 ($MH^+$).

Step III: To a stirred solution of 9-benzyl-7-methylene-3-oxa-9-azabicyclo[3.3.1]nonane (Compound U) (0.070 g, 0.30 mmol) in acetone (2 mL) and $H_2O$ (0.5 mL) was added N-methylmorpholine-N-oxide (0.140 mg, 0.9 mmol) and osmium tetroxide (0.05 ml, 4% in water, 0.01 mmol) at room temperature. The mixture was stirred at room temperature overnight. The mixture was quenched with saturated $Na_2S_2O_3$ (10 mL) and then extracted with EtOAc (20 ml×2). The organic layer was dried, and then concentrated. The residue was purified to give Compound V (0.070 g, 88.7%). LC/MS: calc'd 264 ($MH^+$), exp 264 ($MH^+$).

Step IV: A mixture of 9-benzyl-7-hydroxymethyl-3-oxa-9-aza-bicyclo[3.3.1]nonan-7-ol (Compound V) (0.080 g, 0.30 mmol) and Pd/C (20 mg) in MeOH (2 mL) was stirred under $H_2$ at room temperature overnight. The mixture was filtered and the filtrate was concentrated to give Compound S (0.040 g, 77.0%). LC/MS: calc'd 174 ($MH^+$), exp 174 ($MH^+$).

Example 11

(R)-4-(2-Chloro-4-fluoro-phenyl)-6-(7-methanesulfonyl-3-oxa-7,9-diaza-bicyclo[3.3.1]non-9-ylmethyl)-2-thiazol-2-yl-1,4-dihydro-pyrimidine-5-carboxylic acid methyl ester

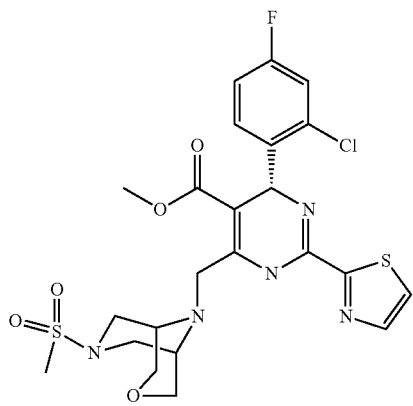 [SMILES: COC(=O)C1=C(CN2C3COCC2CN(S(C)(=O)=O)C3)NC(c2nccs2)=N[C@H]1c1ccc(F)cc1Cl]

The title compound was prepared in analogy to Example 1a with the procedure shown in Scheme 3 by using 7-methanesulfonyl-3-oxa-7,9-diaza-bicyclo[3.3.1]nonane (Compound W) instead of 3-oxa-9-aza-bicyclo[3.3.1]nonane-7-carboxylic acid methyl ester.

Preparation of 7-methanesulfonyl-3-oxa-7,9-diaza-bicyclo[3.3.1]nonane (Compound W)

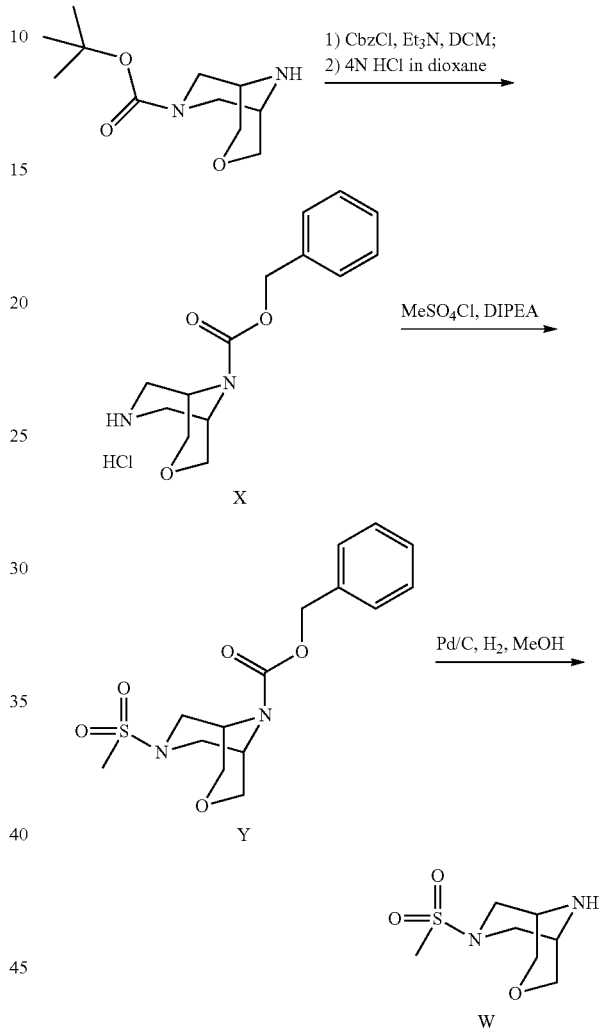

To a solution of 3-oxa-7,9-diaza-bicyclo[3.3.1]nonane-7-carboxylic acid tert-butyl ester (WuXi AppTec (Wuhan) Co., Ltd, CAS: 864448-41-9) (173 mg, 0.76 mmol) in $CH_2Cl_2$ (20 mL) at 0° C. was added DIPEA (195 mg, 1.52 mmol) and CbzCl (155 mg, 0.91 mmol). The reaction mixture was warmed up to room temperature and then stirred for 2 hours. The mixture was quenched with sat. $NH_4Cl$, and then extracted with EtOAc (60 mL). The organic layer was washed with sat. $NH_4Cl$, sat. $NaHCO_3$ and brine (20 mL) respectively, and then dried over $Na_2SO_4$. The solvent was removed to give a white solid (250 mg, 78%), which was dissolved in $CH_2Cl_2$ (2 mL). To the solution was added HCl in dioxane (4 M, 2 mL). The reaction mixture was stirred at room temperature for 2 hours. The solvent was removed to give 3-oxa-7,9-diaza-bicyclo[3.3.1]nonane-9-carboxylic acid benzyl ester (Compound X) (205 mg, 100%) as a white solid. MS: calc'd ($MH^+$) 263, measured ($MH^+$) 263.

To a solution of 3-oxa-7,9-diaza-bicyclo[3.3.1]nonane-9-carboxylic acid benzyl ester (Compound X) (100 mg, 0.33 mmol) in CH₂Cl₂ (5 mL) was added DIPEA (0.23 mL, 1.32 mmol) and methanesulfonyl chloride (57 mg, 0.49 mol). The reaction mixture was stirred at room temperature for 1 hour, and then quenched with sat. NH₄Cl, then diluted with EtOAc (60 mL). The mixture was washed with sat. NH₄Cl, sat. NaHCO₃ and brine (20 mL) respectively. The organic layer was dried over Na₂SO₄. The solvent was removed under reduced pressure to give 7-methanesulfonyl-3-oxa-7,9-diaza-bicyclo[3.3.1]nonane-9-carboxylic acid benzyl ester (Compound Y) (105 mg, 95%) as yellowish oil. MS: calc'd (MH⁺) 341, measured (MH⁺) 341.

To a solution of the crude Compound Y in MeOH (20 mL) was added 10% Pd on carbon (20 mg). The mixture was stirred under one atmosphere pressure of hydrogen at room temperature. After the reaction was completed, the mixture was filtered and concentrated to give 7-methanesulfonyl-3-oxa-7,9-diaza-bicyclo[3.3.1]nonane (Compound W) (50 mg, 78%) which was directly used for next step. MS: calc'd (MH⁺) 207, measured (MH⁺) 207.

To a solution of 3-oxa-7,9-diaza-bicyclo[3.3.1]nonane-9-carboxylic acid benzyl ester (Compound X) (84 mg, 0.28 mmol) in MeOH (5 mL) was added paraformaldehyde (41 mg, 1.38 mmol) and NaBH₄ (21 mg, 0.56 mmol). The reaction mixture was refluxed for 16 hours under argon atmosphere, and then quenched with sat. NaHCO₃, then extracted with EtOAc (20 mL) three times. The combined organic layer was washed successively with sat. NH₄Cl, NaHCO₃ and brine, and then dried over Na₂SO₄. The solvent was concentrated under reduced pressure. The residue was dissolved in MeOH (20 mL). To the solution was added 10% Pd on carbon (20 mg). The mixture was stirred under one atmosphere pressure of hydrogen at room temperature. After the reaction was completed, the mixture was filtered and concentrated to give the crude 7-methyl-3-oxa-7,9-diaza-bicyclo[3.3.1]nonane (Compound Z) (32 mg, 81%) which was directly used for next step. MS: calc'd (MH⁺) 143, measured (MH⁺) 143.

Example 12

(R)-4-(2-Chloro-4-fluoro-phenyl)-6-(7-methyl-3-oxa-7,9-diaza-bicyclo[3.3.1]non-9-ylmethyl)-2-thiazol-2-yl-1,4-dihydro-pyrimidine-5-carboxylic acid methyl ester

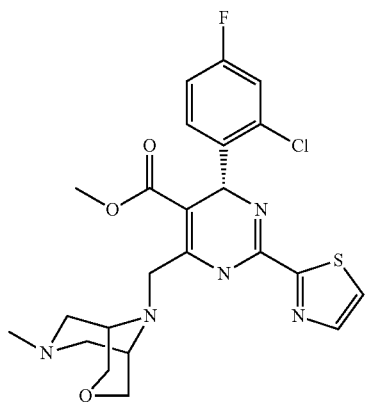 [SMILES: COC(=O)C1=C(CN2C3COCC2CN(C)C3)NC(c2nccs2)=N[C@H]1c1ccc(F)cc1Cl]

The title compound was prepared in analogy to Example 1a with the procedure shown in Scheme 3 by using 7-methyl-3-oxa-7,9-diaza-bicyclo[3.3.1]nonane (Compound Z) instead of 3-oxa-9-aza-bicyclo[3.3.1]nonane-7-carboxylic acid methyl ester.

Preparation of 7-methyl-3-oxa-7,9-diaza-bicyclo[3.3.1]nonane (Compound Z)

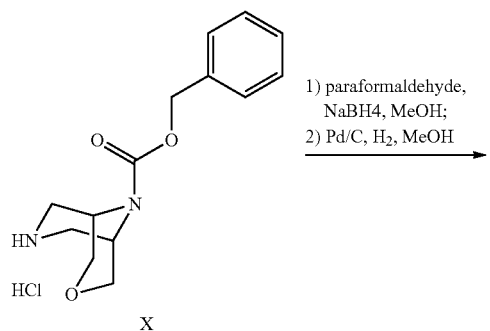

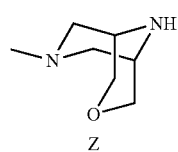

Example 13

(R)-4-(2-Chloro-4-fluoro-phenyl)-6-(7-isopropyl-3-oxa-7,9-diaza-bicyclo[3.3.1]non-9-ylmethyl)-2-thiazol-2-yl-1,4-dihydro-pyrimidine-5-carboxylic acid methyl ester

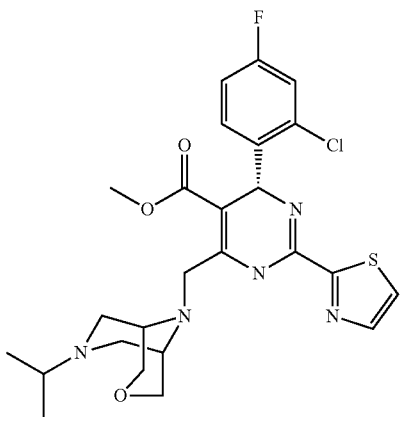 [SMILES: COC(=O)C1=C(CN2C3COCC2CN(C(C)C)C3)NC(c2nccs2)=N[C@H]1c1ccc(F)cc1Cl]

The title compound was prepared in analogy to Example 1a with the procedure shown in Scheme 3 by using 7-isopropyl-3-oxa-7,9-diaza-bicyclo[3.3.1]nonane (Compound AA) instead of 3-oxa-9-aza-bicyclo[3.3.1]nonane-7-carboxylic acid methyl ester.

Preparation of 7-isopropyl-3-oxa-7,9-diaza-bicyclo[3.3.1]nonane (Compound AA)

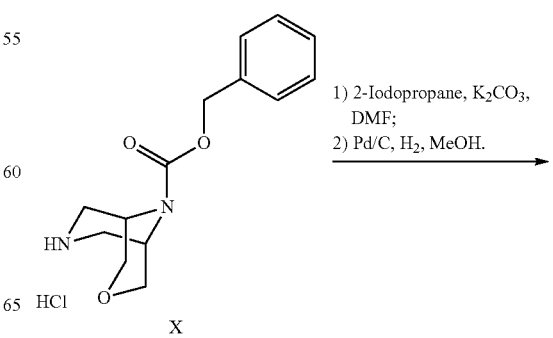

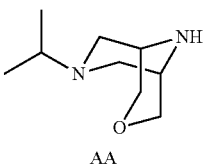

AA

To a solution of 3-oxa-7,9-diaza-bicyclo[3.3.1]nonane-9-carboxylic acid benzyl ester (Compound X) (100 mg, 0.33 mmol) in DMF (5 mL) was added $K_2CO_3$ (91 mg, 0.66 mmol) and 2-iodopropane (111 mg, 0.66 mmol). The reaction mixture was heated to 80° C. and stirred for 16 hours. The mixture was diluted with EtOAc (60 mL), and then washed with sat. $NH_4Cl$, sat. $NaHCO_3$ and brine (20 mL) respectively. The organic layer was dried over $Na_2SO_4$, and then concentrated to give the crude product which was dissolved in MeOH (20 mL). To the solution was added 10% Pd on carbon (20 mg). The mixture was stirred under one atmosphere pressure of $H_2$ at room temperature. After the reaction was completed, the mixture was filtered and concentrated to give the crude 7-isopropyl-3-oxa-7,9-diaza-bicyclo[3.3.1]nonane (Compound AA) (32 mg, 57%) which was directly used for next step. MS: calc'd (MH⁺) 171, measured (MH⁺) 171.

Example 14

(R)-4-(2-Chloro-4-fluoro-phenyl)-6-[7-(2,2-difluoro-ethyl)-3-oxa-7,9-diaza-bicyclo[3.3.1]non-9-ylmethyl]-2-thiazol-2-yl-1,4-dihydro-pyrimidine-5-carboxylic acid methyl ester

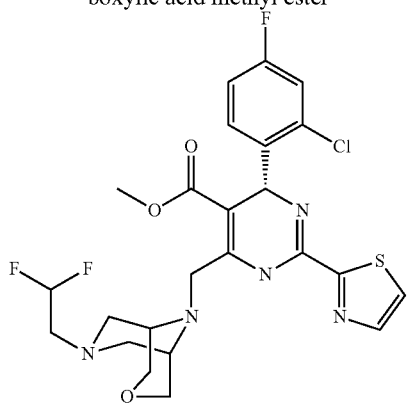

The title compound was prepared in analogy to Example 1a with the procedure shown in Scheme 3 by using 7-(2,2-difluoro-ethyl)-3-oxa-7,9-diaza-bicyclo[3.3.1]nonane (Compound AB) instead of 3-oxa-9-aza-bicyclo[3.3.1]nonane-7-carboxylic acid methyl ester.

Preparation of 7-(2,2-difluoro-ethyl)-3-oxa-7,9-diaza-bicyclo[3.3.1]nonane (Compound AB)

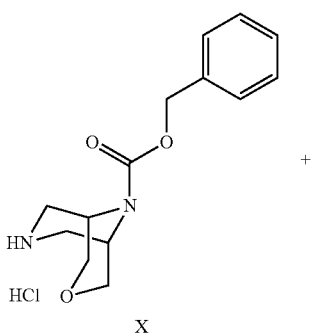

X

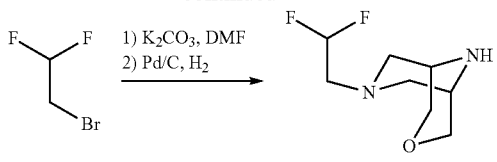

AB

To a solution of 3-oxa-7,9-diaza-bicyclo[3.3.1]nonane-9-carboxylic acid benzyl ester (Compound X) (100 mg, 0.33 mmol) in DMF (5 mL) was added $K_2CO_3$ (91 mg, 0.66 mmol) and 2-iodopropane (95 mg, 0.76 mmol). The reaction mixture was heated to 80° C. and stirred for 16 hours. The mixture was diluted with EtOAc (60 mL), and then washed with sat. $NH_4Cl$, sat. $NaHCO_3$ and brine (20 mL) respectively. The organic layer was dried over $Na_2SO_4$, and then concentrated to give the crude product which was dissolved in MeOH (20 mL). To the solution was added 10% Pd on carbon (20 mg). The mixture was stirred under hydrogen atmosphere at room temperature. After the reaction was completed, the mixture was filtered and concentrated to give the crude 7-(2,2-difluoro-ethyl)-3-oxa-7,9-diaza-bicyclo[3.3.1]nonane (Compound AB) (51 mg, 81%) which was directly used for next step. MS: calc'd (MH⁺) 193, measured (MH⁺) 193.

Example 15

(R)-6-(7-Acetyl-3-oxa-7,9-diaza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester

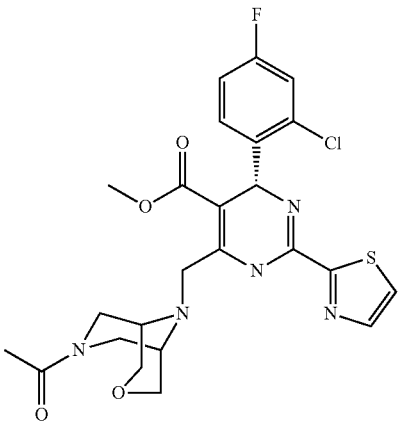 [SMILES: COC(=O)C1=C(CN2C3COCC2CN(C(C)=O)C3)NC(c2nccs2)=N[C@H]1c1ccc(F)cc1Cl]

The title compound was prepared by the procedure shown below (Scheme 5).

Scheme 5

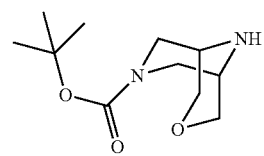

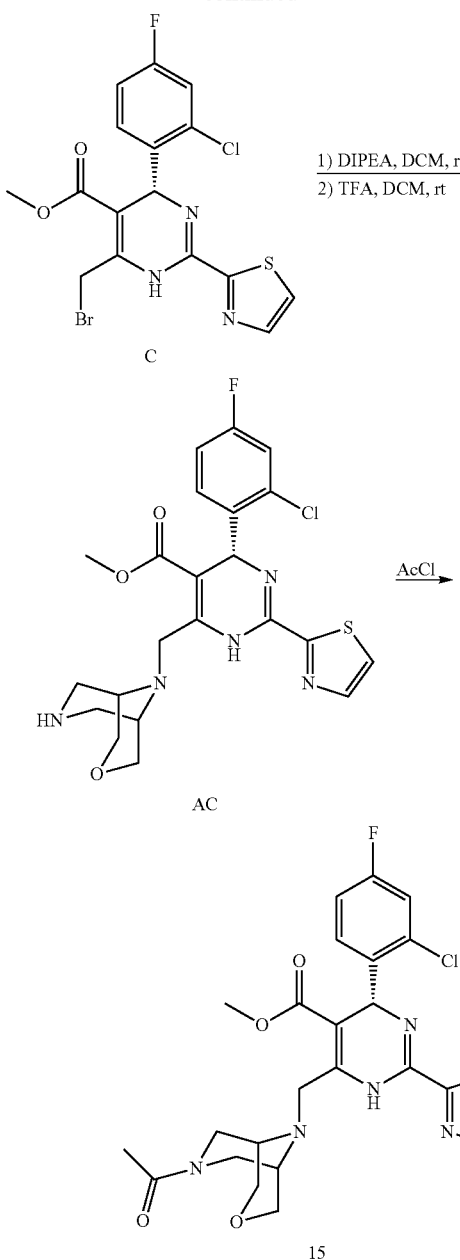

1) DIPEA, DCM, rt
2) TFA, DCM, rt

C

AcCl

AC

15

To a solution of (R)-4-(2-chloro-4-fluoro-phenyl)-6-(3-oxa-7,9-diaza-bicyclo[3.3.1]non-9-ylmethyl)-2-thiazol-2-yl-1,4-dihydro-pyrimidine-5-carboxylic acid methyl ester (Compound AC) (50 mg, 0.1 mmol) and triethylamine (0.042 mL, 0.3 mmol) in CH₂Cl₂ (5 mL) was added acetyl chloride (16 mg, 0.2 mmol) dropwise at ice-bath. The mixture was stirred at 0° C. for 2 hours. The mixture was concentrated in vacuo. The residue was extracted with ethyl acetate (20 mL×2) and then washed with saturated aqueous sodium bicarbonate solution (20 mL×2). The organic layer was dried over anhydrous sodium sulfate and then concentrated in vacuo. The residue was purified by prep-HPLC to afford (R)-6-(7-acetyl-3-oxa-7,9-diaza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester (Example 15) as a light yellow solid (45 mg).

Preparation of (R)-4-(2-chloro-4-fluoro-phenyl)-6-(3-oxa-7,9-diaza-bicyclo[3.3.1]non-9-ylmethyl)-2-thiazol-2-yl-1,4-dihydro-pyrimidine-5-carboxylic acid methyl ester (Compound AC)

To a mixture of 3-oxa-7,9-diaza-bicyclo[3.3.1]nonane-7-carboxylic acid tert-butyl ester (171 mg, 0.75 mmol) and DIPEA (0.45 mL, 2.5 mmol) in CH₂Cl₂ (10 mL) was added (R)-6-bromomethyl-4-(2-chloro-4-fluoro-phenyl)-2-thiazol-2-yl-1,4-dihydro-pyrimidine-5-carboxylic acid methyl ester (222 mg, 0.5 mmol). The mixture was stirred at room temperature for 16 hours. The mixture was concentrated in vacuo. The residue was purified by flash column chromatography to afford 9-[(R)-6-(2-chloro-4-fluoro-phenyl)-5-methoxycarbonyl-2-thiazol-2-yl-3,6-dihydro-pyrimidin-4-ylmethyl]-3-oxa-7,9-diaza-bicyclo[3.3.1]nonane-7-carboxylic acid tert-butyl ester as yellow oil (0.28 g, 94%). MS: calc'd (MH⁺) 592, measured (MH⁺) 592.

To a solution of 9-[(R)-6-(2-chloro-4-fluoro-phenyl)-5-methoxycarbonyl-2-thiazol-2-yl-3,6-dihydro-pyrimidin-4-ylmethyl]-3-oxa-7,9-diaza-bicyclo[3.3.1]nonane-7-carboxylic acid tert-butyl ester (280 mg, 0.47 mmol) in CH₂Cl₂ (10 mL) was added TFA (2 mL) dropwise in ice-bath. The mixture was stirred at room temperature for 16 hours. The mixture was neutralized with a saturated aqueous sodium bicarbonate solution and then extracted with CH₂Cl₂ (20 mL×2). The organic layer was washed with saturated aqueous sodium bicarbonate solution (20 mL×2), and then dried over anhydrous sodium sulfate and then concentrated in vacuo to afford (R)-6-(7-acetyl-3-oxa-7,9-diaza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester (Compound AC) as light yellow oil (230 mg, 98%) which was used for next step without further purification. MS: calc'd (MH⁺) 492, measured (MH⁺) 492.

Example 16

(R)-4-(2-Chloro-4-fluoro-phenyl)-6-(7-methylsulfamoyl-3-oxa-7,9-diaza-bicyclo[3.3.1]non-9-ylmethyl)-2-thiazol-2-yl-1,4-dihydro-pyrimidine-5-carboxylic acid methyl ester

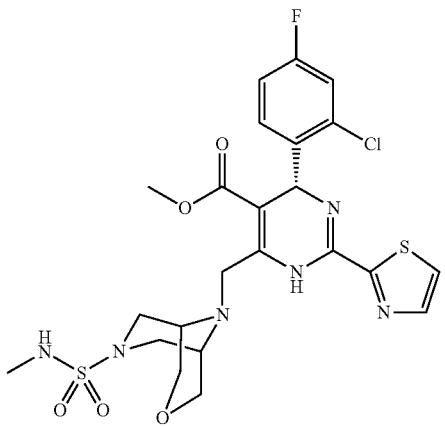 [SMILES: CNS(=O)(=O)N1CC2COCC(C1)N2CC1=C(C(=O)OC)[C@H](c2ccc(F)cc2Cl)N=C(c2nccs2)N1]

105

The title compound was prepared by the procedure shown below.

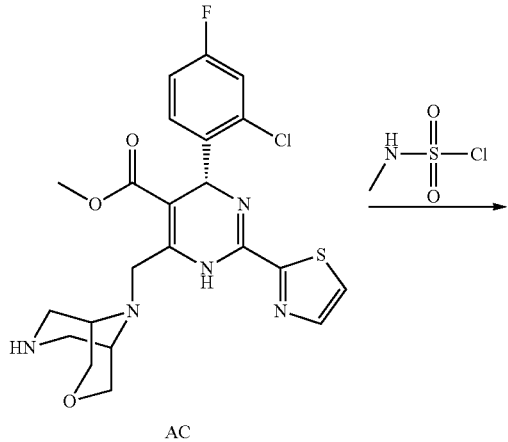

AC

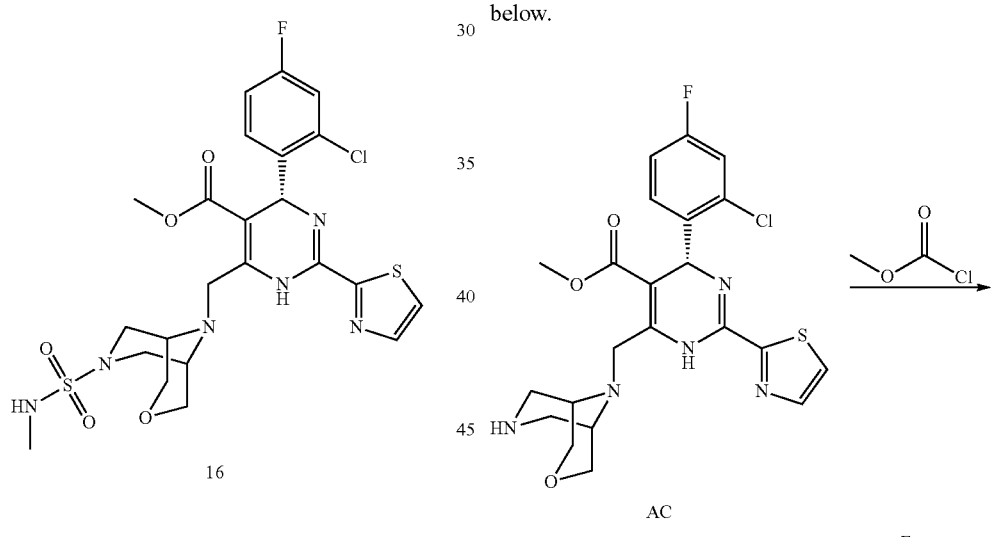

16

To a solution of (R)-4-(2-chloro-4-fluoro-phenyl)-6-(3-oxa-7,9-diaza-bicyclo[3.3.1]non-9-ylmethyl)-2-thiazol-2-yl-1,4-dihydro-pyrimidine-5-carboxylic acid methyl ester (Compound AC) (50 mg, 0.1 mmol) and triethylamine (0.042 mL, 0.3 mmol) in CH$_2$Cl$_2$ (5 mL) was added methylsulfamoyl chloride (26 mg, 0.2 mmol) dropwise in ice-bath. The mixture was stirred at 0° C. for 2 hours. The mixture was concentrated in vacuo. The residue was extracted with ethyl acetate (20 mL×2). The organic layer was washed with saturated aqueous sodium bicarbonate solution (20 mL×2), and then dried over anhydrous sodium sulfate and then concentrated in vacuo. The residue was purified by preparative HPLC to afford Example 16 as a light yellow solid (35 mg)

106

Example 17

9-[(R)-6-(2-Chloro-4-fluoro-phenyl)-5-methoxycarbonyl-2-thiazol-2-yl-3,6-dihydro-pyrimidin-4-ylmethyl]-3-oxa-7,9-diaza-bicyclo[3.3.1]nonane-7-carboxylic acid methyl ester

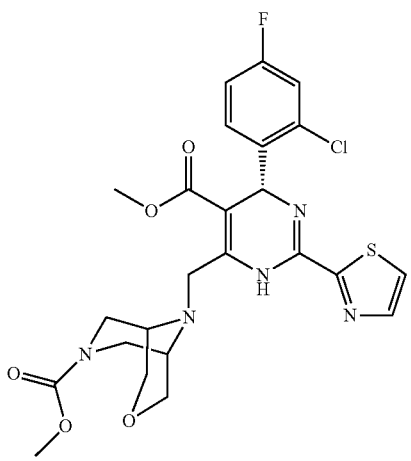 [SMILES: COC(=O)C1=C(CN2C3COCC2CN(C(=O)OC)C3)NC(c2nccs2)=N[C@H]1c1ccc(F)cc1Cl]

The title compound was prepared by the procedure shown below.

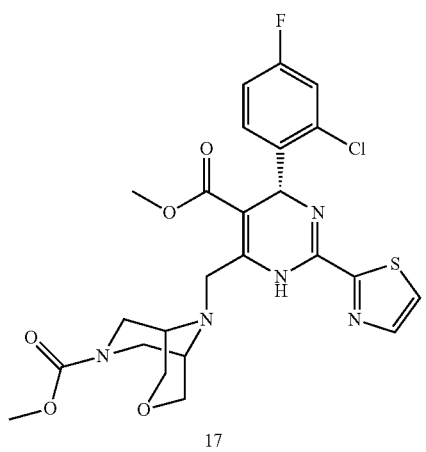

AC

17

To a solution of (R)-4-(2-chloro-4-fluoro-phenyl)-6-(3-oxa-7,9-diaza-bicyclo[3.3.1]non-9-ylmethyl)-2-thiazol-2-yl-1,4-dihydro-pyrimidine-5-carboxylic acid methyl ester (compound AC) (50 mg, 0.1 mmol) and triethylamine (0.042 mL, 0.3 mmol) in CH$_2$Cl$_2$ (5 mL) was added methyl chloroformate (19 mg, 0.2 mmol) dropwise in ice-bath. The mixture was stirred at 0° C. for 3 hours. The mixture was concentrated in vacuo. The residue was extracted with ethyl acetate (20 mL×2). The organic layer was washed with saturated aqueous sodium bicarbonate solution (20 mL×2), and then dried over anhydrous sodium sulfate and then concentrated in vacuo. The residue was purified by preparative HPLC to afford Example 17 as a light yellow solid (19 mg).

Example 18

(R)-6-(7-Carbamoyl-3-oxa-7,9-diaza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester

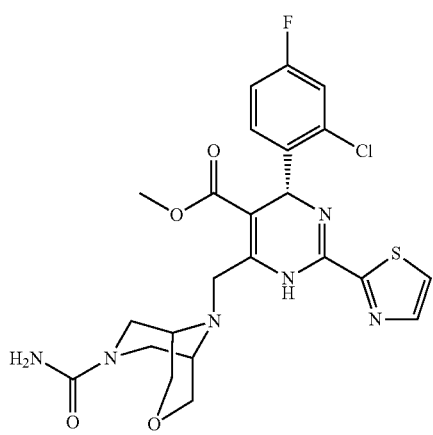 [SMILES: COC(=O)C1=C(CN2C3COCC2CN(C(N)=O)C3)NC(c2nccs2)=N[C@H]1c1ccc(F)cc1Cl]

The title compound was prepared by the procedure shown below.

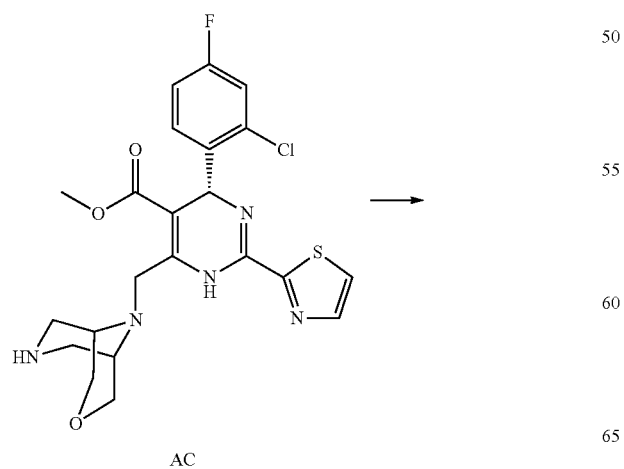

AC

-continued

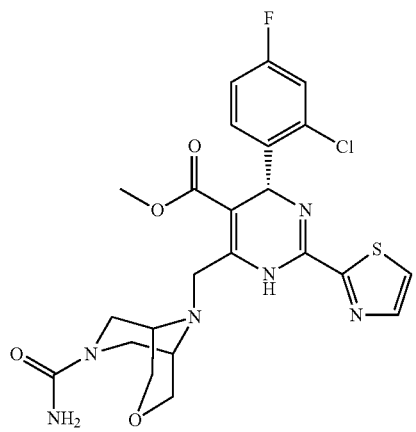

18

To a solution of (R)-4-(2-chloro-4-fluoro-phenyl)-6-(3-oxa-7,9-diaza-bicyclo[3.3.1]non-9-ylmethyl)-2-thiazol-2-yl-1,4-dihydro-pyrimidine-5-carboxylic acid methyl ester (Compound AC) (60 mg, 0.12 mmol) and triethylamine (0.17 mL, 1.2 mmol) in CH$_2$Cl$_2$ (5 mL) was added trimethylsilanyl isocyanate (55 mg, 0.48 mmol) dropwise in ice-bath. The mixture was stirred at 0° C. for 16 hours. The mixture was concentrated in vacuo. The residue was purified by preparative HPLC to afford Example 18 as a light yellow solid (19 mg).

Example 19

(R)-4-(2-Chloro-4-fluoro-phenyl)-6-(7-sulfamoyl-3-oxa-7,9-diaza-bicyclo[3.3.1]non-9-ylmethyl)-2-thiazol-2-yl-1,4-dihydro-pyrimidine-5-carboxylic acid methyl ester

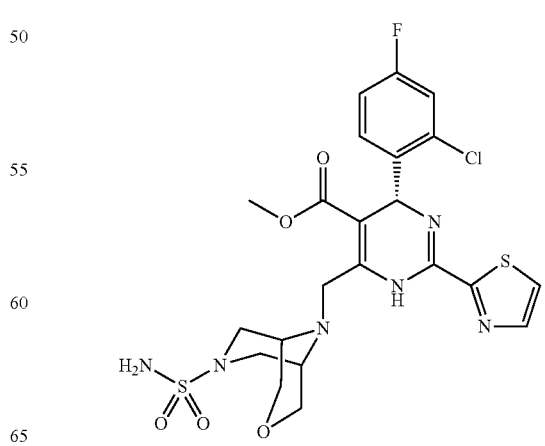

The title compound was prepared by the procedure shown below.

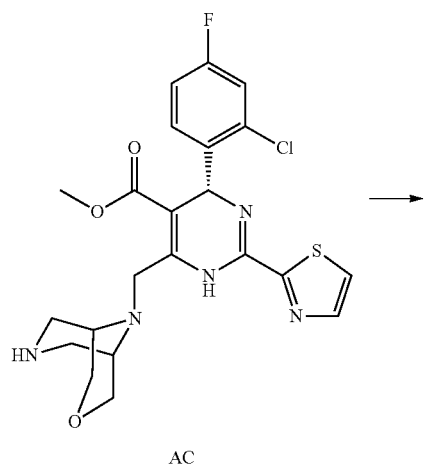

AC

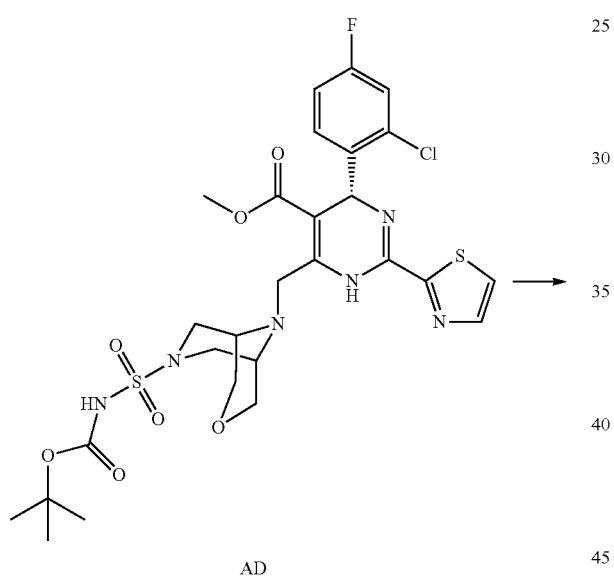

AD

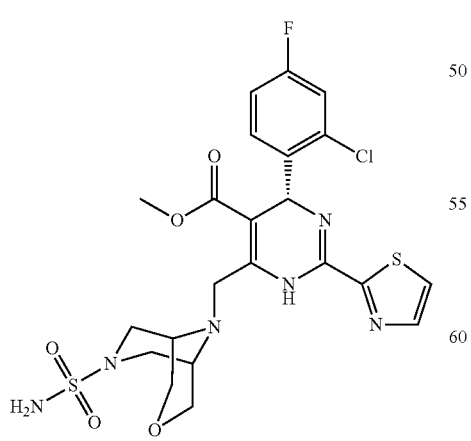

19

To a solution of Compound AD in CH₂Cl₂ (5 mL) was added TFA (0.5 mL) dropwise in ice-bath. The mixture was stirred at room temperature for 2 hours. The mixture was neutralized with a saturated aqueous sodium bicarbonate solution and then extracted with CH₂Cl₂ (20 mL×2). The organic layer was washed with saturated aqueous sodium bicarbonate solution (20 mL×2), and then dried over anhydrous sodium sulfate and then concentrated in vacuo. The residue was purified by preparative HPLC to afford Example 19 as a light yellow solid (18 mg).

Preparation of Compound AD

To a solution of chlorosulfonyl isocyanate (0.087 mL, 1 mmol) in CH₂Cl₂ (20 mL) was added tert-butanol (0.096 mL, 1 mmol) in ice-bath. The mixture was stirred at room temperature for 2 hours. A solution of N-tert-butoxycarbonylsulfamoyl chloride in CH₂Cl₂ (~0.05 M) was obtained, which was used for next step without further purification.

To a solution of (R)-4-(2-chloro-4-fluoro-phenyl)-6-(3-oxa-7,9-diaza-bicyclo[3.3.1]non-9-ylmethyl)-2-thiazol-2-yl-1,4-dihydro-pyrimidine-5-carboxylic acid methyl ester (60 mg, 0.12 mmol) and triethylamine (0.05 mL, 0.36 mmol) in CH₂Cl₂ (10 mL) was added N-tert-butoxycarbonylsulfamoyl chloride in dichloromethane (0.05 M, 2.5 mL, 0.125 mmol) dropwise in ice-bath. The mixture was stirred at 0° C. for 1 hour. The mixture was concentrated in vacuo. The residue was purified by flash column chromatography to afford compound AD as a brown solid (80 mg, 99%). MS: calc'd (MH⁺) 671, measured (MH⁺) 671.

Example 20

(R)-4-(2-Chloro-4-fluoro-phenyl)-6-[7-(1-ethoxycarbonyl-1-methyl-ethyl)-3-oxa-7,9-diaza-bicyclo[3.3.1]non-9-ylmethyl]-2-thiazol-2-yl-1,4-dihydro-pyrimidine-5-carboxylic acid methyl ester

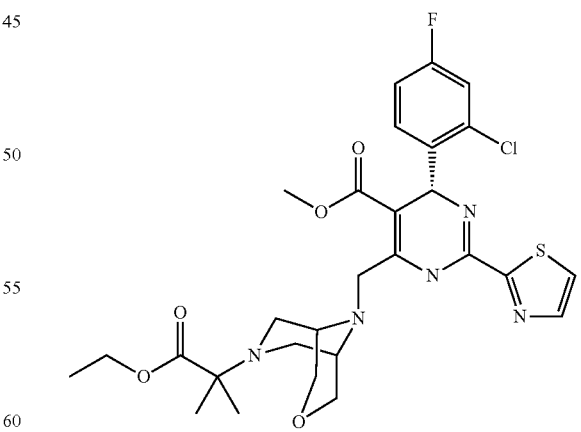

The title compound was prepared in analogy to Example 1a with the procedure shown in Scheme 3 by using 2-methyl-2-(3-oxa-7,9-diaza-bicyclo[3.3.1]non-7-yl)-propionic acid ethyl ester (Compound AE) instead of 3-oxa-9-aza-bicyclo[3.3.1]nonane-7-carboxylic acid methyl ester.

Preparation of 2-methyl-2-(3-oxa-7,9-diaza-bicyclo[3.3.1]non-7-yl)-propionic acid ethyl ester (Compound AE)

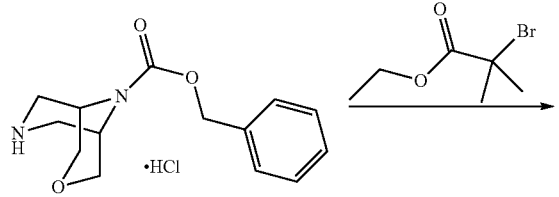

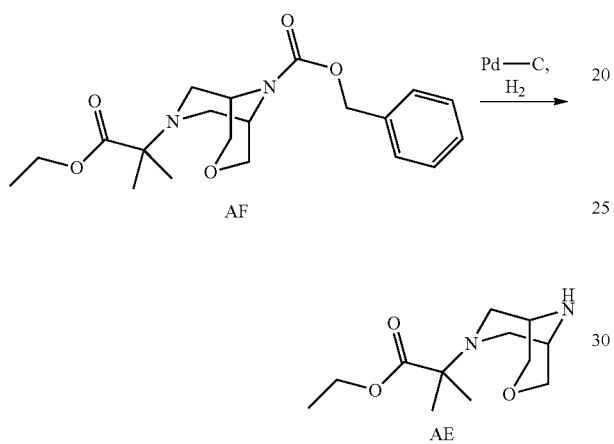

A mixture of 7-(1-ethoxycarbonyl-1-methyl-ethyl)-3-oxa-7,9-diaza-bicyclo[3.3.1]nonane-9-carboxylic acid benzyl ester (Compound X) (130 mg, 0.50 mmol), cesium carbonate (489 mg, 1.5 mmol) and 2-bromo-2-methyl-propionic acid ethyl ester (0.15 mL, 1.0 mmol) in N,N-dimethylformamide (3 mL) was stirred at 80° C. for 5 hours. The mixture was then filtered and washed with ethyl acetate (20 mL×2). The filtrate was concentrated in vacuo and the residue was purified by flash column chromatography to afford 7-(1-ethoxycarbonyl-1-methyl-ethyl)-3-oxa-7,9-diaza-bicyclo[3.3.1]nonane-9-carboxylic acid benzyl ester (Compound AF) as brown oil (0.090 g, 47%). MS: calc'd (MH$^+$) 377, measured (MH$^+$) 377.

A mixture of 2-methyl-2-(3-oxa-7,9-diaza-bicyclo[3.3.1]non-7-yl)-propionic acid ethyl ester (Compound AF) (90 mg, 0.24 mmol) and 10% palladium on activated carbon (20 mg) in methanol (20 mL) was stirred at room temperature under hydrogen pressure (30 psi) for 16 hours. The catalyst was filtered off and the filtrate was concentrate in vacuo to afford 2-methyl-2-(3-oxa-7,9-diaza-bicyclo[3.3.1]non-7-yl)-propionic acid ethyl ester (Compound AE) as light yellow oil (55 mg, 95%) which was used directly in the coupling reaction without further purification. MS: calc'd (MH$^+$) 242, measured (MH$^+$) 242.

Example 21

(R)-4-(2-Chloro-4-fluoro-phenyl)-6-[7-(2-hydroxy-acetyl)-3-oxa-7,9-diaza-bicyclo[3.3.1]non-9-ylmethyl]-2-thiazol-2-yl-1,4-dihydro-pyrimidine-5-carboxylic acid methyl ester

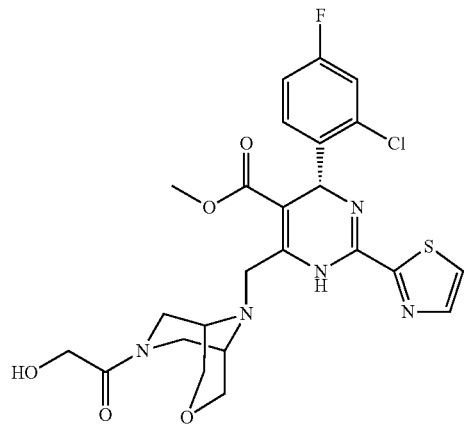 [SMILES: COC(=O)C1=C(CN2C3COCC2CN(C(=O)CO)C3)NC(c2nccs2)=N[C@H]1c1ccc(F)cc1Cl]

Preparation of Example 21

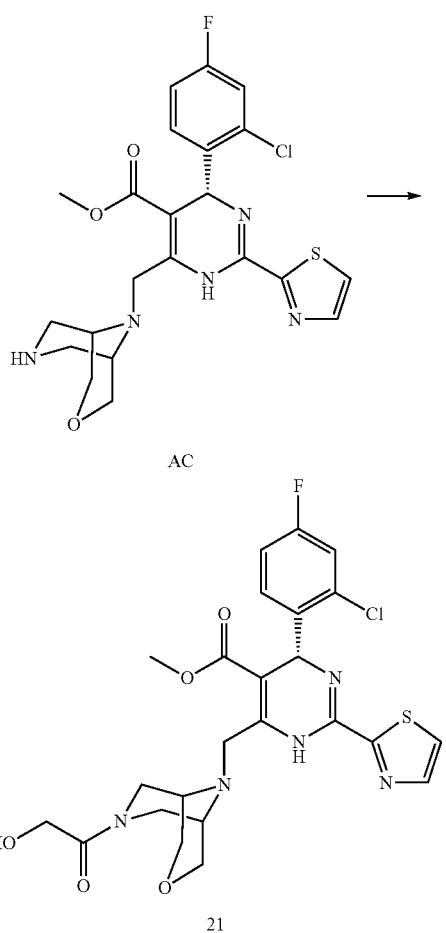

A mixture of (R)-4-(2-chloro-4-fluoro-phenyl)-6-(3-oxa-7,9-diaza-bicyclo[3.3.1]non-9-ylmethyl)-2-thiazol-2-yl-1,4-dihydro-pyrimidine-5-carboxylic acid methyl ester (Compound AC) (61.4 mg, 0.125 mmol), glycolic acid (20 mg, 0.25 mmol), EDCI (48 mg, 0.25 mmol) and triethylamine (0.09 mL, 0.625 mmol) in CH$_2$Cl$_2$ (5 mL) was stirred at room temperature for 16 hours. The mixture was concentrated in

Example 22

7-[(R)-6-(2-Chloro-4-fluoro-phenyl)-5-methoxycarbonyl-2-thiazol-2-yl-3,6-dihydro-pyrimidin-4-ylmethyl]-9-oxa-3,7-diaza-bicyclo[3.3.1]nonane-3-carboxylic acid tert-butyl ester

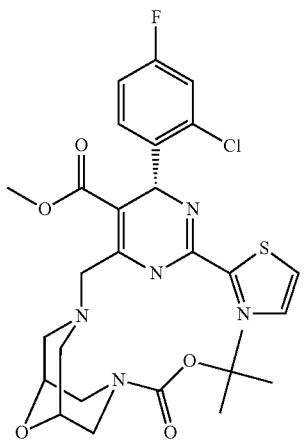 [SMILES: COC(=O)C1=C(CN2CC3CN(C(=O)OC(C)(C)C)CC(C2)O3)NC(c2nccs2)=N[C@H]1c1ccc(F)cc1Cl]

The title compound was prepared in analogy to Example 1a with the procedure shown in Scheme 3 by using 9-oxa-3,7-diaza-bicyclo[3.3.1]nonane-3-carboxylic acid tert-butyl ester (WuXi AppTec (Wuhan) Co., Ltd, CAS: 478647-20-0) instead of 3-oxa-9-aza-bicyclo[3.3.1]nonane-7-carboxylic acid methyl ester.

Example 23

(S)-2-[(R)-6-(2-Chloro-4-fluoro-phenyl)-5-methoxycarbonyl-2-thiazol-2-yl-3,6-dihydro-pyrimidin-4-ylmethyl]-5,5-difluoro-2-aza-bicyclo[2.2.2]octane-3-carboxylic acid

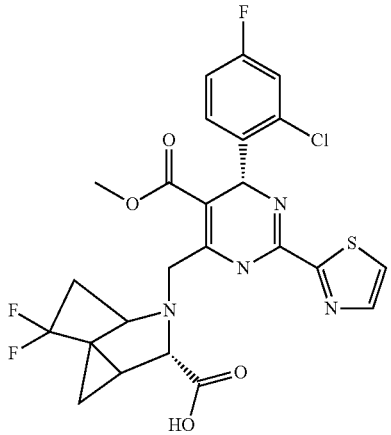 [SMILES: COC(=O)C1=C(CN2C3CC(F)(F)C34CC4[C@H]2C(=O)O)NC(c2nccs2)=N[C@H]1c1ccc(F)cc1Cl]

The title compound was prepared in analogy to Example 1a with the procedure shown in Scheme 3 by using (S)-6,6-difluoro-2-aza-bicyclo[2.2.2]octane-3-carboxylic acid (WuXi AppTec (Wuhan) Co., Ltd, CAS: 1394117-03-3) instead of 3-oxa-9-aza-bicyclo[3.3.1]nonane-7-carboxylic acid methyl ester.

Example 24

(R)-6-(7-Carboxymethyl-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester

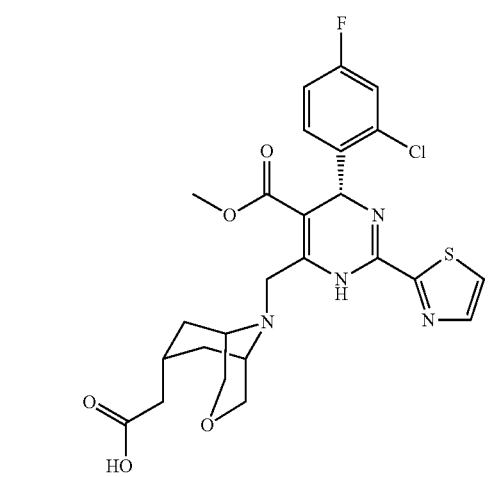 [SMILES: COC(=O)C1=C(CN2C3COCC2CC(CC(=O)O)C3)NC(c2nccs2)=N[C@H]1c1ccc(F)cc1Cl]

The title compound was prepared in analogy to Example 1a with the procedure shown in Scheme 3 by using (3-oxa-9-aza-bicyclo[3.3.1]non-7-yl)-acetic acid (PharmaBlock (Nanjing) R&D Co. Ltd, CAS: 1389441-75-1) instead of 3-oxa-9-aza-bicyclo[3.3.1]nonane-7-carboxylic acid methyl ester.

Example 25

(R)-4-(2-Chloro-4-fluoro-phenyl)-6-(7-methoxycarbonylmethyl-3-oxa-9-aza-bicyclo[3.3.1]non-9-ylmethyl)-2-thiazol-2-yl-1,4-dihydro-pyrimidine-5-carboxylic acid methyl ester

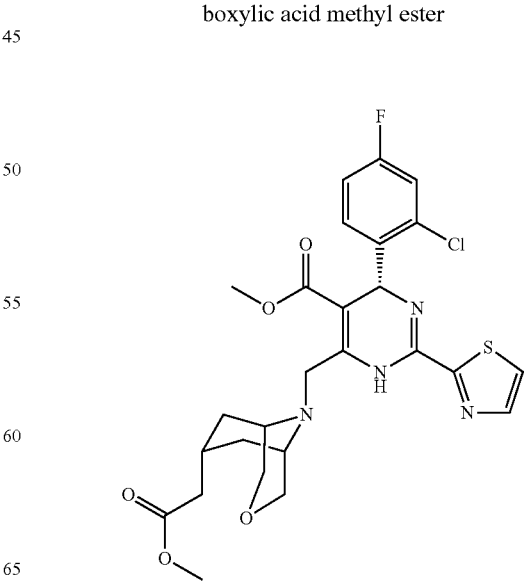

The title compound was prepared in analogy to Example 1a with the procedure shown in Scheme 3 by using (3-oxa-9-aza-bicyclo[3.3.1]non-7-yl)-acetic acid methyl ester (compound AG) instead of 3-oxa-9-aza-bicyclo[3.3.1]nonane-7-carboxylic acid methyl ester.

Preparation of Compound AG

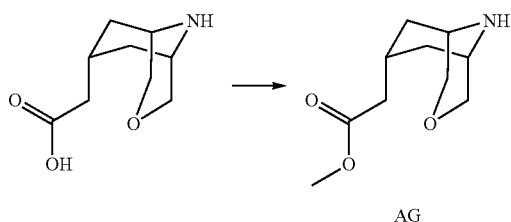

To a solution of (3-oxa-9-aza-bicyclo[3.3.1]non-7-yl)-acetic acid (200 mg, 0.9 mmol) in 10 mL of methanol was added dropwise sulfuryl chloride (0.3 mL, 1.8 mmol) under ice cooling. After the mixture was refluxed for 3 hours, it was concentrated in vacuo. The residue was extracted with ethyl acetate (20 mL×2). The organic layer was washed with saturated aqueous sodium bicarbonate solution (20 mL×2), and then dried over anhydrous sodium sulfate and then concentrated in vacuo to afford (3-oxa-9-aza-bicyclo[3.3.1]non-7-yl)-acetic acid methyl ester (Compound AG) as colorless oil (179 mg, 99%) which was used directly in next step without further purification. MS: calc'd (MH$^+$) 200, measured (MH$^+$) 200.

Example 26

(R)-6-(7-Carboxymethyl-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid ethyl ester

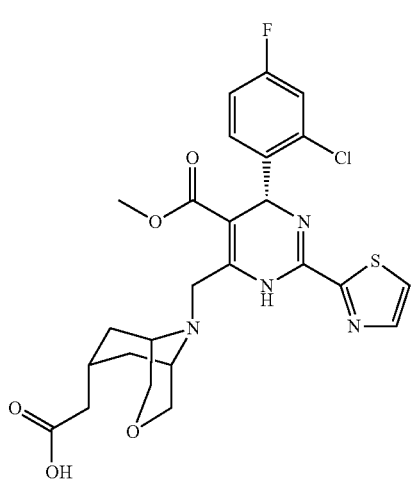 [SMILES: COC(=O)C1=C(CN2C3COCC2CC(CC(=O)O)C3)NC(c2nccs2)=N[C@H]1c1ccc(F)cc1Cl]

The title compound was prepared in analogy to Example 1a with the procedure shown in Scheme 3 by using ethyl acetoacetate instead of methyl acetoacetate and (3-oxa-9-aza-bicyclo[3.3.1]non-7-yl)-acetic acid (PharmaBlock (Nanjing) R&D Co. Ltd, CAS: 1389441-75-1) instead of 3-oxa-9-aza-bicyclo[3.3.1]nonane-7-carboxylic acid methyl ester.

Example 27

6-(7-Carboxymethyl-3-oxa-9-aza-bicyclo[3.3.1]non-9-ylmethyl)-4-(3,4-difluoro-phenyl)-2-thiazol-2-yl-1,4-dihydro-pyrimidine-5-carboxylic acid methyl ester

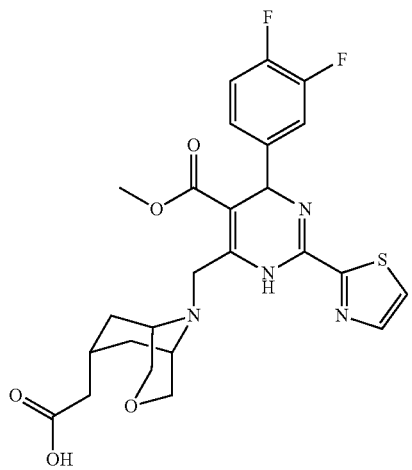 [SMILES: COC(=O)C1=C(CN2C3COCC2CC(CC(=O)O)C3)NC(c2nccs2)=NC1c1ccc(F)c(F)c1]

The title compound was prepared in analogy to Example 3 with the procedure shown in Scheme 4 by using (3-oxa-9-aza-bicyclo[3.3.1]non-7-yl)-acetic acid (PharmaBlock (Nanjing) R&D Co. Ltd, CAS: 1389441-75-1) instead of 3-oxa-9-aza-bicyclo[3.3.1]nonane-7-carboxylic acid methyl ester.

Example 28

(R)-4-(2-Bromo-4-fluoro-phenyl)-6-(7-carboxymethyl-3-oxa-9-aza-bicyclo[3.3.1]non-9-ylmethyl)-2-thiazol-2-yl-1,4-dihydro-pyrimidine-5-carboxylic acid methyl ester

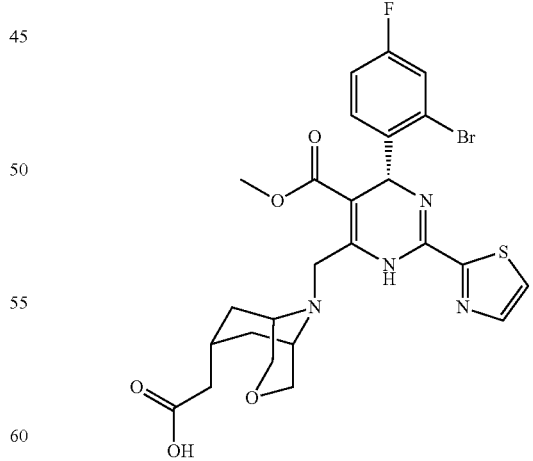

The title compound was prepared in analogy to Example 1a with the procedure shown in Scheme 3 by using 2-bromo-5-fluorobenzaldehyde instead of 2-chloro-5-fluorobenzaldehyde and (3-oxa-9-aza-bicyclo[3.3.1]non-7-yl)-acetic acid (PharmaBlock (Nanjing) R&D Co. Ltd, CAS: 1389441-75-

1) instead of 3-oxa-9-aza-bicyclo[3.3.1]nonane-7-carboxylic acid methyl ester.

Example 29

(S)-6-(7-Carboxymethyl-3-oxa-9-aza-bicyclo[3.3.1]non-9-ylmethyl)-4-(3,4-difluoro-phenyl)-2-thiazol-2-yl-1,4-dihydro-pyrimidine-5-carboxylic acid ethyl ester

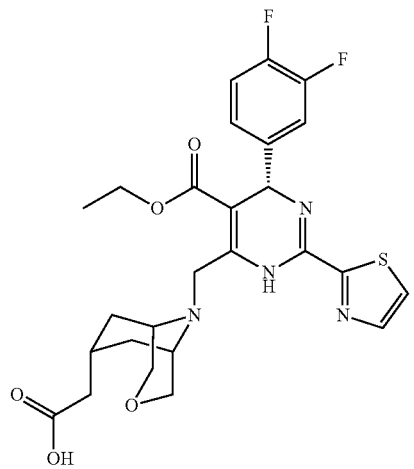 [SMILES: CCOC(=O)C1=C(CN2C3COCC2CC(CC(=O)O)C3)NC(c2nccs2)=N[C@H]1c1ccc(F)c(F)c1]

The title compound was prepared in analogy to Example 1a with the procedure shown in Scheme 3 by using 3,4-diflurobenzaldehyde instead of 2-chloro-5-fluorobenzaldehyde, ethyl acetoacetate and (3-oxa-9-aza-bicyclo[3.3.1]non-7-yl)-acetic acid (PharmaBlock (Nanjing) R&D Co. Ltd, CAS: 1389441-75-1) instead of 3-oxa-9-aza-bicyclo[3.3.1]nonane-7-carboxylic acid methyl ester.

Example 30

(R)-4-(2-Chloro-4-fluoro-phenyl)-6-[7-(hydroxy-methoxycarbonyl-methyl)-3-oxa-9-aza-bicyclo[3.3.1]non-9-ylmethyl]-2-thiazol-2-yl-1,4-dihydro-pyrimidine-5-carboxylic acid methyl ester

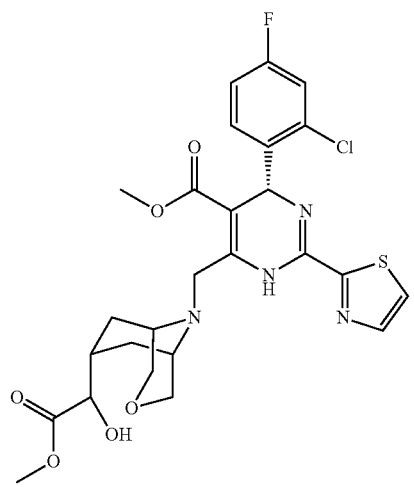 [SMILES: COC(=O)C1=C(CN2C3COCC2CC(C(O)C(=O)OC)C3)NC(c2nccs2)=N[C@H]1c1ccc(F)cc1Cl]

The title compound was prepared in analogy to Example 1a with the procedure shown in Scheme 3 by using hydroxy-(3-oxa-9-aza-bicyclo[3.3.1]non-7-yl)-acetic acid methyl ester (Compound AH) instead of 3-oxa-9-aza-bicyclo[3.3.1]nonane-7-carboxylic acid methyl ester.

Preparation of hydroxy-(3-oxa-9-aza-bicyclo[3.3.1]non-7-yl)-acetic acid methyl ester (Compound AH)

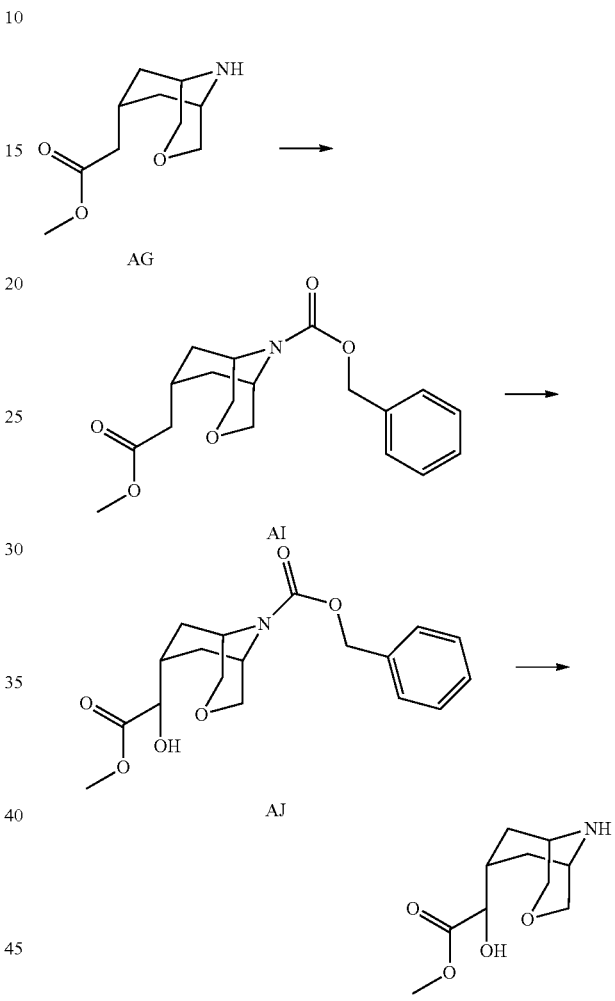

Step I: To a stirred solution of (3-oxa-9-aza-bicyclo[3.3.1]non-7-yl)-acetic acid methyl ester (Compound AG) (179 mg, 0.90 mmol) in 10 mL of dichloromethane was added triethylamine (0.5 mL, 3.6 mmol). The mixture was stirred at room temperature for 15 mins and then benzyl chloroformate (0.25 mL, 1.8 mmol) was added dropwise at 0° C. After the reaction mixture was stirred at room temperature for 2 hours, it was concentrated in vacuo. The residue was purified by flash column chromatography to afford 7-methoxycarbonylmethyl-3-oxa-9-aza-bicyclo[3.3.1]nonane-9-carboxylic acid benzyl ester as colorless oil (Compound AI) (0.13 g, 44%) MS: calc'd (MH$^+$) 334, measured (MH$^+$) 334.

Step II: To a stirred solution of 7-methoxycarbonylmethyl-3-oxa-9-aza-bicyclo[3.3.1]nonane-9-carboxylic acid benzyl ester (Compound AI) (130 mg, 0.39 mmol) in anhydrous THF at −78° C. was added 1 M NaN(trimethylsilyl)$_2$ in THF (0.43 mL, 0.43 mmol) during a period of 5 mins. Then the mixture was stirred for 20 mins at −78° C. To this solution was added a pre-cooled (−78° C.) solution of 2-(phenylsulfonyl)-3-phenyloxaziridine (153 mg, 0.585 mmol) in THF. The solution was stirred for 30 mins at −78° C. and then quenched by rapid addition of 6N HCl. The mixture was stirred at room temperature for 30 mins and then diluted with dichloromethane. The mixture was washed with water and 5% aqueous sodium bicarbonate. The organic layer was dried over anhydrous sodium sulfate and then concentrated in vacuo. The residue was purified by flash column chromatography to afford 7-(hydroxy-methoxycarbonyl-methyl)-3-oxa-9-aza-bicyclo[3.3.1]nonane-9-carboxylic acid benzyl ester (Compound AJ) (0.30 g, 85%). MS: calc'd (MH$^+$) 350, measured (MH$^+$) 350.

Step III: A mixture of 7-(hydroxy-methoxycarbonyl-methyl)-3-oxa-9-aza-bicyclo[3.3.1]nonane-9-carboxylic acid benzyl ester (Compound AJ) (300 mg, 0.86 mmol) and 10% palladium on active carbon (100 mg) in methanol (10 mL) was stirred at room temperature under hydrogen (30 psi) for 16 hours. The catalyst was filtered off. The filtrate was concentrate in vacuo to afford hydroxy-(3-oxa-9-aza-bicyclo[3.3.1]non-7-yl)-acetic acid methyl ester (Compound AH) (107 mg, 57%) which was used for the next step without further purification. MS: calc'd (MH$^+$) 216, measured (MH$^+$) 216.

Example 31

(R)-4-(2-Chloro-4-fluoro-phenyl)-6-(10-oxa-4,5,12-triaza-tricyclo[6.3.1.0*2,6*]dodeca-2(6),3-dien-12-ylmethyl)-2-thiazol-2-yl-1,4-dihydro-pyrimidine-5-carboxylic acid methyl ester

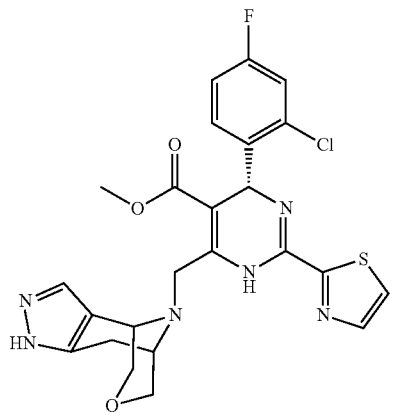 [SMILES: COC(=O)C1=C(CN2C3COCC2c2cn[nH]c2C3)NC(c2nccs2)=N[C@H]1c1ccc(F)cc1Cl]

The title compound was prepared in analogy to Example 1a with the procedure shown in Scheme 3 by using 10-oxa-4,5,12-triaza-tricyclo[6.3.1.0*2,6*]dodeca-2(6),3-diene-12-carboxylic acid tert-butyl ester (WuXi AppTec (Wuhan) Co., Ltd, CAS: 1311183-41-1) instead of 3-oxa-9-aza-bicyclo[3.3.1]nonane-7-carboxylic acid methyl ester.

Example 32

(R)-4-(2-Chloro-4-fluoro-phenyl)-6-(3-methyl-10-oxa-4,5,12-triaza-tricyclo[6.3.1.0*2,6*]dodeca-2(6),3-dien-12-ylmethyl)-2-thiazol-2-yl-1,4-dihydro-pyrimidine-5-carboxylic acid methyl ester

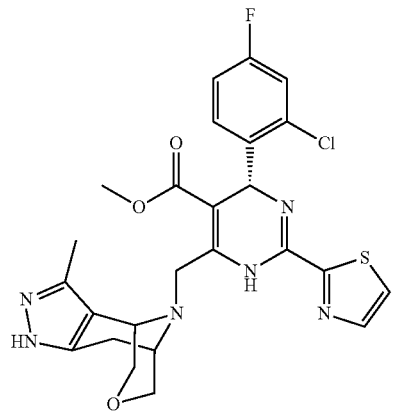 [SMILES: COC(=O)C1=C(CN2C3COCC2c2c(C)n[nH]c2C3)NC(c2nccs2)=N[C@H]1c1ccc(F)cc1Cl]

The title compound was prepared in analogy to Example 1a with the procedure shown in Scheme 3 by using 3-methyl-10-oxa-4,5,12-triaza-tricyclo[6.3.1.0*2,6*]dodeca-2(6),3-diene (Compound AK) instead of 3-oxa-9-aza-bicyclo[3.3.1]nonane-7-carboxylic acid methyl ester.

Preparation of 3-methyl-10-oxa-4,5,12-triaza-tricyclo[6.3.1.0*2,6*]dodeca-2(6),3-diene (Compound AK)

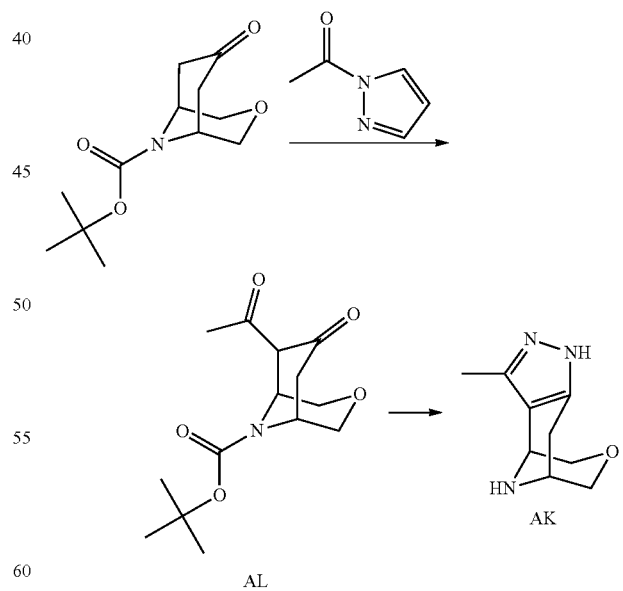

Step I: To a solution of 7-oxo-3-oxa-9-aza-bicyclo[3.3.1]nonane-9-carboxylic acid tert-butyl ester (482 mg, 2 mmol) in THF (5 mL) was added LiHMDS (3 mL, 3 mmol) slowly at −78° C. After 15 mins, 1-pyrazol-1-yl-ethanone (264 mg, 2.4 mmol) was added, and the resulting mixture was stirred at −78° C. for 1 hour and then at room temperature for 1 hour. The reaction mixture was quenched with water, and then extracted with EA (20 mL×2). The organic layer was concentrated in vacuo. The residue was purified by flash chromatography (EA in PE 0%~70%) to afford 6-acetyl-7-oxo-3-oxa-9-aza-bicyclo[3.3.1]nonane-9-carboxylic acid tert-butyl ester (compound AL) as light yellow oil (56 mg, 20%). LC/MS: calc'd 284 (MH⁺), exp 284 (MH⁺).

Step II: To a solution of Compound AL (56 mg, 0.2 mmol) in EtOH (4 mL) was added hydrazine monohydrate (50 mg, 1.0 mmol), then the reaction mixture was sealed and heated at 80° C. for 2 hours. The reaction mixture was concentrated in vacuo. The residue was dissolved in DCM/TFA (3 mL, 2:1) and then stirred at room temperature for 2 hours. The solvent was removed and the residue was dried under vacuum to afford 3-methyl-10-oxa-4,5,12-triaza-tricyclo[6.3.1.0*2,6*]dodeca-2(6),3-diene (Compound AK) as yellow foam (crude 50 mg, 100%). LC/MS: calc'd 184 (MH⁺), exp 184 (MH⁺).

Example 33

(R)-4-(2-Chloro-4-fluoro-phenyl)-6-(5-methyl-3-oxo-10-oxa-4,5,12-triaza-tricyclo[6.3.1.0*2,6*]dodec-2(6)-en-12-ylmethyl)-2-thiazol-2-yl-1,4-dihydro-pyrimidine-5-carboxylic acid methyl ester

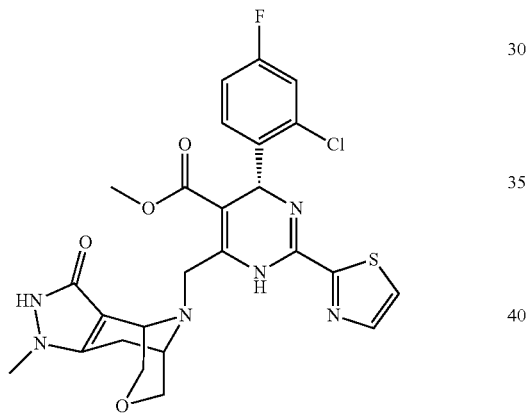

The title compound was prepared in analogy to Example 1a with the procedure shown in Scheme 3 by using 5-methyl-10-oxa-4,5,12-triaza-tricyclo[6.3.1.0*2,6*]dodec-2(6)-en-3-one (Compound AM) instead of 3-oxa-9-aza-bicyclo[3.3.1]nonane-7-carboxylic acid methyl ester.

Preparation of 5-methyl-10-oxa-4,5,12-triaza-tricyclo[6.3.1.0*2,6*]dodec-2(6)-en-3-one (Compound AM)

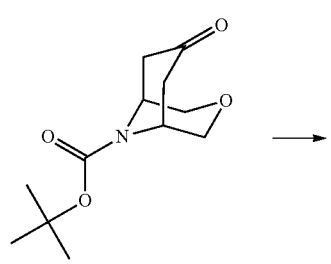

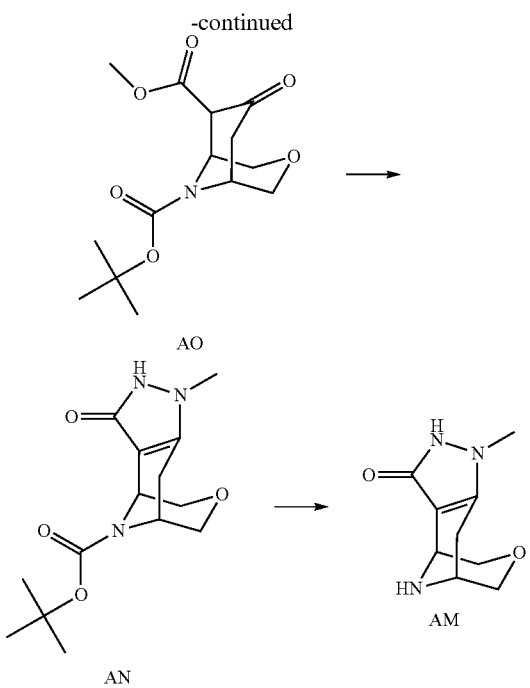

Step I: To a suspension of t-BuOK (1.82 g, 16.26 mmol) in toluene (30 mL) was added dimethyl carbonate (0.98 g, 10.84 mmol). The mixture was heated at 90° C. for 5 mins, and then 7-oxo-3-oxa-9-aza-bicyclo[3.3.1]nonane-9-carboxylic acid tert-butyl ester (1.3 g, 5.4 mmol) was added. After the resulting mixture was stirred at 90° C. for 30 mins, the mixture was turned to brown gel, and then DMF (1.5 mL) was added to get a brown solution. The mixture was stirred at 90° C. for 3 hours. After it was cooled to room temperature, silica gel (25 g, 100200 mesh) was added and the solvent was concentrated in vacuo. The residue was purified by flash column chromatography (EtOAc in PE 0%~70%) to give 7-oxo-3-oxa-9-aza-bicyclo[3.3.1]nonane-6,9-dicarboxylic acid 9-tert-butyl ester 6-methyl ester (Compound AO) as light yellow oil (0.8 g, 49%). LC/MS: calc'd 300 (MH+), exp 300 (MH+); ¹HNMR (400 MHz, CDCl₃) δ 1.40-1.45 (m, 9H), 2.29-2.41 (m, 1H), 2.68-2.84 (m, 1H), 3.47-3.79 (m, 7H), 3.88-3.96 (m, 0.5H), 4.09-4.16 (m, 0.3H), 4.30-4.45 (m, 1H), 4.55-4.67 (m, 0.8H), 11.86 (s, 0.3H).

Step II: To a solution of Compound AO (250 mg, 0.84 mmol) in EtOH (4 mL) was added 40% methyl hydrazine in water (483 mg, 4.2 mmol). The mixture was sealed and heated at 80° C. for 2 hours. The reaction mixture was concentrated in vacuo. The residue was purified by preparative HPLC to afford 5-methyl-3-oxo-10-oxa-4,5,12-triaza-tricyclo

[6.3.1.0*2,6*]dodec-2(6)-ene-12-carboxylic acid tert-butyl ester (Compound AN) as a white solid (99 mg, 40%). LC/MS: calc'd 296 (MH⁺), exp 296 (MH⁺).

Step III: Compound AN (99 mg, 0.33 mmol) was dissolved in DCM/TFA (3 mL, 2:1) and stirred at room temperature for 2 hours. The solvent was removed and the residue was dried under vacuum to afford 5-methyl-10-oxa-4,5,12-triaza-tricyclo[6.3.1.0*2,6*]dodec-2(6)-en-3-one (Compound AM) as a yellow foam (crude 100 mg, 100%). LC/MS: calc'd 196 (MH⁺), exp 196 (MH⁺).

Example 34

(R)-4-(2-Chloro-4-fluoro-phenyl)-6-(4-oxo-8-oxa-3,10-diaza-bicyclo[4.3.1]dec-10-ylmethyl)-2-thiazol-2-yl-1,4-dihydro-pyrimidine-5-carboxylic acid methyl ester

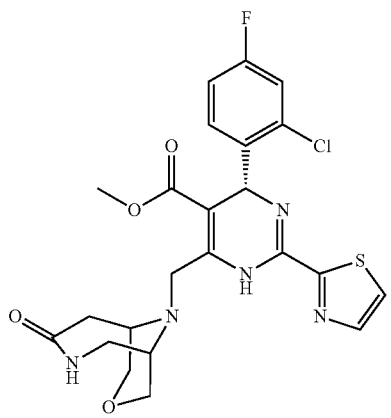 [SMILES: COC(=O)C1=C(CN2C3CNC(=O)CC2COC3)NC(c2nccs2)=N[C@H]1c1ccc(F)cc1Cl]

The title compound was prepared in analogy to Example 1a with the procedure shown in Scheme 3 by using 4-oxo-8-oxa-3,10-diaza-bicyclo[4.3.1]decane-10-carboxylic acid tert-butyl ester (WuXi AppTec (Wuhan) Co., Ltd, CAS: 1160248-56-5) instead of 3-oxa-9-aza-bicyclo[3.3.1]nonane-7-carboxylic acid methyl ester.

Example 35

(R)-6-(7-Acetylamino-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester

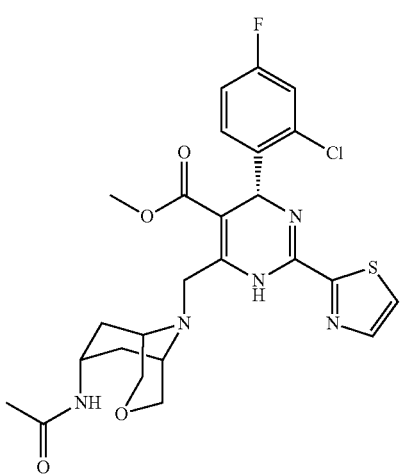 [SMILES: COC(=O)C1=C(CN2C3COCC2CC(NC(C)=O)C3)NC(c2nccs2)=N[C@H]1c1ccc(F)cc1Cl]

The title compound was prepared by the procedure shown below (Scheme 6).

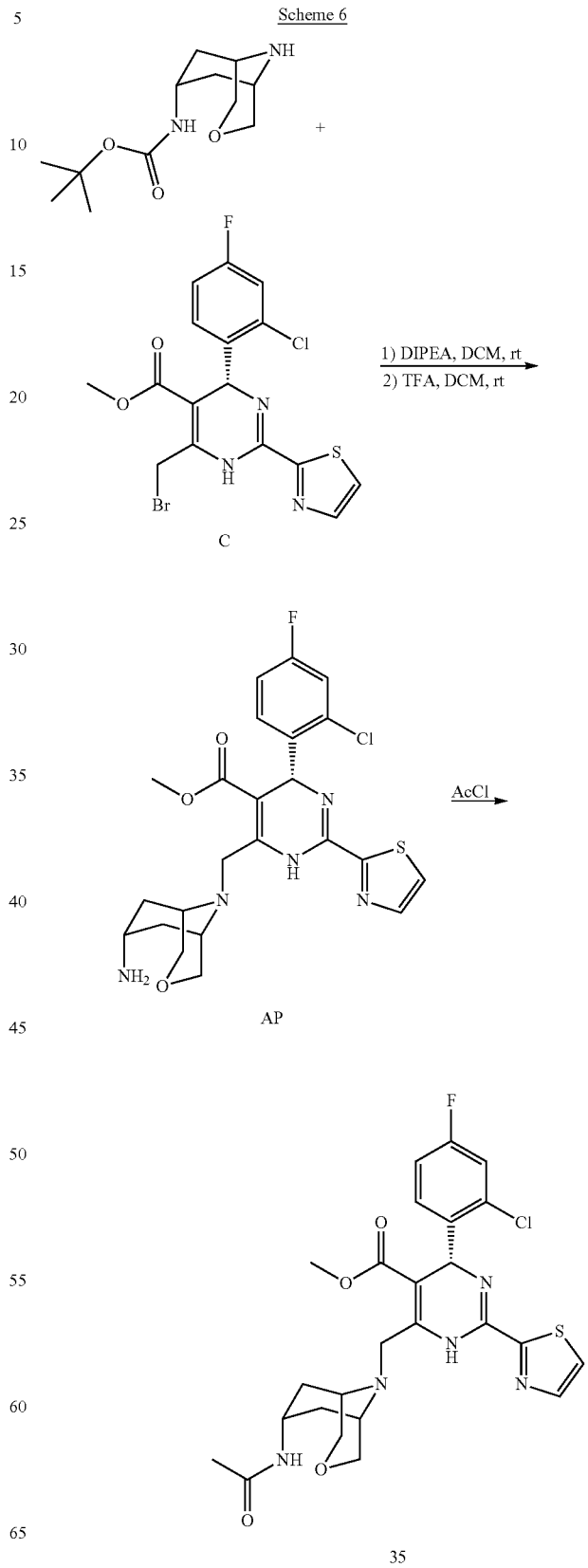

To the solution of (3-oxa-9-aza-bicyclo[3.3.1]non-7-yl)-carbamic acid tert-butyl ester (PharmaBlock (Nanjing) R&D Co. Ltd, catalog number: PB05636) (106 mg, 0.44 mmol) and Compound C (100 mg, 0.22 mmol) in CH$_2$Cl$_2$ (5 mL) was added DIPEA (0.14 mL, 0.44 mmol) at room temperature. The reaction mixture was stirred overnight at room temperature, then diluted with EtOAc (60 mL). The organic layer was washed with sat. NH$_4$Cl, sat. NaHCO$_3$ and brine (20 mL) respectively. The organic layer was dried over Na$_2$SO$_4$, and then concentrated under reduced pressure to give the crude product which was dissolved in CH$_2$Cl$_2$ (5 mL). To the solution was added trifluoroacetic acid (2 mL) at 0° C. The mixture was stirred at room temperature for 2 hours. The solvent was removed under reduced pressure to give the crude (R)-6-(7-amino-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester (Compound AP) which was directly used for next step.

To a solution of Compound AP and DIPEA (0.19 mL, 1.10 mmol) in CH$_2$Cl$_2$ (5 mL) was added acetyl chloride (31 µl, 0.44 mmol) at 0° C. The reaction mixture was stirred at room temperature for 2 hours, and then quenched with sat. NH$_4$Cl, then diluted with EtOAc (60 mL). The organic layer was washed with sat. NH$_4$Cl, sat. NaHCO$_3$ and brine respectively. The organic layer was dried over Na$_2$SO$_4$, and then concentrated, then purified by reverse phase HPLC to give (R)-6-(7-acetylamino-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester (Example 35) (36 mg) as a light yellow powder.

Example 36

(R)-4-(2-Chloro-4-fluoro-phenyl)-6-(7-methane-sulfonylamino-3-oxa-9-aza-bicyclo[3.3.1]non-9-ylmethyl)-2-thiazol-2-yl-1,4-dihydro-pyrimidine-5-carboxylic acid methyl ester

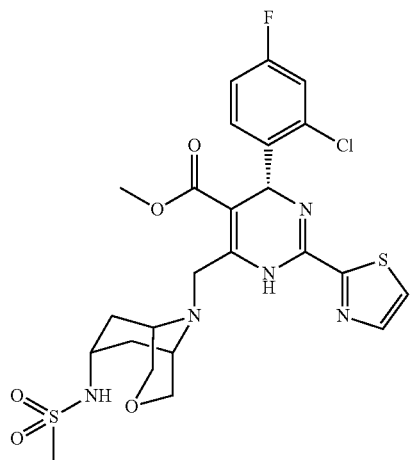 [SMILES: COC(=O)C1=C(CN2C3COCC2CC(NS(C)(=O)=O)C3)NC(c2nccs2)=N[C@H]1c1ccc(F)cc1Cl]

The title compound was prepared in analogy to Example 35 with the procedure shown in Scheme 6 by using methane-sulfonyl chloride instead of acetyl chloride.

Example 37

(R)-4-(2-Chloro-4-fluoro-phenyl)-6-(2-methoxymethyl-azetidin-1-ylmethyl)-2-thiazol-2-yl-1,4-dihydro-pyrimidine-5-carboxylic acid methyl ester

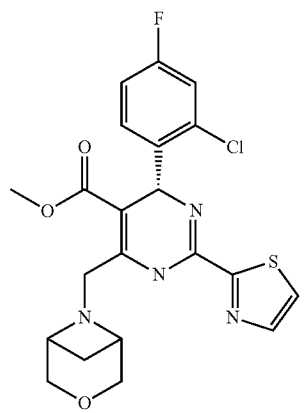 [SMILES: COC(=O)C1=C(CN2C3COCC2C3)NC(c2nccs2)=N[C@H]1c1ccc(F)cc1Cl]

The title compound was prepared in analogy to Example 1a with the procedure shown in Scheme 3 by using 3-oxa-6-azabicyclo[3.1.1]heptane (WuXi AppTec (Wuhan) Co., Ltd, CAS: 286390-20-3) instead of 3-oxa-9-aza-bicyclo[3.3.1]nonane-7-carboxylic acid methyl ester.

Example 38

(R)-4-(2-Chloro-4-fluoro-phenyl)-6-(6-oxa-3-aza-bicyclo[3.1.1]hept-3-ylmethyl)-2-thiazol-2-yl-1,4-dihydro-pyrimidine-5-carboxylic acid methyl ester

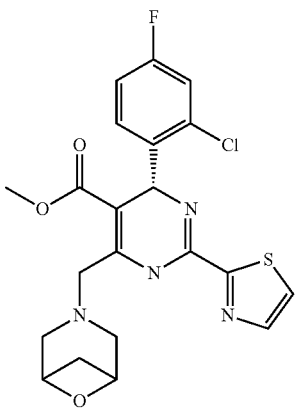 [SMILES: COC(=O)C1=C(CN2CC3CC(C2)O3)NC(c2nccs2)=N[C@H]1c1ccc(F)cc1Cl]

The title compound was prepared in analogy to Example 1a with the procedure shown in Scheme 3 by using 6-oxa-3-aza-bicyclo[3.1.1]heptane instead of 3-oxa-9-aza-bicyclo[3.3.1]nonane-7-carboxylic acid methyl ester.

Example 39

(S)-3-[(R)-6-(2-Chloro-4-fluoro-phenyl)-5-methoxy-carbonyl-2-thiazol-2-yl-3,6-dihydro-pyrimidin-4-ylmethyl]-3,6-diaza-bicyclo[3.2.1]octane-7-carboxylic acid

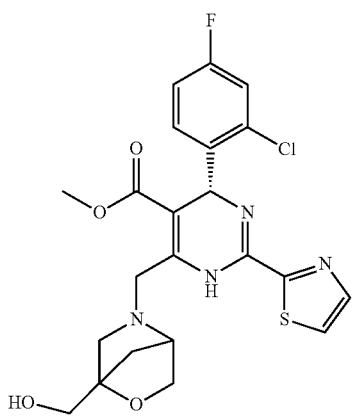 [SMILES: COC(=O)C1=C(CN2CC3(CO)CC2CO3)NC(c2nccs2)=N[C@H]1c1ccc(F)cc1Cl]

The title compound was prepared in analogy to Example 1a with the procedure shown in Scheme 3 by using (2-oxa-5-aza-bicyclo[2.2.1]hept-1-yl)-methanol (the corresponding Boc protected precursor was purchased from WuXi AppTec (Wuhan) Co., Ltd, CAS: 1357351-86-0) instead of 3-oxa-9-aza-bicyclo[3.3.1]nonane-7-carboxylic acid methyl ester.

Example 40

2-[(R)-6-(2-Chloro-4-fluoro-phenyl)-5-methoxycarbonyl-2-thiazol-2-yl-3,6-dihydro-pyrimidin-4-ylmethyl]-4-fluoro-2-aza-bicyclo[2.1.1]hexane-1-carboxylic acid

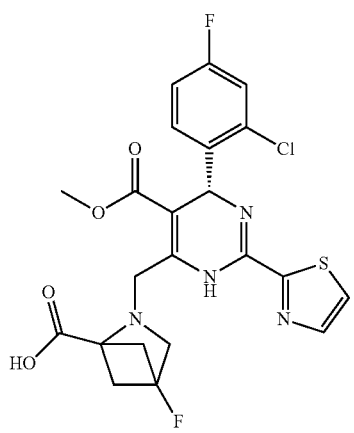 [SMILES: COC(=O)C1=C(CN2CC3(F)CC2(C(=O)O)C3)NC(c2nccs2)=N[C@H]1c1ccc(F)cc1Cl]

The title compound was prepared in analogy to Example 1a with the procedure shown in Scheme 3 by using 4-fluoro-2-aza-bicyclo[2.1.1]hexane-1-carboxylic acid instead of 3-oxa-9-aza-bicyclo[3.3.1]nonane-7-carboxylic acid methyl ester.

Preparation of Literature Known 4-fluoro-2-aza-bicyclo[2.1.1]hexane-1-carboxylic acid (AR)

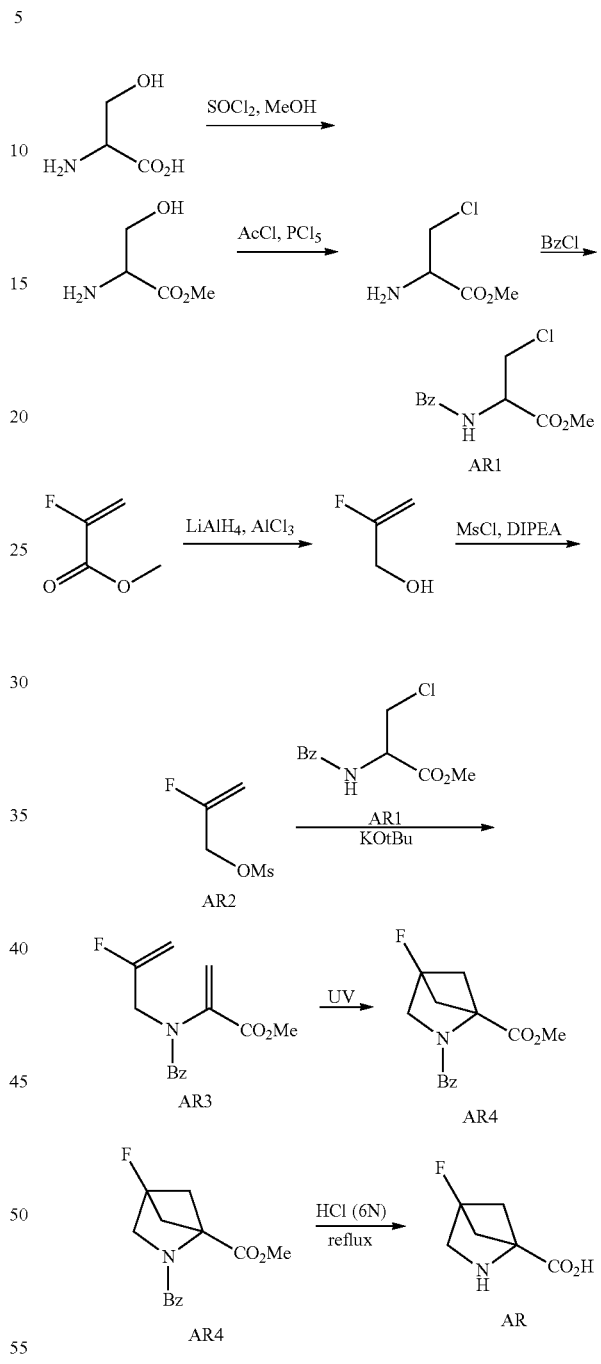

Step I: To a solution of serine (10.5 g, 100 mmol) in MeOH (100 mL) at 0° C. was added thionyl chloride (8.3 g, 5.1 mL, 70 mmol) over 5 minutes. After the reaction mixture was allowed to warm to room temperature and stirred for 48 hours, it was concentrated to a solid through repetitive evaporation with MeOH (3×20 mL), toluene (1×20 mL), and hexane (20 mL). The crude white solid was dissolved in acetyl chloride (120 mL), chilled to 0° C., and phosphorus pentachloride (22.5 g, 107 mmol) was added. The reaction mixture was allowed to warm to room temperature and was stirred for an additional 9 hours. Then the reaction mixture was cooled, and the solid precipitate was filtered and collected to yield 13.5 g of a light-yellow solid. This solid was suspended in THF (100 mL) and water (5 mL) at 0° C. and reacted with potassium carbonate (27 g, 195 mmol) and benzoyl chloride (26.6 g, 22 mL, 190 mmol) for 1 hour at 0° C. The reaction was stirred for 4 hours at room temperature, then diluted with water (600 mL) and chilled to 0° C. overnight. The solid formed in this reaction mixture was filtered off and dried to yield methyl 2-benzamido-3-chloro-propanoate (AR1) (11 g, 42%). LC/MS: calc'd 242 (MH$^+$), exp 242 (MH$^+$).

Step II: A suspension of LiAlH$_4$ (6.6 g, 0.17 mol) in Et$_2$O (150 mL) was treated carefully with AlCl$_3$ (7.6 g, 0.057 mol) at −5° C. The resulting mixture was stirred for 30 minutes at −5° C., and methyl 2-fluoroacrylate (12 g, 0.114 mmol) was added dropwise. The mixture was stirred at −5° C. for additional 1 hour. Thereafter, an excess of wet Na$_2$SO$_4$ was added to decompose excess of AlCl$_3$. Solid phase was separated by filtration and Et$_2$O was carefully removed at atmospheric pressure to give 7.4 g of 40% solution of 2-fluoroprop-2-en-1-ol in Et$_2$O which was further diluted with CH$_2$Cl$_2$ (20 mL). To this solution, DIPEA (6.33 mL, 0.036 mol) was added. The resulting solution was cooled to −30° C., and MsCl (2.42 mL, 0.031 mol) was added dropwise. The reaction mixture was allowed to warm to room temperature, and stirred for additional 1 hour. The mixture was washed with water, 10% solution of citric acid, brine, dried over Na$_2$SO$_4$, and evaporated under reduced pressure to give 2-fluoroallyl methanesulfonate (AR2) (3.77 g, 0.024 mol, 93%). The product is relatively unstable and has to be used immediately in the next step.

Step III: A solution of KOtBu (2.35 g, 0.209 mol) in THF (145 mL) was treated under argon at −78° C. with a solution of methyl methyl 2-benzamido-3-chloro-propanoate (AR1) (2.35 g, 9.72 mmol) in THF (60 mL), followed by addition of 2-fluoroallyl methanesulfonate (AR2) (1.5 g, 9.72 mmol). The reaction mixture was allowed to warm to room temperature, stirred for 28 hours, and partitioned between CH$_2$Cl$_2$ and H$_2$O. The organic layer was washed with 10% solution of citric acid, brine, dried over Na$_2$SO$_4$, and evaporated under reduced pressure. The crude product was purified by flash column chromatography (hexane/EtOAc=9/1) to give methyl 2-[benzoyl(2-fluoroallyl)amino]prop-2-enoate (AR3) (633 mg, 2.44 mmol, 25%). LC/MS: calc'd 264 (MH$^+$), exp 264 (MH$^+$).

Step IV: Methyl 2-[benzoyl(2-fluoroallyl)amino]prop-2-enoate (AR3) (380 mg, 1.44 mmol), acetophenone (30 mg), benzophenone (40 mg) were dissolved in 25 mL of benzene. The solution formed was irradiated in a quartz reactor by 500 W medium pressure mercury lamp at room temperature for 10 hours. The reaction mixture was concentrated, and the residue was purified by flash column chromatography (hexane/EtOAc=3/1) to give methyl 1-fluoro-3-methyl-3-azabicyclo[2.1.1]hexane-4-carboxylate (AR4) (240 mg, 0.913 mmol, 63%). LC/MS: calc'd 264 (MH$^+$), exp 264 (MH$^+$).

Step V: To a solution of methyl 1-fluoro-3-methyl-3-azabicyclo[2.1.1]hexane-4-carboxylate (AR4) (150 mg, 0.57 mmol) in CH$_2$Cl$_2$ (1.0, mL) was added an aqueous of HCl (6.0N, 8.0 mL). The reaction mixture was heated to reflux and stirred for 3 hours. After cooled to room temperature, the solution was filtered. The filtrate was evaporated in vacuo, and the residue was washed with MeCN to give 4-fluoro-2-aza-bicyclo[2.1.1]hexane-1-carboxylic acid as a white solid (45 mg). LC/MS: calc'd 146 (MH$^+$), exp 146 (MH$^+$).

Example 41

(R)-6-(5-Acetyl-2,5-diaza-bicyclo[2.2.1]hept-2-ylmethyl)-4-(2-chloro-4-fluoro-phenyl)-2-thiazol-2-yl-1,4-dihydro-pyrimidine-5-carboxylic acid methyl ester

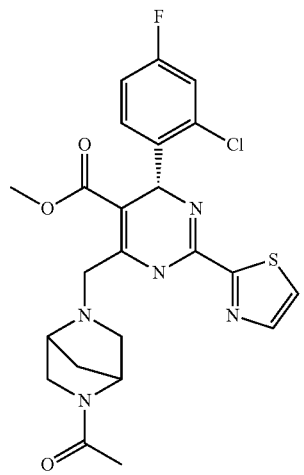 [SMILES: COC(=O)C1=C(CN2CC3CC2CN3C(C)=O)NC(c2nccs2)=N[C@H]1c1ccc(F)cc1Cl]

The title compound was prepared in analogy to Example 1a with the procedure shown in Scheme 3 by using 1-(2,5-diaza-bicyclo[2.2.1]hept-2-yl)-ethanone instead of 3-oxa-9-aza-bicyclo[3.3.1]nonane-7-carboxylic acid methyl ester.

Example 42

6-(7-Carboxymethyl-3-thia-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester

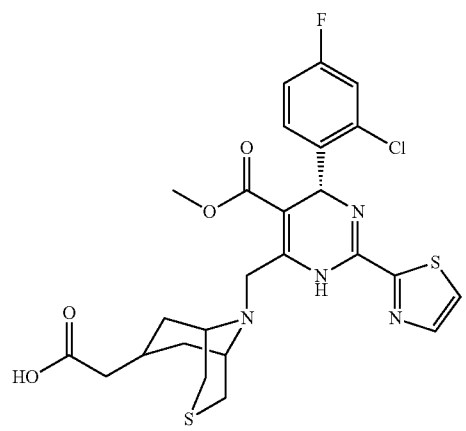 [SMILES: COC(=O)C1=C(CN2C3CSCC2CC(CC(=O)O)C3)NC(c2nccs2)=N[C@H]1c1ccc(F)cc1Cl]

The title compound was prepared in analogy to Example 1a with the procedure shown in Scheme 3 by using 3-thia-9-azabicyclo[3.3.1]nonan-7-one hydrochloride (PharmaBlock (Nanjing) R&D Co. Ltd, CAS: 1205682-24-1) instead of 3-oxa-9-aza-bicyclo[3.3.1]nonane-7-carboxylic acid methyl ester.

Example 43

(R)-6-(7-Diazirine-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester

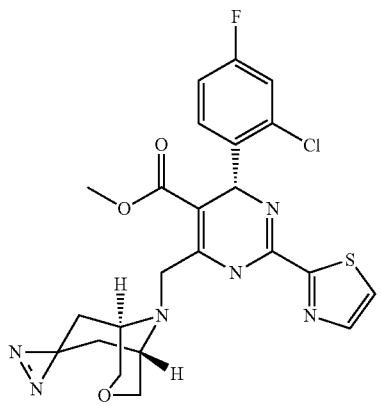 [SMILES: COC(=O)C1=C(CN2[C@@H]3COC[C@H]2CC2(C3)N=N2)NC(c2nccs2)=N[C@H]1c1ccc(F)cc1Cl]

The title compound was prepared in analogy to Example 1a with the procedure shown in Scheme 3 by using 7-diazirine-3-oxa-9-aza-bicyclo[3.3.1]nonane (Compound AQ) instead of 3-oxa-9-aza-bicyclo[3.3.1]nonane-7-carboxylic acid methyl ester.

Preparation of 7-diazirine-3-oxa-9-aza-bicyclo[3.3.1]nonane (Compound AQ)

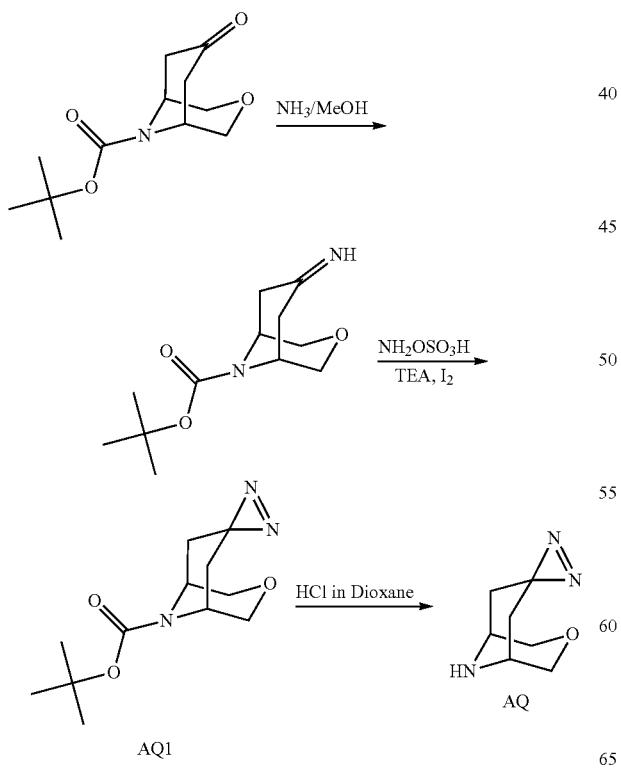

Step I & II: 7-Oxo-3-oxa-9-aza-bicyclo[3.3.1]nonane-9-carboxylic acid tert-butyl ester (200 mg, 0.83 mmol) was added to a solution of $NH_3$/MeOH (4.0 M, 4 mL). The reaction was heated to 60° C. and stirred for 16 hours. After the solution was cooled to room temperature, $NH_2OSO_3H$ (94 mg, 0.83 mmol) was added. The mixture was stirred at room temperature for 2 hours, and then TEA (84 mg, 0.83 mmol) was added. The solution was cooled to 0° C., a solution of $I_2$ (1.0 M) was added until an orange color appeared. The solvent was removed and the residue was dissolved in water (5 mL). The aqueous layer was extracted with EA (10 mL) three times. The combined organic layer was dried over $Na_2SO_4$. The solvent was removed to give crude Compound AQ1 as brown oil (180 mg) which was used at next step without further purification. LC/MS: calc'd 254 ($MH^+$), exp 254 ($MH^+$).

Step III: To a solution of crude Compound AQ1 (180 mg) in DCM (3.0 mL) was added a solution of HCl/dioxane (4 M, 2.0 mL). After the reaction mixture was stirred at room temperature for 16 hours, the solvent was removed and the residue was dissolved in water (3 mL). The aqueous solution was washed with DCM to remove water insoluble impurity and the water solution was then lyophilized to give 7-diazirine-3-oxa-9-aza-bicyclo[3.3.1]nonane (Compound AQ) as a white solid (80 mg). LC/MS: calc'd 154 ($MH^+$), exp 154 ($MH^+$).

Example 44

(R)-4-(2-Chloro-4-fluoro-phenyl)-6-((1R,3R,5S)-3-hydroxy-8-aza-bicyclo[3.2.1]oct-8-ylmethyl)-2-thiazol-2-yl-1,4-dihydro-pyrimidine-5-carboxylic acid methyl ester

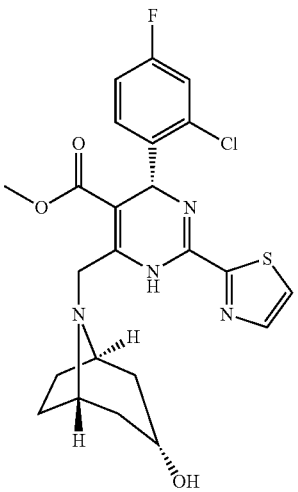 [SMILES: COC(=O)C1=C(CN2[C@@H]3CC[C@H]2C[C@@H](O)C3)NC(c2nccs2)=N[C@H]1c1ccc(F)cc1Cl]

The title compound was prepared in analogy to Example 1a with the procedure shown in Scheme 3 by using (1R,3R,5S)-8-aza-bicyclo[3.2.1]octan-3-ol (BePharm (Shanghai) Ltd, CAS: 14383-51-8) instead of 3-oxa-9-aza-bicyclo[3.3.1]nonane-7-carboxylic acid methyl ester.

Example 45

(R)-4-(2-Chloro-4-fluoro-phenyl)-6-(9-oxa-3,4,11-triaza-tricyclo[5.3.1.0*2,6*]undeca-2(6),4-dien-11-ylmethyl)-2-thiazol-2-yl-1,4-dihydro-pyrimidine-5-carboxylic acid methyl ester

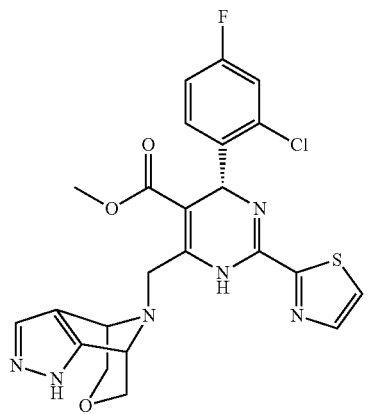 [SMILES: COC(=O)C1=C(CN2C3COCC2c2[nH]ncc23)NC(c2nccs2)=N[C@H]1c1ccc(F)cc1Cl]

The title compound was prepared in analogy to compound 1a in example 1 starting from compound C and compound 45c.

Preparation of Compound 45c

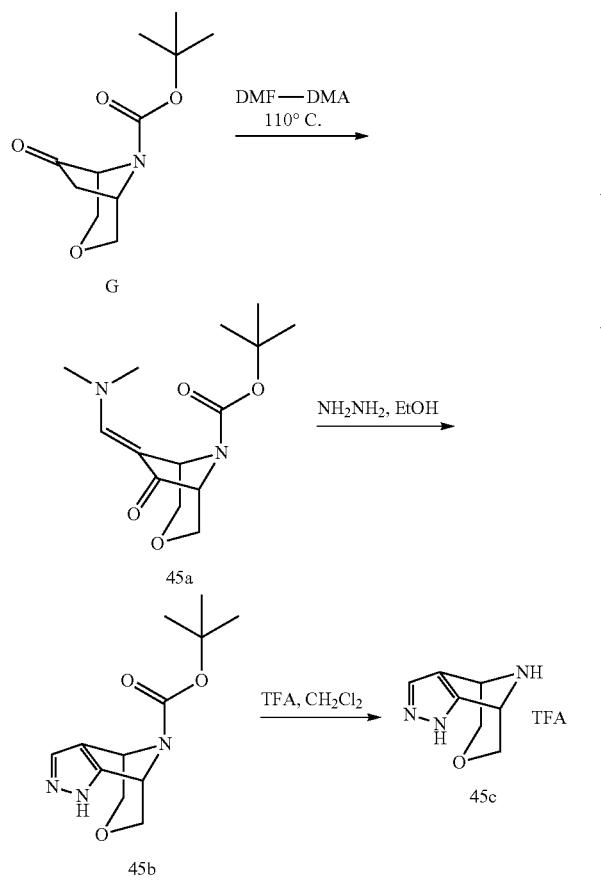

Step I: A mixture of compound G (227 mg, 1 mmol) and DMF-DMA (10 mL) was heated to reflux at 110° C. for 48 hours. After the starting material disappeared as monitored by LCMS and TLC, the mixture was cooled to room temperature and poured into 50 mL ice-water. The mixture was extracted with ethyl acetate and the combined organic layer was washed with brine and dried over anhydrous $Na_2SO_4$. The organic solvent was removed to give compound 45a as crude product, which was directly used for next step without further purification. LC/MS: calc'd 283 ($MH^+$), exp 283 ($MH^+$).

Step II: The crude compound 45a was dissolved into 15 mL of ethanol. To this solution, 0.5 mL hydrazine monohydrate and 3 mL acetic acid were added. The reaction mixture was sealed, heated to 110° C. and stirred overnight. The solvents were removed by reduced pressure and the residue was purified by Prep-HPLC to give white pure product 45b (32 mg, 13%). MS: calc'd ($MH^+$) 252, measured ($MH^+$) 252 $^1$H NMR ($CDCl_3$, 400 MHz): 7.30 (s, 1H), 5.07 (m, 1H), 4.96 (m, 1H), 3.90 (m, 2H), 3.72 (d, J=10.8 Hz, 1H), 3.57 (d, J=10.8 Hz, 1H), 1.49 (s, 9H) ppm.

Step III: To the solution of compound 45b (32 mg, 0.13 mmol) in $CH_2Cl_2$ (4 mL) was added trifluoroacetic acid (2 mL). The mixture was stirred at room temperature for 1 h. The solvent was removed under reduced pressure to give the crude product 45c (35 mg, 100%) which was directly used for next step without further purification. LC/MS: calc'd 152 ($MH^+$), exp 152 ($MH^+$).

Example 46

2-[[(1R,5S)-9-[[(4R)-4-(2-chloro-4-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]oxy]acetic acid

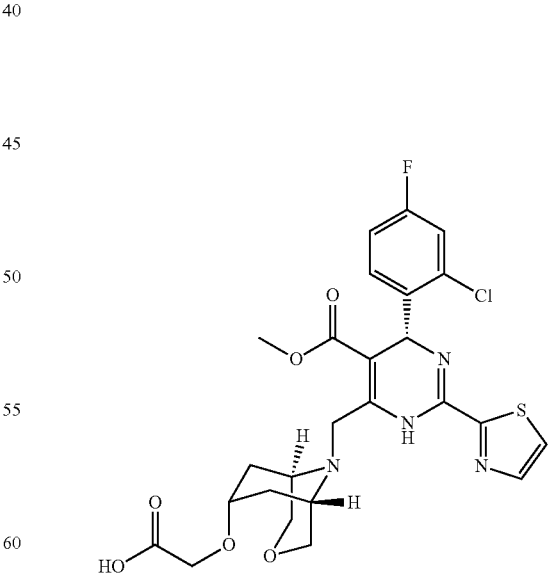

The title compound was prepared in analogy to Example 1 with the procedure shown in Scheme 3 by using ethyl 2-(3- oxa-9-azabicyclo[3.3.1]nonan-7-yloxy)acetate 46a instead of 3-oxa-9-aza-bicyclo[3.3.1]nonane-7-carboxylic acid methyl ester.

Preparation of ethyl 2-(3-oxa-9-azabicyclo[3.3.1]nonan-7-yloxy)acetate 46a

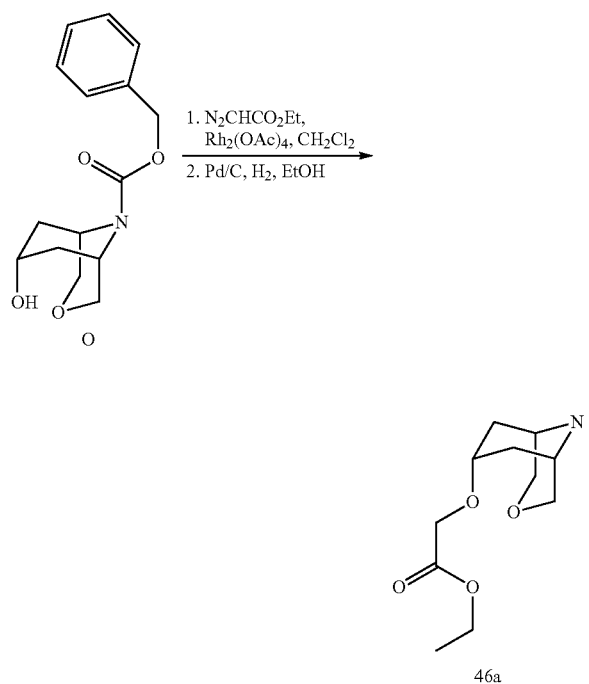

46a

Step I: To a solution of benzyl 7-hydroxy-3-oxa-9-azabicyclo[3.3.1]nonane-9-carboxylate O (200 mg, 0.72 mmol) in DCM (4 mL) was added ethyl 2-diazoacetate (202 mg, 1.44 mmol) and Rhodium(II) acetate (319 mg, 0.72 mmol) at 0° C. The resulting mixture was stirred at room temperature for overnight, and then diluted with EtOAc. The organic layer was separated, and the aqueous phase was extracted with EtOAc. The combined organic phases were washed with water and brine and dried (Na$_2$SO$_4$). The organic solvent was removed in vacuo to give the crude product, which was purified by column chromatography to give the intermediate benzyl 7-(2-ethoxy-2-oxo-ethoxy)-3-oxa-9-azabicyclo[3.3.1]nonane-9-carboxylate (144 mg, 55%). LC/MS: calc'd 364 (MH$^+$), exp 364 (MH$^+$).

Step II: To a solution of intermediate benzyl 7-(2-ethoxy-2-oxo-ethoxy)-3-oxa-9-azabicyclo[3.3.1]nonane-9-carboxylate (144 mg, 0.40 mmol) in EtOH (10 mL) was added 10% Pd/C (20 mg). The mixture was charged with H$_2$ and being stirred at room temperature for 2 h. The mixture was filtered through a pad of Celite and washed with EtOH. The resulting filtrate was concentrated in vacuo to give compound 46a (83 mg, 91%). LC/MS: calc'd 230 (MH$^+$), exp 230 (MH$^+$); $^1$H NMR (MeOD, 400 MHz): 4.18 (dd, J=14.0, 6.8 Hz, 2H), 4.13 (s, 2H), 3.74 (m, 1H), 3.68 (m, 4H), 2.98 (m, 2H), 2.27 (m, 2H), 1.77 (m, 2H), 1.27 (t, J=7.2 Hz, 3H).

Example 47

2-[[(1R,5S)-9-[[(4S)-4-(3,4-difluorophenyl)-5-methoxycarbonyl-2-thiazol-2-yl-1,4-dihydropyrimidin-6-yl]methyl]-3-oxa-9-azabicyclo[3.3.1]nonan-7-yl]oxy]acetic acid

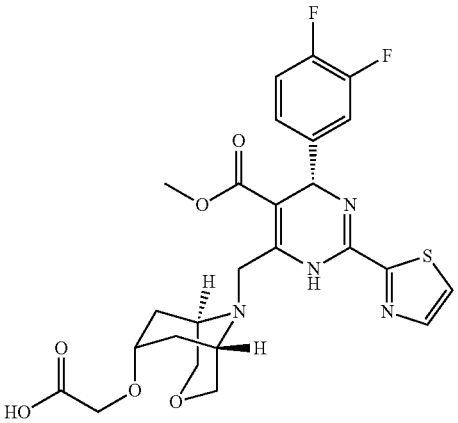 [SMILES: COC(=O)C1=C(CN2[C@@H]3COC[C@H]2CC(OCC(=O)O)C3)NC(c2nccs2)=N[C@H]1c1ccc(F)c(F)c1]

The title compound was prepared in analogy to Example 1 with the procedure shown in Scheme 3 by using 3,4-difluoro-benzaldehyde and ethyl 2-(3-oxa-9-azabicyclo[3.3.1]nonan-7-yloxy)acetate instead of 2-chloro-4-fluoro-benzaldehyde and 3-oxa-9-aza-bicyclo[3.3.1]nonane-7-carboxylic acid methyl ester, respectively.

Example 48

Methyl (4R)-6-[(6-acetamido-3-oxa-8-azabicyclo[3.2.1]octan-8-yl)methyl]-4-(2-chloro-4-fluoro-phenyl)-2-thiazol-2-yl-1,4-dihydropyrimidine-5-carboxylate

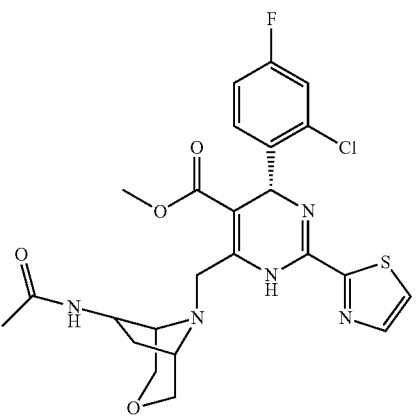 [SMILES: COC(=O)C1=C(CN2C3COCC2C(NC(C)=O)C3)NC(c2nccs2)=N[C@H]1c1ccc(F)cc1Cl]

The title compound was prepared in analogy to Example 1 with the procedure shown in Scheme 3 by using N-(3-oxa-8-azabicyclo[3.2.1]octan-6-yl)acetamide (48b) instead of 3-oxa-9-azabicyclo[3.3.1]nonane-7-carboxylic acid methyl ester. Preparation of N-(3-oxa-8-azabicyclo[3.2.1]octan-6-yl)acetamide 48b

137

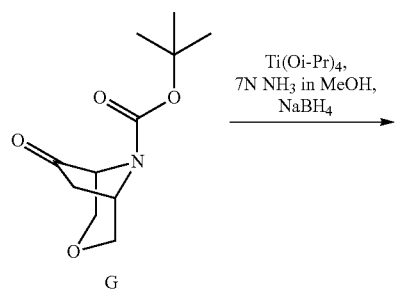

138

Example 49

Methyl (4R)-4-(2-chloro-4-fluoro-phenyl)-6-[(6-hydroxy-3-oxa-8-azabicyclo[3.2.1]octan-8-yl)methyl]-2-thiazol-2-yl-1,4-dihydropyrimidine-5-carboxylate

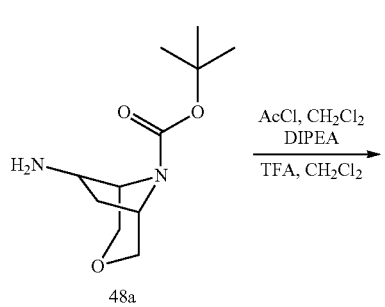

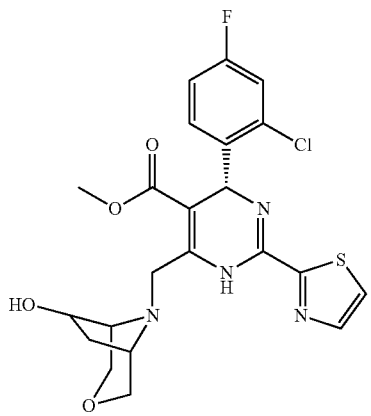 [SMILES: COC(=O)C1=C(CN2C3COCC2C(O)C3)NC(c2nccs2)=N[C@H]1c1ccc(F)cc1Cl]

The title compound was prepared in analogy to compound 1a in Example 1 by using compound 49a instead of 3-oxa-9-azabicyclo[3.3.1]nonane-7-carboxylic acid methyl ester.

Preparation of 3-oxa-8-azabicyclo[3.2.1]octan-6-ol (49a)

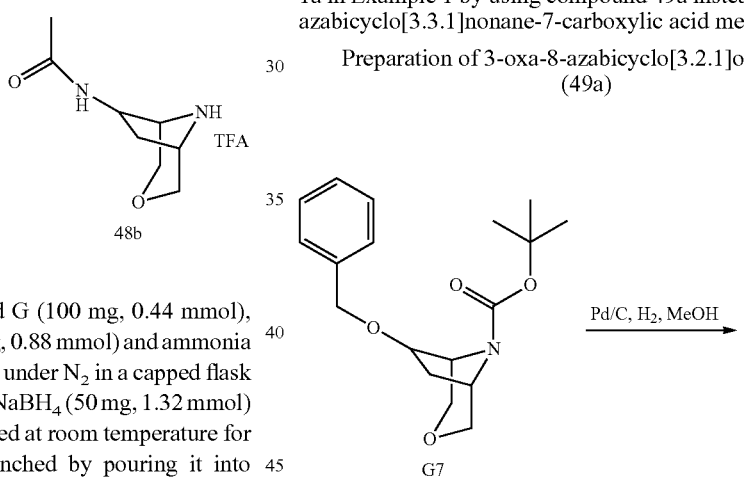

Step I: A mixture of compound G (100 mg, 0.44 mmol), titanium(IV) isopropylate (250 mg, 0.88 mmol) and ammonia in $CH_3OH$ (20 ml, 7N) was stirred under $N_2$ in a capped flask at room temperature for 6 h. Then $NaBH_4$ (50 mg, 1.32 mmol) was added to the mixture and stirred at room temperature for 3 h. The reaction was then quenched by pouring it into $NH_3 \cdot H_2O$ (2M, 20 ml) and extracted with EA. The organic layer was dried over $Na_2SO_4$ and concentrated. The resulting residue was purified by pre-HPLC to give the product 48a (30 mg, 30%) as white solid. LC/MS: calc'd 229 ($MH^+$), exp 229 ($MH^+$). $^1HNMR$ (400 MHz, $CDCl_3$): 1.48-1.64 (m, 12H), 2.51-2.58 (m, 1H), 3.56-3.63 (m, 2H), 3.72-3.89 (m, 3H), 4.04-4.13 (m, 2H).

Step II: To the solution of compound 48a (30 mg, 0.13 mmol) and i-PrNEt2 (0.22 mL, 1.3 mmol) in $CH_2Cl_2$ (5 mL) at 0° C. was added AcCl (46 μL, 0.65 mmol). The mixture was stirred at room temperature for 1 h, quenched with Sat. $NH_4Cl$, diluted with EtOAc (50 mL). The organic layer was separated, washed with sat. $NH_4Cl$, sat. $NaHCO_3$ and brine, dried over $Na_2SO_4$ and concentrated to give a crude residue (30 mg, 86%), which was treated with 30% TFA in DCM. The mixture was stirred at room temperature for 1 h, solvent was evaporated to give a crude product 48b (30 mg, 95%) which was directly used for next step. LC/MS: calc'd 171 ($MH^+$), exp 171 ($MH^+$).

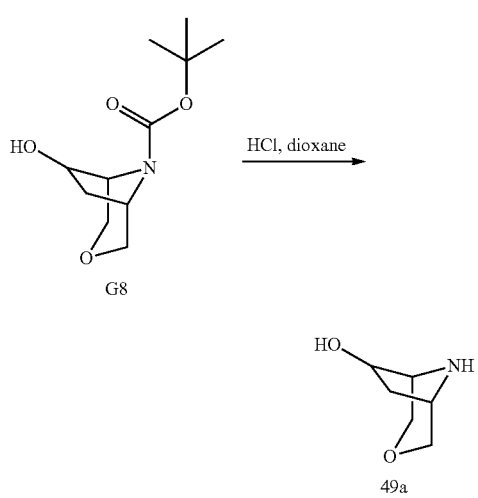

Step I: A mixture of (1R,5R,6R)-tert-butyl 6-(benzyloxy)-3-oxa-8-azabicyclo[3.2.1]octane-8-carboxylate G7 (racemic, 800 mg, 2.51 mmol), 10% Pd/C (300 mg) and MeOH (20 mL) was hydrogenated under 50 psi at 40° C. for 24 h. The mixture was filtered through a pad of Celite and washed with MeOH. The resulting filtrate was concentrated in vacuo to give compound G8 (520 mg, 91%). LC/MS: calc'd 252 (MH$^+$), exp 252 (MH$^+$); $^1$H NMR (METHANOL-d4, 400 MHz): 4.39 (m, 1H), 4.13 (m, 1H), 3.75 (m, 1H), 3.60 (d, J=11.2 Hz, 1H), 3.43 (m, 2H), 3.20 (m, 1H), 2.23 (m, 1H), 1.68 (m, 1H), 1.39 (s, 9H).

Step II: Compound G8 (100 mg, 0.44 mmol) was dissolved in 4M HCl in Dioxane (5 mL). The solution was being stirred at room temperature for 1 h, then the solvent was evaporated under reduced pressure to give compound 49a (70 mg, 95%) as white solid. LC/MS: calc'd 130 (MH$^+$), exp 130 (MH$^+$).

Example 50

2-[[8-[[(4R)-4-(2-bromo-4-fluoro-phenyl)-5-ethoxycarbonyl-2-thiazol-2-yl-1,4-dihydropyrimidin-6-yl]methyl]-3-oxa-8-azabicyclo[3.2.1]octan-6-yl]oxy]acetic acid

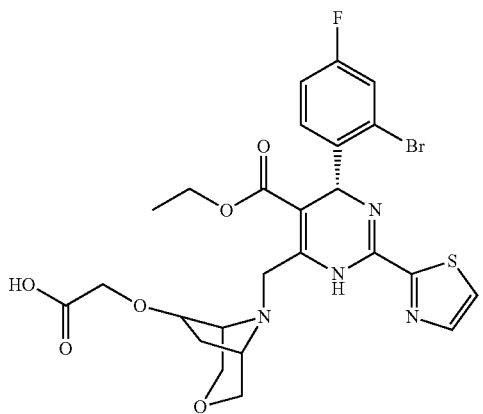 [SMILES: CCOC(=O)C1=C(CN2C3COCC2C(OCC(=O)O)C3)NC(c2nccs2)=N[C@H]1c1ccc(F)cc1Br]

The title compound was prepared in analogy to Example 1 with the procedure shown in Scheme 3 by using ethyl 3-oxobutanoate, 2-bromo-4-fluoro-benzaldehyde and ethyl 2-(3-oxa-8-azabicyclo[3.2.1]octan-6-yloxy)acetate 50b instead of methyl acetoacetate, 2-chloro-4-fluoro-benzaldehyde and 3-oxa-9-azabicyclo[3.3.1]nonane-7-carboxylic acid methyl ester, respectively.

Preparation of ethyl 2-(3-oxa-8-azabicyclo[3.2.1]octan-6-yloxy)acetate (50b)

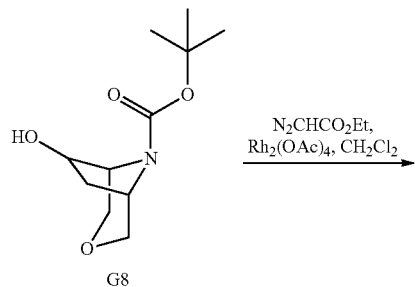

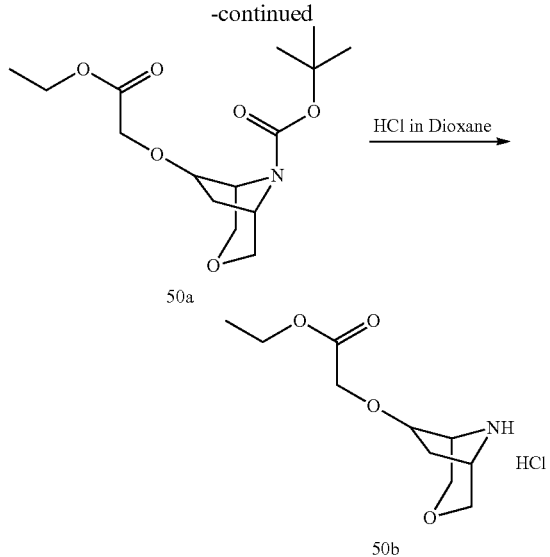

Step I: To a solution of tert-butyl 6-hydroxy-3-oxa-8-azabicyclo[3.2.1]octane-8-carboxylate G8 (racemic, 200 mg, 0.87 mmol) in DCM (4 mL) was added ethyl 2-diazoacetate (246 mg, 1.75 mmol) and Rhodium(II) acetate (386 mg, 0.87 mmol) at 0° C. The resulting mixture was stirred at room temperature for overnight, and then diluted with EtOAc. The organic layer was separated, and the aqueous phase was extracted with EtOAc. The combined organic phases were washed with water and brine and dried (Na$_2$SO$_4$). The organic solvent was removed in vacuo to give the crude product, which was purified by column chromatography on silica gel with EtOAc/PE (50:100) to give the compound 50a (205 mg, 75%). LC/MS: calc'd 216 (M-Boc+H$^+$), exp 216 (M-Boc+H$^+$).

Step II: To a solution of (1R,5R,6R)-tert-butyl 6-(2-ethoxy-2-oxoethoxy)-3-oxa-8-azabicyclo[3.2.1]octane-8-carboxylate 50a (racemic, 200 mg, 0.63 mmol) in DCM (10 mL) was added HCl/dioxane (2 mL, 7 M). The resulting mixture was stirred at room temperature for 2 h. The organic solvent was removed in vacuo to give the compound 50b (150 mg, 94%). MS: calc'd (MH$^+$) 216, measured (MH$^+$) 216; $^1$H NMR (CDCl$_3$, 400 MHz): 4.28 (m, 8H), 3.79 (m, 1H), 3.70 (s, 1H), 3.57 (d, J=12.4 Hz, 1H), 2.50 (m, 1H), 2.31 (m, 1H), 1.28 (m, 3H).

Example 51

Methyl (4R)-4-(2-chloro-4-fluoro-phenyl)-6-[(6-fluoro-3-oxa-8-azabicyclo[3.2.1]octan-8-yl)methyl]-2-thiazol-2-yl-1,4-dihydropyrimidine-5-carboxylate

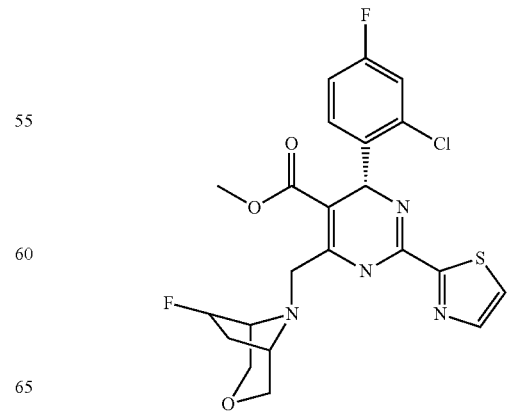

The title compound was prepared in analogy to compound 1a in Example 1 starting from compound C and compound 6-fluoro-3-oxa-8-azabicyclo[3.2.1]octane 51a. Preparation of 6-fluoro-3-oxa-8-azabicyclo[3.2.1]octane 51a:

Compound 51a was prepared from tert-butyl 6-hydroxy-3-oxa-8-azabicyclo[3.2.1]octane-8-carboxylate G8 by treatment with DAST (diethylaminosulfur trifluoride) followed by HCl/dioxane to remove the N-Boc protection.

Example 52

8-[[(4R)-4-(2-bromo-4-fluoro-phenyl)-5-ethoxycarbonyl-2-thiazol-2-yl-1,4-dihydropyrimidin-6-yl]methyl]-3-oxa-8-azabicyclo[3.2.1]octane-6-carboxylic acid

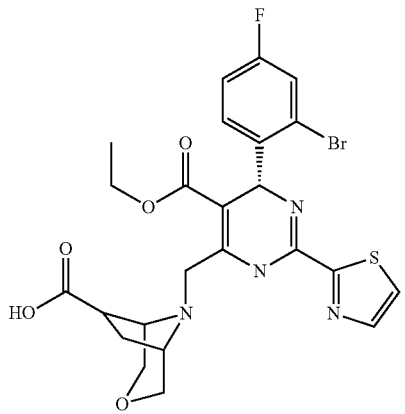 [SMILES: CCOC(=O)C1=C(CN2C3COCC2C(C(=O)O)C3)NC(c2nccs2)=N[C@H]1c1ccc(F)cc1Br]

The title compound was prepared in analogy to Example 1a with the procedure shown in Scheme 3 by using ethyl 3-oxobutanoate, 2-bromo-4-fluoro-benzaldehyde and 3-oxa-8-azabicyclo[3.2.1]octane-6-carboxylic acid F instead of methyl acetoacetate, 2-chloro-4-fluoro-benzaldehyde and 3-oxa-9-azabicyclo[3.3.1]nonane-7-carboxylic acid methyl ester, respectively.

Example 53

Methyl (4R)-4-(2-bromo-4-fluoro-phenyl)-6-[[7-(2-hydroxyacetyl)-3-oxa-7,9-diazabicyclo[3.3.1]nonan-9-yl]methyl]-2-thiazol-2-yl-1,4-dihydropyrimidine-5-carboxylate

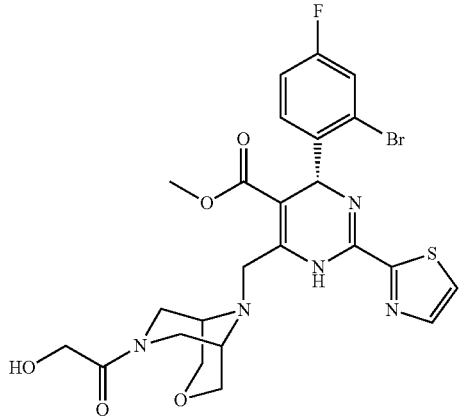 [SMILES: COC(=O)C1=C(CN2C3COCC2CN(C(=O)CO)C3)NC(c2nccs2)=N[C@H]1c1ccc(F)cc1Br]

The title compound was prepared in analogy to Example 21 by using methyl (4R)-4-(2-bromo-4-fluoro-phenyl)-6-(3-oxa-7,9-diazabicyclo[3.3.1]nonan-9-ylmethyl)-2-thiazol-2-yl-1,4-dihydropyrimidine-5-carboxylate 53b instead of Compound AC. 53b (67 mg, 0.125 mmol) and glycolic acid (20 mg, 0.25 mmol) afforded 14 mg of Example 53.

Preparation of methyl (4R)-4-(2-bromo-4-fluorophenyl)-6-(3-oxa-7,9-diazabicyclo[3.3.1]nonan-9-ylmethyl)-2-thiazol-2-yl-1,4-dihydropyrimidine-5-carboxylate 53b

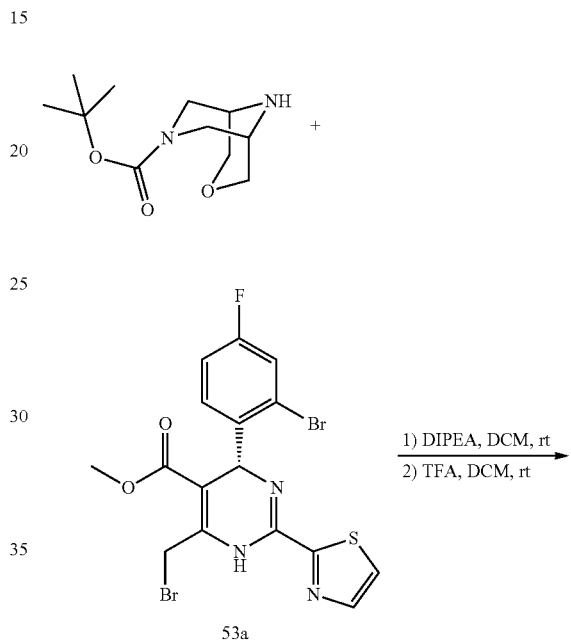

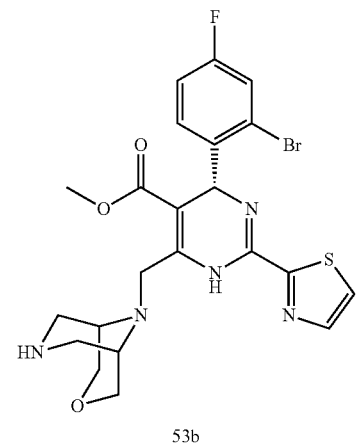

Compound 53b was prepared in analogy to intermediate AC in Example 15, starting from 3-oxa-7,9-diaza-bicyclo[3.3.1]nonane-7-carboxylic acid tert-butyl ester and methyl (4R)-4-(2-bromo-4-fluoro-phenyl)-6-(bromomethyl)-2-thiazol-2-yl-1,4-dihydropyrimidine-5-carboxylate 53a, while 53a was prepared in analogy to compound C in Example 1.

Example 54

Methyl (4R)-4-(2-bromo-4-fluoro-phenyl)-6-[(7-carbamoyl-3-oxa-7,9-diazabicyclo[3.3.1]nonan-9-yl)methyl]-2-thiazol-2-yl-1,4-dihydropyrimidine-5-carboxylate

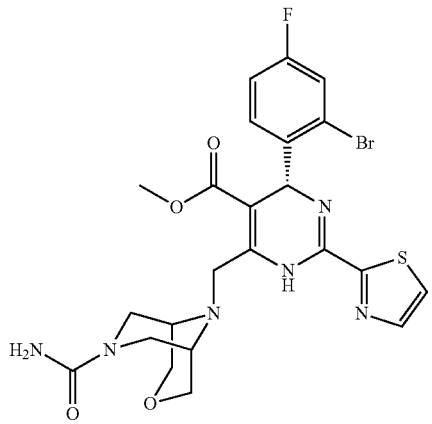 [SMILES: COC(=O)C1=C(CN2C3COCC2CN(C(N)=O)C3)NC(c2nccs2)=N[C@H]1c1ccc(F)cc1Br]

The title compound was prepared in analogy to Example 18 starting from methyl (4R)-4-(2-bromo-4-fluoro-phenyl)-6-(3-oxa-7,9-diazabicyclo[3.3.1]nonan-9-ylmethyl)-2-thiazol-2-yl-1,4-dihydropyrimidine-5-carboxylate 53b (50 mg, 0.09 mmol) and isocyanato(trimethyl)silane (43 mg, 0.37 mmol). 37 mg of the title compound was isolated as a light yellow powder.

Example 55

2-[(1R,5)-9-[[(4R)-4-(2-chloro-3-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid

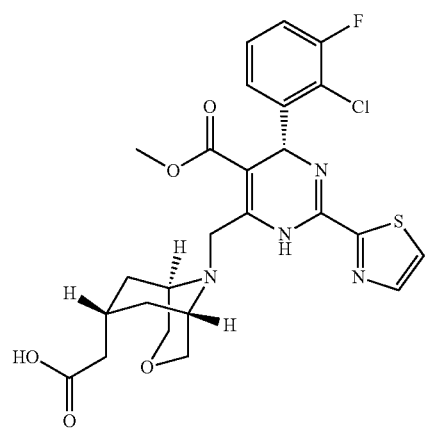 [SMILES: COC(=O)C1=C(CN2[C@@H]3COC[C@H]2C[C@@H](CC(=O)O)C3)NC(c2nccs2)=N[C@H]1c1cccc(F)c1Cl]

The title compound was prepared in analogy to Example 1a with the procedure shown in Scheme 3 by using 2-chloro-3-fluoro-benzaldehyde and (3-oxa-9-aza-bicyclo[3.3.1]non-7-yl)-acetic acid (PharmaBlock (Nanjing) R&D Co. Ltd, PBN20121752, CAS: 1389441-75-1) instead of 2-chloro-4-fluoro-benzaldehyde and 3-oxa-9-azabicyclo[3.3.1]nonane-7-carboxylic acid methyl ester, respectively.

Example 56

Methyl (4R)-4-(2-chloro-4-fluoro-phenyl)-6-[[(1R,5S)-7-endo-(sulfamoylamino)-3-oxa-9-azabicyclo[3.3.1]nonan-9-yl]methyl]-2-thiazol-2-yl-1,4-dihydropyrimidine-5-carboxylate

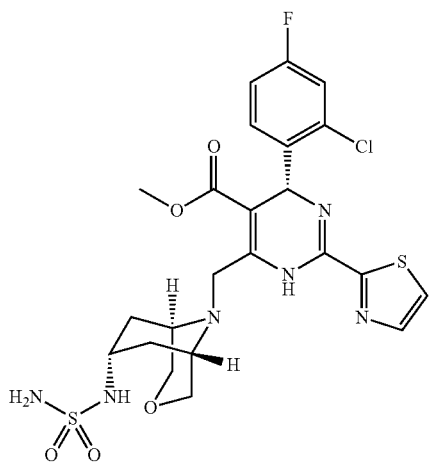 [SMILES: COC(=O)C1=C(CN2[C@@H]3COC[C@H]2C[C@@H](NS(N)(=O)=O)C3)NC(c2nccs2)=N[C@H]1c1ccc(F)cc1Cl]

Preparation of Example 56

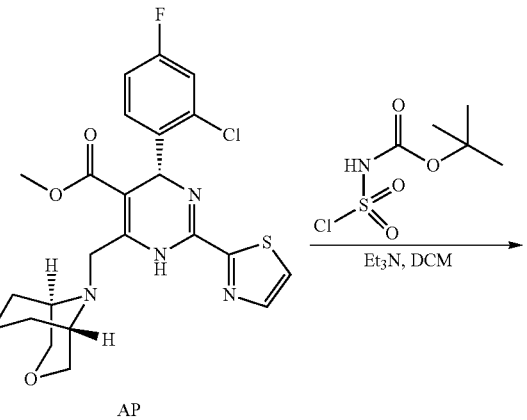

AP

-continued

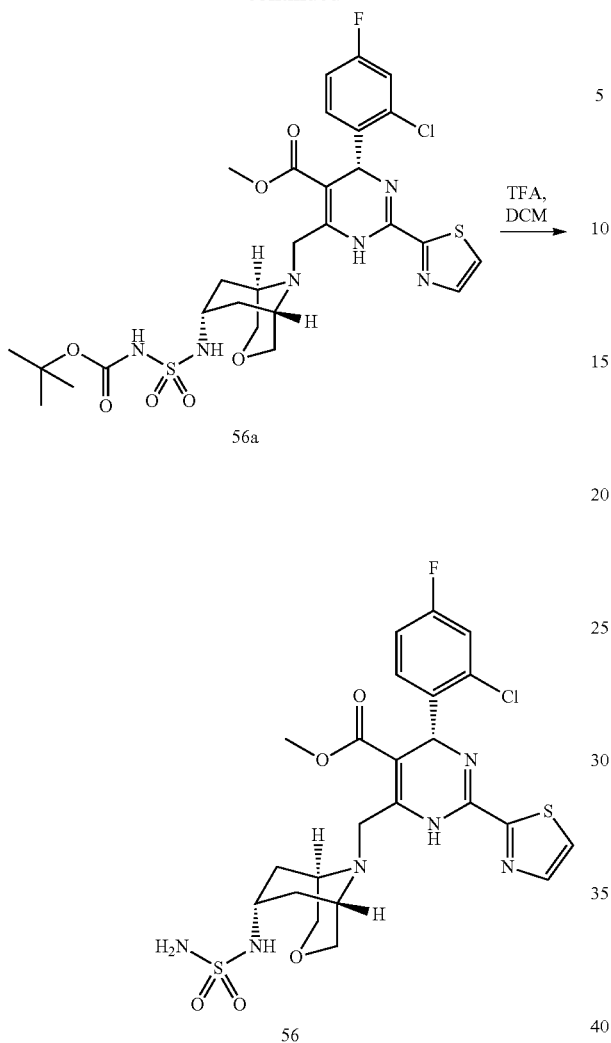

56a

56

Step I: To a solution of methyl (4R)-6-[[(1S,5R)-7-amino-3-oxa-9-azabicyclo[3.3.1]nonan-9-yl]methyl]-4-(2-chloro-4-fluoro-phenyl)-2-thiazol-2-yl-1,4-dihydropyrimidine-5-carboxylate AP (60 mg, 0.12 mmol) and triethyl-amine (0.05 mL, 0.36 mmol) in DCM (5 mL) was added a 0.05 M solution of tert-butyl N-chlorosulfonylcarbamate in DCM (2.5 mL, 0.125 mmol) dropwise at 0° C. The mixture was allowed to warm to room temperature while stirred for 16 h. Then the mixture was concentrated in vacuo. The residue was purified by flash silica gel chromatography to afford 0.08 g of the product 56a as a yellow oil (yield was 97%). MS: calc'd (MH+) 684, measured (MH+) 684.

Step II: To a solution of methyl (4R)-6-[[(1S,5R)-7-(tert-butoxycarbonylsulfamoylamino)-3-oxa-9-azabicyclo[3.3.1]nonan-9-yl]methyl]-4-(2-chloro-4-fluoro-phenyl)-2-thiazol-2-yl-1,4-dihydropyrimidine-5-carboxylate 56a (80 mg, 0.12 mmol) in DCM (5 mL) was added TFA (0.5 mL). The mixture was stirred at 25° C. for 3 h. The mixture was concentrated in vacuo. The residue was purified by Preparative HPLC to afford 30 mg of the Example 56 as a light yellow powder (yield was 42%).

Example 57

Methyl (4R)-4-(2-chloro-4-fluoro-phenyl)-2-thiazol-2-yl-6-[[(1S,5R)-7-endo-ureido-3-oxa-9-azabicyclo[3.3.1]nonan-9-yl]methyl]-1,4-dihydropyrimidine-5-carboxylate

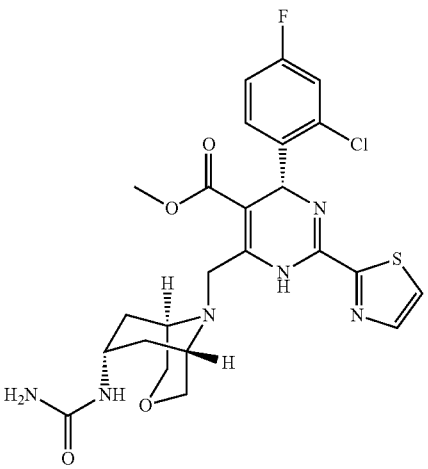 [SMILES: COC(=O)C1=C(CN2[C@@H]3COC[C@H]2C[C@@H](NC(N)=O)C3)NC(c2nccs2)=N[C@H]1c1ccc(F)cc1Cl]

To a solution of methyl (4R)-6-[[(1S,5R)-7-(tert-butoxycarbonylamino)-3-oxa-9-azabicyclo[3.3.1]nonan-9-yl]methyl]-4-(2-chloro-4-fluoro-phenyl)-2-thiazol-2-yl-1,4-dihydropyrimidine-5-carboxylate AP (60 mg, 0.12 mmol) and triethyl-amine (0.17 mL, 1.2 mmol) in DCM (5 mL) was added isocyanato(trimethyl)silane (55 mg, 0.48 mmol) dropwise at 0° C. The mixture was allowed to warm to room temperature while stirred for 16 h. Then the mixture was concentrated in vacuo. The residue was purified by preparative HPLC to afford 30 mg of the Example 57 as a light yellow powder (yield was 45%).

Example 58

2-[(1S,5R)-9-[[(4R)-4-(2-bromo-4-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid

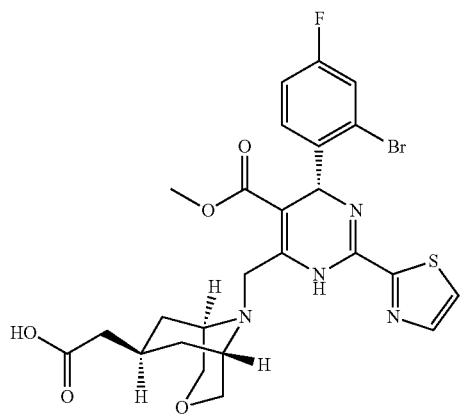 [SMILES: COC(=O)C1=C(CN2[C@@H]3COC[C@H]2C[C@H](CC(=O)O)C3)NC(c2nccs2)=N[C@H]1c1ccc(F)cc1Br]

The title compound was prepared in analogy to Example 1a with the procedure shown in Scheme 3 by using 2-bromo-4-fluoro-benzaldehyde and exo-(3-oxa-9-aza-bicyclo[3.3.1]non-7-yl)-acetic acid (PharmaBlock (Nanjing) R&D Co. Ltd, PB05416) instead of 2-chloro-4-fluoro-benzaldehyde and 3-oxa-9-azabicyclo[3.3.1]nonane-7-carboxylic acid methyl ester, respectively.

Example 59

Exo-2-[(1S,5R)-9-[[(4R)-4-(2-chloro-3-fluoro-phenyl)-5-methoxycarbonyl-2-thiazol-2-yl-1,4-dihydro-pyrimidin-6-yl]methyl]-3-oxa-9-azabicyclo[3.3.1]nonan-7-yl]acetic acid

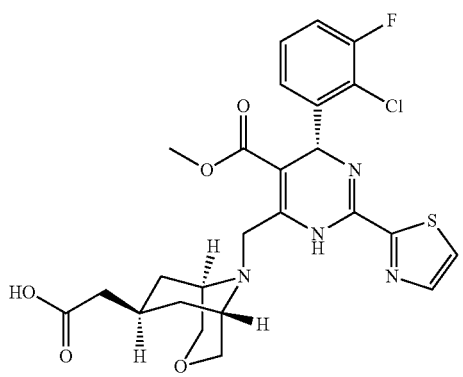 [SMILES: COC(=O)C1=C(CN2[C@@H]3COC[C@H]2C[C@H](CC(=O)O)C3)NC(c2nccs2)=N[C@H]1c1cccc(F)c1Cl]

The title compound was prepared in analogy to Example 1a with the procedure shown in Scheme 3 by using 2-chloro-3-fluoro-benzaldehyde and exo-(3-oxa-9-aza-bicyclo[3.3.1]non-7-yl)-acetic acid (PharmaBlock (Nanjing) R&D Co. Ltd, PB05416) instead of 2-chloro-4-fluoro-benzaldehyde and 3-oxa-9-azabicyclo[3.3.1]nonane-7-carboxylic acid methyl ester, respectively.

Example 60

Methyl (4R)-4-(2-chloro-4-fluoro-phenyl)-6-[[(1R,5S)-7-exo-(methanesulfonamido)-3-oxa-9-azabicyclo[3.3.1]nonan-9-yl]methyl]-2-thiazol-2-yl-1,4-dihydropyrimidine-5-carboxylate

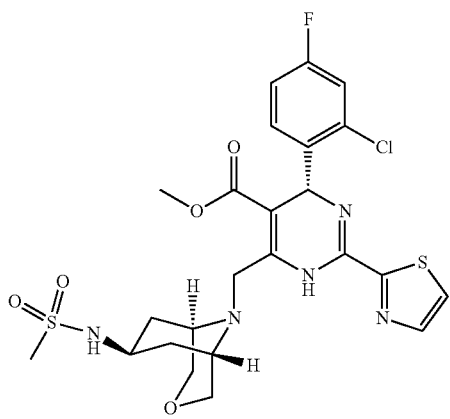 [SMILES: COC(=O)C1=C(CN2[C@@H]3COC[C@H]2C[C@H](NS(C)(=O)=O)C3)NC(c2nccs2)=N[C@H]1c1ccc(F)cc1Cl]

Preparation of Example 60

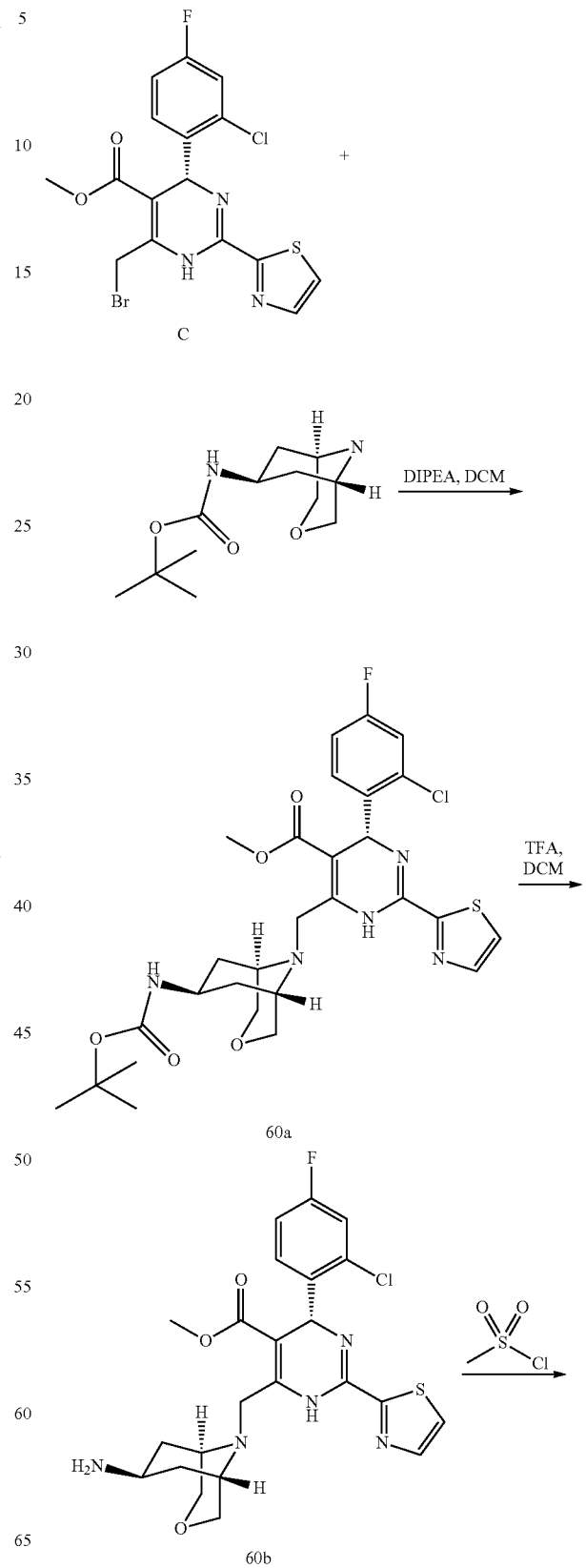

149
-continued

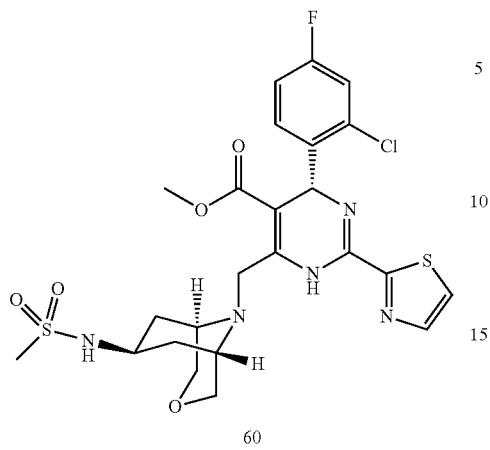

Step I: A mixture of methyl (4R)-4-(2-chloro-4-fluoro-phenyl)-6-(3-oxa-7,9-diazabicyclo[3.3.1]nonan-9-ylmethyl)-2-thiazol-2-yl-1,4-dihydropyrimidine-5-carboxylate (222 mg, 0.5 mmol, compound C, tert-butyl exo-N-[(1R,5S)-3-oxa-9-azabicyclo[3.3.1]nonan-7-yl]carbamate (158 mg, 0.65 mmol) and DIPEA (0.26 mL, 1.5 mmol) in dichloromethane (10 mL). The mixture was stirred at 25° C. for 16 h. The mixture was concentrated in vacuo. The residue was purified by silica gel chromatography to afford 0.3 g of the product 60a as a yellow oil (yield was 99%). MS: calc'd (MH$^+$) 606, measured (MH$^+$) 606.

Step II: To a solution of methyl (4R)-6-[[(1S,5R)-7-(tert-butoxycarbonylamino)-3-oxa-9-azabicyclo[3.3.1]nonan-9-yl]methyl]-4-(2-chloro-4-fluoro-phenyl)-2-thiazol-2-yl-1,4-dihydropyrimidine-5-carboxylate 60a (300 mg, 0.49 mmol) in DCM (5 mL) was added TFA (2 mL). The mixture was stirred at 25° C. for 5 h. The mixture was concentrated in vacuo to afford methyl (4R)-6-[[(1S,5R)-7-amino-3-oxa-9-azabicyclo[3.3.1]nonan-9-yl]methyl]-4-(2-chloro-4-fluoro-phenyl)-2-thiazol-2-yl-1,4-dihydropyrimidine-5-carboxylate 60b (240 mg, 96%) which was used for next step without further purification. MS: calc'd (MH$^+$) 506, measured (MH$^+$) 506.

Step III: To a solution of methyl (4R)-6-[[(1S,5R)-7-amino-3-oxa-9-azabicyclo[3.3.1]nonan-9-yl]methyl]-4-(2-chloro-4-fluoro-phenyl)-2-thiazol-2-yl-1,4-dihydropyrimidine-5-carboxylate 60b (60 mg, 0.12 mmol) and triethyl-amine (0.05 mL, 0.3 mmol) in DCM (5 mL) was added methanesulfonyl chloride (0.018 mL, 0.24 mmol) dropwise at 0° C. The mixture was allowed to warm to room temperature while stirred for 1 h. Then the mixture was concentrated in vacuo. The residue was purified by preparative HPLC to afford 20 mg of the product 60 as a light yellow powder (yield was 28%).

150

Example 61

Methyl (4R)-6-[[(1S,5R)-7-exo-acetamido-3-oxa-9-azabicyclo[3.3.1]nonan-9-yl]methyl]-4-(2-chloro-4-fluoro-phenyl)-2-thiazol-2-yl-1,4-dihydropyrimidine-5-carboxylate

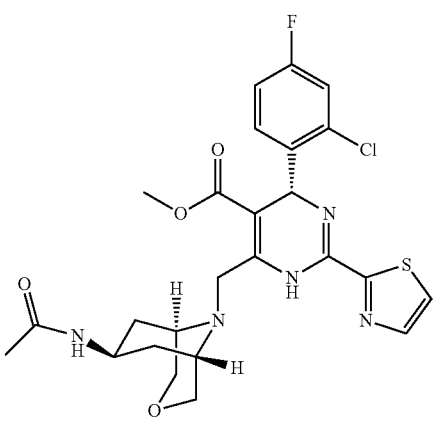 [SMILES: COC(=O)C1=C(CN2[C@@H]3COC[C@H]2C[C@H](NC(C)=O)C3)NC(c2nccs2)=N[C@H]1c1ccc(F)cc1Cl]

To a solution of methyl (4R)-6-[[(1S,5R)-7-amino-3-oxa-9-azabicyclo[3.3.1]nonan-9-yl]methyl]-4-(2-chloro-4-fluoro-phenyl)-2-thiazol-2-yl-1,4-dihydropyrimidine-5-carboxylate 60b (60 mg, 0.12 mmol) and triethyl-amine (0.05 mL, 0.3 mmol) in DCM (5 mL) was added acetyl chloride (0.018 mL, 0.24 mmol) dropwise at 0° C. The mixture was allowed to warm to room temperature while stirred for 1 h, and then concentrated in vacuo. The residue was purified by preparative HPLC to afford 23 mg of the title compound 61 as a light yellow powder (yield was 34%).

Example 62

Methyl (4R)-4-(2-chloro-4-fluoro-phenyl)-2-thiazol-2-yl-6-[[(1S,5R)-7-exo-ureido-3-oxa-9-azabicyclo[3.3.1]nonan-9-yl]methyl]-1,4-dihydropyrimidine-5-carboxylate

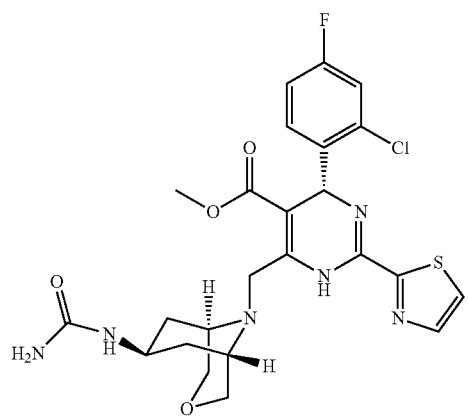 [SMILES: COC(=O)C1=C(CN2[C@@H]3COC[C@H]2C[C@H](NC(N)=O)C3)NC(c2nccs2)=N[C@H]1c1ccc(F)cc1Cl]

To a solution of methyl (4R)-6-[[(1S,5R)-7-amino-3-oxa-9-azabicyclo[3.3.1]nonan-9-yl]methyl]-4-(2-chloro-4-fluoro-phenyl)-2-thiazol-2-yl-1,4-dihydropyrimidine-5-carboxylate 60b (60 mg, 0.12 mmol) and triethyl-amine (0.17 mL, 1.2 mmol) in DCM (5 mL) was added isocyanato(trimethyl)silane (55 mg, 0.48 mmol) dropwise at 0° C. The mixture was allowed to warm to room temperature while stirred for 3 h. Then the mixture was concentrated in vacuo. The residue was purified by Preparative HPLC to afford 23 mg of the title compound 62 as a light yellow powder (yield was 34%).

Example 63

Methyl (4R)-4-(2-chloro-4-fluoro-phenyl)-6-[[(1R, 5S)-7-exo-(sulfamoylamino)-3-oxa-9-azabicyclo[3.3.1]nonan-9-yl]methyl]-2-thiazol-2-yl-1,4-dihydropyrimidine-5-carboxylate Preparation of Example 63

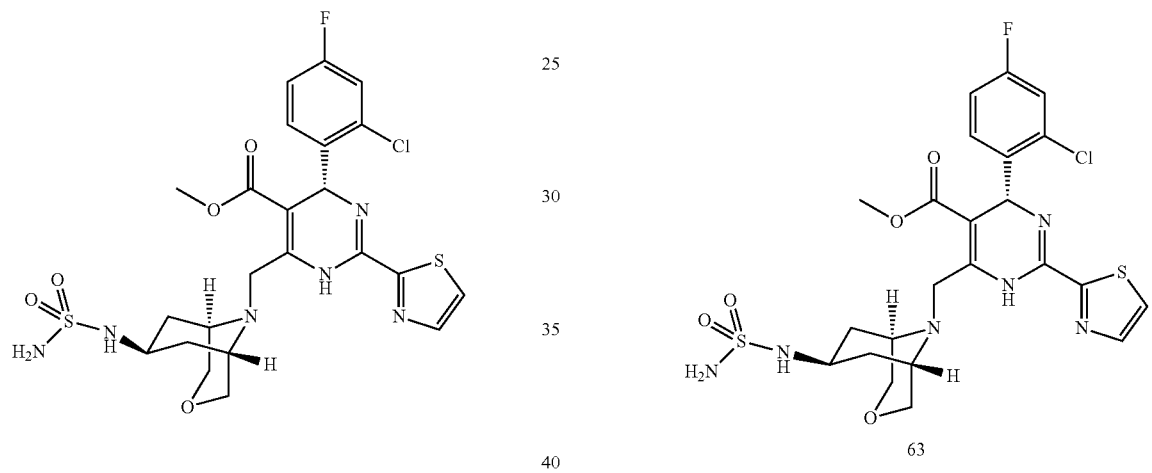

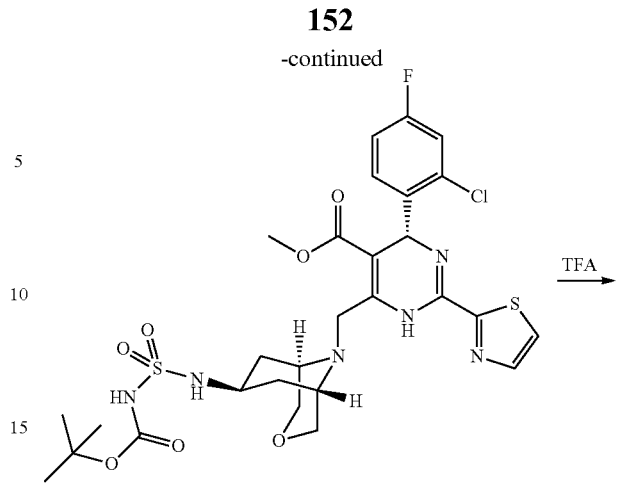

Step I: To a solution of methyl (4R)-6-[[(1S,5R)-7-amino-3-oxa-9-azabicyclo[3.3.1]nonan-9-yl]methyl]-4-(2-chloro-4-fluoro-phenyl)-2-thiazol-2-yl-1,4-dihydropyrimidine-5-carboxylate 60b (60 mg, 0.12 mmol) and triethylamine (0.17 mL, 1.2 mmol) in DCM (5 mL) was added a 0.05 M solution of tert-butyl N-chlorosulfonylcarbamate in DCM (2.5 mL, 0.125 mmol) dropwise at 0° C. The mixture was allowed to warm to room temperature while stirred for 16 h, and then concentrated in vacuo. The residue was purified by silica gel chromatography to afford 0.08 g of methyl (4R)-6-[[(1S,5R)-7-(tert-butoxycarbonylsulfamoylamino)-3-oxa-9-azabicyclo[3.3.1]nonan-9-yl]methyl]-4-(2-chloro-4-fluoro-phenyl)-2-thiazol-2-yl-1,4-dihydropyrimidine-5-carboxylate 63a as a yellow oil (yield was 97%). MS: calc'd (MH$^+$) 684, measured (MH$^+$) 684.

Step II: To a solution of methyl (4R)-6-[[(1S,5R)-7-(tert-butoxycarbonylsulfamoylamino)-3-oxa-9-azabicyclo[3.3.1]nonan-9-yl]methyl]-4-(2-chloro-4-fluoro-phenyl)-2-thiazol-2-yl-1,4-dihydropyrimidine-5-carboxylate 63a (80 mg, 0.12 mmol) in DCM (5 mL) was added TFA (0.5 mL), The mixture was stirred at 25° C. for 3 h, and then concentrated in vacuo. The residue was purified by preparative HPLC to afford 14 mg of the title compound 63 as a light yellow powder (yield was 20%).

Example 64

2-[(1R,5S,6S)-8-[[(4R)-4-(2-bromo-4-fluoro-phenyl)-5-methoxycarbonyl-2-thiazol-2-yl-1,4-dihydro-pyrimidin-6-yl]methyl]-3-oxa-8-azabicyclo[3.2.1]octan-6-yl]acetic acid

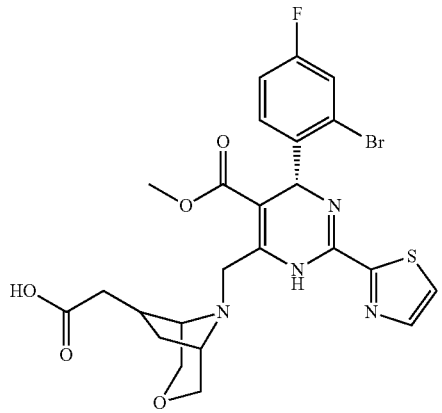 [SMILES: COC(=O)C1=C(CN2C3COCC2C(CC(=O)O)C3)NC(c2nccs2)=N[C@H]1c1ccc(F)cc1Br]

The title compound was prepared in analogy to compound 1a in Example 1 starting from methyl (4R)-4-(2-bromo-4-fluoro-phenyl)-6-(bromomethyl)-2-thiazol-2-yl-1,4-dihydropyrimidine-5-carboxylate 53a (73 mg, 0.15 mmol) and 2-(3-oxa-8-azabicyclo[3.2.1]octan-6-yl)acetic acid (121 mg, 0.7 mmol) 64c. 21 mg of the title compound was isolated by preparative HPLC as a yellow powder (yield was 16%).

Preparation of
2-(3-oxa-8-azabicyclo[3.2.1]octan-6-yl)acetic acid
64c

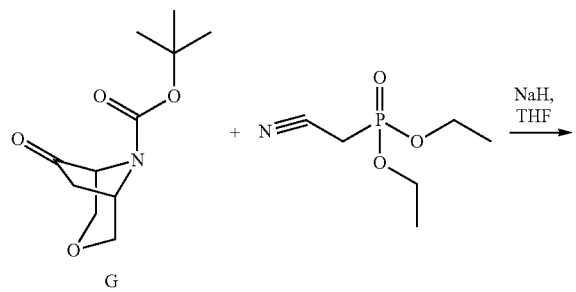

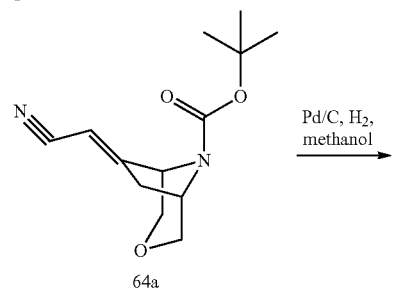

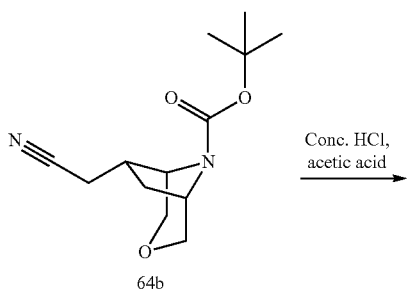

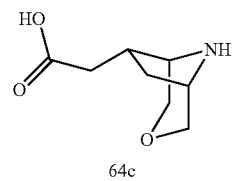

Step I: To a solution of tert-butyl 6-oxo-3-oxa-8-azabicyclo[3.2.1]octane-8-carboxylate G (1.43 mL, 8.81 mmol) in THF (50 mL) was added NaH (350 mg, 8.81 mmol) at ice-bath. After 15 min, 2-diethoxyphosphorylacetonitrile (1 g, 4.4 mmol) was added. The mixture was stirred at 25° C. for 2 h, quenched with water (5 mL) and then extracted with ethyl acetate (200 mL) two times. The combined organic layers were washed with water (200 mL) three times, dried over anhydrous sodium sulfate and concentrated in vacuo. The residue was purified by silica gel chromatography to afford 970 mg of the product 64a as a white solid (yield was 88%). MS: calc'd (MH+) 251, measured (MH+) 251.

Step II: A mixture of tert-butyl (6E)-6-(cyanomethylene)-3-oxa-8-azabicyclo[3.2.1]octane-8-carboxylate 64a (970 mg, 3.9 mmol) and 10% palladium on active carbon (200 mg) in methanol (100 mL) was stirred at 25° C. under 30 psi of $H_2$ pressure for 5 hours. Then the catalyst was filtered off and washed with ethyl acetate. The filtrate was concentrate in vacuo. The residue was purified by silica gel chromatography to afford 180 mg of the product 64b as a colorless oil (yield was 18%). MS: calc'd (MH+) 253, measured (MH+) 253.

Step III: A solution of tert-butyl (6S)-6-(cyanomethyl)-3-oxa-8-azabicyclo[3.2.1]octane-8-carboxylate 64b (180 mg, 0.71 mmol) in Conc. HCl (5 mL) and acetic acid (1 mL) was stirred at 100° C. for 4 h. Then the mixture concentrated in vacuo to afford 2-[(6S)-3-oxa-8-azabicyclo[3.2.1]octan-6-yl]acetic acid 64c (121 mg, 99%) which was used for next step without further purification. MS: calc'd (MH+) 172, measured (MH+) 172.

Example 65

Endo-2-[(1S,5R)-9-[[(4R)-4-(2-chloro-3-fluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid

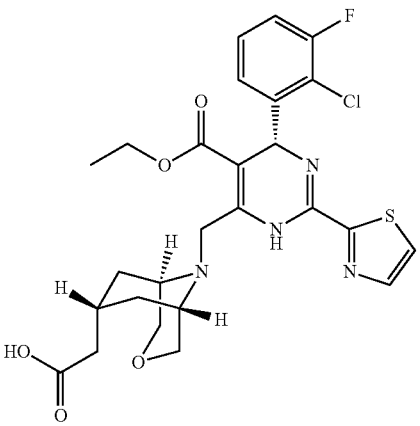 [SMILES: CCOC(=O)C1=C(CN2[C@@H]3COC[C@H]2C[C@@H](CC(=O)O)C3)NC(c2nccs2)=N[C@H]1c1cccc(F)c1Cl]

The title compound was prepared in analogy to Example 1a with the procedure shown in Scheme 3 by using ethyl acetoacetate, 2-chloro-3-fluoro-benzaldehyde and in the three component reaction step, and (3-oxa-9-aza-bicyclo [3.3.1]non-7-yl)-acetic acid (CAS: 1389441-75-1) instead of methyl acetoacetate, 2-chloro-4-fluoro-benzaldehyde and 3-oxa-9-azabicyclo[3.3.1]nonane-7-carboxylic acid methyl ester, respectively.

Example 66

Exo-2-[(1S,5R)-9-[[(4R)-4-(2-chloro-3-fluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid

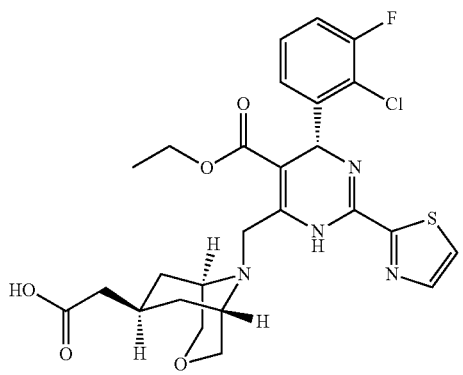 [SMILES: CCOC(=O)C1=C(CN2[C@@H]3COC[C@H]2C[C@H](CC(=O)O)C3)NC(c2nccs2)=N[C@H]1c1cccc(F)c1Cl]

The title compound was prepared in analogy to Example 1a with the procedure shown in Scheme 3 by using ethyl acetoacetate, 2-chloro-3-fluoro-benzaldehyde and exo-(3-oxa-9-aza-bicyclo[3.3.1]non-7-yl)-acetic acid in (PharmaBlock (Nanjing) R&D Co. Ltd, PB05416) instead of methyl acetoacetate, 2-chloro-4-fluoro-benzaldehyde and 3-oxa-9-azabicyclo[3.3.1]nonane-7-carboxylic acid methyl ester, respectively.

Example 67

Exo-2-[(1S,5R)-9-[[(4R)-4-(2-bromo-4-fluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid

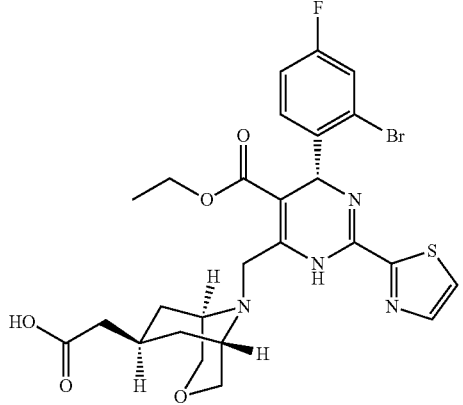 [SMILES: CCOC(=O)C1=C(CN2[C@@H]3COC[C@H]2C[C@H](CC(=O)O)C3)NC(c2nccs2)=N[C@H]1c1ccc(F)cc1Br]

The title compound was prepared in analogy to Example 1a with the procedure shown in Scheme 3 by using ethyl acetoacetate and 2-bromo-4-fluoro-benzaldehyde and exo-(3-oxa-9-aza-bicyclo[3.3.1]non-7-yl)-acetic acid (PharmaBlock (Nanjing) R&D Co. Ltd, PB05416) instead of methyl acetoacetate, 2-chloro-4-fluoro-benzaldehyde and 3-oxa-9-azabicyclo[3.3.1]nonane-7-carboxylic acid methyl ester, respectively.

Example 68

Exo-2-[(1S,5R)-9-[[(4R)-4-(2-bromo-3-fluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid

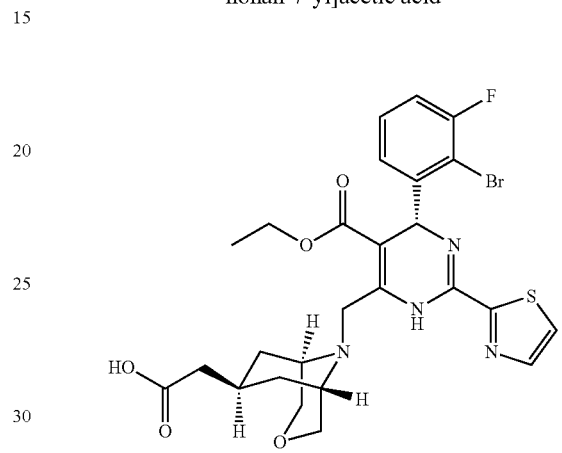

The title compound was prepared in analogy to Example 1a with the procedure shown in Scheme 3 by using ethyl acetoacetate, 2-bromo-3-fluoro-benzaldehyde and exo-(3-oxa-9-aza-bicyclo[3.3.1]non-7-yl)-acetic acid (PharmaBlock (Nanjing) R&D Co. Ltd, PB05416) instead of methyl acetoacetate, 2-chloro-4-fluoro-benzaldehyde and 3-oxa-9-azabicyclo[3.3.1]nonane-7-carboxylic acid methyl ester, respectively.

Example 69

Exo-2-[(1S,5R)-9-[[(4R)-4-(2-chloro-3,4-difluorophenyl)-5-ethoxycarbonyl-2-thiazol-2-yl-1,4-dihydropyrimidin-6-yl]methyl]-3-oxa-9-azabicyclo[3.3.1]nonan-7-yl]acetic acid

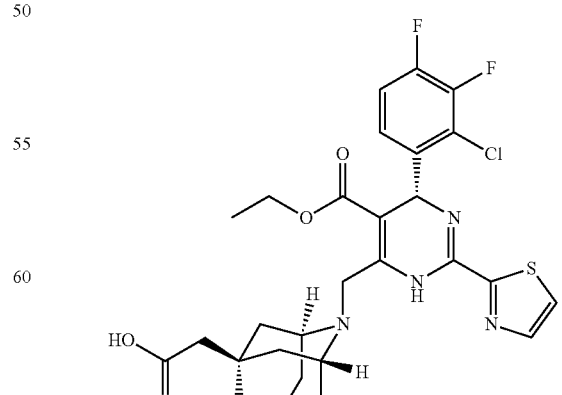

The title compound was prepared in analogy to Example 1a with the procedure shown in Scheme 3 by using ethyl acetoacetate, 2-chloro-3,4-difluoro-benzaldehyde and exo-(3-oxa-9-aza-bicyclo[3.3.1]non-7-yl)-acetic acid (PharmaBlock (Nanjing) R&D Co. Ltd, PB05416) instead of methyl acetoacetate, 2-chloro-4-fluoro-benzaldehyde and 3-oxa-9-azabicyclo[3.3.1]nonane-7-carboxylic acid methyl ester, respectively.

Example 70

Ethyl (4R)-6-[[(1S,5R)-7-endo-acetamido-3-oxa-9-azabicyclo[3.3.1]nonan-9-yl]methyl]-4-(2-bromo-4-fluoro-phenyl)-2-thiazol-2-yl-1,4-dihydropyrimidine-5-carboxylate

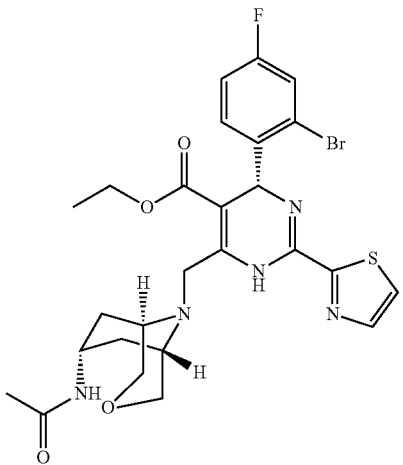 [SMILES: CCOC(=O)C1=C(CN2[C@@H]3COC[C@H]2C[C@@H](NC(C)=O)C3)NC(c2nccs2)=N[C@H]1c1ccc(F)cc1Br]

The title compound was prepared in analogy to Example 35 by using ethyl (4R)-4-(2-bromo-4-fluoro-phenyl)-6-(bromomethyl)-2-thiazol-2-yl-1,4-dihydropyrimidine-5-carboxylate 70a instead of compound C.
Ethyl (4R)-4-(2-bromo-4-fluoro-phenyl)-6-(bromomethyl)-2-thiazol-2-yl-1,4-dihydropyrimidine-5-carboxylate 70a was prepared in analogy to compound C with procedures shown in Example 1 by using ethyl acetoacetate and 2-bromo-4-fluoro-benzaldehyde instead of methyl acetoacetate and 2-chloro-4-fluoro-benzaldehyde, respectively.

Example 71

Ethyl (4R)-6-[[(1S,5R)-7-exo-acetamido-3-oxa-9-azabicyclo[3.3.1]nonan-9-yl]methyl]-4-(2-bromo-4-fluoro-phenyl)-2-thiazol-2-yl-1,4-dihydropyrimidine-5-carboxylate

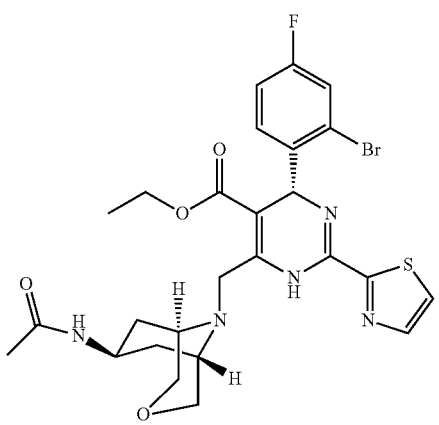 [SMILES: CCOC(=O)C1=C(CN2[C@@H]3COC[C@H]2C[C@H](NC(C)=O)C3)NC(c2nccs2)=N[C@H]1c1ccc(F)cc1Br]

To a solution of ethyl (4R)-6-[[(1S,5R)-7-amino-3-oxa-9-azabicyclo[3.3.1]nonan-9-yl]methyl]-4-(2-bromo-4-fluoro-phenyl)-2-thiazol-2-yl-1,4-dihydropyrimidine-5-carboxylate (75 mg, 0.133 mmol) 71a and triethylamine (0.06 mL, 0.4 mmol) in DCM (5 mL) was added acetyl chloride (0.018 mL, 0.24 mmol) dropwise at 0° C. The mixture was allowed to warm to room temperature while stirred for 1 h. Then the mixture was concentrated in vacuo. The residue was purified by preparative HPLC to afford 27 mg of Example 71 as a light yellow powder (yield was 33%).

Preparation of ethyl (4R)-6-[[(1S,5R)-7-amino-3-oxa-9-azabicyclo[3.3.1]nonan-9-yl]methyl]-4-(2-bromo-4-fluoro-phenyl)-2-thiazol-2-yl-1,4-dihydropyrimidine-5-carboxylate 71a Compound 71a was prepared in analogy to 60b in Example 60 by using ethyl (4R)-4-(2-bromo-4-fluoro-phenyl)-6-(bromomethyl)-2-thiazol-2-yl-1,4-dihydropyrimidine-5-carboxylate 70a instead of compound C.

Example 72

Exo-2-[(1S,5R)-9-[[(4R)-4-(2-chlorophenyl)-5-ethoxycarbonyl-2-thiazol-2-yl-1,4-dihydropyrimidin-6-yl]methyl]-3-oxa-9-azabicyclo[3.3.1]nonan-7-yl] acetic acid

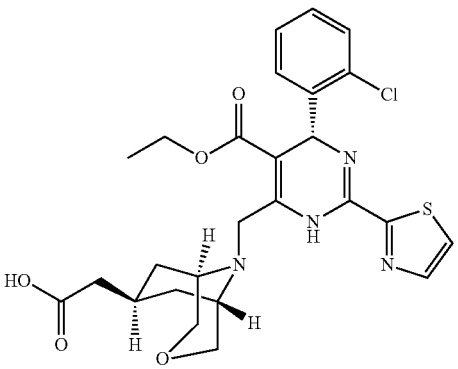 [SMILES: CCOC(=O)C1=C(CN2[C@@H]3COC[C@H]2C[C@H](CC(=O)O)C3)NC(c2nccs2)=N[C@H]1c1ccccc1Cl]

The title compound was prepared in analogy to Example 1a with the procedure shown in Scheme 3 by using ethyl acetoacetate, 2-chloro-benzaldehyde and exo-(3-oxa-9-azabicyclo[3.3.1]non-7-yl)-acetic (PharmaBlock (Nanjing) R&D Co. Ltd, PB05416) acid (PharmaBlock (Nanjing) R&D Co. Ltd, PB05416) instead of methyl acetoacetate, 2-chloro-4-fluoro-benzaldehyde and 3-oxa-9-azabicyclo[3.3.1]nonane-7-carboxylic acid methyl ester, respectively.

Example 73

Exo-2-[(1S,5R)-9-[[(4R)-4-(2-chloro-3,4-difluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid

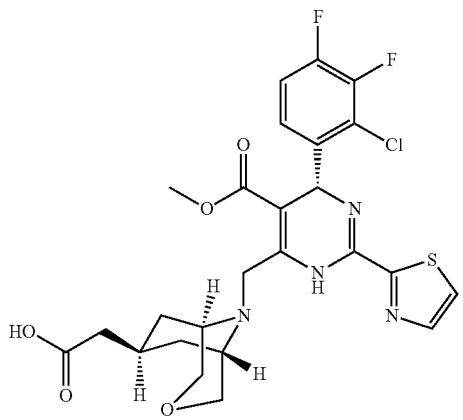 [SMILES: COC(=O)C1=C(CN2[C@@H]3COC[C@H]2C[C@H](CC(=O)O)C3)NC(c2nccs2)=N[C@H]1c1ccc(F)c(F)c1Cl]

The title compound was prepared in analogy to Example 1a with the procedure shown in Scheme 3 by using 2-chloro-3,4-difluoro-benzaldehyde and exo-(3-oxa-9-aza-bicyclo[3.3.1]non-7-yl)-acetic acid (PharmaBlock (Nanjing) R&D Co. Ltd, PB05416) instead of 2-chloro-4-fluoro-benzaldehyde and 3-oxa-9-azabicyclo[3.3.1]nonane-7-carboxylic acid methyl ester, respectively.

Example 74

Exo-2-[(1S,5R)-9-[[(4R)-4-(2-bromo-3-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid

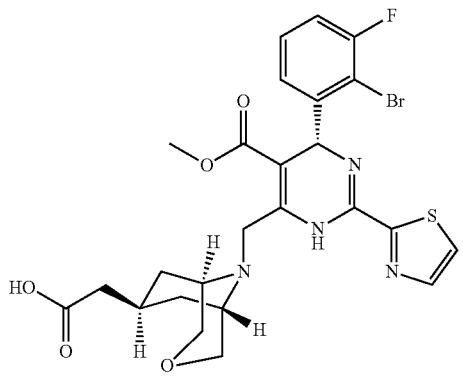 [SMILES: COC(=O)C1=C(CN2[C@@H]3COC[C@H]2C[C@H](CC(=O)O)C3)NC(c2nccs2)=N[C@H]1c1cccc(F)c1Br]

The title compound was prepared in analogy to Example 1a with the procedure shown in Scheme 3 by using 2-bromo-3-fluoro-benzaldehyde and exo-(3-oxa-9-aza-bicyclo[3.3.1]non-7-yl)-acetic acid (PharmaBlock (Nanjing) R&D Co. Ltd, PB05416) instead of 2-chloro-4-fluoro-benzaldehyde and 3-oxa-9-azabicyclo[3.3.1]nonane-7-carboxylic acid methyl ester, respectively.

Example 75

Exo-2-[(1S,5R)-9-[[(4R)-4-(2,3-difluorophenyl)-5-ethoxycarbonyl-2-thiazol-2-yl-1,4-dihydropyrimidin-6-yl]methyl]-3-oxa-9-azabicyclo[3.3.1]nonan-7-yl]acetic acid

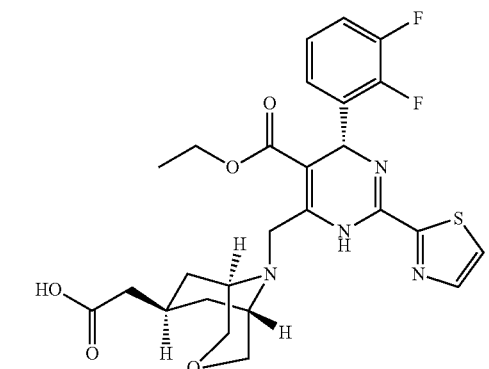

The title compound was prepared in analogy to Example 1a with the procedure shown in Scheme 3 by using ethyl acetoacetate, 2,3-difluoro-benzaldehyde and exo-(3-oxa-9-aza-bicyclo[3.3.1]non-7-yl)-acetic acid instead of methyl acetoacetate, 2-chloro-4-fluoro-benzaldehyde and 3-oxa-9-azabicyclo[3.3.1]nonane-7-carboxylic acid methyl ester, respectively.

Example 76

Exo-2-[(1S,5R)-9-[[(4R)-4-(2-bromophenyl)-5-methoxycarbonyl-2-thiazol-2-yl-1,4-dihydropyrimidin-6-yl]methyl]-3-oxa-9-azabicyclo[3.3.1]nonan-7-yl]acetic acid

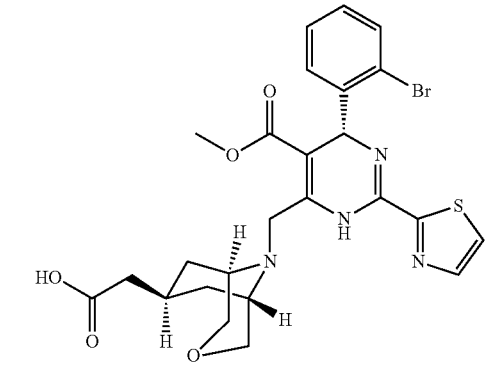 [SMILES: COC(=O)C1=C(CN2[C@@H]3COC[C@H]2C[C@H](CC(=O)O)C3)NC(c2nccs2)=N[C@H]1c1ccccc1Br]

The title compound was prepared in analogy to Example 1a with the procedure shown in Scheme 3 by using 2-bromo-benzaldehyde and exo-(3-oxa-9-aza-bicyclo[3.3.1]non-7-yl)-acetic acid (PharmaBlock (Nanjing) R&D Co. Ltd, PB05416) instead of 2-chloro-4-fluoro-benzaldehyde and 3-oxa-9-azabicyclo[3.3.1]nonane-7-carboxylic acid methyl ester, respectively.

Example 77

Exo-2-[(1S,5R)-9-[[(4R)-4-(2-bromophenyl)-5-ethoxycarbonyl-2-thiazol-2-yl-1,4-dihydropyrimidin-6-yl]methyl]-3-oxa-9-azabicyclo[3.3.1]nonan-7-yl]acetic acid

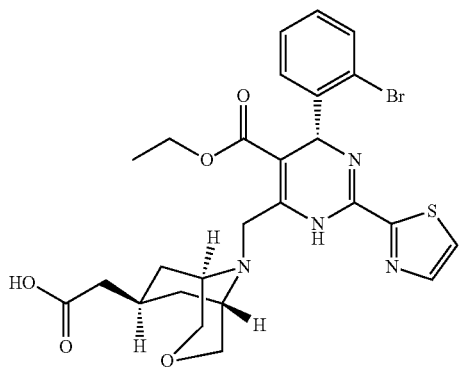 [SMILES: CCOC(=O)C1=C(CN2[C@@H]3COC[C@H]2C[C@H](CC(=O)O)C3)NC(c2nccs2)=N[C@H]1c1ccccc1Br]

The title compound was prepared in analogy to Example 1a with the procedure shown in Scheme 3 by using ethyl acetoacetate, 2-bromo-benzaldehyde and exo-(3-oxa-9-azabicyclo[3.3.1]non-7-yl)-acetic acid (PharmaBlock (Nanjing) R&D Co. Ltd, PB05416) instead of methyl acetoacetate, 2-chloro-4-fluoro-benzaldehyde and 3-oxa-9-azabicyclo[3.3.1]nonane-7-carboxylic acid methyl ester, respectively.

Example 78

Exo-2-[(1S,5R)-9-[[(4S)-4-(3,4-difluoro-2-methyl-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid

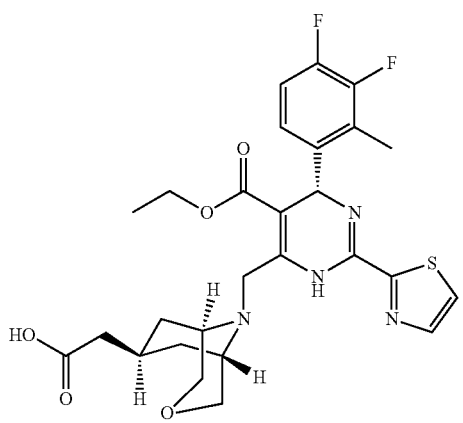 [SMILES: CCOC(=O)C1=C(CN2[C@@H]3COC[C@H]2C[C@H](CC(=O)O)C3)NC(c2nccs2)=N[C@H]1c1ccc(F)c(F)c1C]

The title compound was prepared in analogy to Example 1a with the procedure shown in Scheme 3 by using ethyl acetoacetate, 2-methyl-3,4-difluoro-benzaldehyde and exo-(3-oxa-9-aza-bicyclo[3.3.1]non-7-yl)-acetic acid (PharmaBlock (Nanjing) R&D Co. Ltd, PB05416) instead of methyl acetoacetate, 2-chloro-4-fluoro-benzaldehyde and 3-oxa-9-azabicyclo[3.3.1]nonane-7-carboxylic acid methyl ester, respectively.

Example 79

3-[(1S,5R)-9-[[(4R)-4-(2-chloro-4-fluoro-phenyl)-5-methoxycarbonyl-2-thiazol-2-yl-1,4-dihydropyrimidin-6-yl]methyl]-3-oxa-7,9-diazabicyclo[3.3.1]nonan-7-yl]-2,2-dimethyl-3-oxo-propanoic acid

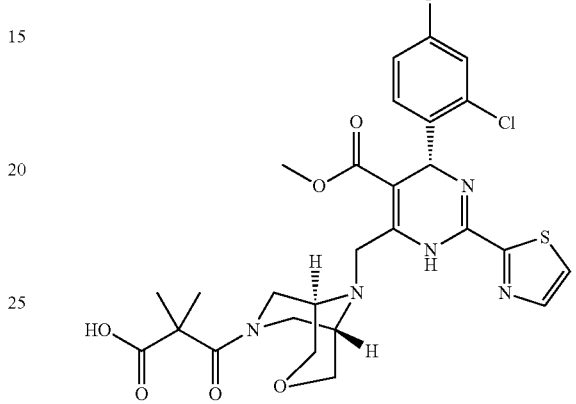

A mixture of methyl (4R)-4-(2-chloro-4-fluoro-phenyl)-6-(3-oxa-7,9-diazabicyclo[3.3.1]nonan-9-ylmethyl)-2-thiazol-2-yl-1,4-dihydropyrimidine-5-carboxylate (50 mg, 0.1 mmol), 2,2-dimethylpropanedioic acid (prepared as shown in Example 15) (26.4 mg, 0.2 mmol), HATU (48 mg, 0.25 mmol) and triethyl-amine (0.09 mL, 0.625 mmol) in dichloromethane (5 mL). The mixture was stirred at 25° C. for 16 h, and then concentrated in vacuo. The resulting residue was purified by preparative HPLC to afford 10 mg of the title compound as a white powder (yield was 18%).

Example 80

Exo-2-[(1S,5R)-9-[[(4R)-4-(2-bromo-3,4-difluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid

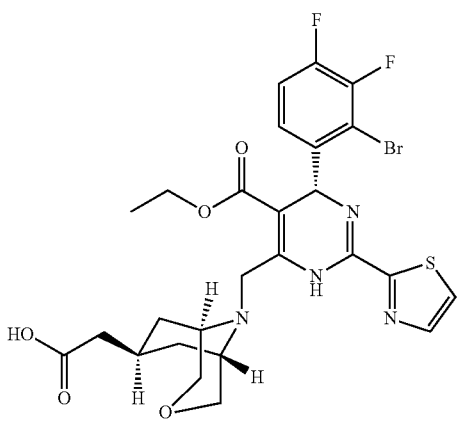 [SMILES: CCOC(=O)C1=C(CN2[C@@H]3COC[C@H]2C[C@H](CC(=O)O)C3)NC(c2nccs2)=N[C@H]1c1ccc(F)c(F)c1Br]

The title compound was prepared in analogy to Example 1a with the procedure shown in Scheme 3 by using ethyl acetoacetate, 2-bromo-3,4-difluoro-benzaldehyde and exo-(3-oxa-9-aza-bicyclo[3.3.1]non-7-yl)-acetic acid (PharmaBlock (Nanjing) R&D Co. Ltd, PB05416) instead of methyl acetoacetate, 2-chloro-4-fluoro-benzaldehyde and 3-oxa-9-azabicyclo[3.3.1]nonane-7-carboxylic acid methyl ester, respectively.

Examples 81 and 82

(1S,5R)-8-[[(4R)-4-(2-chloro-4-fluoro-phenyl)-5-methoxycarbonyl-2-thiazol-2-yl-1,4-dihydropyrimidin-6-yl]methyl]-3-oxa-8-azabicyclo[3.2.1]octane-5-carboxylic acid and (1R,5S)-8-[[(4R)-4-(2-chloro-4-fluoro-phenyl)-5-methoxycarbonyl-2-thiazol-2-yl-1,4-dihydropyrimidin-6-yl]methyl]-3-oxa-8-azabicyclo[3.2.1]octane-5-carboxylic acid

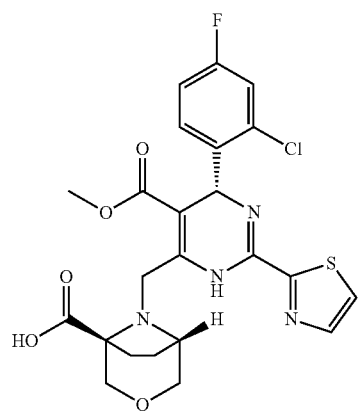

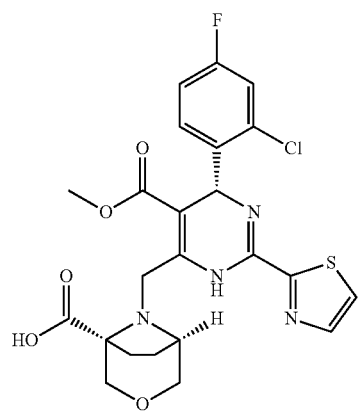

A mixture of methyl (4R)-6-(bromomethyl)-4-(2-chloro-4-fluoro-phenyl)-2-thiazol-2-yl-1,4-dihydropyrimidine-5-carboxylate (compound C, 61 mg, 0.138 mmol), 3-oxa-8-azabicyclo[3.2.1]octane-5-carboxylic acid 81a (20 mg, 0.127 mmol) and DIPEA (0.07 mL, 0.4 mmol) in DCM (5 mL) was stirred at 25° C. for 16 h. Then the mixture was concentrated in vacuo. The residue was purified by preparative HPLC to afford a pair of diastereomers, Example 81 and Example 82.

Preparation of
3-oxa-8-azabicyclo[3.2.1]octane-5-carboxylic acid
81a

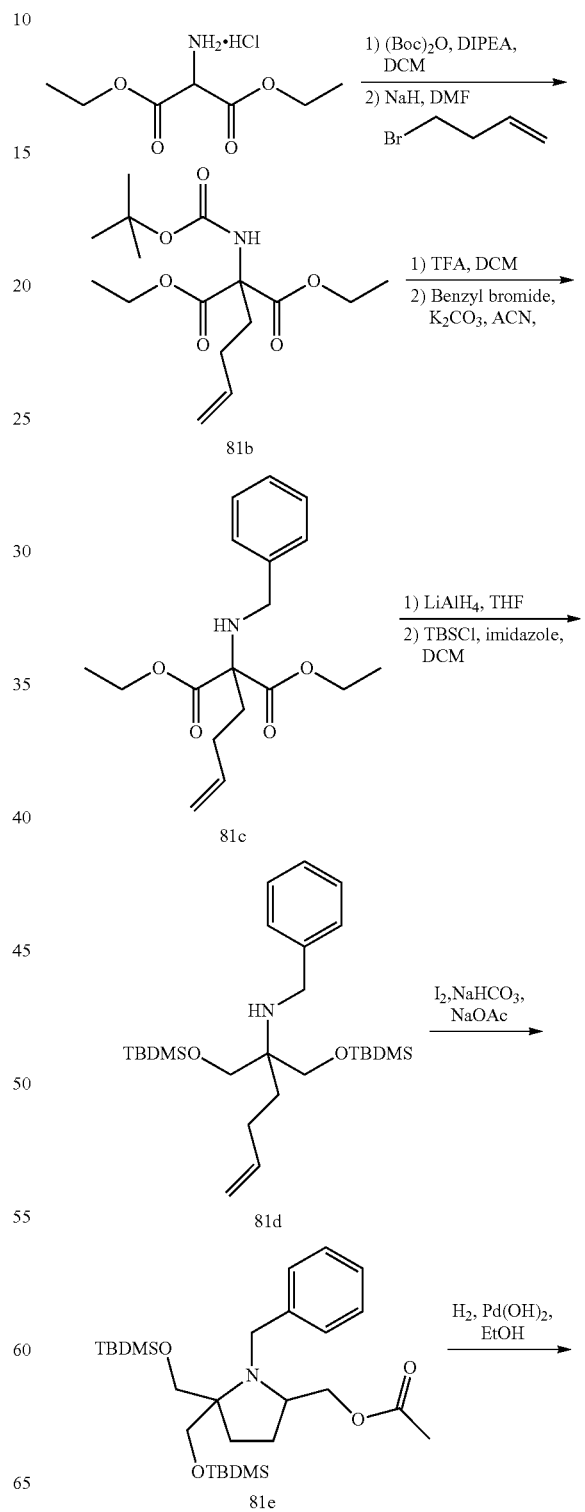

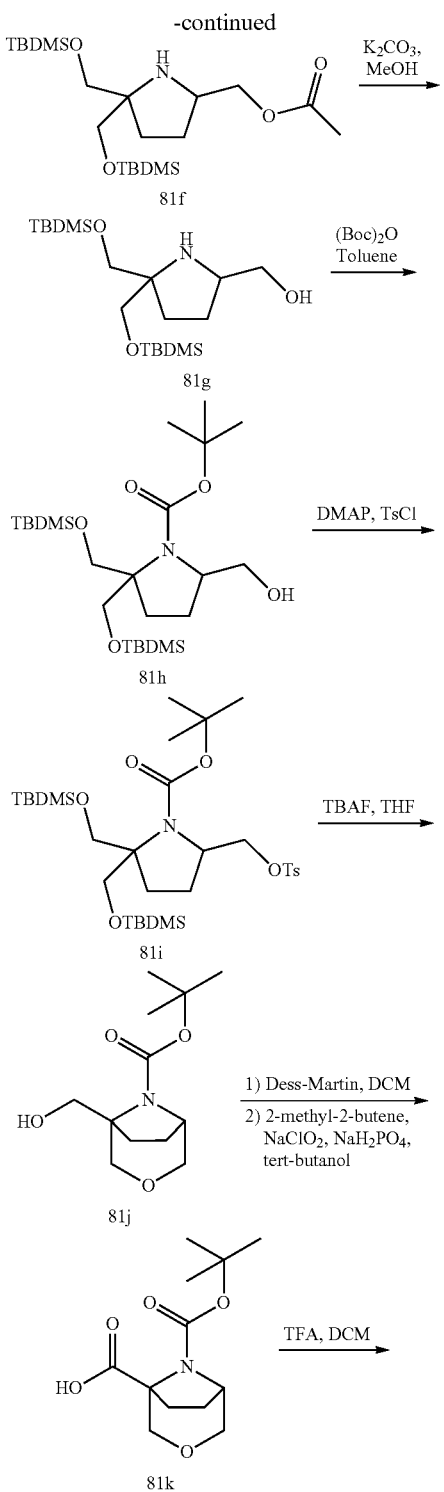

(250 mL) was added di-tert-butyl dicarbonate (20.8 g, 96 mmol) at ice-bath. The mixture was allowed to warm to room temperature while stirred for 16 h. Then the mixture was concentrated in vacuo. And the residue was extracted with DCM (150 mL) two times. The combined organic layers were washed with saturated NaHCO$_3$ (100 mL) three times, dried over anhydrous sodium sulfate and concentrated in vacuo to afford 22 g of crude product diethyl 2-(tert-butoxycarbonylamino)propanedioate as a colorless oil (yield was 100%). MS: calc'd (MH$^+$) 276, measured (MH$^+$) 276.

Step II. To a solution of diethyl 2-(tert-butoxycarbonylamino)propanedioate (20 g, 72.7 mmol) in DMF (100 mL) was added NaH (3.5 g, 87.3 mmol). The mixture was allowed to warm to room temperature while stirred for 0.5 h. Then 4-bromo-1-butene (10.8 g, 80 mmol) was added. The mixture was stirred at 90° C. for 4 h. The mixture was cooled to room temperature, quenched with water (20 mL), and concentrated in vacuo. The residue was purified by silica gel chromatography to afford 14.5 g of the product 81b as a brown oil (yield was 60%). MS: calc'd (MH$^+$) 330, measured (MH$^+$) 330.

Step III. To a solution of diethyl 2-but-3-enyl-2-(tert-butoxycarbonylamino)propanedioate 81b (14.5 g, 4.4 mmol) in DCM (30 mL) was added TFA (10 mL), The mixture was stirred at room temperature for 16 h, quenched with saturated NaHCO$_3$ (50 mL) and then extracted with DCM (150 mL) two times, washed with saturated NaHCO$_3$ (100 mL) three times, dried over anhydrous sodium sulfate and concentrated in vacuo to afford diethyl 2-amino-2-but-3-enyl-propanedioate as a crude product (9.5 g, 94%), which was used for next step without further purification. MS: calc'd (MH$^+$) 230, measured (MH$^+$) 230.

Step IV. To a mixture of diethyl 2-amino-2-but-3-enyl-propanedioate (9.5 g, 41.5 mmol) and K$_2$CO$_3$ (17.3 g, 125 mmol) in ACN (250 mL) was added benzyl bromide (5.9 mL, 49.8 mmol). The mixture was stirred at 80° C. for 16 h. Then the insoluble solid was filtered off and the filtrate was concentrated in vacuo and the residue was extracted with ethyl acetate (200 mL) two times, washed with water (100 mL) three times, dried over anhydrous sodium sulfate and concentrated in vacuo. The residue was purified by silica gel chromatography to afford 11.3 g of 81c as a colorless oil (yield was 85%). MS: calc'd (MH$^+$) 320, measured (MH$^+$) 320.

Step V. To a mixture of diethyl 2-(benzylamino)-2-but-3-enyl-propanedioate 81c (13.9 g, 43.6 mmol) in THF (200 mL) was added standard solution of 2 M LiAlH$_4$ in THF (44 ml) dropwise at ice-bath. The mixture was allowed to warm to room temperature for 3 h. Then the reaction mixture was poured into a mixture of anhydrous sodium sulfate (500 g) and water (50 mL) in ether (300 mL), Then the insoluble solid was filtered off and the filtrate was concentrated in vacuo to afford 2-(benzylamino)-2-but-3-enyl-propane-1,3-diol (9.4 g, 91%) which was used for next step without further purification. MS: calc'd (MH$^+$) 236, measured (MH$^+$) 236.

Step VI. To a solution of 2-(benzylamino)-2-but-3-enyl-propane-1,3-diol (9.4 g, 40 mmol) and imidazole (6 g, 88 mmol) in DCM (150 mL) was added a solution of tert-butyldimethylsilyl chloride (16.4 mL, 88 mL) in DCM (50 mL) dropwise at ice-bath. The mixture was allowed to warm to room temperature while stirred for 16 h. The mixture was quenched with water (100 mL) and then extracted with DCM (100 mL) two times, washed with water (100 mL) three times, dried over anhydrous sodium sulfate and concentrated in vacuo. The residue was purified by silica gel chromatography to afford 17 g of N-benzyl-1-[tert-butyl(dimethyl)silyl]oxy-2-[[tert-butyl(dimethyl)silyl]oxymethyl]hex-5-en-2-amine 81d as a white solid (yield was 92%). MS: calc'd (MH$^+$) 461, measured (MH$^+$) 461.

Step I. To a solution of diethyl aminomalonate hydrochloride (17 g, 80 mmol) and DIPEA (44 mL, 250 mmol) in DCM Step VII. To a mixture of N-benzyl-1-[tert-butyl(dimethyl)silyl]oxy-2-[[tert-butyl(dimethyl)silyl]oxymethyl]hex-5-en-2-amine (1.2 g, 2.59 mmol), NaHCO₃ (435 mg, 5.18 mmol) and sodium acetate (637 mg, 7.77 mmol) in ACN (100 mL) was added I₂ (658 mg, 2.59 mmol) at room temperature. After 3 h, another batch of sodium acetate (637 mg, 7.77 mmol) was added. The mixture was stirred at 50° C. for 16 h. Then the insoluble solid was filtered off and the filtrate was concentrated in vacuo. The residue was extracted with ethyl acetate (100 mL) two times, washed with water (100 mL) three times, dried over anhydrous sodium sulfate and concentrated in vacuo. The residue was purified by flash silica gel chromatography to afford 5.7 g of the product 81e as a brown oil (yield was 45%). MS: calc'd (MH⁺) 522, measured (MH⁺) 522.

Step VIII: The mixture of [1-benzyl-5,5-bis[[tert-butyl(dimethyl)silyl]oxymethyl]pyrrolidin-2-yl]methyl acetate 81e (5.7 g, 10.94 mmol) and 20% palladium hydroxide on active carbon (1 g) in ethanol (150 mL) was stirred at 50° C. under 2.5 Mpa of H₂ pressure for 16 hours. Then the catalyst was filtered off and washed with ethyl acetate. The filtrate was concentrated in vacuo to afford [5,5-bis[[tert-butyl(dimethyl)silyl]oxymethyl]pyrrolidin-2-yl]methyl acetate 81f (4.48 g, 95%) which was used for next step without further purification. MS: calc'd (MH⁺) 432, measured (MH⁺) 432.

Step VIII: A mixture of [5,5-bis[[tert-butyl(dimethyl)silyl]oxymethyl]pyrrolidin-2-yl]methyl acetate (4.48 g, 10.4 mmol) and K₂CO₃ (g, mmol) in methanol (50 mL) was stirred at 25° C. for 2 h. Then the insoluble solid was filtered off and the filtrate was concentrated in vacuo. And then the residue was extracted with ethyl acetate (50 mL) two times, washed with water (20 mL) three times, dried over anhydrous sodium sulfate and concentrated in vacuo to afford [5,5-bis[[tert-butyl(dimethyl)silyl]oxymethyl]pyrrolidin-2-yl]methanol 81g (4 g, 98%) which was used for next step without further purification. MS: calc'd (MH⁺) 390, measured (MH⁺) 390.

Step IX: A mixture of [5,5-bis[[tert-butyl(dimethyl)silyl]oxymethyl]pyrrolidin-2-yl]methanol (2 g, 5.14 mmol) and di-tert-butyl dicarbonate (2.22 g, 10.28 mmol) in toluene (20 mL) was stirred at 90° C. for 4 h. Then the mixture was concentrated in vacuo and the residue was extracted with ether (50 mL) two times, washed with saturated NaHCO₃ (50 mL) three times, dried over anhydrous sodium sulfate and concentrated in vacuo to afford 4.26 g of the product 81h as a brown oil (yield was 96%). MS: calc'd (MH⁺) 490, measured (MH⁺) 490.

Step X: To a mixture of tert-butyl 2,2-bis[[tert-butyl(dimethyl)silyl]oxymethyl]-5-(hydroxymethyl)pyrrolidine-1-carboxylate (400 mg, 0.82 mmol) and 4-dimethylaminopyridine (300 mg, 2.45 mmol) in DCM (20 mL) was added 4-toluenesulfonyl chloride (312 mg, 1.64 mmol) at 0° C. The mixture was stirred at 25° C. for 16 h. Then the mixture was diluted with DCM (50 mL) and washed with saturated NH₄Cl (50 mL) three times, saturated NaHCO₃ (50 mL) three times and water (50 mL) three times, dried over anhydrous sodium sulfate and concentrated in vacuo to afford tert-butyl 2,2-bis[[tert-butyl(dimethyl)silyl]oxymethyl]-5-(p-tolylsulfonyloxymethyl)pyrrolidine-1-carboxylate 81i (410 mg, 77%) which was used for next step without further purification. MS: calc'd (MH⁺) 644, measured (MH⁺) 644.

Step XI: A mixture of tert-butyl 2,2-bis[[tert-butyl(dimethyl)silyl]oxymethyl]-5-(p-tolylsulfonyloxymethyl)pyrrolidine-1-carboxylate (410 mg, 0.64 mmol) and TBAF (1 M in THF, 4 mL) in THF (2 mL) was stirred at 50° C. for 16 h. Then the mixture was diluted with ethyl acetate (50 mL) and washed with saturated NH₄Cl (50 mL) three times and water (50 mL) three times, dried over anhydrous sodium sulfate and concentrated in vacuo to afford isopropyl 5-(hydroxymethyl)-3-oxa-8-azabicyclo[3.2.1]octane-8-carboxylate 81j (73 mg, 47%) which was used for next step without further purification. MS: calc'd (MH⁺) 244, measured (MH⁺) 244.

Step XII: To a solution of isopropyl 5-(hydroxymethyl)-3-oxa-8-azabicyclo[3.2.1]octane-8-carboxylate (73 mg, 0.3 mmol) in DCM (mL) was added Dess-Martin (191 mg, 0.45 mmol) at ice-bath. The mixture was allowed to warm to room temperature while stirred for 2 h. Then the mixture was diluted with DCM (50 mL) and washed with saturated NaHCO₃ (50 mL) three times and water (50 mL) three times, dried over anhydrous sodium sulfate and concentrated in vacuo to afford tert-butyl 5-formyl-3-oxa-8-azabicyclo[3.2.1]octane-8-carboxylate (71 mg, 98%) which was used for next step without further purification. MS: calc'd (MH⁺) 242, measured (MH⁺) 242.

Step XIII: A 50 ml of flask fitted with magnetic stirrer was charged with 5 ml of THF and was cooled to –78° C., to which 2-methyl-2-butene (0.15 mL, 3 mmol) was added and stirred for 5 minutes. Another 50 ml of flask fitted with magnetic stirrer was charged with tert-butyl 5-formyl-3-oxa-8-azabicyclo[3.2.1]octane-8-carboxylate (71 mg, 0.3 mmol) and tert butanol (5 mL) and was stirred at 25° C., to which the above prepared 2-methyl-2-butene THF solution was added. The resulting mixture was cooled to 0° C., and then a solution of NaH₂PO₄ (81 mg, 0.52 mmol) in water (5 mL) and a solution of NaClO₂ (20 mg, 0.22 mmol) in water (5 mL) were added subsequently. After stirring for 20 minutes at 0° C., the reaction mixture was diluted with water (10 mL), acidified to pH 5-6 using 1N HCl, and extracted with ethyl acetate (50 mL) three times. The combined organic phases were dried over Na₂SO₄, and concentrated in vacuo to afford 8-tert-butoxycarbonyl-3-oxa-8-azabicyclo[3.2.1]octane-5-carboxylic acid 81k (40 mg, 51%), which was used for next step without further purification. MS: calc'd (MH⁺) 258, measured (MH⁺) 258

Step XIV: To a solution of 8-tert-butoxycarbonyl-3-oxa-8-azabicyclo[3.2.1]octane-5-carboxylic acid (40 mg, 0.15 mmol) in DCM (3 mL) was added TFA (1 mL), The mixture was stirred at room temperature for 4 h. The mixture was concentrated in vacuo to afford 3-oxa-8-azabicyclo[3.2.1]octane-5-carboxylic acid 81a (20 mg, 85%) which was used for next step without further purification. MS: calc'd (MH⁺) 158, measured (MH⁺) 158.

Example 83

8-[[(4R)-4-(2-chloro-3-fluoro-phenyl)-5-ethoxycarbonyl-2-thiazol-2-yl-1,4-dihydropyrimidin-6-yl]methyl]-3-oxa-8-azabicyclo[3.2.1]octane-5-carboxylic acid

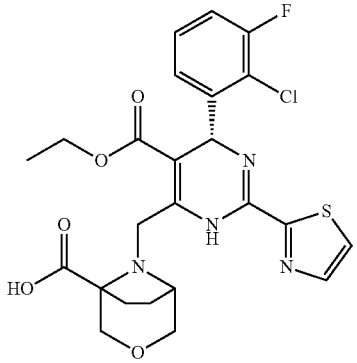 [SMILES: CCOC(=O)C1=C(CN2C3CCC2(C(=O)O)COC3)NC(c2nccs2)=N[C@H]1c1cccc(F)c1Cl]

The title compound was prepared in analogy to Example 1a with the procedure shown in Scheme 3 by using ethyl acetoacetate, 2-chloro-3-fluoro-benzaldehyde and 3-oxa-8-azabicyclo[3.2.1]octane-5-carboxylic acid 81a instead of methyl acetoacetate, 2-chloro-4-fluoro-benzaldehyde and 3-oxa-9-azabicyclo[3.3.1]nonane-7-carboxylic acid methyl ester, respectively.

Examples 84 and 85

(1S,5R)-8-[[(4S)-4-(3,4-difluoro-2-methyl-phenyl)-5-methoxycarbonyl-2-thiazol-2-yl-1,4-dihydropyrimidin-6-yl]methyl]-3-oxa-8-azabicyclo[3.2.1]octane-5-carboxylic acid and (1R,5S)-8-[[(4S)-4-(3,4-difluoro-2-methyl-phenyl)-5-methoxycarbonyl-2-thiazol-2-yl-1,4-dihydropyrimidin-6-yl]methyl]-3-oxa-8-azabicyclo[3.2.1]octane-5-carboxylic acid

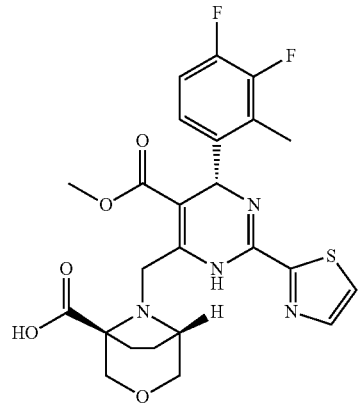

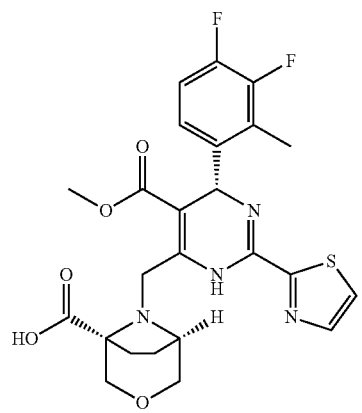

The title compounds were prepared in analogy to Example 1a with the procedure shown in Scheme 3 by using 2-methyl-3,4-difluoro-benzaldehyde and 3-oxa-8-azabicyclo[3.2.1]octane-5-carboxylic acid 81a instead of 2-chloro-4-fluoro-benzaldehyde and 3-oxa-9-azabicyclo[3.3.1]nonane-7-carboxylic acid methyl ester, respectively. Purification by HPLC afforded two diastereomers, Example 84 and Example 85.

Examples 86 and 87

2-[(1R,3S,5S)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid and 2-[(1S,3R,5R)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid

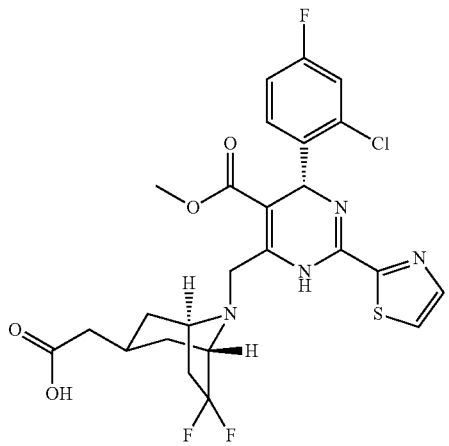

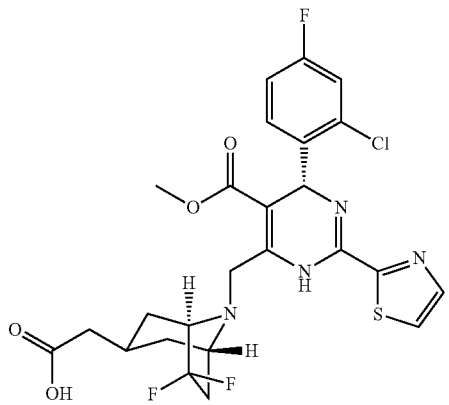

Preparation of Examples 86 and 87

To a solution of 86j, which was one of the two enantiomers of methyl 2-exo-[6,6-difluoro-8-azabicyclo[3.2.1]octan-3-yl]acetate, in dimethylformamide (5 mL) was added methyl (4R)-6-(bromomethyl)-4-(2-chloro-4-fluoro-phenyl)-2-thiazol-2-yl-1,4-dihydropyrimidine-5-carboxylate (compound C, 76 mg, 0.17 mmol), potassium iodide (35 mg, 0.21 mmol) and N,N-diisopropylethylamine (0.05 mL). The reaction mixture was heated to 55° C. for 3 hours. The reaction mixture was cooled down to room temperature, and then NaOH (35 mg, 0.87 mmol) in $H_2O$ (0.5 mL) was added. The mixture was then stirred at room temperature for three hours. Afterwards, the reaction mixture was quenched by adding ice-water, and then neutralized to pH 7.0 with 1N hydrochloride solution. The mixture was extracted with ethyl acetate (50 mL) three times. The organic phase was separated and concentrated. The residue was purified by silica gel chromatography and then by prepare-HPLC to give Example 86 (18 mg, 22%).

Example 87 was prepared in analogy to Example 86 starting from 86k, which was the other enantiomer of methyl 2-exo-[6,6-difluoro-8-azabicyclo[3.2.1]octan-3-yl]acetate, and methyl (4R)-6-(bromomethyl)-4-(2-chloro-4-fluorophenyl)-2-thiazol-2-yl-1,4-dihydropyrimidine-5-carboxylate C.

Preparation of the Two Enantiomers of methyl 2-exo-[6,6-difluoro-8-azabicyclo[3.2.1]octan-3-yl] acetate, 86j and 86k

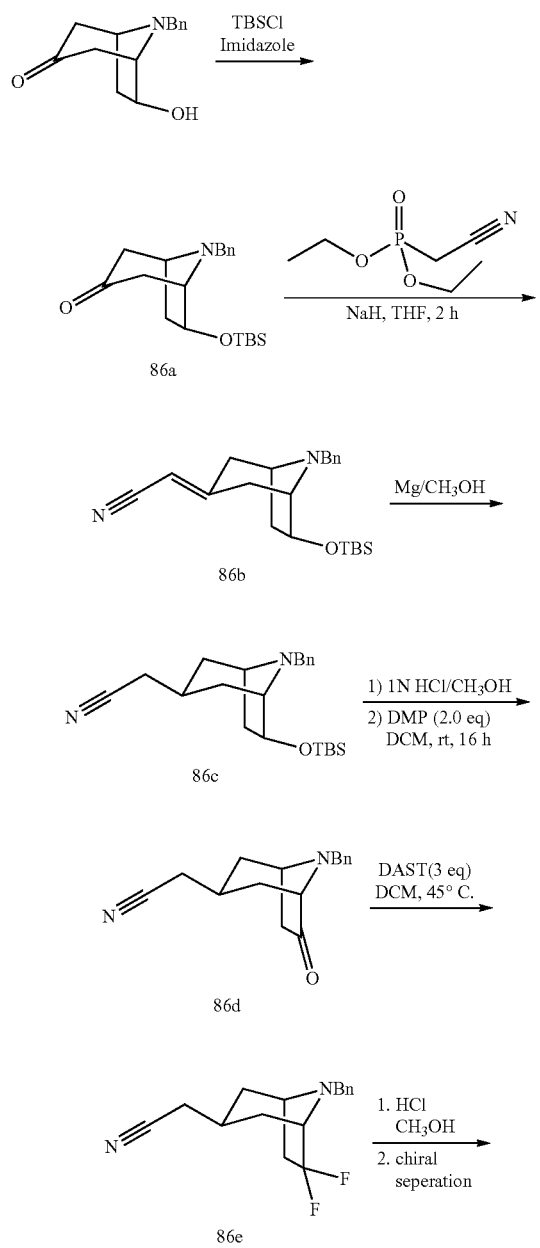

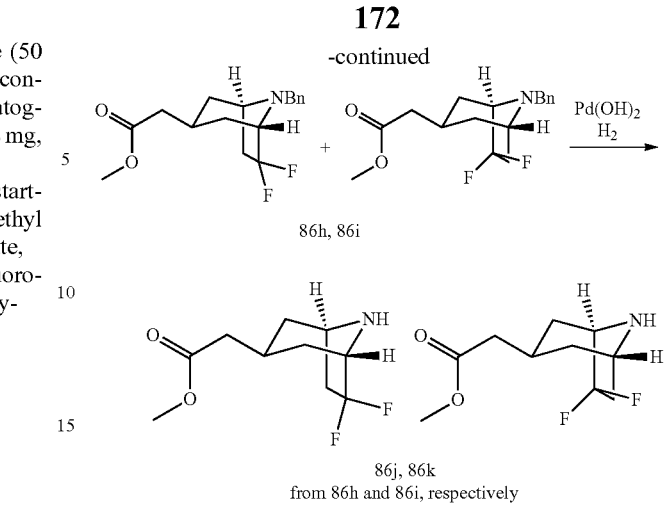

86h, 86i 86j, 86k
from 86h and 86i, respectively

Step I: To a mixture of 8-benzyl-6-hydroxy-8-azabicyclo [3.2.1]octan-3-one (prepared according to the procedure reported in Journal of Heterocyclic Chemistry 1992, 29(6), 1541-4; 46.2 g, 0.2 mol, 1.0 eq) and imidazole (16.3 g, 0.24 mol, 1.2 eq) in DCM (500 mL) was added TBSCl (33.1 g, 0.22 mol, 1.1 eq) in DCM (100 mL) slowly at room temperature in 10 min, then the mixture was stirred at room temperature for 2 h, washed with water (300 mL) and brine (300 mL), the organic layer was dried over $Na_2SO_4$ and concentrated to give 8-benzyl-6-[tert-butyl(dimethyl)silyl]oxy-8-azabicyclo [3.2.1]octan-3-one 86a as a colorless oil, 62 g, yield: 90%. MS: calc'd ($MH^+$) 232, measured ($MH^+$) 232.

Step II: To a suspension of NaH (6.98 g, 173 mmol) in tetrahydrofuran (460 mL) at 0° C. was added dropwise a solution of diethyl cyanomethylphosphonate (18.5 mL, 103.8 mmol) in tetrahydrofuran (80 mL). The reaction was refluxed for 1 hour and then cooled at 0° C. again. To the reaction mixture was added a solution of compound 86a (26.0 g, 75 mol) in tetrahydrofuran (80 mL). The reaction was allowed to warm up to room temperature and stirred 2 hours. The reaction mixture was then quenched with saturated aqueous solution of $NaHCO_3$, and most of the THF was removed under reduced pressure. Ethyl acetate (200 mL) was added, washed with water, brine, dried over $Na_2SO_4$ and evaporated to dryness. The residue was purified on silica gel, eluting with 0 to 20% EtOAc in hexanes, to give the desired product (2E)-2- [8-benzyl-6-[tert-butyl(dimethyl)silyl]oxy-8-azabicyclo [3.2.1]octan-3-ylidene]acetonitrile 86b (27 g, 98%). MS: calc'd ($MH^+$) 369, measured ($MH^+$) 369.

Step III: A solution of compound 86b (27.8 g, 75.3 mmol) in anhydrous methanol (300 mL) was placed in a flask equipped with a condenser, to it was added Mg (2 g, 87 mmol). The reaction mixture was stirred at room temperature for 30 min. The reaction mixture was then cooled with ice-water bath. After another 1 h stirring, another batch of Mg (2 g, 87 mmol) was added, and the reaction mixture was allowed to stir for 2 hours at 0° C. The mixture was diluted with ethyl acetate (500 mL), and quenched by adding slowly 12 N HCl (13 mL). The solvents were removed under reduced pressure, and the residue was dissolved in ethyl acetate (500 mL), which was then washed with water, brine, dried over $Na_2SO_4$ and evaporated to dryness. The above procedure was repeated until compound 86b was completely consumed. A crude product (14 g) with 2-exo-[8-benzyl-6-[tert-butyl(dimethyl) silyl]oxy-8-azabicyclo[3.2.1]octan-3-yl]acetonitrile 86c as the major product was obtained, and used without further purification in the next step. Around 20% of the endo-isomer was observed.

173

Step IV: The crude 86c (14 g) was dissolved in 1N HCl in methanol (350 mL). The reaction mixture was stirred at room temperature for 4 hours. The solvent was evaporated under reduced pressure. Ethyl acetate (300 mL) and water (50 mL) were added, and basified with 2N NaOH aqueous solution to pH 10. The organic phase was separated and the aqueous phase was extracted with ethyl acetate 3 times. The combined organic layers were washed with brine, dried over MgSO$_4$ and evaporated to dryness. The residue was dissolved in DCM (200 mL), and DMP (23 g, 56.5 mmol) was added. After stirred overnight, 20 mL of water was added, and the solid in the reaction mixture was filtered off. The filtrate was extracted with DCM. The organic layers were combined and washed with water, brine, dried over Na$_2$SO$_4$, and concentrated under reduced pressure. The crude product was purified on silica gel, eluting with 0 to 50% EtOAc in hexanes, to give the desired product 2-exo-(8-benzyl-6-oxo-8-azabicyclo [3.2.1]octan-3-yl)acetonitrile 86d (8 g). Around 10% of the endo-isomer was observed.

Step V: To a stirred solution of compound 86d (8 g, 31.3 mmol) in 20 mL of dichloromethane was added diethylaminosulfur trifluoride (12 mL, 94 mmol). The mixture was stirred at 50° C. overnight, then quenched with saturated NaHCO$_3$ aqueous solution at 0° C., and extracted three times with DCM (100 mL). The combined organic layers were washed with water, brine, dried over anhydrous MgSO$_4$, filtered, concentrated and purified by silica gel column chromatography (EtOAc/Hexane 5:95) to yield 2-exo-(8-benzyl-6, 6-difluoro-8-azabicyclo[3.2.1]octan-3-yl)acetonitrile 86e (7 g, 81%).

Step VI: Acetyl chloride (48 mL) was added into methanol (100 mL) at 0° C., and the mixture was stirred at room temperature for 1 hour. To it was added compound 86e (2 g, 7.2 mmol), and the resulting mixture was stirred for 18 hours at 80° C. After cooling to room temperature, the solvents were removed under reduced pressure. The residue was dissolved in ethyl acetate, neutralized carefully with aqueous NaHCO$_3$ solution. The organic phase was washed with brine, dried over Na$_2$SO$_4$ and evaporated to dryness. The crude mixture was purified on silica gel to give methyl 2-exo-(8-benzyl-6, 6-difluoro-8-azabicyclo[3.2.1]octan-3-yl)acetate (2 g, 88%), which was further purified by chiral SFC (ChiralCel OJ 250*30 mm, Sum 15% ethanol) to give a pair of enantiomers of methyl 2-exo-[8-benzyl-6,6-difluoro-8-azabicyclo[3.2.1] octan-3-yl]acetate, 86h (peak 1) and 86i (peak 2).

Step VII: To a solution of 86h (2 g 6.4 mmol) in 15 mL of methanol was added 200 mg of Pd(OH)$_2$ (20% loading on carbon, wet with 50% water content). The mixture reaction was stirred at room temperature under 1 atm H$_2$ for 6 h, and then filtered, and washed with additional methanol. The filtrates were concentrated under reduced pressure to yield one of the two enantiomers of methyl 2-exo-[6,6-difluoro-8-azabicyclo[3.2.1]octan-3-yl]acetate, 86j (1.26 g).

The other enantiomer of methyl 2-exo-[6,6-difluoro-8-azabicyclo[3.2.1]octan-3-yl]acetate, 86k, was prepared in analogy to 86j from 86i.

174

Examples 88 and 89

2-[(1R,3S,5S)-8-[[(4R)-4-(2-chloro-3-fluoro-phenyl)-5-methoxycarbonyl-2-thiazol-2-yl-1,4-dihydro-pyrimidin-6-yl]methyl]-6,6-difluoro-8-azabicyclo [3.2.1]octan-3-yl]acetic acid and 2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo [3.2.1]octan-3-yl]acetic acid

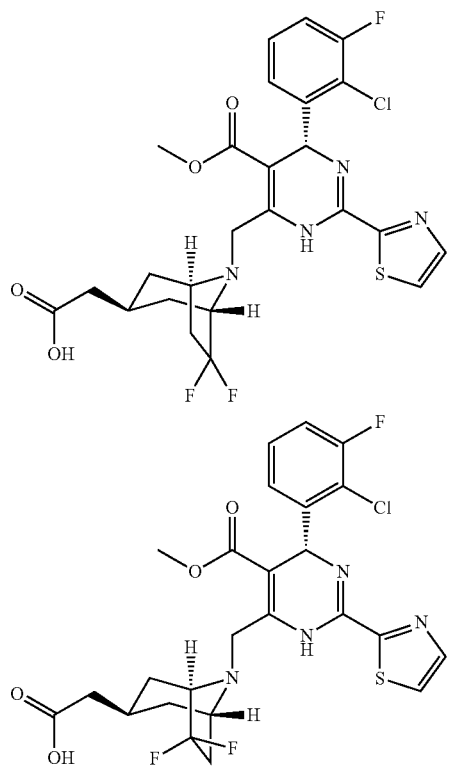

Preparation of Examples 88 and 89

Example 88 was prepared in analogy to Example 86 starting from 86j (30 mg) and methyl (4R)-6-(bromomethyl)-4-(2-chloro-3-fluoro-phenyl)-2-thiazol-2-yl-1,4-dihydropyrimidine-5-carboxylate 88a (76 mg). 18 mg of the title compound 88 was isolated after purification by preparative HPLC. Methyl (4R)-6-(bromomethyl)-4-(2-chloro-3-fluoro-phenyl)-2-thiazol-2-yl-1,4-dihydropyrimidine-5-carboxylate 88a was prepared in analogy to compound C with procedures shown in Example 1 by using 2-chloro-3-fluoro-benzaldehyde instead of 2-chloro-4-fluoro-benzaldehyde in the three component reaction.

Example 89 was prepared in analogy to Example 86 starting from 86k (30 mg) and methyl (4R)-6-(bromomethyl)-4-(2-chloro-3-fluoro-phenyl)-2-thiazol-2-yl-1,4-dihydropyrimidine-5-carboxylate 88a (76 mg). 14 mg of compound 89 was isolated after purification by preparative HPLC.

Examples 90 and 91

2-[(1R,3S,5S)-8-[[(4R)-4-(2-chlorophenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid and 2-[(1S,3R,5R)-8-[[(4R)-4-(2-chlorophenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid

Examples 92 and 92

2-[(1R,3S,5S)-8-[[(4R)-4-(2-bromophenyl)-5-ethoxycarbonyl-2-thiazol-2-yl-1,4-dihydropyrimidin-6-yl]methyl]-6,6-difluoro-8-azabicyclo[3.2.1]octan-3-yl]acetic acid and 2-[(1S,3R,5R)-8-[[(4R)-4-(2-bromophenyl)-5-ethoxycarbonyl-2-thiazol-2-yl-1,4-dihydropyrimidin-6-yl]methyl]-6,6-difluoro-8-azabicyclo[3.2.1]octan-3-yl]acetic acid

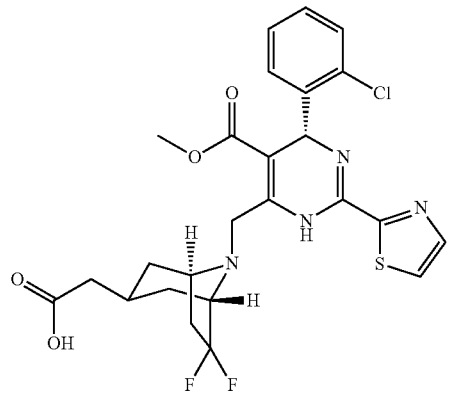

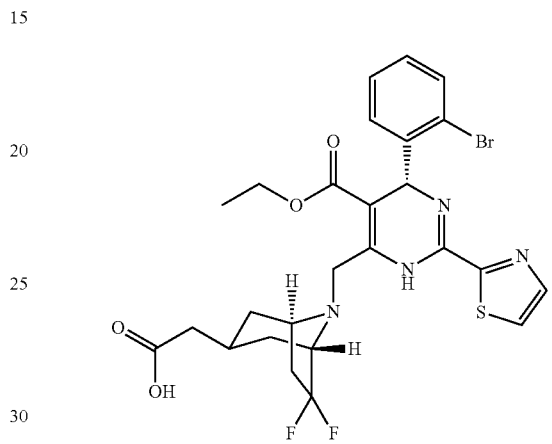

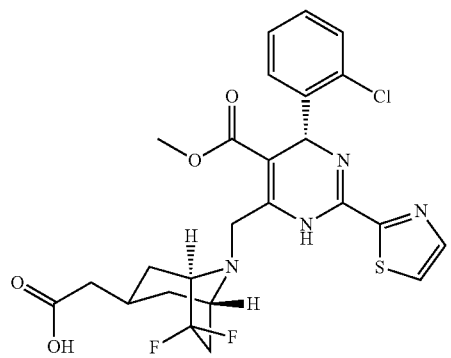

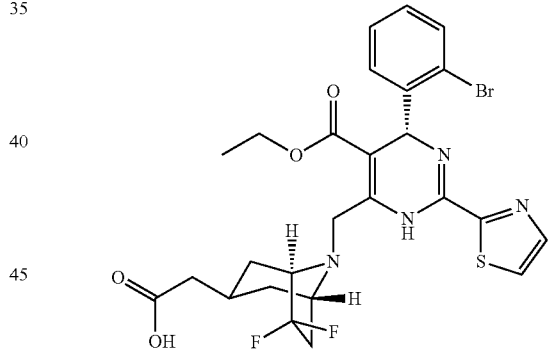

Preparation of Examples 90 and 91

Example 90 was prepared in analogy to Example 86 starting from 86j and methyl (4R)-6-(bromomethyl)-4-(2-chlorophenyl)-2-thiazol-2-yl-1,4-dihydropyrimidine-5-carboxylate 90a. Methyl (4R)-6-(bromomethyl)-4-(2-chlorophenyl)-2-thiazol-2-yl-1,4-dihydropyrimidine-5-carboxylate 90a was prepared in analogy to compound C with procedures shown in Example 1 by using 2-chlorobenzaldehyde instead of 2-chloro-4-fluoro-benzaldehyde in the three component reaction.

Example 91 was prepared in analogy to Example 86 starting from 86k and methyl (4R)-6-(bromomethyl)-4-(2-chlorophenyl)-2-thiazol-2-yl-1,4-dihydropyrimidine-5-carboxylate 90a.

Preparation of Examples 92 and 93

Example 92 was prepared in analogy to Example 86 starting from 86j and ethyl (4R)-6-(bromomethyl)-4-(2-bromophenyl)-2-thiazol-2-yl-1,4-dihydropyrimidine-5-carboxylate 92a. (4R)-6-(bromomethyl)-4-(2-bromophenyl)-2-thiazol-2-yl-1,4-dihydropyrimidine-5-carboxylate 92a was prepared in analogy to compound C with procedures shown in Example 1 by using ethyl acetoacetate and 2-bromobenzaldehyde instead of methyl acetoacetate and 2-chloro-4-fluoro-benzaldehyde in the three component reaction.

Example 93 was prepared in analogy to Example 86 starting from 86k and ethyl (4R)-6-(bromomethyl)-4-(2-bromophenyl)-2-thiazol-2-yl-1,4-dihydropyrimidine-5-carboxylate 92a.

Examples 94 and 95

2-[(1R,3S,5S)-8-[[(4R)-4-(2-bromo-3-fluoro-phenyl)-5-methoxycarbonyl-2-thiazol-2-yl-1,4-dihydro-pyrimidin-6-yl]methyl]-6,6-difluoro-8-azabicyclo[3.2.1]octan-3-yl]acetic acid and 2-[(1S,3R,5R)-8-[[(4R)-4-(2-bromo-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid

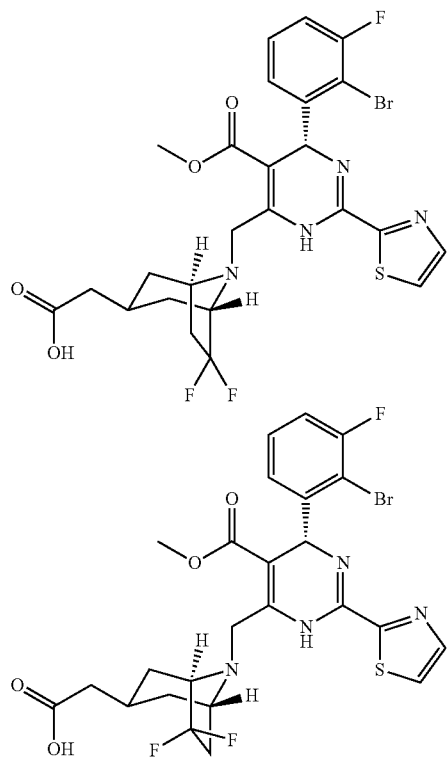

Preparation of Examples 94 and 95

Example 94 was prepared in analogy to Example 86 starting from 86j (30 mg) and methyl (4R)-4-(2-bromo-3-fluoro-phenyl)-6-(bromomethyl)-2-thiazol-2-yl-1,4-dihydropyrimidine-5-carboxylate 94a (86 mg). 13 mg of the title compound was isolated.

Methyl (4R)-4-(2-bromo-3-fluoro-phenyl)-6-(bromomethyl)-2-thiazol-2-yl-1,4-dihydropyrimidine-5-carboxylate 94a was prepared in analogy to compound C with procedures shown in Example 1 by using 2-bromo-3-fluorobenzaldehyde instead of 2-chloro-4-fluoro-benzaldehyde.

Example 95 was prepared in analogy to Example 86 starting from 86k (30 mg) and methyl (4R)-4-(2-bromo-3-fluorophenyl)-6-(bromomethyl)-2-thiazol-2-yl-1,4-dihydropyrimidine-5-carboxylate 94a (86 mg). 56 mg of the title compound was isolated.

Examples 96 and 97

2-[(1R,3S,5S)-8-[[(4S)-4-(4-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid and 2-[(1S,3R,5R)-8-[[(4S)-4-(4-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid

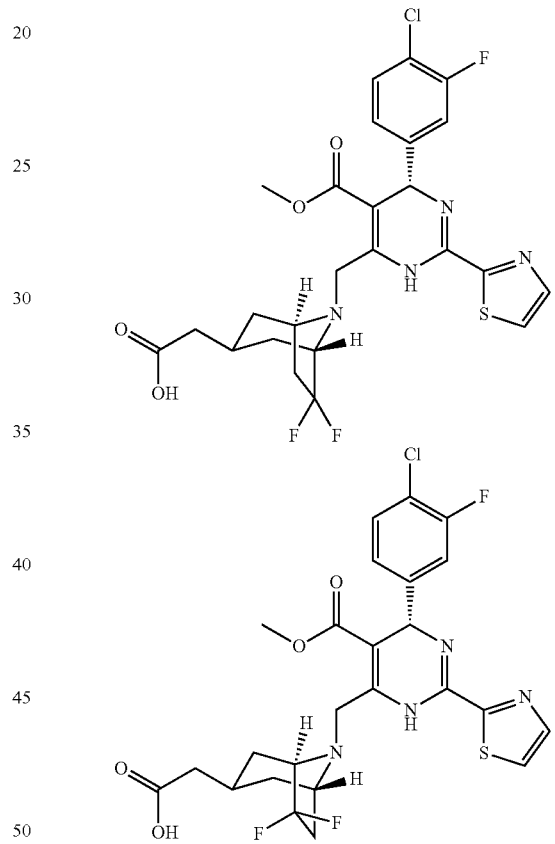

Preparation of Examples 96 and 97

Example 96 was prepared in analogy to Example 86 starting from 86j (30 mg) and methyl (4S)-6-(bromomethyl)-4-(4-chloro-3-fluoro-phenyl)-2-thiazol-2-yl-1,4-dihydropyrimidine-5-carboxylate 96a (78 mg). 12 mg of Example 96 was isolated. Methyl (4S)-6-(bromomethyl)-4-(4-chloro-3-fluoro-phenyl)-2-thiazol-2-yl-1,4-dihydropyrimidine-5-carboxylate 96a was prepared in analogy to compound C with procedures shown in Example 1 by using 4-chloro-3-fluorobenzaldehyde instead of 2-chloro-4-fluoro-benzaldehyde in the three component reaction step.

Example 97 was prepared in analogy to Example 86 starting from 86k (30 mg) and methyl (4S)-6-(bromomethyl)-4-

(4-chloro-3-fluoro-phenyl)-2-thiazol-2-yl-1,4-dihydropyrimidine-5-carboxylate 96a (78 mg). 14 mg of the title compound was isolated.

Examples 98 and 99

2-[(1R,3S,5S)-8-[[(4R)-4-(2-chloro-3-fluoro-phenyl)-5-ethoxycarbonyl-2-thiazol-2-yl-1,4-dihydropyrimidin-6-yl]methyl]-6,6-difluoro-8-azabicyclo[3.2.1]octan-3-yl]acetic acid and 2-[(1S,3R,5R)-8-[[(4R)-4-(2-chloro-3-fluoro-phenyl)-5-ethoxycarbonyl-2-thiazol-2-yl-1,4-dihydropyrimidin-6-yl]methyl]-6,6-difluoro-8-azabicyclo[3.2.1]octan-3-yl]acetic acid

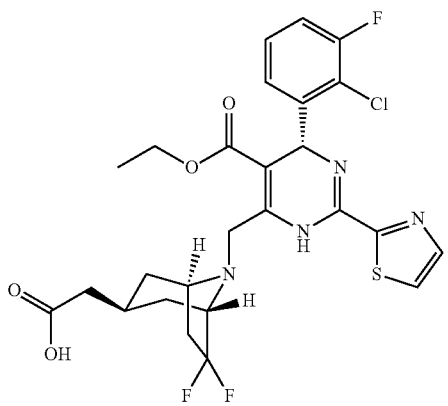

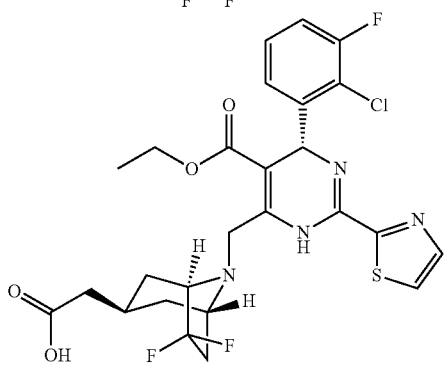

Preparation of Examples 98 and 99

Example 98 was prepared in analogy to Example 86 starting from 86j (30 mg) and ethyl (4R)-6-(bromomethyl)-4-(2-chloro-3-fluoro-phenyl)-2-thiazol-2-yl-1,4-dihydropyrimidine-5-carboxylate 98a (80 mg). 25 mg of Example 98 was isolated. Ethyl (4R)-6-(bromomethyl)-4-(2-chloro-3-fluoro-phenyl)-2-thiazol-2-yl-1,4-dihydropyrimidine-5-carboxylate 98a was prepared in analogy to compound C with procedures shown in Example 1 by using ethyl acetoacetate and 2-chloro-3-fluorobenzaldehyde instead of methyl acetoacetate and 2-chloro-4-fluoro-benzaldehyde, respectively.

Example 99 was prepared in analogy to Example 86 starting from 86k (30 mg) and ethyl (4R)-6-(bromomethyl)-4-(2-chloro-3-fluoro-phenyl)-2-thiazol-2-yl-1,4-dihydropyrimidine-5-carboxylate 98a (80 mg). 25 mg of the title compound was isolated.

Examples 100 and 101

2-[(1S,5S,6R,7R)-9-[[(4R)-4-(2-chloro-3-fluoro-phenyl)-5-methoxycarbonyl-2-thiazol-2-yl-1,4-dihydropyrimidin-6-yl]methyl]-6-fluoro-3-oxa-9-azabicyclo[3.3.1]nonan-7-yl]acetic acid and 2-[(1R,5R,6S,7S)-9-[[(4R)-4-(2-chloro-3-fluoro-phenyl)-5-methoxycarbonyl-2-thiazol-2-yl-1,4-dihydropyrimidin-6-yl]methyl]-6-fluoro-3-oxa-9-azabicyclo[3.3.1]nonan-7-yl]acetic acid

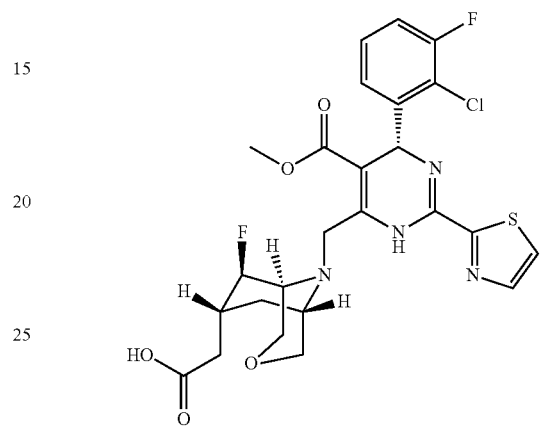

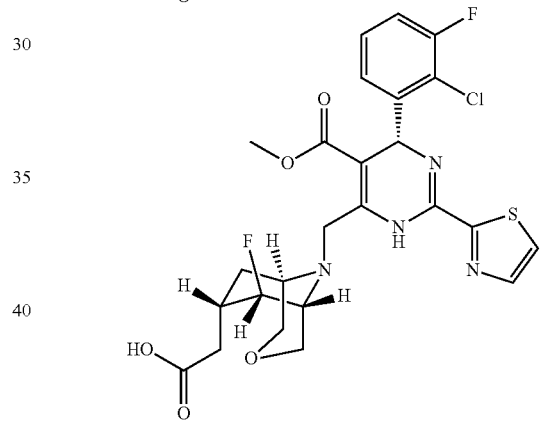

The title compounds were prepared in analogy to Example 86 starting from methyl 2-(6-fluoro-3-oxa-9-azabicyclo[3.3.1]nonan-7-yl)acetate 100a (100 mg) and methyl (4R)-6-(bromomethyl)-4-(2-chloro-3-fluoro-phenyl)-2-thiazol-2-yl-1,4-dihydropyrimidine-5-carboxylate 88a (208 mg). The crude product was purified by silica gel chromatography first, and then by preparative HPLC to give Example 101 and Example 102.

Preparation of methyl 2-(6-fluoro-3-oxa-9-azabicyclo[3.3.1]nonan-7-yl)acetate 100a

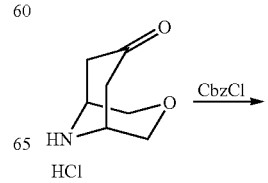

-continued

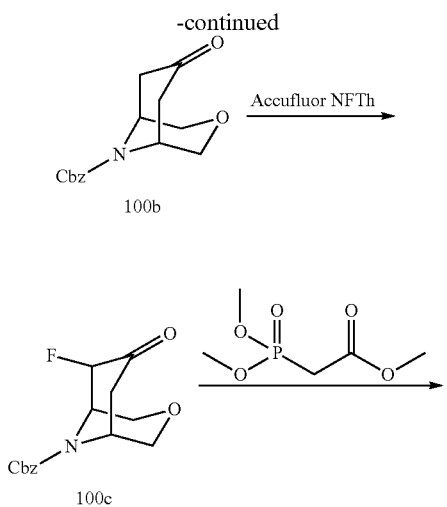

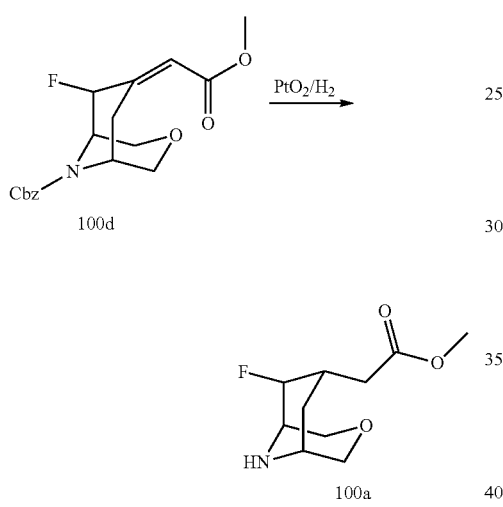

benzyl 6-fluoro-7-oxo-3-oxa-9-azabicyclo[3.3.1]nonane-9-carboxylate 100c (4.1 g, 50%). MS: calc'd (MH+) 294, measured (MH+) 294.

Step III: To a solution of NaH (273 mg, 11.4 mmol) in tetrahydrofuran (30 mL) at 0° C. was added dropwise a solution of methyl 2-dimethoxyphosphorylacetate (2.1 g, 11.4 mmol) in tetrahydrofuran (10 mL). The reaction was stirred at 70° C. for 1 hour and then cooled to 0° C. again. To the reaction mixture was added a solution of benzyl 6-fluoro-7-oxo-3-oxa-9-azabicyclo[3.3.1]nonane-9-carboxylate 100c (1.7 g, 5.7 mmol) in tetrahydrofuran (8 mL). The reaction was allowed to warm up to room temperature and stirred 2 hours. After being quenched with 1 N HCl, the solvent was evaporated under reduced pressure. Ethyl acetate (20 mL) was added. The mixture was washed with water, brine, dried over Na$_2$SO$_4$ and evaporated to dryness. The crude mixture was purified on silica gel, eluted with 0 to 20% EtOAc in hexanes, to give the desired product benzyl (7Z/E)-6-fluoro-7-(2-methoxy-2-oxo-ethylidene)-3-oxa-9-azabicyclo[3.3.1]nonane-9-carboxylate 100d (1.8 g, 89%). MS: calc'd (MH+) 350, measured (MH+) 350.

Step IV: To a solution of (7Z/E)-6-fluoro-7-(2-methoxy-2-oxo-ethylidene)-3-oxa-9-azabicyclo[3.3.1]nonane-9-carboxylate 100d (1.8 g, 5.1 mmol) in THF (50 ml) and H$_2$O (2 ml) was add of PtO$_2$ (250 mg, 1.1 mmol). The mixture reaction was stirred at room temperature under hydrogen balloon for 6 h, then filtered and washed with additional THF. The filtrates were concentrated under reduced pressure to yield methyl 2-(6-fluoro-3-oxa-9-azabicyclo[3.3.1]nonan-7-yl)acetate 100a (910 mg, 70%).

Examples 102 and 103

2-[(1S,5S,6R,7R)-9-[[(4R)-4-(2-chlorophenyl)-5-ethoxycarbonyl-2-thiazol-2-yl-1,4-dihydropyrimidin-6-yl]methyl]-6-fluoro-3-oxa-9-azabicyclo[3.3.1]nonan-7-yl]acetic acid Step I: 3-oxa-9-azabicyclo[3.3.1]nonan-7-one hydrochloride (CAS 1126795-00-3) (10 g) was dissolved in 200 ml of dichloromethane which was cooled to 0° C. Then, CbzCl (14.3 g, 84.7 mmol) was added to the mixture followed by the dropwise addition of a solution of TEA (14.6 ml, 112.8 mmol) in 20 ml of dichloromethane. The mixture was allowed to warm up to room temperature. After stirring 2 h, it was quenched with 20 ml of a saturated aqueous solution of NaHCO$_3$. The two layers were separated and the aqueous layer was extracted with dichloromethane (3×150 ml). The combined organic layers were washed with water, dried over Na$_2$SO$_4$ and the solvent was evaporated under reduced pressure. The crude product was purified by chromatography on silica gel, yielding 10.1 g of benzyl 7-oxo-3-oxa-9-azabicyclo[3.3.1]nonane-9-carboxylate 100b (64%).

Step II: To a solution of benzyl 7-oxo-3-oxa-9-azabicyclo[3.3.1]nonane-9-carboxylate 100b (7.6 g, 27.6 mmol) in methanol (150 mL) at 0° C. was added Accufluor NFTh (17.5 g, 55.2 mmol). The reaction was stirred at 90° C. for 3 hours and then cooled to room temperature. After filtration, the filtrate was evaporated under reduced pressure, and the residue was dissolved in ethyl acetate (20 mL), washed with water and brine, dried over Na$_2$SO$_4$ and evaporated to dryness. The crude mixture was purified on silica gel, eluting with 0 to 50% EtOAc in hexanes, to give the desired product and 2-[(1R,5R,6S,7S)-9-[[(4R)-4-(2-chlorophenyl)-5-ethoxycarbonyl-2-thiazol-2-yl-1,4-dihydropyrimidin-6-yl]methyl]-6-fluoro-3-oxa-9-azabicyclo[3.3.1]nonan-7-yl]acetic acid

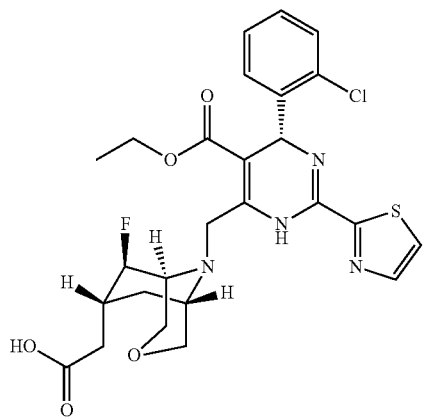

-continued

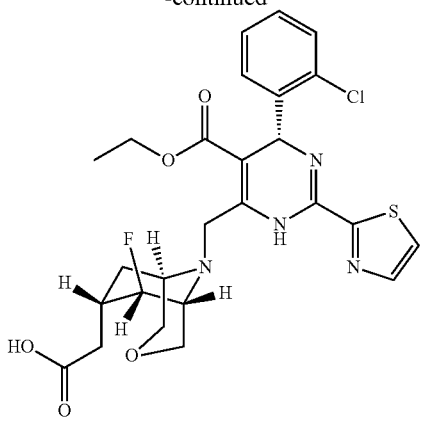

The title compounds were prepared in analogy to Example 86 starting from methyl 2-(6-fluoro-3-oxa-9-azabicyclo[3.3.1]nonan-7-yl)acetate 100a (100 mg) and ethyl (4R)-6-(bromomethyl)-4-(2-chloro-phenyl)-2-thiazol-2-yl-1,4-dihydropyrimidine-5-carboxylate 102a (215 mg). The crude product was purified by silica gel chromatography first, and then by preparative HPLC to give Example 102 (27 mg), and Example 103 (21 mg). Ethyl (4R)-6-(bromomethyl)-4-(2-chloro-phenyl)-2-thiazol-2-yl-1,4-dihydropyrimidine-5-carboxylate 102a was prepared in analogy to compound C with procedures shown in Example 1 by using ethyl acetoacetate and 2-chloro-benzaldehyde instead of methyl acetoacetate and 2-chloro-4-fluoro-benzaldehyde in the three component reaction.

Example 104

(4R)-4-(2-Chloro-4-fluoro-phenyl)-6-(4,10-dioxa-5,12-diaza-tricyclo[6.3.1.0*2,6*]dodeca-2,5-dien-12-ylmethyl)-2-thiazol-2-yl-1,4-dihydro-pyrimidine-5-carboxylic acid methyl ester

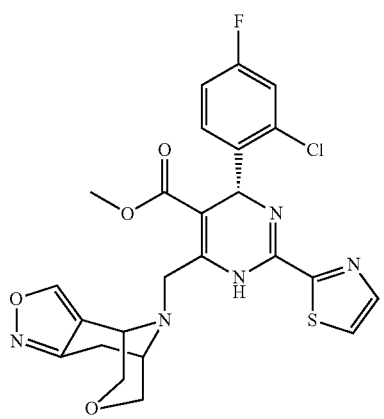 [SMILES: COC(=O)C1=C(CN2C3COCC2c2conc2C3)NC(c2nccs2)=N[C@H]1c1ccc(F)cc1Cl]

The title compound was prepared in analogy to Example 1a in Scheme 3 by using methyl (4R)-4-(2-chloro-4-fluoro-phenyl)-6-(bromomethyl)-2-thiazol-2-yl-1,4-dihydropyrimidine-5-carboxylate C (200 mg) and 4,10-Dioxa-5,12-diaza-tricyclo[6.3.1.0*2,6*]dodeca-2,5-diene 104a (100 mg). 15 mg of the title compound was isolated as yellow powder.

Preparation of 4,10-Dioxa-5,12-diaza-tricyclo[6.3.1.0*2,6*]dodeca-2,5-diene 104a

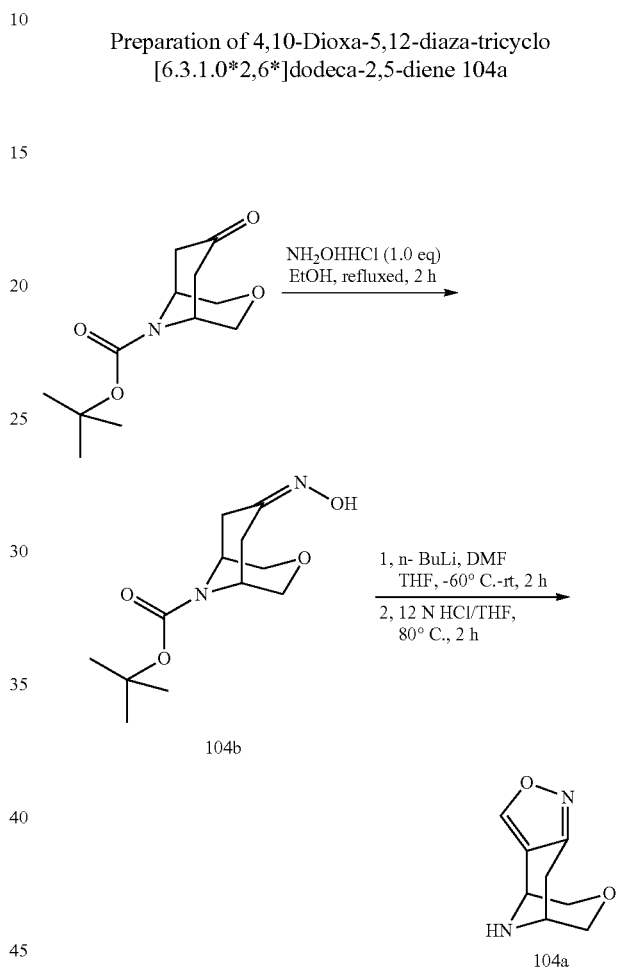

Step I: A solution of tert-butyl 7-oxo-3-oxa-9-azabicyclo[3.3.1]nonane-9-carboxylate (482 mg, 2 mmol, 1.0 eq) and NH$_2$OH.HCl (462 mg, 3 mmol, 3.0 eq) in EtOH (10 mL) was refluxed for 2 h. The reaction mixture was concentrated to give tert-butyl 7-hydroxyimino-3-oxa-9-azabicyclo[3.3.1]nonane-9-carboxylate 104b as a white solid, which was used in next step without further purification. MS: calc'd (MH$^+$) 267, measured (MH$^+$) 267.

Step II: To a solution of compound 104b (512 mg, 2 mmol, 1.0 eq) in THF (10 mL) was added n-BuLi (5 mL, 2.0 M, 5.0 eq) dropwise at −50° C. After 30 min, dry DMF (740 mg, 10 mmol, 5.0 eq) in THF (2 mL) was added dropwise, the mixture was stirred for another 2 h from −60° C. to room temperature. To it 12 N HCl (1 mL) was added and refluxed for 2 h. The reaction mixture was concentrated to give 4,10-Dioxa-5,12-diaza-tricyclo[6.3.1.0*2,6*]dodeca-2,5-diene 104a (332 mg) as an oil. MS: calc'd (MH$^+$) 167, measured (MH$^+$) 167.

Example 105

(4R)-4-(2-Chloro-4-fluoro-phenyl)-6-(5,10-dioxa-4,12-diaza-tricyclo[6.3.1.0*2,6*]dodeca-2(6),3-dien-12-ylmethyl)-2-thiazol-2-yl-1,4-dihydro-pyrimidine-5-carboxylic acid methyl ester

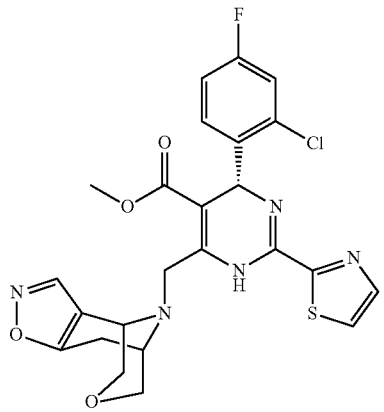 [SMILES: COC(=O)C1=C(CN2C3COCC2c2cnoc2C3)NC(c2nccs2)=N[C@H]1c1ccc(F)cc1Cl]

The title compound was prepared in analogy to Example 1a in Scheme 3 by using methyl (4R)-4-(2-chloro-4-fluoro-phenyl)-6-(bromomethyl)-2-thiazol-2-yl-1,4-dihydropyrimidine-5-carboxylate C (200 mg) and 5,10-Dioxa-4,12-diaza-tricyclo[6.3.1.0*2,6*]dodeca-2(6),3-diene 105a (100 mg). 20 mg of the title compound was isolated as yellow powder.

Preparation of 5,10-Dioxa-4,12-diaza-tricyclo[6.3.1.0*2,6*]dodeca-2(6),3-diene 105a A solution of tert-butyl 7-oxo-3-oxa-9-azabicyclo[3.3.1]nonane-9-carboxylate (482 mg, 2 mmol) and tert-butoxy-N,N,N',N'-tetra-methyl-methanediamine (522 mg) in dioxane (10 mL) was stirred at 60° C. for 16 h. The solvent was removed in vacuo, and the residue was dissolved in EtOH (10 mL). To it NH$_2$OH.HCl (462 mg, 3 mmol) was added. After stirring at room temperature for 2 h, 12 N HCl (1 mL) was added and refluxed for 2 h. The reaction mixture was concentrated to give 5,10-Dioxa-4,12-diaza-tricyclo[6.3.1.0*2,6*]dodeca-2(6),3-diene 105a as an oil (yield 100%), which was used without further purification. MS: calc'd (MH$^+$) 167, measured (MH$^+$) 167.

Example 106

(4R)-4-(2-Chloro-4-fluoro-phenyl)-6-(7-fluoro-5,10-dioxa-4,12-diaza-tricyclo[6.3.1.0*2,6*]dodeca-2(6),3-dien-12-ylmethyl)-2-thiazol-2-yl-1,4-dihydropyrimidine-5-carrboxylic acid methyl ester

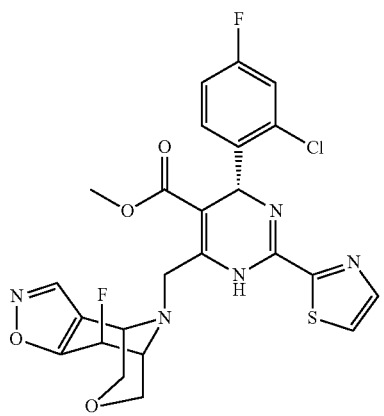 [SMILES: COC(=O)C1=C(CN2C3COCC2C(F)c2oncc23)NC(c2nccs2)=N[C@H]1c1ccc(F)cc1Cl]

The title compound was prepared in analogy to Example 1a in Scheme 3 by using methyl (4R)-4-(2-chloro-4-fluoro-phenyl)-6-(bromomethyl)-2-thiazol-2-yl-1,4-dihydropyrimidine-5-carboxylate C (200 mg) and 7-fluoro-5,10-dioxa-4,12-diaza-tricyclo[6.3.1.0*2,6*]dodeca-2(6),3-diene 106a (140 mg). 8 mg of the title compound was isolated as yellow powder.

Preparation of 7-fluoro-5,10-dioxa-4,12-diaza-tricyclo[6.3.1.0*2,6*]dodeca-2(6),3-dien 106a

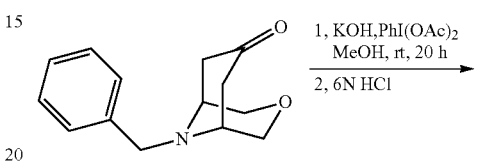

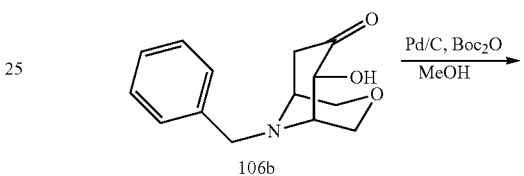

106b

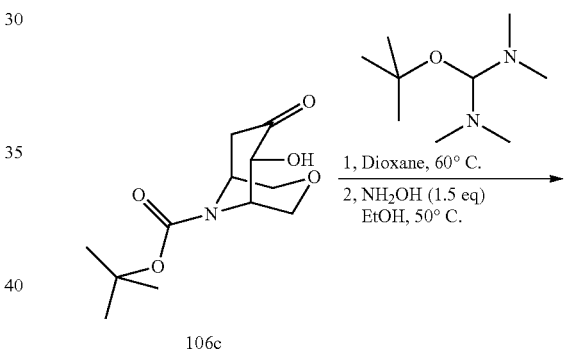

106c

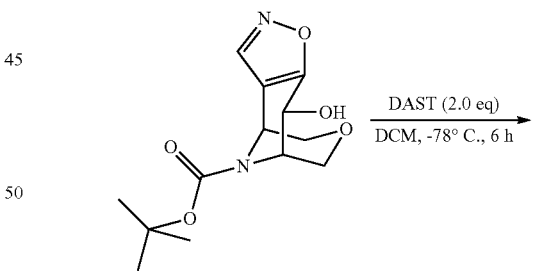

106d

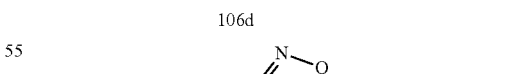

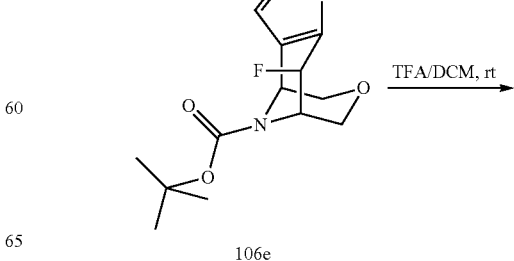

106e

187
-continued

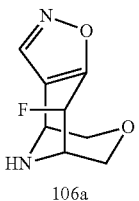
106a

Step I: To a stirred solution of potassium hydroxide (730 mg, 13 mmol) in dry MeOH (50 mL) at 0° C. under nitrogen was added a solution of 9-benzyl-3-oxa-9-azabicyclo[3.3.1]nonan-7-one (CAS: 81514-40-1, 1 g, 4.3 mmol) in dry MeOH (20 mL) dropwise over 10 min. The reaction mixture was stirred at 0° C. for another 10 min, and PhI(OAc)2 (1.83 g, 5.5 mmol) was added portion wise over 10 min. The reaction mixture was warmed to room temperature, with stirring, overnight. After the starting material disappeared as monitored by TLC, MeOH was removed under reduced pressure and the residue was cooled to 0° C. and 10 ml of 6N HCl was added carefully. The mixture was stirred at room temperature for 2 hours, and then ethyl acetate and water (50 mL, 1:1) were added. The aqueous layer was separated and was added into $K_2CO_3$ till the solution was saturated. The mixture was extracted with ethyl acetate (20 mL) three times, dried and concentrated, the residue was purified by silica gel (EA/PE=1:2) to give 9-benzyl-6-hydroxy-3-oxa-9-azabicyclo[3.3.1]nonan-7-one 106b as colorless oil, 270 mg, yield: 25%. MS: calc'd (MH$^+$) 248, measured (MH$^+$) 248.

Step II: A mixture of compound 106b (247 mg, 1 mmol, 1.0 eq), Boc$_2$O (654 mg, 3 mmol, 3.0 eq) and Pd/C (50 mg, 20%) in MeOH (10 mL) was stirred at room temperature for 16 h. Then the solid was filtered off, the solvent was removed in vacuo, the residue was purified by silica gel (EA/PE=1:1) to give tert-butyl 6-hydroxy-7-oxo-3-oxa-9-azabicyclo[3.3.1]nonane-9-carboxylate 106c as a colorless oil. 260 mg, yield: 100%. MS: calc'd (MH$^+$) 258, measured (MH$^+$) 258.

Step III: 7-Hydroxy-5,10-dioxa-4,12-diaza-tricyclo[6.3.1.0*2,6*]dodeca-2(6),3-diene-12-carboxylic acid tert-butyl ester 106d was prepared in analogy to compound 105a in Example 105, starting with 106c (260 mg). 141 mg of 106d was obtained as a colorless oil. MS: calc'd (MH$^+$) 283, measured (MH$^+$) 283.

Step IV: To a solution of 7-Hydroxy-5,10-dioxa-4,12-diaza-tricyclo[6.3.1.0*2,6*]dodeca-2(6),3-diene-12-carboxylic acid tert-butyl ester 106d (141 mg, 0.5 mmol, 1.0 eq) in DCM (5 mL) was added DAST (166 mg, 1 mmol, 2.0 eq) at –78° C. Then mixture was stirred for 6 h from –78° C. to room temperature. The reaction was diluted with EA (20 mL), and washed with aqueous NaHCO$_3$ (5%, 20 mL). The organic layer was dried and concentrated to give 7-Fluoro-5,10-dioxa-4,12-diaza-tricyclo[6.3.1.0*2,6*]dodeca-2(6),3-diene-12-carboxylic acid tert-butyl ester as an oil, 150 mg, crude yield: 100%. MS: calc'd (MH$^+$) 285, measured (MH$^+$) 285.

Step V: A solution of 7-Fluoro-5,10-dioxa-4,12-diaza-tricyclo[6.3.1.0*2,6*]dodeca-2(6),3-diene-12-carboxylic acid tert-butyl ester (150 mg) in TFA/DCM (5 mL, 1:2) was stirred at room temperature for 1 h. The solvent was removed in vacuo to give 7-fluoro-5,10-dioxa-4,12-diaza-tricyclo[6.3.1.0*2,6*]dodeca-2(6),3-diene 106a (141 mg) as yellow oil, crude yield: 100%. MS: calc'd (MH$^+$) 185, measured (MH$^+$) 185.

188
Example 107

(R)-4-(2-Chloro-4-fluoro-phenyl)-6-(7,7-difluoro-10-oxa-4,5,12-triaza-tricyclo[6.3.1.0*2,6*]dodeca-2(6),3-dien-12-ylmethyl)-2-thiazol-2-yl-1,4-dihydro-pyrimidine-5-arboxylic acid methyl ester

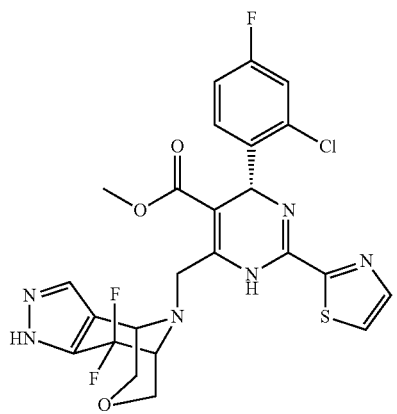 [SMILES: COC(=O)C1=C(CN2C3COCC2C(F)(F)c2[nH]ncc23)NC(c2nccs2)=N[C@H]1c1ccc(F)cc1Cl]

The title compound was prepared in analogy to Example 1a in Scheme 3 by using methyl (4R)-4-(2-chloro-4-fluoro-phenyl)-6-(bromomethyl)-2-thiazol-2-yl-1,4-dihydropyrimidine-5-carboxylate C (100 mg) and 7,7-difluoro-5,10-dioxa-4,12-diaza-tricyclo[6.3.1.0*2,6*]dodeca-2(6),3-diene 107a (50 mg). 8 mg of the title compound was isolated as yellow powder.

Preparation of 7,7-difluoro-5,10-dioxa-4,12-diaza-tricyclo[6.3.1.0*2,6*]dodeca-2(6),3-diene 107a

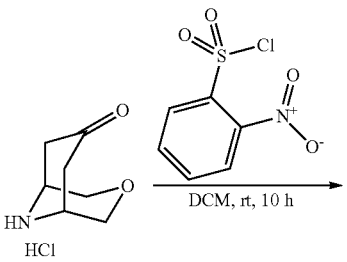

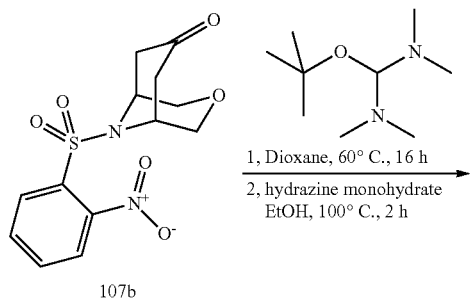
107b

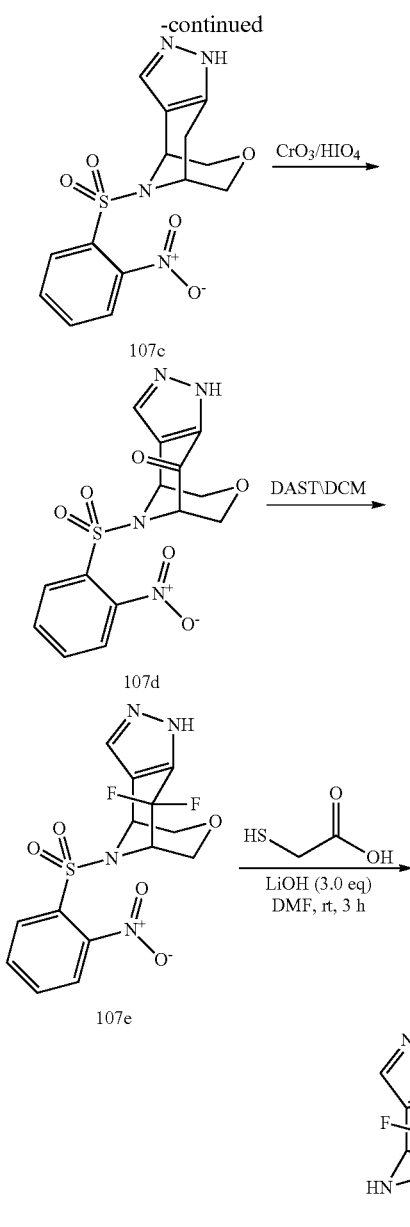

Step III: A solution of CrO₃ (100 mg, 1.0 mmol, 0.33 eq) and H₅IO₆ (2.05 g, 9 mmol, 3.0 eq) in MeCN (50 mL) was stirred at room temperature for 5 min, compound 107c (1.05 g, 3 mmol, 1.0 eq) in MeCN (5 mL) was added and then stirred at 70° C. for 12 h. The solid was filtered off and the filtrate was diluted with EA (50 mL), washed with Na₂S₂O₃ (10%, 50 mL) and brine (50 mL). The organic layer was concentrated, and the residue was purified by silica gel (EA/PE=1:2) to give 12-(2-nitro-benzenesulfonyl)-10-oxa-4,5,12-triaza-tricyclo[6.3.1.0*2,6*]dodeca-2(6),3-dien-7-one 107d as a white solid, 270 mg, yield: 25%. MS: calc'd (MH⁺) 365, measured (MH⁺) 365.

Step IV: A mixture of compound 107d (270 mg, 0.74 mmol, 1.0 eq) and DAST (1 mL, 7.4 mmol, 10.0 eq) in DCM (1 mL) was stirred at 60° C. in sealed tube for 18 h. The mixture was added dropwise to a cooled aqueous NaHCO₃ (20 mL, 5%) solution, then the mixture was extracted with EA (20 mL) two times, the organic layer was dried (Na₂SO₄) and concentrated. The residue was purified by silica gel (EA/PE=1:3) to give 7,7-difluoro-12-(2-nitro-benzenesulfonyl)-10-oxa-4,5,12-triaza-tricyclo[6.3.1.0*2,6*]dodeca-2(6),3-diene 107e as a slight yellow oil. 100 mg, yield: 35%. MS: calc'd (MH⁺) 387, measured (MH⁺) 387.

Step V: To a mixture of compound 107e (100 mg, 0.26 mmol, 1.0 eq) and LiOH (33 mg, 0.78 mmol, 3.0 eq) in DMF (5 mL) was added mercaptoacetic acid (36 mg, 0.4 mmol, 1.5 eq) slowly, the mixture was stirred at room temperature for 3 h. The solvent was removed in vacuo to give 7,7-difluoro-5,10-dioxa-4,12-diaza-tricyclo[6.3.1.0*2,6*]dodeca-2(6),3-diene 107a as an oil, used in next step without further purification. MS: calc'd (MH⁺) 202, measured (MH⁺) 202.

Example 108

Methyl (4R)-4-(2-chloro-4-fluorophenyl)-6-[(6,6-difluoro-3-oxa-8-azabicyclo[3.2.1]octan-8-yl)methyl]-2-(1,3-thiazol-2-yl)-1,4-dihydropyrimidine-5-carboxylate Step I: A solution of 3-oxa-9-azabicyclo[3.3.1]nonan-7-one hydrochloride (CAS 1126795-00-3, 2.82 g), TEA (6.12 g, 60 mmol, 3.0 eq) and 2-Nitro-benzenesulfonyl chloride (8.84 g, 40 mmol, 2.0 eq) in DCM (100 mL) was stirred at room temperature for 10 h. Then the solvent was removed in vacuo, the residue was purified by silica gel (EA/PE=1:3) to give 9-(2-nitrophenyl)sulfonyl-3-oxa-9-azabicyclo[3.3.1]nonan-7-one 107b as a white solid, 4.90 g, yield: 75%. MS: calc'd (MH⁺) 327, measured (MH⁺) 327.

Step II: A mixture of compound 107b (4.9 g, 15 mmol, 1.0 eq) and tert-butoxy-N,N,N',N'-tetra-methyl-methanediamine (3.92 g, 22.5 mmol, 1.5 eq) in dioxane (50 mL) was stirred at 60° C. for 16 h, then the solvent was removed in vacuo, the residue was dissolved in EtOH (50 mL), NH₂NH₂.H₂O (3.5 mg, 75 mmol, 5.0 eq) was added and then stirred at 60° C. for 2 h. The reaction mixture was concentrated and then purified by silica gel (EA/PE=1:2) to give 12-(2-Nitro-benzenesulfonyl)-10-oxa-4,5,12-triaza-tricyclo[6.3.1.0*2,6*]dodeca-2(6),3-diene 107c as a slight yellow oil, 1.57 g, yield: 29.8%. MS: calc'd (MH⁺) 351, measured (MH⁺) 351.

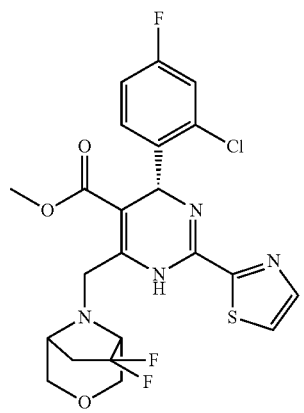 [SMILES: COC(=O)C1=C(CN2C3COCC2C(F)(F)C3)NC(c2nccs2)=N[C@H]1c1ccc(F)cc1Cl]

The title compound was prepared in analogy to Example 1a in Scheme 3 by using methyl (4R)-4-(2-chloro-4-fluoro-phenyl)-6-(bromomethyl)-2-thiazol-2-yl-1,4-dihydropyrimidine-5-carboxylate (compound C, 100 mg) and 6,6-difluoro- 3-oxa-8-azabicyclo[3.2.1]octane 108a (200 mg). 6 mg of the title compound was isolated as yellow powder.

Preparation of 6,6-difluoro-3-oxa-8-azabicyclo[3.2.1]octane 108a

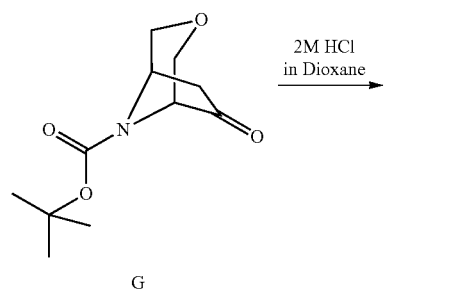

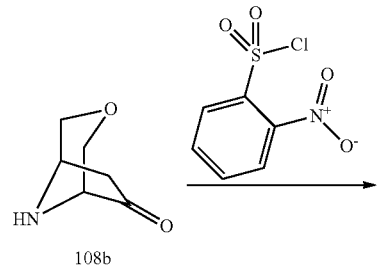

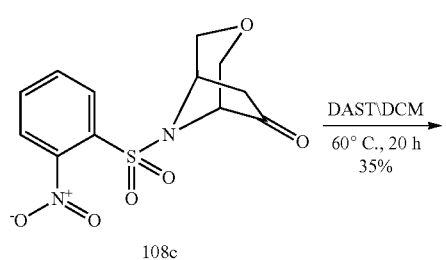

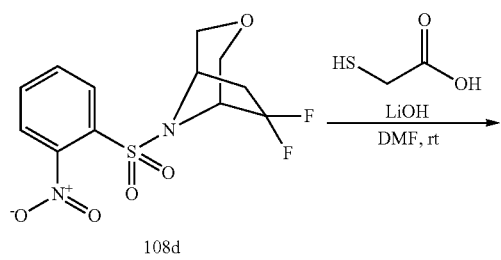

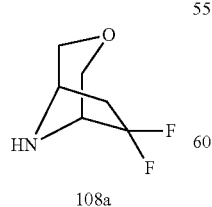

108a

Step I: A mixture of compound G (227 mg, 1 mmol, 1.0 eq) in HCl/Dioxane (2 mL) was stirred at room temperature for 2 h. Then the solvent was removed in vacuo to give 3-oxa-8-azabicyclo[3.2.1]octan-6-one 108b as white solid (200 mg), which was used in the next step without further purification. MS: calc'd (MH+) 128, measured (MH+) 128.

Step II: A mixture of compound 108b (100 mg), TEA (102 mg), $K_2CO_3$ (207 mg, 1.5 mmol, 3.0 eq) and 2-nitro-benzenesulfonyl chloride (222 mg) in MeCN (10 mL) was stirred at room temperature for 10 h. Then the solvent was removed in vacuo, the residue was purified by silica gel (EA/PE=1:3) to give 8-(2-nitrophenyl)sulfonyl-3-oxa-8-azabicyclo[3.2.1]octan-6-one 108c as a white solid, 100 mg. MS: calc'd (MH+) 313, measured (MH+) 313.

Step III: A mixture of compound 108c (100 mg) and DAST (1 mL) in DCM (1 mL) was stirred at 50° C. in sealed tube for 18 h. The mixture was added dropwise to a cooled aqueous $NaHCO_3$ (20 mL, 5%) solution, then the mixture was extracted with EA (20 mL) two times, the organic layer was dried ($Na_2SO_4$) and concentrated. The residue was purified by silica gel (EA/PE=1:3) to give 6,6-difluoro-8-(2-nitrophenyl)sulfonyl-3-oxa-8-azabicyclo[3.2.1]octane 108d as a slight yellow oil. 90 mg. MS: calc'd (MH+) 335, measured (MH+) 335.

Step IV: To a solution of compound 108d (90 mg) and LiOH (36 mg) in DMF (5 mL) was added mercaptoacetic acid (36 mg) slowly, the mixture was stirred at room temperature for 3 h. The solvent was removed in vacuo to give 6,6-difluoro-3-oxa-8-azabicyclo[3.2.1]octane 108a as an oil, which was used in next step without purification. MS: calc'd (MH+) 150, measured (MH+) 150.

Examples 109 and 110

2-[(1R,3R,5S)-8-[[(4R)-4-(2-chloro-4-fluoro-phenyl)-5-methoxycarbonyl-2-thiazol-2-yl-1,4-dihydro-pyrimidin-6-yl]methyl]-6,6-difluoro-8-azabicyclo[3.2.1]octan-3-yl]acetic acid and 2-[(1S,3S,5R)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid

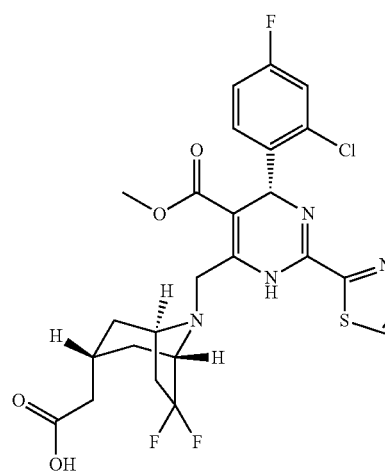

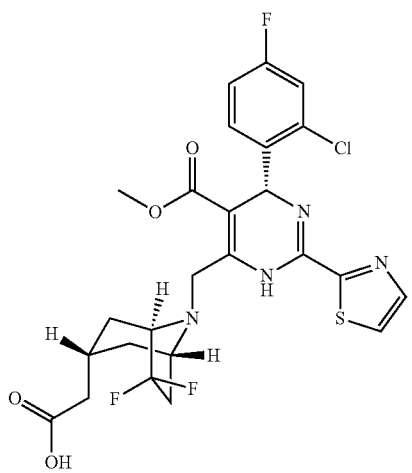

Preparation of Examples 109 and 110

Example 109 was prepared in analogy to Example 86 by using (4R)-4-(2-chloro-4-fluoro-phenyl)-6-(bromomethyl)-2-thiazol-2-yl-1,4-dihydropyrimidine-5-carboxylate (compound C, 45 mg) and 109a (one of the two enantiomers of methyl 2-endo-[6,6-difluoro-8-azabicyclo[3.2.1]octan-3-yl]acetate, 22 mg). 22 mg of Example 109 was isolated as yellow powder.

Example 110 was prepared in analogy to Example 86 by using (4R)-4-(2-chloro-4-fluoro-phenyl)-6-(bromomethyl)-2-thiazol-2-yl-1,4-dihydropyrimidine-5-carboxylate (compound C, 44 mg) and 109b (the other enantiomer of methyl 2-endo-[6,6-difluoro-8-azabicyclo[3.2.1]octan-3-yl]acetate-3-yl]acetate, 22 mg). 20 mg of Example 110 was isolated as yellow powder.

Preparation of the Two Enantiomers of methyl 2-endo-[(6,6-difluoro-8-azabicyclo[3.2.1]octan-3-yl]acetate, 109a and 109b

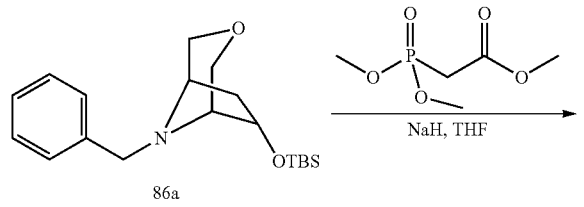

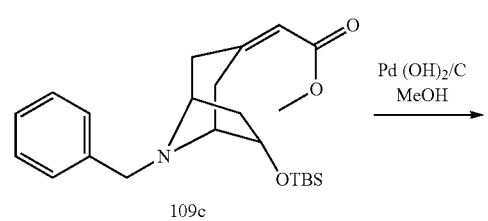

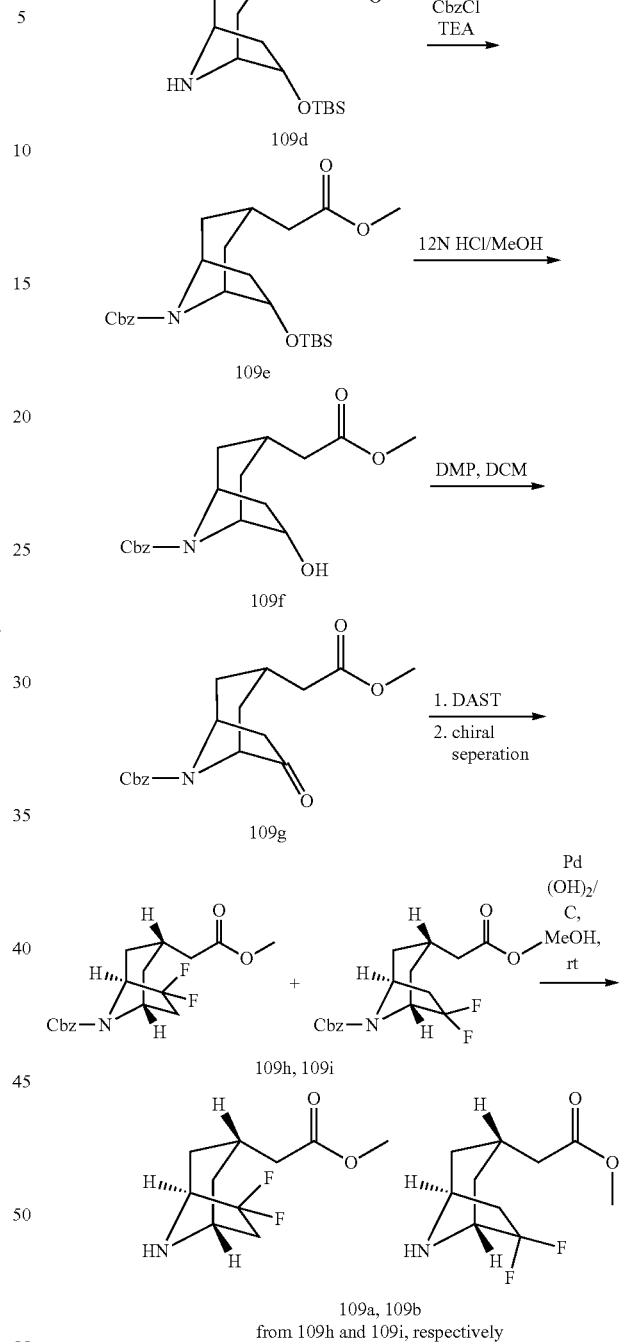

Step I: To a solution of Trimethyl phosphoroacetate (36.4 g, 0.2 mol, 2.0 eq) in THF (800 mL) was added NaH (8 g, 0.2 mol, 2.0 eq) slowly at room temperature, then the mixture was refluxed for 1 h. After the reaction was cooled to room temperature, compound 86a (34.5 g, 0.1 mol, 1.0 eq) in THF (150 mL) was added dropwise and then refluxed for 16 h. The mixture was quenched with water, extracted with EA (500 mL) two times, the organic layers were combined, dried over $Na_2SO_4$ and concentrated. The residue was purified by silica gel (EA/PE=1:10) to give methyl (2E/Z)-2-[8-benzyl-6-[tert-butyl(dimethyl)silyl]oxy-8-azabicyclo[3.2.1]octan-3- ylidene]acetate 109c as a white solid, 34 g, yield: 85%. ¹H NMR (400 MHz, DMSO-d6) δ: 7.45-7.11 (m, 5H), 5.75 (s, 0.6H), 5.70 (s, 0.4H), 4.13-3.99 (m, 1H), 3.99-3.82 (m, 2H), 3.66-3.53 (m, 3H), 3.52-3.45 (m, 1H), 3.45 (br, 1H), 3.35-3.29 (m, 1H), 3.07 (br, 1H), 2.53 (br, 1H), 2.27 (d, J=15.6 Hz, 0.4H), 2.13 (d, J=14.0 Hz, 0.6H), 1.94-1.76 (m, 2H), 0.91-0.81 (m, 9H), 0.06-0.07 (m, 6H); MS: calc'd (MH⁺) 402, measured (MH⁺) 402.

Step II: A mixture of compound 109c (32 g, 0.08 mol, 1.0 eq) and Pd(OH)₂/C (3 g, 15%) in MeOH (800 mL) was stirred at 60° C. for 20 h under 1 atm hydrogen, then the mixture was filtered, the filtrate was concentrated to give methyl 2-[6-[tert-butyl(dimethyl)silyl]oxy-8-azabicyclo[3.2.1]octan-3-ylidene]acetate 109d as a colorless oil, 22.4 g, yield: 90%. ¹HNMR (400 MHz, DMSO-d6) δ: 4.21 (dd, J=1.8, 6.4 Hz, 1H), 3.58 (s, 3H), 3.45 (t, J=6.8 Hz, 1H), 3.03 (d, J=6.0 Hz, 1H), 2.31-2.24 (m, 2H), 2.17-2.08 (m, 1H), 2.03 (dd, J=6.0, 13.6 Hz, 1H), 1.98-1.82 (m, 2H), 1.53 (dd, J=7.8, 13.6 Hz, 1H), 1.10-0.95 (m, 2H), 0.89-0.84 (m, 9H), 0.07-0.02 (m, 6H); MS: calc'd (MH⁺) 312, measured (MH⁺) 312.

Step III: To a solution of compound 109d (40 g, 0.13 mol, 1.0 eq) and TEA (40 g, 0.39 mol, 3.0 eq) in DCM (800 mL) was added a solution of CbzCl (45 g, 0.26 mol, 2.0 eq) in DCM (150 mL) slowly. The resulting mixture was stirred at room temperature for 16 h. The mixture was quenched with water, washed with 1N HCl (500 mL), the organic layer was dried over Na₂SO₄ and concentrated to give benzyl 6-[tert-butyl(dimethyl)silyl]oxy-3-(2-methoxy-2-oxo-ethyl)-8-azabicyclo[3.2.1]octane-8-carboxylate 109e as a crude product.

Step IV: crude 109e was dissolved in MeOH (400 mL), 12 N HCl (40 mL, 3.0 eq) was added and then stirred at room temperature for 30 min. The mixture was diluted with water (800 mL), and extracted two times with EA (500 mL). The organic layers were combined, dried over Na₂SO₄ and concentrated, the residue was purified by silica gel (EA/PE=1:3) to give benzyl 6-hydroxy-3-(2-methoxy-2-oxo-ethyl)-8-azabicyclo[3.2.1]octane-8-carboxylate 109f as a colorless oil, 30 g, yield for two steps, 70%. ¹H NMR (400 MHz, DMSO-d6) δ: 7.43-7.26 (m, 5H), 5.09 (s, 2H), 4.90 (dd, J=3.6, 6.8 Hz, 1H), 4.23 (d, J=6.4 Hz, 1H), 4.16-4.09 (m, 1H), 4.12-3.92 (m, 1H), 3.59 (s, 3H), 2.38 (d, J=7.2 Hz, 2H), 2.14-1.93 (m, 5H), 1.72 (br, 1H); MS: calc'd (MH⁺) 334, measured (MH⁺) 334.

Step V: To a solution of compound 109f (30 g, 0.09 mol, 1.0 eq) in DCM (800 mL) was added DMP (Dess-Martin Periodinane, 76.5 g, 0.18 mol, 2.0 eq) slowly at 0° C. The resulting mixture was stirred at room temperature for 16 h, and quenched with water. The solid was filtered off, the filtrate was washed with brine (500 mL), dried over Na₂SO₄ and concentrated. The residue was purified by silica gel (EA/PE=1:3) to give benzyl 3-(2-methoxy-2-oxo-ethyl)-6-oxo-8-azabicyclo[3.2.1]octane-8-carboxylate 109g as a colorless oil (26.5 g, yield 88%). ¹H NMR (400 MHz, DMSO-d6) δ: 7.46-7.30 (m, 5H), 5.15 (s, 2H), 4.61 (br, 1H), 4.00 (br, 1H), 3.58 (s, 3H), 2.77 (dd, J=7.2, 18.2 Hz, 1H), 2.41-2.30 (m, 3H), 2.28-2.10 (m, 3H), 1.49 (d, J=13.2 Hz, 1H), 1.38 (d, J=11.8 Hz, 1H); MS: calc'd (MH⁺) 332, measured (MH⁺) 332.

Step VI: A mixture of compound 109g (16 g, 0.04 mol, 1.0 eq) and DAST (32 g, 0.2 mol, 5.0 eq) in DCM (30 mL) was stirred at 60° C. in sealed tube for 3 days. The mixture was added dropwise to a cooled aqueous NaHCO₃ (500 mL, 5%) solution, then the mixture was extracted with EA (300 mL) two times, the organic layers were combined, washed with 1N HCl (200 mL) and brine (300 mL), dried over Na₂SO₄ and concentrated. The crude product contained the desired difluorinated product and a byproduct, vinyl fluoride in a ratio of about 1:1. The crude product was dissolved in DCM (200 mL), to it m-CPBA (20 g, 0.12 mol, 3.0 eq) was added slowly. The reaction mixture was stirred at room temperature for 16 h. the solid was filtered off, the filtrate was washed with NaHCO₃ (200 mL, 5% aq. solution) three times, Na₂S₂O₃ (200 mL, 5% aqueous solution) two times and brine (300 mL). The organic layer was concentrated and purified by preparative HPLC to remove the epoxide derived from vinyl fluoride. The obtained difluoro-product was further purified by chiral SFC (ChiralPak AD 250*30 mm, 5 um, 15% ethanol) to give a pair of enantiomers of benzyl 6,6-difluoro-3-endo-(2-methoxy-2-oxo-ethyl)-8-azabicyclo[3.2.1]octane-8-carboxylate, 109h (2 g, peak 1), and 109i (2 g, peak 2).

Step VII: A mixture of 109h (2 g, 5.5 mmol, 1.0 eq) and Pd(OH)₂/C (200 mg, 10%) in MeOH (30 mL) was stirred at room temperature for 16 h under hydrogen, then the mixture was filtered, the filtrate was concentrated to give one of the two enantiomers of methyl 2-endo-[6,6-difluoro-8-azabicyclo[3.2.1]octan-3-yl]acetate, 109a, as a colorless oil (1.15 g, yield 92%). ¹H NMR (400 MHz, DMSO-d6) δ: 3.58 (s, 3H), 3.47 (t, J=7.4 Hz, 1H), 3.29-3.18 (m, 1H), 2.77 (br, 1H), 2.37-2.16 (m, 4H), 2.12-1.85 (m, 3H), 1.36 (dd, J=7.0, 14.2 Hz, 1H), 1.10 (dd, J=6.4, 13.6 Hz, 1H); ¹⁹F NMR (376 MHz, DMSO-d6) d=(−87.44)-(−89.12) (m, 1F), (−107.59)-(−109.06) (m, 1F). MS: calc'd (MH⁺) 220, measured (MH⁺) 220.

The other enantiomer of methyl 2-endo-[6,6-difluoro-8-azabicyclo[3.2.1]octan-3-yl]acetate, 109b, was prepared from 109i in analogy to 109a.

Examples 111 and 112

2-[(1R,3R,5S)-8-[[(4S)-4-(3,4-difluoro-2-methyl-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid and 2-[(1S,3S,5R)-8-[[(4S)-4-(3,4-difluoro-2-methyl-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid

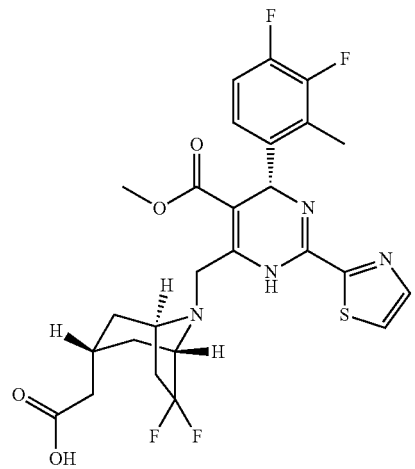

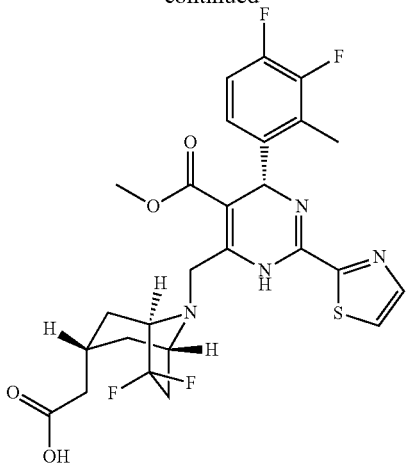

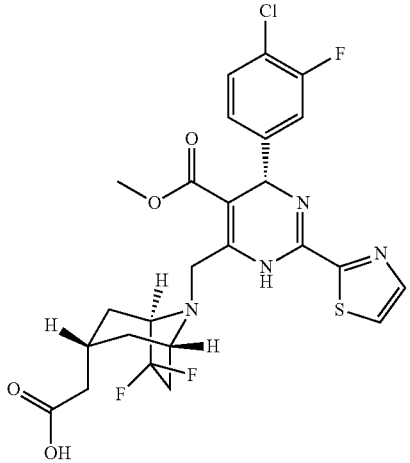

Preparation of Examples 111 and 112

Example 111 was prepared in analogy to Example 86 starting from methyl (4S)-6-(bromomethyl)-4-(3,4-difluoro-2-methyl-phenyl)-2-thiazol-2-yl-1,4-dihydropyrimidine-5-carboxylate 111a (50 mg) and 109a (22 mg). 4 mg of Example 111 was isolated as yellow powder.

Methyl (4S)-6-(bromomethyl)-4-(3,4-difluoro-2-methyl-phenyl)-2-thiazol-2-yl-1,4-dihydropyrimidine-5-carboxylate 111a was prepared in analogy to compound C with procedures shown in Example 1 by using 3,4-difluoro-2-methyl-benzaldehyde instead of 2-chloro-4-fluoro-benzaldehyde.

Example 112 was prepared in analogy to Example 86 starting from methyl (4S)-6-(bromomethyl)-4-(3,4-difluoro-2-methyl-phenyl)-2-thiazol-2-yl-1,4-dihydropyrimidine-5-carboxylate 111a (50 mg) and 109b (22 mg). 3.5 mg of Example 112 was isolated as yellow powder.

Example 113

2-[(1R,3R,5S)-8-[[(4S)-4-(4-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid or 2-[(1S,3S,5R)-8-[[(4S)-4-(4-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid The title compound was prepared in analogy to Example 86 starting from methyl (4S)-6-(bromomethyl)-4-(4-chloro-3-fluoro-phenyl)-2-thiazol-2-yl-1,4-dihydropyrimidine-5-carboxylate 96a (50 mg) and 109a (22 mg). 15 mg of the title compound was isolated as yellow powder.

Examples 114 and 115

2-[(1R,3S,5S)-8-[[(4S)-4-(3,4-difluorophenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid and 2-[(1S,3R,5R)-8-[[(4S)-4-(3,4-difluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid

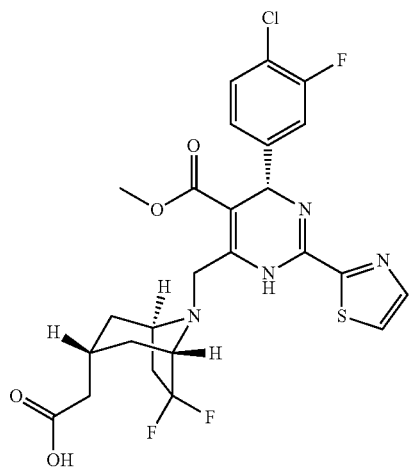

or

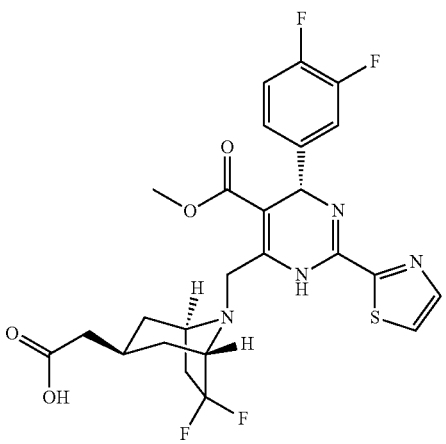

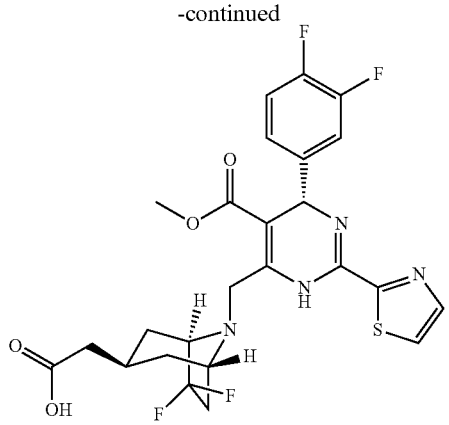

Preparation of Examples 114 and 115

Example 114 was prepared in analogy to Example 86 starting from 86j (22 mg) and methyl (4S)-6-(bromomethyl)-4-(3,4-difluorophenyl)-2-thiazol-2-yl-1,4-dihydropyrimidine-5-carboxylate 114a (50 mg). 6 mg of Example 114 was isolated.

Methyl (4S)-6-(bromomethyl)-4-(3,4-difluorophenyl)-2-thiazol-2-yl-1,4-dihydropyrimidine-5-carboxylate 114a was prepared in analogy to compound C with procedures shown in Example 1 by using 3,4-difluoro-benzaldehyde instead of and 2-chloro-4-fluoro-benzaldehyde.

Example 115 was prepared in analogy to Example 86 starting from 86k (22 mg) and methyl (4S)-6-(bromomethyl)-4-(3,4-difluorophenyl)-2-thiazol-2-yl-1,4-dihydropyrimidine-5-carboxylate 114a (50 mg). 8 mg of Example 115 was isolated.

Examples 116 and 117

2-[(3R)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid and 2-[(3S)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid

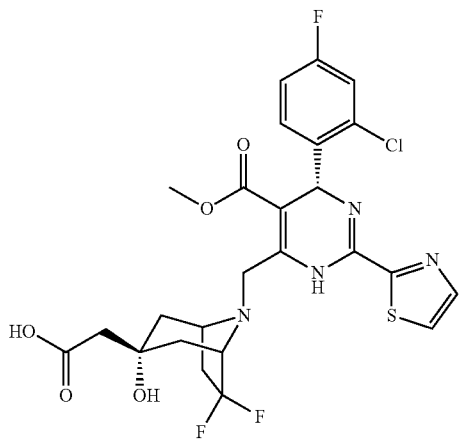

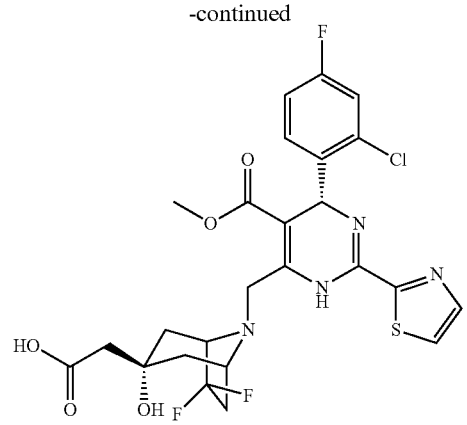

The title compounds were prepared in analogy to Example 86 starting from (4R)-4-(2-chloro-4-fluoro-phenyl)-6-(bromomethyl)-2-thiazol-2-yl-1,4-dihydropyrimidine-5-carboxylate (compound C, 225 mg) and ethyl 2-(6,6-difluoro-3-hydroxy-8-azabicyclo[3.2.1]octan-3-yl)acetate 116a (120 mg). The crude product was purified by preparative HPLC first, and then chiral SFC, to afford Example 116 and Example 117.

Ethyl 2-(6,6-difluoro-3-hydroxy-8-azabicyclo[3.2.1]octan-3-yl)acetate 116a

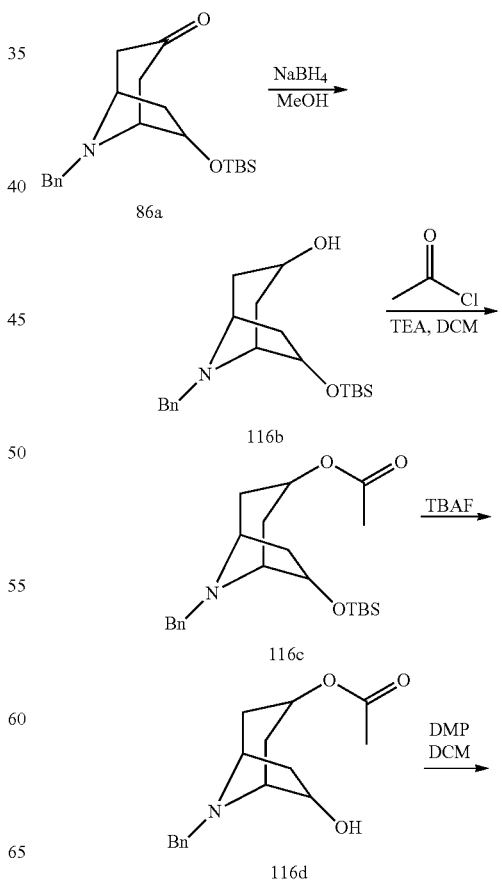

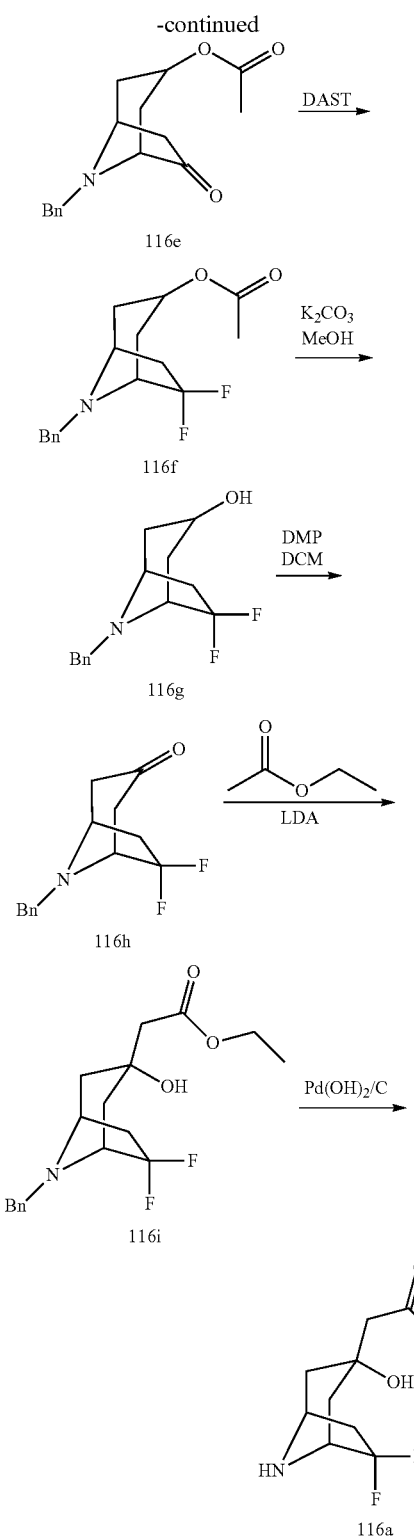

ethyl)silyl]oxy-8-azabicyclo[3.2.1]octan-3-ol 116b as a colorless oil, 6.24 g, yield: 90%. MS: calc'd (MH+) 348, measured (MH+) 348.

Step II: A mixture of compound 116b (6.24 g, 18 mmol, 1.0 eq) and TEA (9.2 g, 9 mmol, 5.0 eq) in DCM (100 mL) was added AcCl (4.2 g, 54 mmol) slowly and then stirred at room temperature for 2 h. The mixture was quenched with water (100 mL), extracted with DCM (100 mL), the organic layer was combined, dried over Na$_2$SO$_4$ and concentrated to give [8-benzyl-6-[tert-butyl(dimethyl)silyl]oxy-8-azabicyclo [3.2.1]octan-3-yl]acetate 116c as a colorless oil, 6.66 g, yield: 95%. MS: calc'd (MH+) 390, measured (MH+) 390.

Step III: A solution of compound 116c (6.24 g, 16 mmol, 1.0 eq) and TBAF (6.26 g, 24 mmol, 1.5 eq) in THF (100 mL) was stirred at 70° C. for 20 h. The mixture was diluted with EA (100 mL), and washed with water (100 mL) two times. The organic layer was extracted with 1N HCl (100 mL), the aqueous layer was adjust to PH=8 with NaHCO$_3$, extracted with DCM (100 mL) two times, the DCM layer was dried over Na$_2$SO$_4$ and concentrated to give (8-benzyl-6-hydroxy-8-azabicyclo[3.2.1]octan-3-yl)acetate 116d as a colorless oil, 4.4 g, crude yield: 100%. MS: calc'd (MH+) 276, measured (MH+) 276.

Step IV: To a mixture of compound 116d (4.4 g, 16 mmol, 1.0 eq) in DCM (50 mL) was added DMP (13.6 g, 32 mmol, 2.0 eq) slowly at 0° C., then the mixture was stirred at room temperature for 16 h. The reaction mixture was quenched with water, the solid was filtered off, the filtrate was diluted with DCM (100 mL), washed with NaHCO$_3$ (100 mL) three times and brine (100 mL). The organic layer was dried over Na$_2$SO$_4$ and concentrated. The residue was purified by silica gel (EA/PE=1:3) to give (8-benzyl-6-oxo-8-azabicyclo [3.2.1]octan-3-yl)acetate 116e as a colorless oil. 2.2 g, two step yield: 50%. MS: calc'd (MH+) 274, measured (MH+) 274.

Step V: A mixture of ketone 116e (2.2 g, 8 mmol, 1.0 eq) and DAST (6.44 g, 40 mmol, 5.0 eq) in DCM (15 mL) was stirred at 60° C. in sealed tube for 18 h. The mixture was added dropwise to a cooled aqueous NaHCO$_3$ (50 mL, 5%) solution, then the mixture was extracted with EA (50 mL) two times, the organic layer was dried over Na$_2$SO$_4$ and concentrated. The residue was purified by silica gel (EA/PE=1:3) to give (8-benzyl-6,6-difluoro-8-azabicyclo[3.2.1]octan-3-yl) acetate 116f as a slight yellow oil. 1.48 g, yield: 50%. MS: calc'd (MH+) 296, measured (MH+) 296.

Step VI: A solution of compound 116f (1.48 g, 4 mmol, 1.0 eq) and K$_2$CO$_3$ (1.1 g, 8 mmol, 2.0 eq) in MeOH (20 mL) was stirred at room temperature for 16 h. The mixture was quenched with water (100 mL), extracted with EA (100 mL) two times, the organic layer was combined, dried over Na$_2$SO$_4$ and concentrated to give 8-benzyl-6,6-difluoro-8-azabicyclo[3.2.1]octan-3-ol 116g as a colorless oil, 1.02 g, crude yield: 100° A. MS: calc'd (MH+) 254, measured (MH+) 254.

Step VII: To a mixture of compound 116g (1.02 g, 4 mmol, 1.0 eq) in DCM (20 mL) was added DMP (3.4 g, 8 mmol, 2.0 eq) slowly at 0° C., then the mixture was stirred at room temperature for 16 h. The reaction mixture was quenched with water, the solid was filtered off, the filtrate was diluted with DCM (100 mL), washed with NaHCO$_3$ (100 mL) three times and brine (100 mL). The organic layer was dried over Na$_2$SO$_4$ and concentrated. The residue was purified by silica gel (EA/PE=1:4) to give 8-benzyl-6,6-difluoro-8-azabicyclo [3.2.1]octan-3-one 116h as a colorless oil. 0.5 g. MS: calc'd (MH+) 252, measured (MH+) 2520.

Step I: To a solution of compound 86a (6.9 g, 20 mmol, 1.0 eq) in MeOH (100 mL) was added NaBH$_4$ (1.5 g, 40 mmol, 2.0 eq) slowly at room temperature, then the mixture was stirred at room temperature for 1 h. The mixture was quenched with water (100 mL), extracted with EA (100 mL) two times. The organic layer was combined, dried over Na$_2$SO$_4$ and concentrated to give 8-benzyl-6-[tert-butyl(dim- Step VIII: To a solution of diisopropylamine (1.02 g, 10 mmol, 5.0 eq) in THF (10 mL) was added n-BuLi (5 mL, 2.0 M, 5.0 eq) dropwise at −50° C. After 30 min, dry EA (880 mg, 10 mmol, 5.0 eq) in NMP/THF (11 mL, 1:10) was added dropwise. After 1 h at −50° C., a solution of compound 116h (500 mg, 2 mmol, 1.0 eq) in THF (5 mL) was added slowly, and the resulting mixture was warmed from −50° C. to room temperature for 2 h. The reaction mixture was quenched with water (50 mL), extracted with EA (100 mL). The organic layer was dried over Na$_2$SO$_4$ and concentrated. The residue was purified by silica gel (EA/PE=1:3) to give ethyl 2-(8-benzyl-6,6-difluoro-3-hydroxy-8-azabicyclo[3.2.1]octan-3-yl)acetate 116i as a colorless oil. 490 mg, yield: 72%. $^1$H NMR (400 MHz, DMSO-d6) ppm 7.37-7.19 (m, 5H), 4.45 (s, 1H), 4.09 (q, J=7.0 Hz, 2H), 3.84-3.70 (m, 2H), 3.27 (d, J=5.0 Hz, 1H), 3.08 (d, J=11.3 Hz, 1H), 2.70 (q, J=13.6 Hz, 1H), 2.43 (s, 2H), 2.37-2.26 (m, 1H), 2.13-2.00 (m, 2H), 1.84-1.72 (m, 1H), 1.52 (d, J=14.3 Hz, 1H), 1.22 (t, J=7.0 Hz, 3H); MS: calc'd (MH$^+$) 340, measured (MH$^+$) 340.

Step VIIII: A mixture of compound 116i (340 mg, 1 mmol, 1.0 eq) and Pd(OH)$_2$/C (100 mg, 30%) in MeOH (20 mL) was stirred at room temperature for 16 h under 1 atmosphere of hydrogen. The mixture was filtered, and the filtrate was concentrated to give ethyl 2-(6,6-difluoro-3-hydroxy-8-azabicyclo[3.2.1]octan-3-yl)acetate 116a as a colorless oil, 224 mg, yield: 90%. MS: calc'd (MH$^+$) 250, measured (MH$^+$) 250.

Examples 118 and 119

2-[(3R)-8-[[(4R)-4-(3,4-difluoro-2-methyl-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid and 2-[(3S)-8-[[(4S)-4-(3,4-difluoro-2-methyl-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid

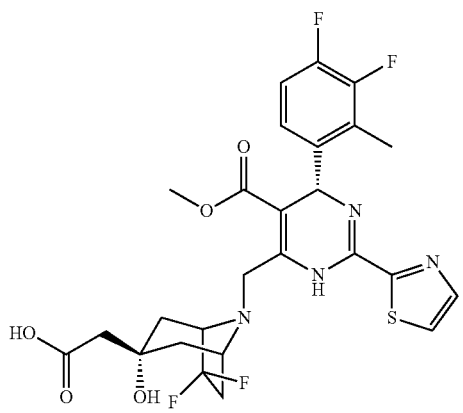

The title compounds were prepared in analogy to Example 86 starting from methyl (4S)-6-(bromomethyl)-4-(3,4-difluoro-2-methyl-phenyl)-2-thiazol-2-yl-1,4-dihydropyrimidine-5-carboxylate 111a (220 mg) and ethyl 2-(6,6-difluoro-3-hydroxy-8-azabicyclo[3.2.1]octan-3-yl)acetate 116a (120 mg). The crude product was purified by preparative HPLC first, and then chiral SFC, to give Example 118 (20 mg) and Example 119 (15 mg).

Examples 120 and 121

2-[(3R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid and 2-[(3S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid

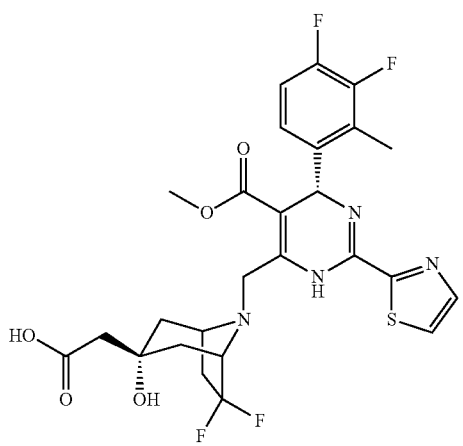

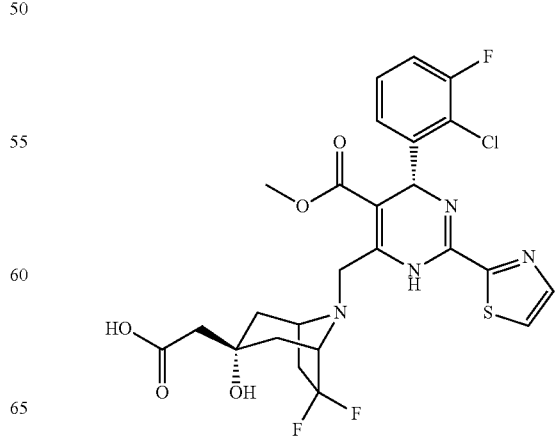

-continued

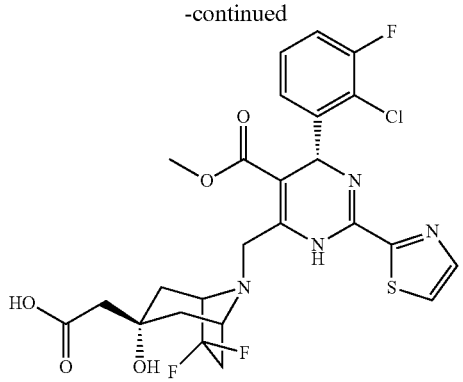

The title compounds were prepared in analogy to Example 86 starting from methyl (4R)-6-(bromomethyl)-4-(2-chloro-3-fluoro-phenyl)-2-thiazol-2-yl-1,4-dihydropyrimidine-5-carboxylate 88a (220 mg) and ethyl 2-(6,6-difluoro-3-hydroxy-8-azabicyclo[3.2.1]octan-3-yl)acetate 116a (120 mg). The crude product was purified by preparative HPLC first, and then chiral SFC, to give Example 120 (30 mg) and Example 121 (30 mg).

Example 122

Methyl (4R)-6-[(3-acetyl-3,8-diazabicyclo[3.2.1]octan-8-yl)methyl]-4-(2-chloro-4-fluoro-phenyl)-2-thiazol-2-yl-1,4-dihydropyrimidine-5-carboxylate

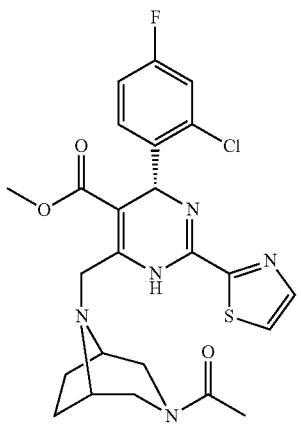 [SMILES: COC(=O)C1=C(CN2C3CCC2CN(C(C)=O)C3)NC(c2nccs2)=N[C@H]1c1ccc(F)cc1Cl]

To a solution of methyl (4R)-6-(bromomethyl)-4-(2-chloro-4-fluoro-phenyl)-2-thiazol-2-yl-1,4-dihydropyrimidine-5-carboxylate (compound C, 80 mg, 0.13 mmol) in dimethylformamide (3.0 mL) was added compound tert-butyl 3,8-diazabicyclo[3.2.1]octane-3-carboxylate (28 mg, 0.13 mmol) and potassium carbonate (40 mg, 0.29 mmol). The reaction mixture was stirred at room temperature overnight. The reaction mixture was poured into ice-water, extracted with EA (20 mL) three times. The combined organic phase was concentrated to give a crude tert-butyl 8-[[(4R)-4-(2-chloro-4-fluoro-phenyl)-5-methoxycarbonyl-2-thiazol-2-yl-1,4-dihydropyrimidin-6-yl]methyl]-3,8-diazabicyclo[3.2.1]octane-3-carboxylate (80 mg).

A mixture of tert-butyl 8-[[(4R)-4-(2-chloro-4-fluoro-phenyl)-5-methoxycarbonyl-2-thiazol-2-yl-1,4-dihydropyrimidin-6-yl]methyl]-3,8-diazabicyclo[3.2.1]octane-3-carboxylate (80 mg), trifluoroacetic acid (1.0 mL) and dichloromethane (2.0 mL) was stirred at room temperature for one hour, and then concentrated. The residue was dissolved in dichloromethane (5.0 mL), followed by adding diisopropylethylamine (0.2 mL) and acetic chloride (0.1 mL). The result mixture was stirred at room temperature overnight. The reaction mixture was concentrated and purified by prep-HPLC to give Methyl (4R)-6-[(3-acetyl-3,8-diazabicyclo[3.2.1]octan-8-yl)methyl]-4-(2-chloro-4-fluoro-phenyl)-2-thiazol-2-yl-1,4-dihydropyrimidine-5-carboxylate 122 (11.3 mg).

Examples 123 and 124

2-[(7S)-9-[[(4R)-4-(2-chloro-4-fluoro-phenyl)-5-methoxycarbonyl-2-thiazol-2-yl-1,4-dihydropyrimidin-6-yl]methyl]-6-hydroxy-3-oxa-9-azabicyclo[3.3.1]nonan-7-yl]acetic acid and 2-[(7R)-9-[[(4R)-4-(2-chloro-4-fluoro-phenyl)-5-methoxycarbonyl-2-thiazol-2-yl-1,4-dihydropyrimidin-6-yl]methyl]-6-hydroxy-3-oxa-9-azabicyclo[3.3.1]nonan-7-yl]acetic acid

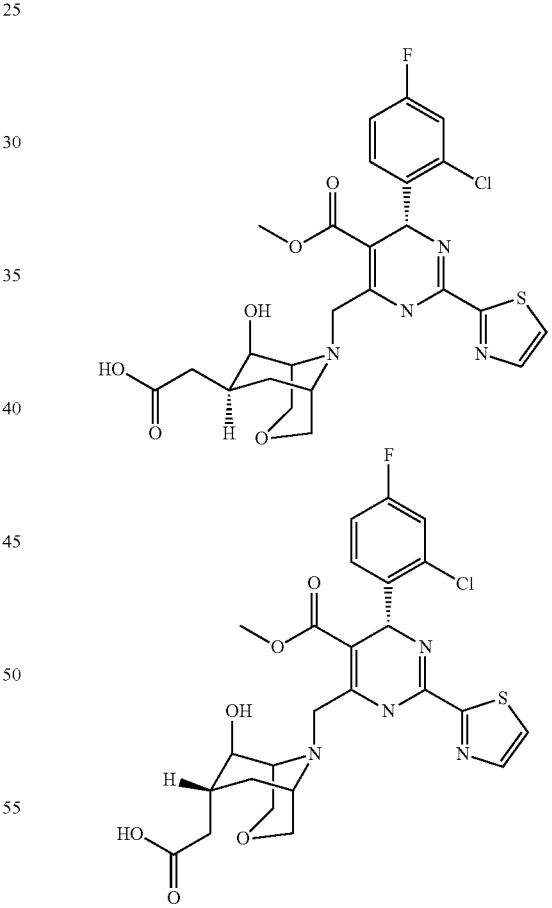

The title compounds were prepared in analogy to Example 1 with ethyl 2-(6-hydroxy-3-oxa-9-azabicyclo[3.3.1]nonan-7-yl)acetate 123a and methyl (4R)-6-(bromomethyl)-4-(2-chloro-4-fluoro-phenyl)-2-thiazol-2-yl-1,4-dihydropyrimidine-5-carboxylate (compound C). The crude product from the final step was purified by preparative HPLC to give two compounds, Example 123, and Example 124.

Preparation of ethyl 2-(6-hydroxy-3-oxa-9-azabicyclo[3.3.1]nonan-7-yl)acetate 123a

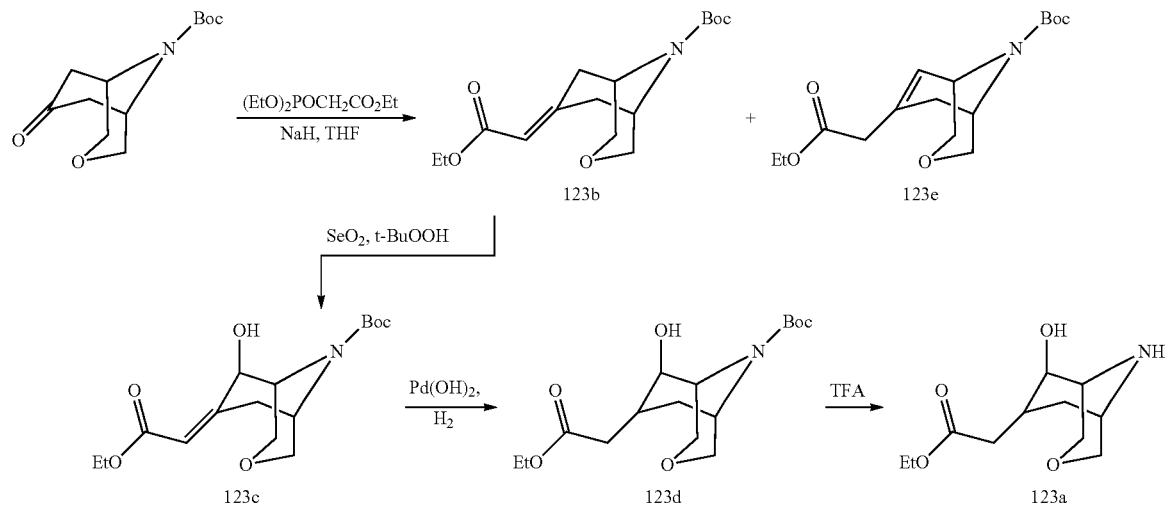

Step I: To a suspension of sodium hydride (396 mg, 60% dispersion in mineral oil, 9.9 mmol) in dry THF (5 ml) was added 2-diethoxyphosphorylacetic acid ethyl ester (2.40 g, 10.8 mmol) at 0° C. The resulting mixture was stirred at room temperature for 10 mins, and then heated at 80° C. for 20 mins. The reaction mixture was cooled down to room temperature. To the reaction mixture was added a solution of tert-butyl 7-oxo-3-oxa-9-azabicyclo[3.3.1]nonane-9-carboxylate (2.00 g, 8.3 mmol) in dry THF (20 ml). The resulting mixture was stirred at 80° C. overnight. The solvent was removed and the residue was partitioned between ethyl acetate and water. The organic phase was dried, concentrated and purified by silica gel chromatography to give tert-butyl 7-(2-ethoxy-2-oxo-ethylidene)-3-oxa-9-azabicyclo[3.3.1]nonane-9-carboxylate 123b (1.20 g, 46.5%) and tert-butyl 7-(2-ethoxy-2-oxo-ethyl)-3-oxa-9-azabicyclo[3.3.1]non-6-ene-9-carboxylate 123e (0.800 g, 30.8%). Compound 123b: $^1$H NMR (400 MHz, CDCl$_3$): d=5.72-5.66 (m, 1H), 4.29-4.23 (m, 1H), 4.15 (d, J=7.3 Hz, 3H), 4.05-3.97 (m, 1H), 3.88-3.77 (m, 2H), 3.76-3.65 (m, 2H), 2.77-2.61 (m, 1H), 2.38 (d, J=15.3 Hz, 2H), 1.53-1.48 (m, 9H), 1.30-1.26 (m, 3H).

Step II: To a solution of tert-butyl hydroperoxide in 1,2-dichloroethane (8.0 mL, v/v 1:5, pre-dried over Na$_2$SO$_4$) was added compound 123b (600 mg, 2.0 mmol) and selenium dioxide (220 mg, 2.0 mmol). The reaction mixture was sealed and heated to 70° C. under microwave for one hour. The reaction mixture was cooled down to room temperature, washed with saturated Na$_2$SO$_3$ solution, and extracted with DCM (30 mL) three times. The organic phases were combined and dried over Na$_2$SO$_4$. After filtration and concentration, the residue was purified by silica gel column to give tert-butyl (7E/Z)-7-(2-ethoxy-2-oxo-ethylidene)-6-hydroxy-3-oxa-9-azabicyclo[3.3.1]nonane-9-carboxylate 123c (563 mg, yield: 90%). $^1$H NMR (400 MHz, CDCl$_3$): d=5.83-5.44 (m, 1H), 4.36-4.08 (m, 5H), 3.93-3.55 (m, 5H), 3.13-3.05 (m, 0.5H), 2.82-2.74 (m, 0.5H), 2.30-2.22 (m, 0.5H), 2.10-2.03 (m, 0.5H), 1.53-1.49 (m, 9H), 1.30-1.26 (m, 3H).

Step III: To a solution of compound 123c (18 g, 55 mmol) in ethanol (200 mL) was added palladium hydroxide (3.0 g). The reaction mixture was stirred at 40° C. overnight under 1 atm H$_2$. The reaction mixture was filtrated and concentrated to give tert-butyl 7-(2-ethoxy-2-oxo-ethyl)-6-hydroxy-3-oxa-9-azabicyclo[3.3.1]nonane-9-carboxylate 123d (18 g, crude). $^1$H NMR (400 MHz, CDCl3): d=4.24-3.98 (m, 4H), 3.90-3.78 (m, 1H), 3.70-3.48 (m, 4H), 2.79 (dd, J=5.3, 15.6 Hz, 0.5H), 2.59 (d, J=7.0 Hz, 0.5H), 2.41 (dd, J=5.5, 15.8 Hz, 0.5H), 2.30 (dd, J=8.2, 15.7 Hz, 0.5H), 2.25-2.16 (m, 1H), 1.77-1.64 (m, 1H), 1.54-1.50 (m, 9H), 1.42-1.26 (m, 5H).

Step IV: To a solution of compound 123d (100 mg) in dichloromethane (2.0 mL) was added trifluoroacetic acid (1.0 mL). The reaction mixture was stirred at room temperature for one hour, and concentrated under reduced pressure to give ethyl 2-(6-hydroxy-3-oxa-9-azabicyclo[3.3.1]nonan-7-yl)acetate 123a, which was used directly in next step without purification.

Examples 125 and 126

2-[(7R)-9-[[(4R)-4-(2-chloro-4-fluoro-phenyl)-5-methoxycarbonyl-2-thiazol-2-yl-1,4-dihydropyrimidin-6-yl]methyl]-6,6-difluoro-3-oxa-9-azabicyclo [3.3.1]nonan-7-yl]acetic acid and 2-[(7S)-9-[[(4R)-4-(2-chloro-4-fluoro-phenyl)-5-methoxycarbonyl-2-thiazol-2-yl-1,4-dihydropyrimidin-6-yl]methyl]-6,6-difluoro-3-oxa-9-azabicyclo [3.3.1]nonan-7-yl]acetic acid

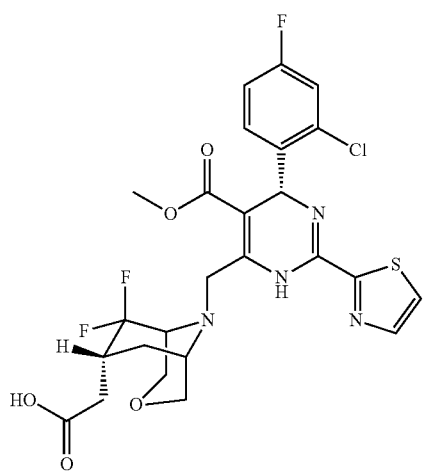

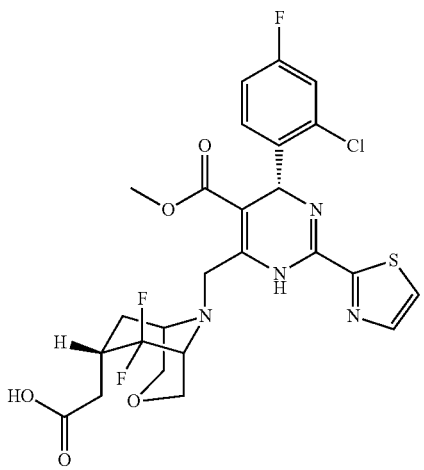

Preparation of Examples 125 and 126

Example 125 was prepared in analogy to Example 86 starting from methyl (4R)-6-(bromomethyl)-4-(2-chloro-4-fluoro-phenyl)-2-thiazol-2-yl-1,4-dihydropyrimidine-5-carboxylate (compound C) and 125a (one of the two enantiomers of ethyl 2-endo-[6,6-difluoro-3-oxa-9-azabicyclo[3.3.1]nonan-7-yl]acetate).

Example 126 was prepared in analogy to Example 86 starting from methyl (4R)-6-(bromomethyl)-4-(2-chloro-4-fluoro-phenyl)-2-thiazol-2-yl-1,4-dihydropyrimidine-5-carboxylate (compound C) and 126a (the other enantiomer of ethyl 2-endo-[6,6-difluoro-3-oxa-9-azabicyclo[3.3.1]nonan-7-yl]acetate).

Preparation of the two enantiomers of ethyl 2-endo-[6,6-difluoro-3-oxa-9-azabicyclo[3.3.1]nonan-7-yl] acetate, 125a and 126a

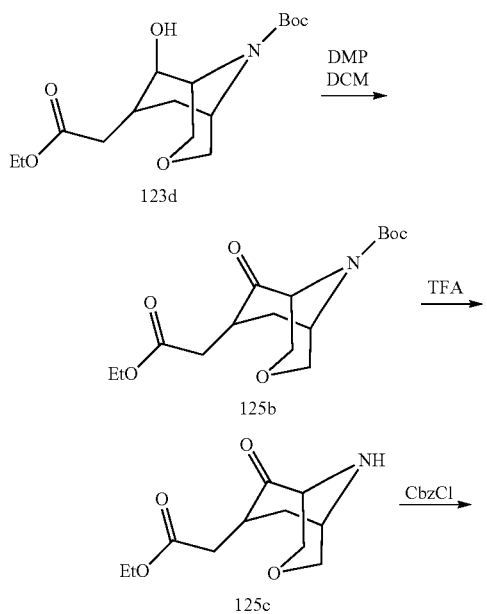

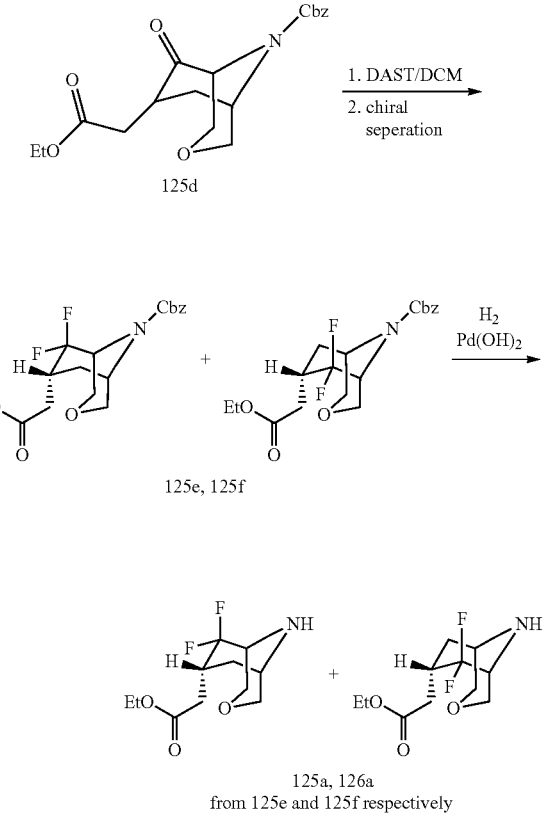

Step I: To a solution of compound 123d (960 mg, 3.0 mmol) in dichloromethane (30 mL) was added Dess-Martin reagent (2.54 g, 6.0 mmol) at 40° C. The reaction mixture was stirred for three hours, then another batch of Dess-Martin reagent (1.27 g, 3.0 mmol) was added. The reaction mixture was stirred overnight. The reaction mixture was poured into ice-water, and filtrated. The filtrate was washed with sodium bicarbonate solution and sodium sulphite solution, extracted with dichloromethane (50 mL) three times. The organic phase was dried over $Na_2SO_4$, and concentrated. The residue was purified by silica gel column to give tert-butyl 7-(2-ethoxy-2-oxo-ethyl)-6-oxo-3-oxa-9-azabicyclo[3.3.1]nonane-9-carboxylate 125b (780 mg, yield: 80%).

Step II and III: a mixture of tert-butyl 7-(2-ethoxy-2-oxo-ethyl)-6-oxo-3-oxa-9-azabicyclo[3.3.1]nonane-9-carboxylate 125b (654 mg, 2.0 mmol), trifluoroacetic acid (1.0 mL) and dichloromethane (2.0 mL) was stirred at room temperature for one hour. The reaction mixture was concentrated. The residue was dissolved in dimethylformamide (5.0 mL), followed by adding potassium carbonate (700 mg, 5.0 mmol) and N,N-diisopropylethylamine (0.3 mL). The result mixture was warmed to 40° C., then added dropwise benzyl chloroformate (311 µL, 2.2 mmol) in dimethylformamide (1.0 mL). The resulting mixture was stirred for another two hours. The reaction was quenched by adding ice-water, extracted with PE: EA=5:1 (30 mL) three times. The combined organic phases were dried over $Na_2SO_4$, and concentrated. The residue was purified by silica gel column to give benzyl 7-(2-ethoxy-2-oxo-ethyl)-6-oxo-3-oxa-9-azabicyclo[3.3.1]nonane-9-carboxylate 125d (650 mg, yield: 90%).

Step IV: To a solution of benzyl 7-(2-ethoxy-2-oxo-ethyl)-6-oxo-3-oxa-9-azabicyclo[3.3.1]nonane-9-carboxylate 125d (14.4 g, 40 mmol) in dichloromethane (84 mL) was added diethylaminosulfur trifluoride (42 mL, 320 mmol). The reaction mixture was stirred at 65° C. overnight. The reaction mixture was cooled down and diluted with ethyl acetate (300 mL). The mixture was poured into ice-water and sodium bicarbonate solution at 0° C. The reaction mixture was extracted with PE: EA=5:1 (150 mL) three times. The combined organic phases were dried over $Na_2SO_4$, filtrated and concentrated. The residue was purified by silica gel column (18% EA in petroleum ether), preparative HPLC, and then chiral SFC (OJ-H, 30*250 mm, 5 um, 5% isopropanol) to give a pair of enantiomers of benzyl 7-endo-(2-ethoxy-2-oxo-ethyl)-6,6-difluoro-3-oxa-9-azabicyclo[3.3.1]nonane-9-carboxylate, 125e (2.0 g, peak 1) and 125f (3 g, peak 2).

Step V: To a solution of 125e (2.0 g, 5.22 mmol) in ethanol (25 mL) was added palladium hydroxide (1.0 g). The reaction mixture was stirred at room temperature overnight, and then diluted with ethyl acetate (300 mL). The mixture was filtrated and concentrated to give 125a, one of the two enantiomers of ethyl 2-endo-[6,6-difluoro-3-oxa-9-azabicyclo[3.3.1]nonan-7-yl]acetate (1.0 g, crude).

The other enantiomer of ethyl 2-endo-[6,6-difluoro-3-oxa-9-azabicyclo[3.3.1]nonan-7-yl]acetate, 126a, was prepared from 125f in analogy to compound 125a.

Examples 127 and 128

2-[(7R)-9-[[(4S)-4-(3,4-difluoro-2-methyl-phenyl)-5-ethoxycarbonyl-2-thiazol-2-yl-1,4-dihydropyrimidin-6-yl]methyl]-6,6-difluoro-3-oxa-9-azabicyclo[3.3.1]nonan-7-yl]acetic acid and 2-[(7S)-9-[[(4S)-4-(3,4-difluoro-2-methyl-phenyl)-5-ethoxycarbonyl-2-thiazol-2-yl-1,4-dihydropyrimidin-6-yl]methyl]-6,6-difluoro-3-oxa-9-azabicyclo[3.3.1]nonan-7-yl]acetic acid

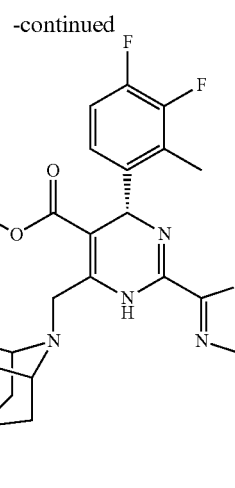

-continued

Preparation of Examples 127 and 128

Example 127 was prepared in analogy to Example 86 starting from ethyl (4S)-6-(bromomethyl)-4-(3,4-difluoro-2-methyl-phenyl)-2-thiazol-2-yl-1,4-dihydropyrimidine-5-carboxylate 127a and 125a. Compound 127a was prepared in analogy to methyl (4R)-6-(bromomethyl)-4-(2-chloro-4-fluoro-phenyl)-2-thiazol-2-yl-1,4-dihydropyrimidine-5-carboxylate (compound C) in Example 1, by using ethyl acetoacetate and 3,4-difluoro-2-methyl-benzaldehyde instead of methyl acetoacetate and 2-chloro-4-fluoro-benzaldehyde, respectively.

Example 128 was prepared in analogy to Example 86 starting from ethyl (4S)-6-(bromomethyl)-4-(3,4-difluoro-2-methyl-phenyl)-2-thiazol-2-yl-1,4-dihydropyrimidine-5-carboxylate 127a and 126a.

Examples 129 and 130

2-[(7R)-9-[[(4R)-4-(2-chloro-3-fluoro-phenyl)-5-ethoxycarbonyl-2-thiazol-2-yl-1,4-dihydropyrimidin-6-yl]methyl]-6,6-difluoro-3-oxa-9-azabicyclo[3.3.1]nonan-7-yl]acetic acid and 2-[(7S)-9-[[(4R)-4-(2-chloro-3-fluoro-phenyl)-5-ethoxycarbonyl-2-thiazol-2-yl-1,4-dihydropyrimidin-6-yl]methyl]-6,6-difluoro-3-oxa-9-azabicyclo[3.3.1]nonan-7-yl]acetic acid

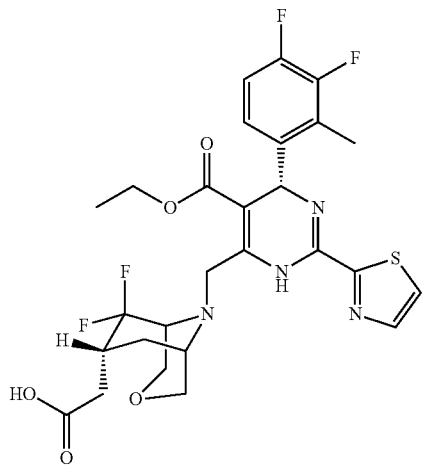

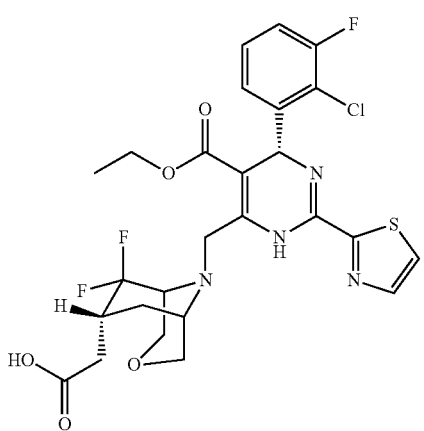

213

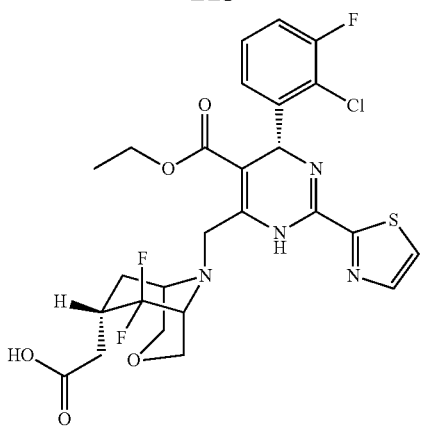

Preparation of Examples 129 and 130

Example 129 was prepared in analogy to Example 86 starting from ethyl (4R)-6-(bromomethyl)-4-(2-chloro-3-fluorophenyl)-2-thiazol-2-yl-1,4-dihydropyrimidine-5-carboxylate 98a and 125a.

Example 130 was prepared in analogy to Example 86 starting from ethyl (4R)-6-(bromomethyl)-4-(2-chloro-3-fluorophenyl)-2-thiazol-2-yl-1,4-dihydropyrimidine-5-carboxylate 98a and 126a.

Example 131

2-[(1R,5R,7S)-9-[[(4R)-4-(2-chloro-3,4-difluorophenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid or 2-[(1S,5S,7R)-9-[[(4R)-4-(2-chloro-3,4-difluorophenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid

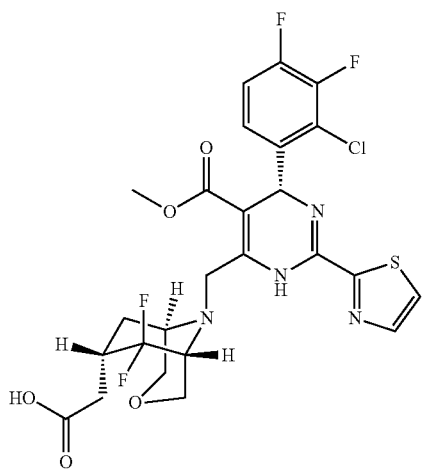

or

214

-continued

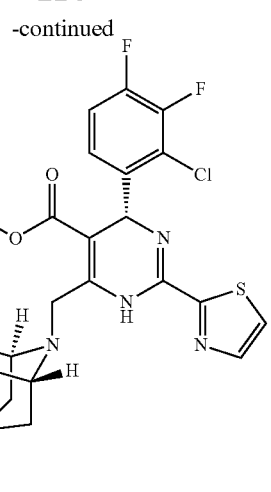

The title compound was prepared in analogy to Example 86 starting from methyl (4R)-6-(bromomethyl)-4-(2-chloro-3,4-difluoro-phenyl)-2-thiazol-2-yl-1,4-dihydropyrimidine-5-carboxylate 131a and 126a.

Methyl (4R)-6-(bromomethyl)-4-(2-chloro-3,4-difluorophenyl)-2-thiazol-2-yl-1,4-dihydropyrimidine-5-carboxylate 131a was prepared in analogy to methyl (4R)-6-(bromomethyl)-4-(2-chloro-4-fluoro-phenyl)-2-thiazol-2-yl-1,4-dihydropyrimidine-5-carboxylate (compound C) in Example 1, by using 2-chloro-3,4-difluoro-benzaldehyde instead of 2-chloro-4-fluoro-benzaldehyde.

Example 132

2-[(1R,5R,7S)-9-[[(4S)-4-(3,4-difluoro-2-methylphenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid or 2-[(1S,5S,7R)-9-[[(4S)-4-(3,4-difluoro-2-methylphenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid or

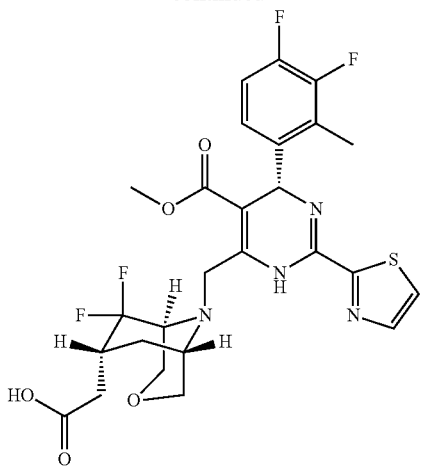

The title compound was prepared in analogy to Example 86 starting from methyl (4S)-6-(bromomethyl)-4-(3,4-difluoro-2-methyl-phenyl)-2-thiazol-2-yl-1,4-dihydropyrimidine-5-carboxylate 111a and 126a.

Example 133

Methyl (4R)-4-(2-chloro-4-fluoro-phenyl)-6-[(6-oxo-3-oxa-7,9-diazabicyclo[3.3.1]nonan-9-yl)methyl]-2-thiazol-2-yl-1,4-dihydropyrimidine-5-carboxylate

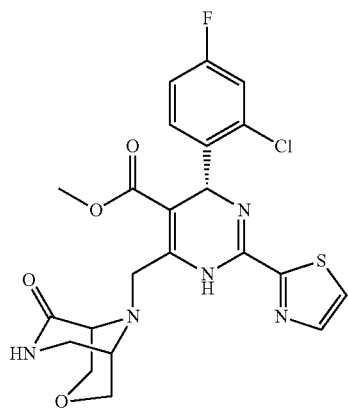 [SMILES: COC(=O)C1=C(CN2C3CNC(=O)C2COC3)NC(c2nccs2)=N[C@H]1c1ccc(F)cc1Cl]

The titled compound was prepared by following procedure. To a solution of methyl (4R)-6-(bromomethyl)-4-(2-chloro-4-fluoro-phenyl)-2-thiazol-2-yl-1,4-dihydropyrimidine-5-carboxylate (compound C, 0.089 g, 0.20 mmol) and tert-butyl 6-oxo-3-oxa-7,9-diazabicyclo[3.3.1]nonane-7-carboxylate 133a (0.096 g) in CH$_2$Cl$_2$ (3 ml) was added DIPEA (0.2 ml, 1.14 mmol) at room temperature. The resulting mixture was stirred at room temperature overnight. The mixture was concentrated, and the residue (0.120 g, MS: calc'd (MH$^+$) 606, measured (MH$^+$) 606) was dissolved in dichloromethane (3 ml). To it was added trifluoroacetic acid (2 ml) at room temperature. The resulting mixture was stirred at room temperature for 2 hours. Then the mixture was concentrated and the residue was purified by preparative HPLC to give the title compound (10 mg).

Preparation of tert-butyl 6-oxo-3-oxa-7,9-diazabicyclo[3.3.1]nonane-7-carboxylate 133a

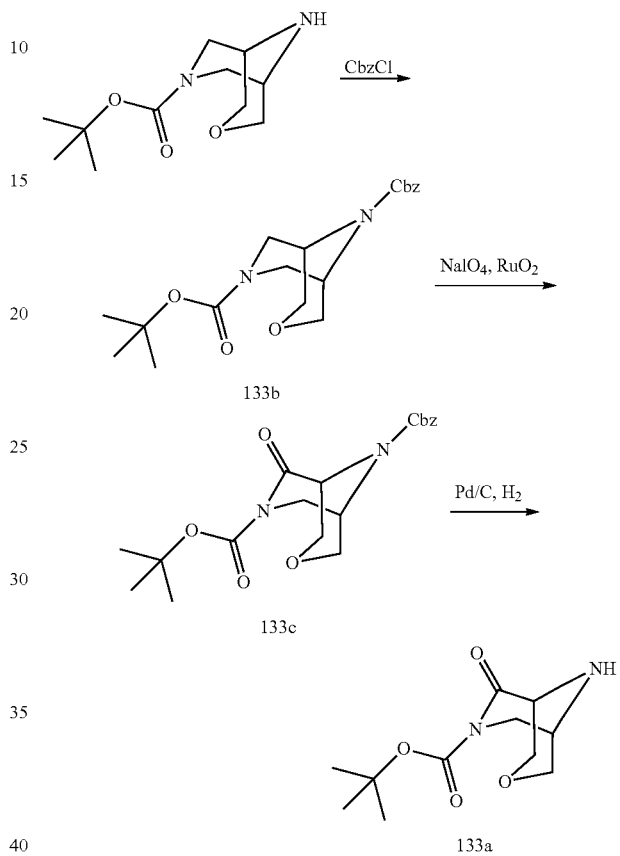

Step I: To a solution of tert-butyl 3-oxa-7,9-diazabicyclo[3.3.1]nonane-7-carboxylate (0.500 g, 2.2 mmol) in dichloromethane (5 ml) was added triethylamine (0.443 g, 4.4 mmol) at room temperature. The mixture was stirred at room temperature for a few mins, and then benzyl chloroformate (0.751 g, 4.4 mmol) was added to the reaction mixture. The resulting mixture was stirred at room temperature overnight. The mixture was partitioned between dichloromethane and water. The organic phase was dried, and concentrated. The residue was purified by silica gel chromatography to give 9-benzyl 7-tert-butyl 3-oxa-7,9-diazabicyclo[3.3.1]nonane-7,9-dicarboxylate 133b (0.637 g, 80.0%). MS: calc'd (MH$^+$) 363, measured (MH$^+$) 363.

Step II: A solution of 133b (0.100 g, 0.28 mmol) in ethyl acetate (1 ml) was added to a mixture of 10% NaIO$_4$ aqueous solution (0.283 mg in 3 ml H$_2$O) and RuO$_2$. The mixture was stirred at room temperature overnight. The organic phase was separated and the aqueous phase was extracted with ethyl acetate (10 ml) two times. The combined organic phases were treated with isopropyl alcohol (2 ml) to decompose RuO$_4$ oxidant, then washed three times with H$_2$O (5 ml), dried, and concentrated. The crude product 9-benzyl-7-tert-butyl 6-oxo-3-oxa-7,9-diazabicyclo[3.3.1]nonane-7,9-dicarboxylate 133c (0.150 g) was used directly in next step. MS: calc'd (MH$^+$) 377, measured (MH$^+$) 377.

Step III: A mixture of 133c (150 mg, 0.40 mmol) and Pd/C (20 mg) in MeOH (5 ml) was stirred under H₂ balloon at room temperature overnight. The reaction mixture was filtered and the filtrate was concentrated to give crude tert-butyl 6-oxo-3-oxa-7,9-diazabicyclo[3.3.1]nonane-7-carboxylate 133a (96 mg), which was used directly in next step. MS: calc'd (MH⁺) 243, measured (MH⁺) 243.

Example 134

Endo-2-[9-[[(4R)-4-(2-bromophenyl)-5-methoxycarbonyl-2-thiazol-2-yl-1,4-dihydropyrimidin-6-yl]methyl]-3-oxa-9-azabicyclo[3.3.1]nonan-7-yl]acetic acid

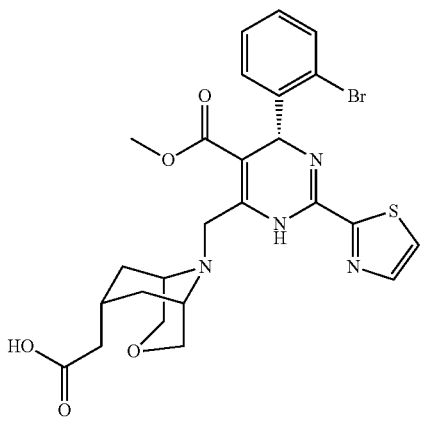 [SMILES: COC(=O)C1=C(CN2C3COCC2CC(CC(=O)O)C3)NC(c2nccs2)=N[C@H]1c1ccccc1Br]

To a stirred solution of (4R)-6-(bromomethyl)-4-(2-bromophenyl)-2-thiazol-2-yl-1,4-dihydropyrimidine-5-carboxylate 134a (122 mg) and endo-(3-oxa-9-aza-bicyclo[3.3.1]non-7-yl)-acetic acid (PharmaBlock (Nanjing) R&D Co. Ltd, PBN20121752, 72 mg) in CH₂Cl₂ (3 ml) was added DIPEA (0.20 ml, 1.14 mmol) at room temperature. The resulting mixture was stirred at room temperature overnight. Then the reaction mixture was concentrated and the residue was purified by prep-HPLC to give the title compound (23 mg). (4R)-6-(bromomethyl)-4-(2-bromophenyl)-2-thiazol-2-yl-1,4-dihydropyrimidine-5-carboxylate 134a was prepared in analogy to compound C in Example 1 by using 2-bromoaldehyde instead of 2-chloro-4-fluoro-benzaldehyde.

Example 135

Endo-2-[9-[[(4R)-4-(2-chloro-3,4-difluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid

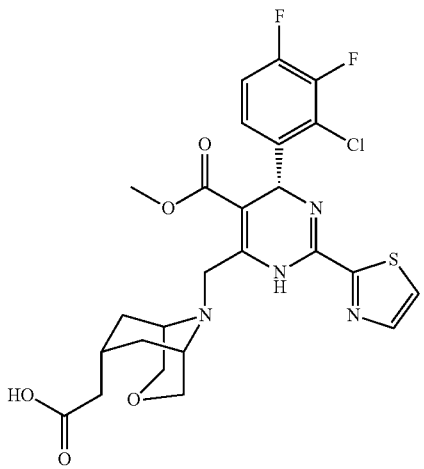 [SMILES: COC(=O)C1=C(CN2C3COCC2CC(CC(=O)O)C3)NC(c2nccs2)=N[C@H]1c1ccc(F)c(F)c1Cl]

The title compound was prepared in analogy to Example 134, starting from methyl (4R)-6-(bromomethyl)-4-(2-chloro-3,4-difluoro-phenyl)-2-thiazol-2-yl-1,4-dihydropyrimidine-5-carboxylate 131a (200 mg) and endo-(3-oxa-9-azabicyclo[3.3.1]non-7-yl)-acetic acid (PharmaBlock (Nanjing) R&D Co. Ltd, PBN20121752, 120 mg). 115 mg of the title compound was isolated.

Example 136

Endo-2-[9-[[(4S)-4-(4-chloro-3-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid

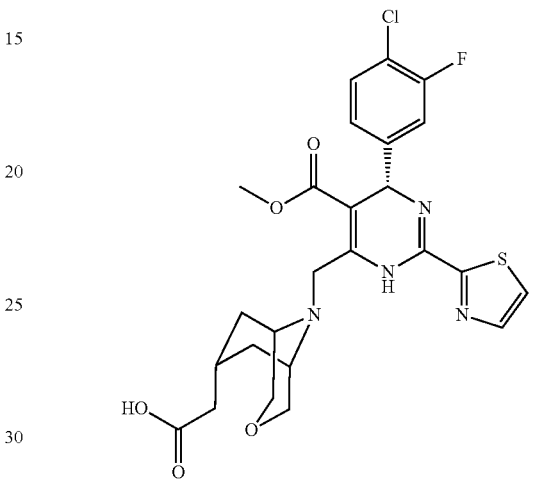

The title compound was prepared in analogy to Example 134, starting from methyl (4S)-6-(bromomethyl)-4-(4-chloro-3-fluoro-phenyl)-2-thiazol-2-yl-1,4-dihydropyrimidine-5-carboxylate 96a (50 mg) and endo-(3-oxa-9-aza-bicyclo[3.3.1]non-7-yl)-acetic acid (PharmaBlock (Nanjing) R&D Co. Ltd, PBN20121752, 40 mg). 10 mg of the title compound was isolated.

Example 137

Methyl (4R)-4-(2-chloro-4-fluoro-phenyl)-6-[[7-(2-ethoxy-1-hydroxy-2-oxo-ethyl)-7-hydroxy-3-oxa-9-azabicyclo[3.3.1]nonan-9-yl]methyl]-2-thiazol-2-yl-1,4-dihydropyrimidine-5-carboxylate

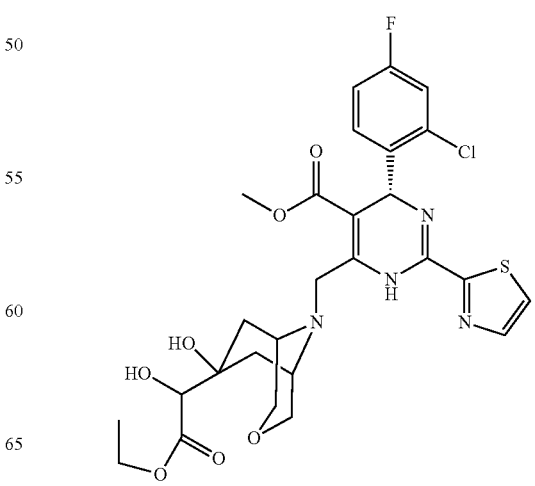

219

The title compound was prepared in analogy to Example 134, starting from methyl (4R)-6-(bromomethyl)-4-(2-chloro-4-fluoro-phenyl)-2-thiazol-2-yl-1,4-dihydropyrimidine-5-carboxylate (compound C, 58 mg) and ethyl 2-hydroxy-2-(7-hydroxy-3-oxa-9-azabicyclo[3.3.1]nonan-7-yl)acetate 137a (96 mg). 7 mg of the title compound was isolated.

Preparation of 2-hydroxy-2-(7-hydroxy-3-oxa-9-azabicyclo[3.3.1]nonan-7-yl)acetate 137a

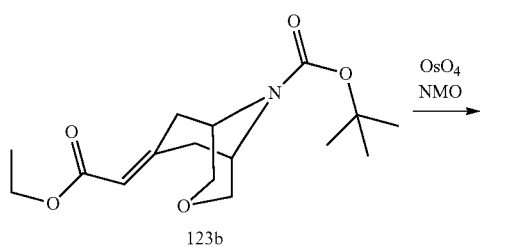

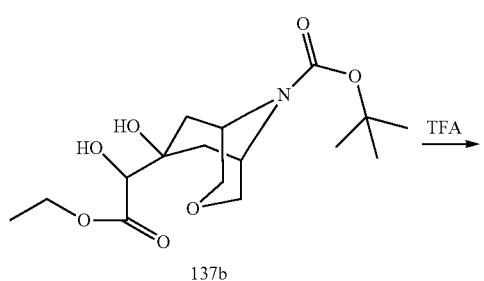

Step I: To a mixture of tert-butyl 7-(2-ethoxy-2-oxo-ethylidene)-3-oxa-9-azabicyclo[3.3.1]nonane-9-carboxylate 123b (0.800 g, 2.6 mmol) in acetone (8 ml) and water (2 ml) were added N-methylmorpholine-N-oxide (0.903 g, 7.7 mmol) and Osmium tetroxide solution (0.3 ml, 4 wt % in H$_2$O, 1.2 mmol) at room temperature. The resulting mixture was stirred at room temperature overnight. The mixture was then concentrated and the crude diol 137b (0.950 g) was used directly in next step without further purification.

Step II: To a solution of diol 137b (150 mg, 0.43 mmol) in dichloromethane (2 ml) was added trifluoroacetic acid (2 ml) at room temperature. The resulting mixture was stirred at room temperature for 2 hours, then concentrated to give 2-hydroxy-2-(7-hydroxy-3-oxa-9-azabicyclo[3.3.1]nonan-7-yl)acetate 137a (120 mg) as a crude product, which was used directly in next step.

220

Example 138

Methyl (4R)-4-(2-chloro-4-fluoro-phenyl)-6-[[7-(2-ethoxy-2-oxo-ethyl)-6,7-dihydroxy-3-oxa-9-azabicyclo[3.3.1]nonan-9-yl]methyl]-2-thiazol-2-yl-1,4-dihydropyrimidine-5-carboxylate

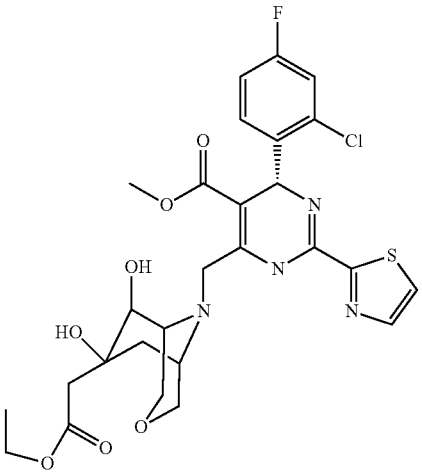 [SMILES: CCOC(=O)CC1(O)CC2COCC(C1O)N2CC1=C(C(=O)OC)[C@H](c2ccc(F)cc2Cl)N=C(c2nccs2)N1]

The title compound was prepared in analogy to Example 134, starting from methyl (4R)-6-(bromomethyl)-4-(2-chloro-4-fluoro-phenyl)-2-thiazol-2-yl-1,4-dihydropyrimidine-5-carboxylate (compound C, 86 mg) and ethyl 2-(6,7-dihydroxy-3-oxa-9-azabicyclo[3.3.1]nonan-7-yl)acetate 138a (142 mg). 6 mg of the title compound was isolated.

Preparation of ethyl 2-(6,7-dihydroxy-3-oxa-9-azabicyclo[3.3.1]nonan-7-yl)acetate 138a

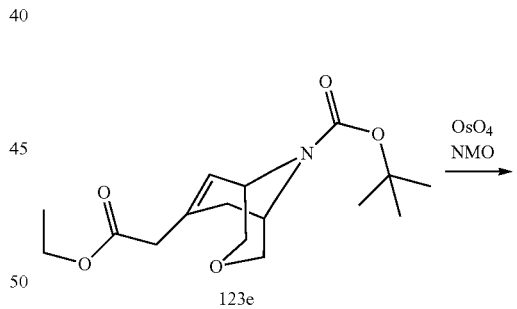

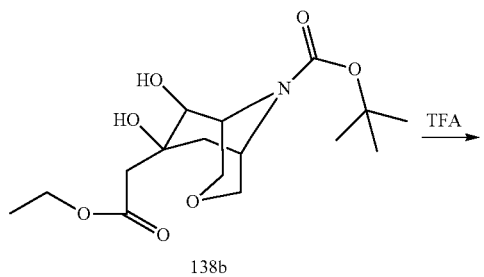

221
-continued

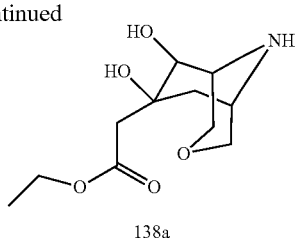

138a

Step I: To a tert-butyl 7-(2-ethoxy-2-oxo-ethyl)-3-oxa-9-azabicyclo[3.3.1]non-6-ene-9-carboxylate 123e (0.800 g, 2.6 mmol) in acetone (8 ml) and water (2 ml) were added N-methylmorpholine-N-oxide (0.903 g, 7.7 mmol) and Osmium tetroxide solution (0.3 ml, 4 wt % in H2O, 1.2 mmol) at room temperature. The resulting mixture was stirred at room temperature overnight. The mixture was then concentrated to give crude diol 138b (0.900 g), which was used directly in next step without further purification. MS: calc'd (MH$^+$) 346, measured (MH$^+$) 346.

Step II: To a solution of diol 138b (200 mg, 0.58 mmol) in dichloromethane (2 ml) was added trifluoroacetic acid (2 ml) at room temperature. The resulting mixture was stirred at room temperature for 2 hours, then concentrated to give 142 mg of ethyl 2-(6,7-dihydroxy-3-oxa-9-azabicyclo[3.3.1]nonan-7-yl)acetate 138a, which was used directly in next step. MS: calc'd (MH$^+$) 246, measured (MH$^+$) 246.

Example 139

7-amino-9-[[(4R)-4-(2-chloro-4-fluoro-phenyl)-5-methoxycarbonyl-2-thiazol-2-yl-1,4-dihydropyrimidin-6-yl]methyl]-3-oxa-9-azabicyclo[3.3.1]nonane-7-carboxylic acid

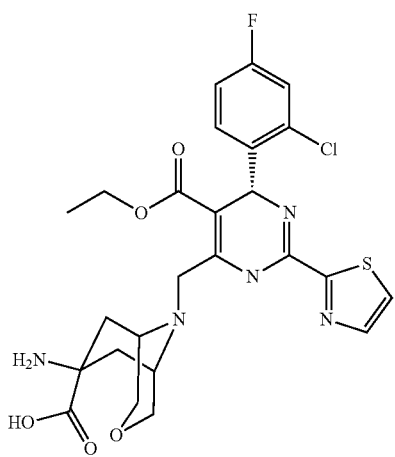 [SMILES: CCOC(=O)C1=C(CN2C3COCC2CC(N)(C(=O)O)C3)NC(c2nccs2)=N[C@H]1c1ccc(F)cc1Cl]

The title compound was prepared in analogy to Example 133 by using 7-(tert-butoxycarbonylamino)-3-oxa-9-azabicyclo[3.3.1]nonane-7-carboxylic acid 139a (40 mg) and methyl (4R)-6-(bromomethyl)-4-(2-chloro-4-fluoro-phenyl)-2-thiazol-2-yl-1,4-dihydropyrimidine-5-carboxylate (compound C, 39 mg). 4 mg of the title compound was isolated.

Preparation of 7-(tert-butoxycarbonylamino)-3-oxa-9-azabicyclo[3.3.1]nonane-7-carboxylic acid 139a

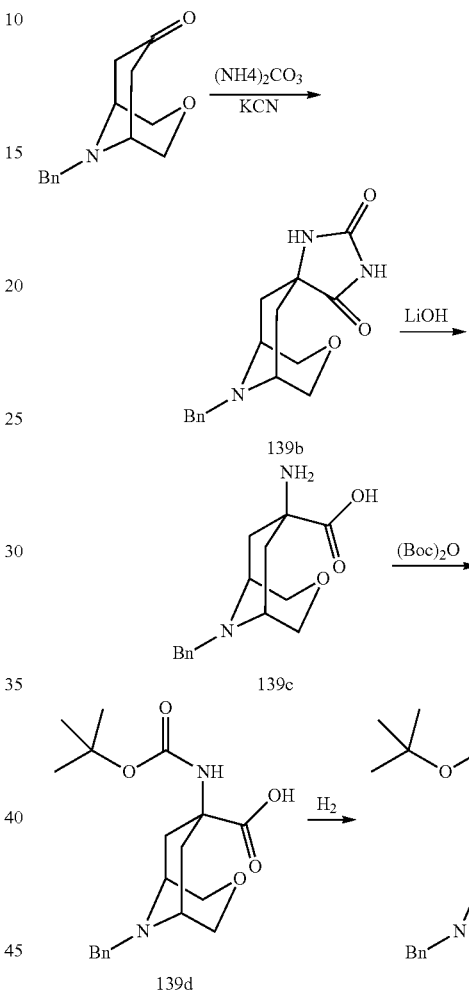

Step I: A mixture of 9-benzyl-3-oxa-9-azabicyclo[3.3.1]nonan-7-one (0.9 g, 3.9 mmol), KCN (760 mg, 11.7 mmol), and (NH$_4$)$_2$CO$_3$ (1.1 g, 11.7 mmol) in EtOH (8 ml) and H$_2$O (8 ml) was stirred at 55° C. for 2 days. Then the mixture was poured into water (100 ml) and extracted with DCM (100 ml) two times. The organic layer was dried and concentrated to obtain a residue. The residue was purified by chromatography on silica gel (PE/EA=1:1 then DCM/MeOH=15:1) to give 9-benzylspiro[3-oxa-9-azabicyclo[3.3.1]nonane-7,5'-imidazolidine]-2',4'-dione 139b (0.6 g, 70%) as white solid. MS: calc'd (MH$^+$) 302, measured (MH$^+$) 302.

Step II: LiOH (240 mg, 10 mmol) was added to a suspension of compound 139 b (0.3 g, 1 mmol) in H$_2$O (30 ml). The result mixture was stirred at 100° C. for 40 h. The mixture was cooled to room temperature and filtered to remove a white solid, and the filtrate was evaporated. The pH of the concentrate was adjusted from 12 to 5 with concentrated HCl, and the solution was evaporated to dryness. The residue was treated with methanol to lead to a suspension. After filtration and being washed with CH₃OH, the solid was dried to give 7-amino-9-benzyl-3-oxa-9-azabicyclo[3.3.1]nonane-7-carboxylic acid 139c (200 mg, 72%) as white solid. MS: calc'd (MH⁺) 277, measured (MH⁺) 277.

Step III: NaOH (45 mg, 1.1 mmol) was added to a mixture of compound 139c (100 mg, 0.36 mmol) and (Boc)₂O (457 mg, 0.72 mmol) in THF (15 ml) and H₂O (15 ml). The mixture was stirred at 70° C. overnight. The THF was evaporated and the water solution was acidified with 1N HCl until pH=5. The water solution was extracted with EA (3×50 ml). The organic layer was dried and concentrated to give a residue. The residue was purified by pre-HPLC to afford 9-benzyl-7-(tert-butoxycarbonylamino)-3-oxa-9-azabicyclo[3.3.1]nonane-7-carboxylic acid 139d (50 mg, 37%) as white solid. MS: calc'd (MH⁺) 377, measured (MH⁺) 377; ¹H NMR (400 MHz, CDCl₃) δ 1.45 (s, 9H), 2.30-2.33 (m, 2H), 2.50-2.55 (m, 2H), 3.02-3.04 (d, 2H), 3.69-3.72 (d, 2H), 4.12-4.22 (m, 4H), 7.35-7.41 (m, 3H), 7.47-7.49 (d, 2H).

Step IV: A mixture of compound 139d (0.050 g, 0.13 mmol) and Pd/C (20 mg) in MeOH (5 ml) was stirred under H₂ balloon at room temperature overnight. The mixture was filtered and the filtrate was concentrated to give 40 mg of the crude 7-(tert-butoxycarbonylamino)-3-oxa-9-azabicyclo[3.3.1]nonane-7-carboxylic acid 139a, which was used directly in next step without further purification. MS: calc'd (MH⁺) 287, measured (MH⁺) 287.

Example 140

7-amino-9-[[(4R)-4-(2,3-difluorophenyl)-5-ethoxycarbonyl-2-thiazol-2-yl-1,4-dihydropyrimidin-6-yl]methyl]-3-oxa-9-azabicyclo[3.3.1]nonane-7-carboxylic acid

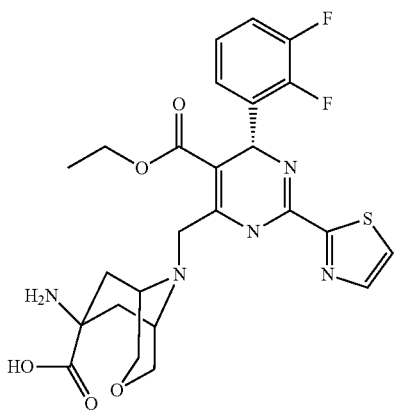 [SMILES: CCOC(=O)C1=C(CN2C3COCC2CC(N)(C(=O)O)C3)NC(c2nccs2)=N[C@H]1c1cccc(F)c1F]

The title compound was prepared in analogy to Example 133 by using 7-(tert-butoxycarbonylamino)-3-oxa-9-azabicyclo[3.3.1]nonane-7-carboxylic acid 139a (49 mg) and ethyl (4R)-6-(bromomethyl)-4-(2,3-difluoro-phenyl)-2-thiazol-2-yl-1,4-dihydropyrimidine-5-carboxylate 140a (48 mg). 5 mg of the title compound was isolated.

Ethyl (4R)-6-(bromomethyl)-4-(2,3-difluoro-phenyl)-2-thiazol-2-yl-1,4-dihydropyrimidine-5-carboxylate 140a was prepared in analogy to compound C in Example 1 by using ethyl acetoacetate and 2,3-difluorobenzaldehyde instead of methyl acetoacetate and 2-chloro-4-fluoro-benzaldehyde, respectively.

Example 141

7-amino-9-[[(4R)-4-(2-bromo-4-fluoro-phenyl)-5-ethoxycarbonyl-2-thiazol-2-yl-1,4-dihydropyrimidin-6-yl]methyl]-3-oxa-9-azabicyclo[3.3.1]nonane-7-carboxylic acid

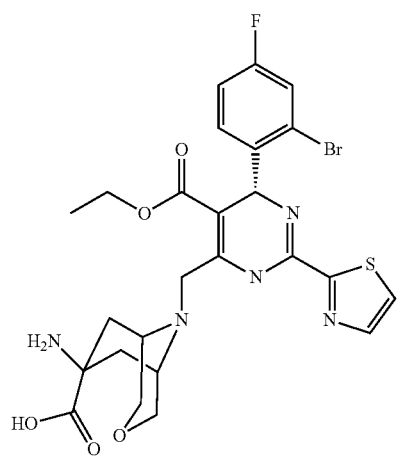 [SMILES: CCOC(=O)C1=C(CN2C3COCC2CC(N)(C(=O)O)C3)NC(c2nccs2)=N[C@H]1c1ccc(F)cc1Br]

The title compound was prepared in analogy to Example 133 by using 7-(tert-butoxycarbonylamino)-3-oxa-9-azabicyclo[3.3.1]nonane-7-carboxylic acid 139a (49 mg) and ethyl (4R)-6-(bromomethyl)-4-(2-bromo-4-fluoro-phenyl)-2-thiazol-2-yl-1,4-dihydropyrimidine-5-carboxylate 70a (55 mg). 15 mg of the title compound was isolated.

Example 142

Methyl (4R)-4-(2-chloro-4-fluoro-phenyl)-6-(8-oxa-3-azabicyclo[3.2.1]octan-3-ylmethyl)-2-thiazol-2-yl-1,4-dihydropyrimidine-5-carboxylate

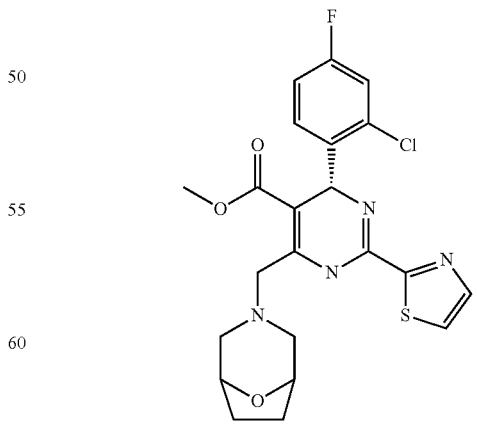

The title compound was prepared in analogy to Example 1a in Example 1 by using methyl (4R)-6-(bromomethyl)-4-(2-chloro-4-fluoro-phenyl)-2-thiazol-2-yl-1,4-dihydropyrimidine-5-carboxylate (compound C, 200 mg) and 8-oxa-3-azabicyclo[3.2.1]octane hydrochloride (100 mg). 44 mg of title compound was isolated.

Example 143

Methyl (4R)-4-(2-chloro-4-fluoro-phenyl)-6-[(5,5-difluoro-2-azabicyclo[2.2.1]heptan-2-yl)methyl]-2-thiazol-2-yl-1,4-dihydropyrimidine-5-carboxylate

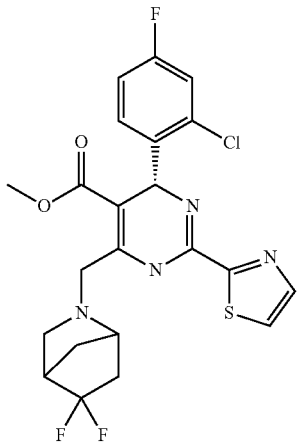 [SMILES: COC(=O)C1=C(CN2CC3CC2CC3(F)F)NC(c2nccs2)=N[C@H]1c1ccc(F)cc1Cl]

The title compound was prepared in analogy to Example 1a in Example 1 by using methyl (4R)-6-(bromomethyl)-4-(2-chloro-4-fluoro-phenyl)-2-thiazol-2-yl-1,4-dihydropyrimidine-5-carboxylate (compound C, 50 mg) and 5,5-difluoro-2-azabicyclo[2.2.1]heptane (Wuxi AppTec Co., Ltd, WX120101, 29 mg). 7 mg of title compound was isolated.

Example 144

Methyl (4R)-4-(2-chloro-4-fluoro-phenyl)-6-[(5,5-difluoro-3-azabicyclo[2.2.1]heptan-3-yl)methyl]-2-thiazol-2-yl-1,4-dihydropyrimidine-5-carboxylate

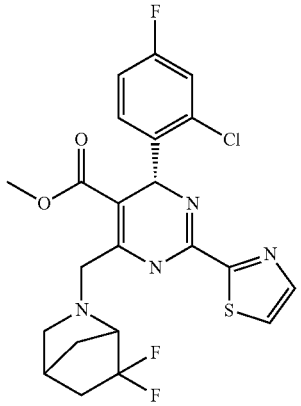 [SMILES: COC(=O)C1=C(CN2CC3CC2C(F)(F)C3)NC(c2nccs2)=N[C@H]1c1ccc(F)cc1Cl]

The title compound was prepared in analogy to Example 1a in Example 1 by using methyl (4R)-6-(bromomethyl)-4-(2-chloro-4-fluoro-phenyl)-2-thiazol-2-yl-1,4-dihydropyrimidine-5-carboxylate (compound C, 50 mg) and 5,5-difluoro-3-azabicyclo[2.2.1]heptane (Wuxi AppTec Co. Ltd, WX120379, 29 mg). 26 mg of title compound was isolated.

Example 145

Methyl (4R)-6-[[4-(acetamidomethyl)-5-oxa-2-azabicyclo[2.2.1]heptan-2-yl]methyl]-4-(2-chloro-4-fluoro-phenyl)-2-thiazol-2-yl-1,4-dihydropyrimidine-5-carboxylate

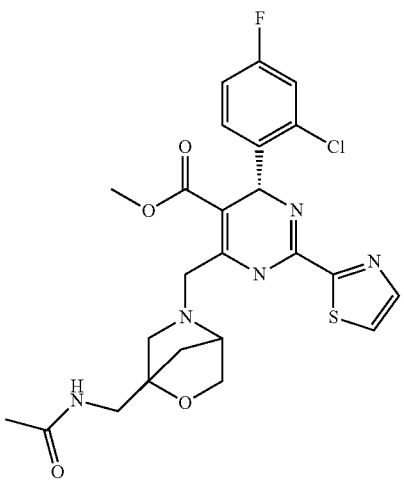 [SMILES: COC(=O)C1=C(CN2CC3(CNC(C)=O)CC2CO3)NC(c2nccs2)=N[C@H]1c1ccc(F)cc1Cl]

The title compound was prepared in analogy to Example 1a in Example 1 by using methyl (4R)-6-(bromomethyl)-4-(2-chloro-4-fluoro-phenyl)-2-thiazol-2-yl-1,4-dihydropyrimidine-5-carboxylate (compound C, 65 mg) and N-(5-oxa-2-azabicyclo[2.2.1]heptan-4-ylmethyl)acetamide (37 mg). 5.5 mg of title compound was isolated.

Preparation of N-(5-oxa-2-azabicyclo[2.2.1]heptan-4-ylmethyl)acetamide

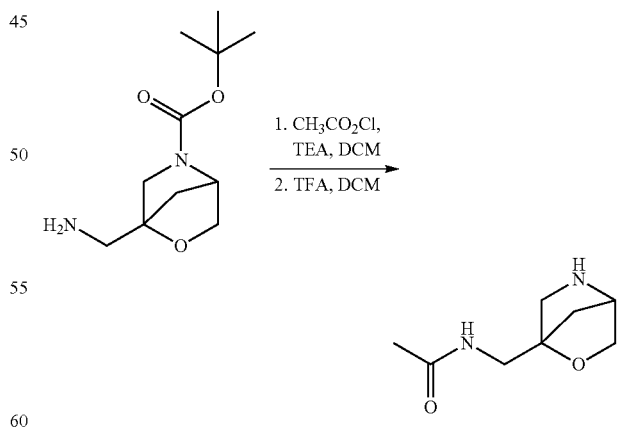

A mixture of tert-butyl 4-(aminomethyl)-5-oxa-2-azabicyclo[2.2.1]heptane-2-carboxylate (Wuxi AppTec, CAS 1357351-98-4) (50 mg, 0.22 mmol), TEA (44.4 mg, 0.44 mmol) in DCM (2 mL) was added CH$_3$CO$_2$Cl (26 mg, 0.33 mmol) at 0° C. After 2 hours, the solvent was removed under reduced pressure. The residue was treated with TFA in DCM.

After stirring for 2 hours at room temperature, the residue was used in next step without purification. MS: calc'd (MH⁺) 271, measured (MH⁺) 271.

Examples 146 and 147

Example 146

Methyl (4R)-4-(2-chloro-4-fluoro-phenyl)-6-[[7-(2-ethoxy-2-oxo-ethyl)-7-(methanesulfonamido)-3-oxa-9-azabicyclo[3.3.1]nonan-9-yl]methyl]-2-thiazol-2-yl-1,4-dihydropyrimidine-5-carboxylate

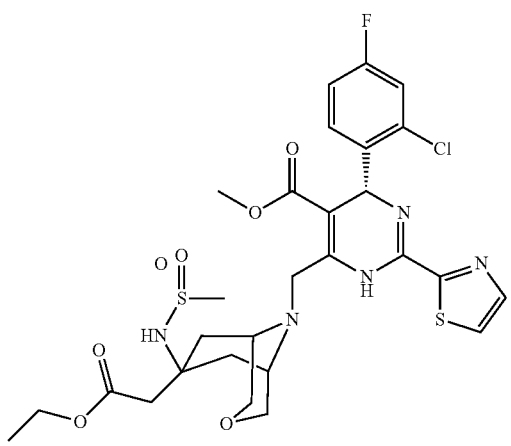

Example 147

Methyl (4R)-4-(2-chloro-4-fluoro-phenyl)-6-[[7-(2-ethoxy-2-oxo-ethyl)-7-[(2,2,2-trifluoroacetyl)amino]-3-oxa-9-azabicyclo[3.3.1]nonan-9-yl]methyl]-2-thiazol-2-yl-1,4-dihydropyrimidine-5-carboxylate

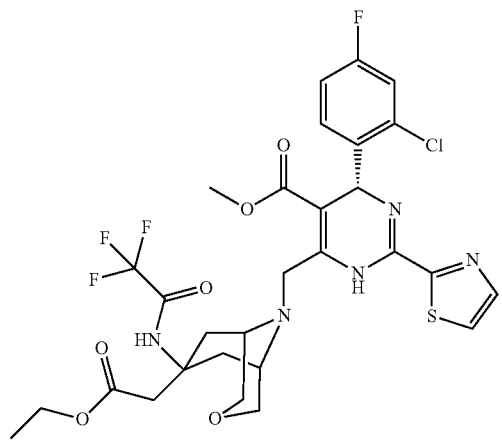 [SMILES: CCOC(=O)CC1(NC(=O)C(F)(F)F)CC2COCC(C1)N2CC1=C(C(=O)OC)[C@H](c2ccc(F)cc2Cl)N=C(c2nccs2)N1]

Preparation of Example 146 and Example 147

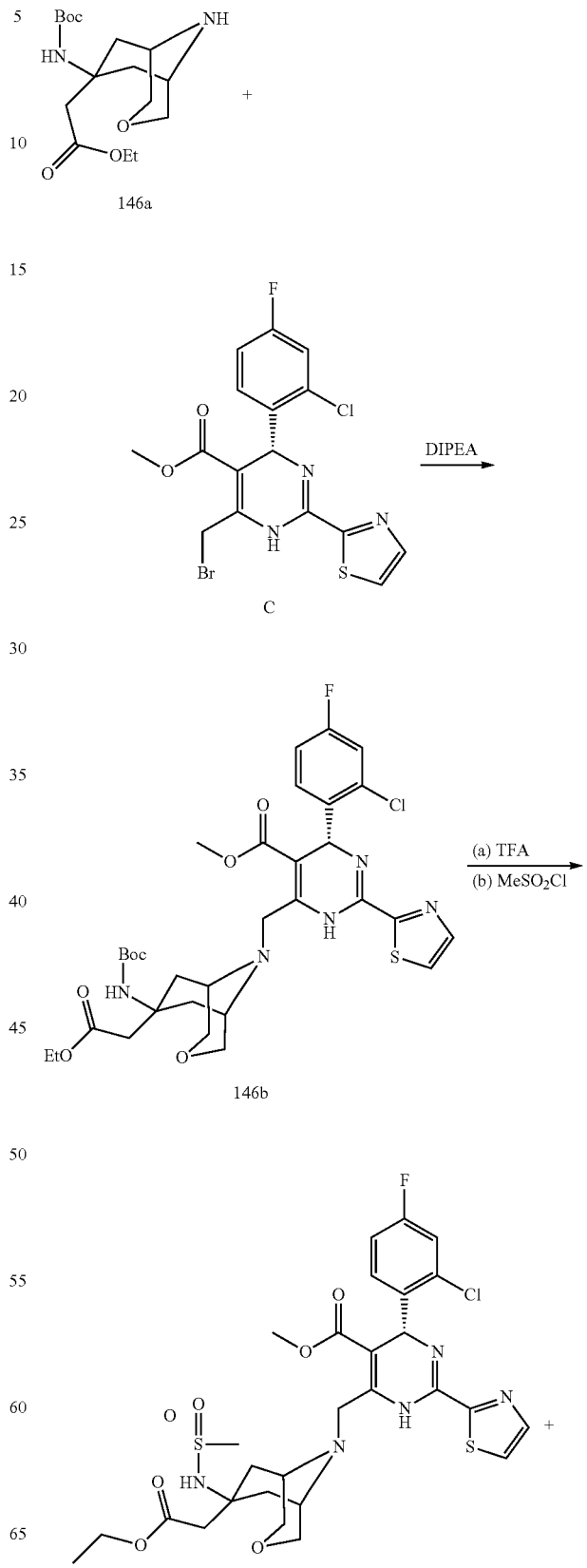

229

-continued

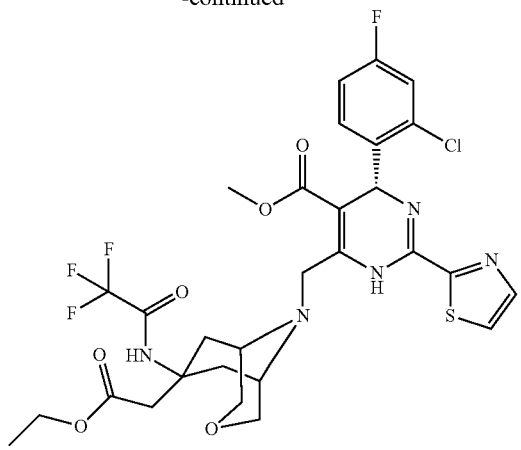

A mixture of ethyl 2-[7-(tert-butoxycarbonylamino)-3-oxa-9-azabicyclo[3.3.1]nonan-7-yl]acetate 146a (0.1 g, 0.3 mmol) and methyl (4R)-6-(bromomethyl)-4-(2-chloro-4-fluoro-phenyl)-2-thiazol-2-yl-1,4-dihydropyrimidine-5-carboxylate C (90 mg, 0.2 mmol), DIPEA (77.4 mg, 0.6 mmol) in DCM (5 mL) was stirred for 12 hours at room temperature. The mixture was concentrated to give crude methyl (4R)-6-[[7-(tert-butoxycarbonylamino)-7-(2-ethoxy-2-oxo-ethyl)-3-oxa-9-azabicyclo[3.3.1]nonan-9-yl]methyl]-4-(2-chloro-4-fluoro-phenyl)-2-thiazol-2-yl-1,4-dihydropyrimidine-5-carboxylate 146b. MS: calc'd (MH+) 692, exp (MH+) 692.

A mixture of 146b (0.14 g, 0.20 mmol), TFA (2 mL) in DCM (5 mL) was stirred for 2 hours. The solvents were removed under reduced pressure to give crude methyl (4R)-6-[[7-amino-7-(2-ethoxy-2-oxo-ethyl)-3-oxa-9-azabicyclo[3.3.1]nonan-9-yl]methyl]-4-(2-chloro-4-fluoro-phenyl)-2-thiazol-2-yl-1,4-dihydropyrimidine-5-carboxylate in TFA salt form. MS: calc'd (MH+) 592, exp (MH+) 592. This TFA salt (35 mg, 0.051 mmol) was dissolved in a mixture of TEA (20.6 mg, 0.204 mmol) in DCM (3 mL). To it was added CH₃SO₂Cl (11.7 mg, 0.102 mmol). The resulting mixture was stirred for 12 hours at room temperature, and concentrated under reduced pressure. The residue was purified by preparative HPLC to give two products, Example 146 and Example 147.

Preparation of ethyl 2-[7-(tert-butoxycarbonylamino)-3-oxa-9-azabicyclo[3.3.1]nonan-7-yl]acetate 146a

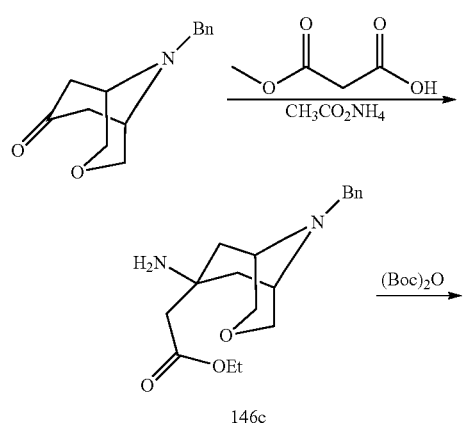

230

-continued

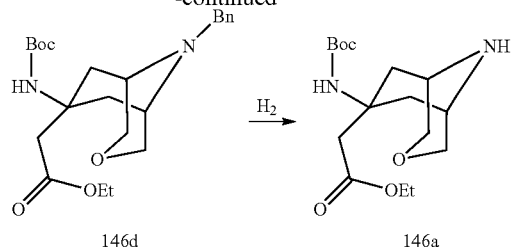

Step I: The mixture of 9-benzyl-3-oxa-9-azabicyclo[3.3.1]nonan-7-one (0.5 g, 2.2 mmol), 3-methoxy-3-oxo-propanoic acid (0.44 g, 3.3 mmol), ammonium acetate (0.33 g, 4.4 mmol) in ethanol (5 mL) was refluxed for 3 hours. After removal of solvent, the residue was purified by flash silica gel chromatography to afford ethyl 2-(7-amino-9-benzyl-3-oxa-9-azabicyclo[3.3.1]nonan-7-yl)acetate 146c. Yield: 5%. MS: calc'd (MH+) 319, measured (MH+) 319.

Step II: A mixture of ethyl 2-(7-amino-9-benzyl-3-oxa-9-azabicyclo[3.3.1]nonan-7-yl)acetate (1.2 g, 3.8 mmol), (Boc)₂O (1.23 g, 5.7 mmol), and TEA (0.77 g, 7.6 mmol) in DCM (15 mL) was stirred for 2 hours at room temperature. After removal of solvent, the residue was purified by flash silica gel chromatography to afford ethyl 2-[9-benzyl-7-(tert-butoxycarbonylamino)-3-oxa-9-azabicyclo[3.3.1]nonan-7-yl]acetate 146d as an oil, 1.5 g, yield, 95%. MS: calc'd (MH+) 419, measured (MH+) 419.

Step III: A mixture of ethyl 2-[9-benzyl-7-(tert-butoxycarbonylamino)-3-oxa-9-azabicyclo[3.3.1]nonan-7-yl]acetate (0.7 g, 1.67 mmol), 10% Pd/C (0.5 g) in methanol (20 mL) was stirred for 12 hours under 1 atm H₂. Filtration followed by removal of the residue gave ethyl 2-[7-(tert-butoxycarbonylamino)-3-oxa-9-azabicyclo[3.3.1]nonan-7-yl]acetate 146a, which was used in next step without purification. Yield: 96%. MS: calc'd (MH+) 329, measured (MH+) 329.

Examples 148 and 149

(1S,4R)-7-[[(4R)-4-(2-chloro-4-fluoro-phenyl)-5-methoxycarbonyl-2-thiazol-2-yl-1,4-dihydropyrimidin-6-yl]methyl]-2,2-difluoro-7-azabicyclo[2.2.1]heptane-4-carboxylic acid and (1R,4S)-7-[[(4R)-4-(2-chloro-4-fluoro-phenyl)-5-methoxycarbonyl-2-thiazol-2-yl-1,4-dihydropyrimidin-6-yl]methyl]-2,2-difluoro-7-azabicyclo[2.2.1]heptane-4-carboxylic acid

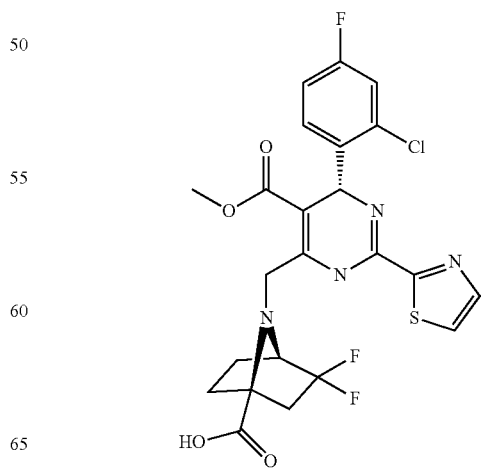

The title compounds were prepared in analogy to Example 1 by using methyl 2,2-difluoro-7-azabicyclo[2.2.1]heptane-4-carboxylate 148a (22 mg) and methyl (4R)-6-(bromomethyl)-4-(2-chloro-4-fluoro-phenyl)-2-thiazol-2-yl-1,4-dihydropyrimidine-5-carboxylate (compound C, 106 mg). Final purification by preparative HPLC afforded two products, Example 148 and example 149.

Preparation of methyl 2,2-difluoro-7-azabicyclo[2.2.1]heptane-4-carboxylate 148a

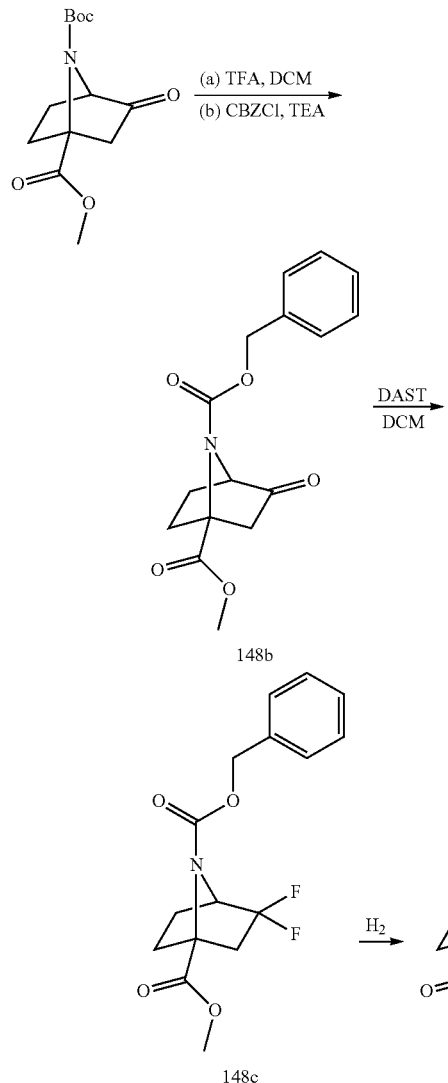

Step I: A mixture of O7-tert-butyl O4-methyl 2-oxo-7-azabicyclo[2.2.1]heptane-4,7-dicarboxylate (prepared according to the literature: Org. Lett., Vol. 9, No. 7, 2007 p 1235-p 1238) (0.34 g, 1.27 mmol), TFA (1.5 ml) in DCM was stirred for 2 hours. After removal of solvent and TFA under reduced pressure, the residue was dissolved into DCM (5 mL). To it was added TEA (0.51 g, 5.08 mmol) and CbzCl (0.43 g, 2.54 mmol). After 12 hours, the mixture was concentrated under reduced pressure. The residue was purified by flash chromatography to give O7-benzyl O4-methyl 2-oxo-7-azabicyclo[2.2.1]heptane-4,7-dicarboxylate 148b. Yield: 30%. MS: calc'd (MH +) 304, measured (MH +) 304.

Step II: A mixture of O7-benzyl O4-methyl 2-oxo-7-azabicyclo[2.2.1]heptane-4,7-dicarboxylate (0.5 g, 1.65 mmol) and DAST (2.66 g, 16.5 mmol) in DCM (2 mL) was heated for 12 hours at 45° C., then quenched with water, extracted with DCM, washed with NaHCO₃ (aq), After removal of solvent, the residue was purified by flash chromatography to give O7-benzyl O4-methyl 2,2-difluoro-7-azabicyclo[2.2.1]heptane-4,7-dicarboxylate 148c, Yield:8%. MS: calc'd (MH +) 326, measured (MH +) 326.

Step III: The mixture of O7-benzyl O4-methyl 2,2-difluoro-7-azabicyclo[2.2.1]heptane-4,7-dicarboxylate (0.24 g, 0.74 mmol), 10% Pd/C (0.3 g) in methanol (20 mL) was stirred for 12 hours under 1 atm H2. Removal of the catalyst solid and solvent gave methyl 2,2-difluoro-7-azabicyclo[2.2.1]heptane-4-carboxylate 148a. This crude product was used in next step without purification. Yield: 69.3%. MS: calc'd (MH +) 192, measured (MH +) 192.

Example 150

8-[[(4R)-4-(2-chloro-3-fluoro-phenyl)-5-ethoxycarbonyl-2-thiazol-2-yl-1,4-dihydropyrimidin-6-yl]methyl]-6,6-difluoro-8-azabicyclo[3.2.1]octane-3-carboxylic acid

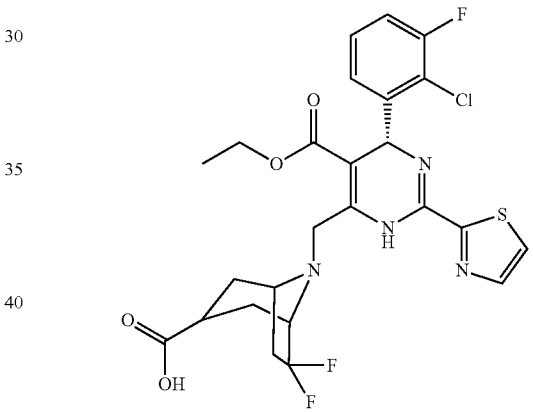

The title compound was prepared in analogy to Example 1, by using methyl 6,6-difluoro-8-azabicyclo[3.2.1]octane-3-carboxylate 150a (200 mg) and ethyl (4R)-6-(bromomethyl)-4-(2-chloro-3-fluoro-phenyl)-2-thiazol-2-yl-1,4-dihydropyrimidine-5-carboxylate 98a (400 mg). 30 mg of the title compound was isolated finally after preparative HPLC purification. Preparation of methyl 6,6-difluoro-8-azabicyclo[3.2.1]octane-3-carboxylate 150a:

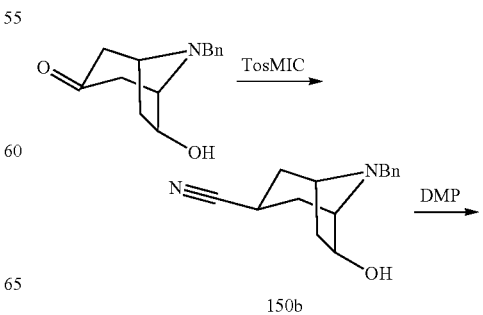

233

-continued

150c

150d 150e  150a

Step I: To a mixture of 8-benzyl-6-hydroxy-8-azabicyclo[3.2.1]octan-3-one (1.2 g) and TosMIC (1.95 g) in a mixture of 20 mL of DME and 0.5 mL of absolute EtOH was added t-BuOK (3.5 g) portionwise while keeping the temperature between 5 and 10° C. The resulting mixture was stirred at room temperature 30 min, and then warmed to 35-40° C. for another 30 minutes. The suspension thus obtained was cooled to room temperature, and the precipitate (TosK) was removed and extracted with DME. The combined DME solutions were concentrated to 3 mL and purified by silica gel chromatography to give 8-benzyl-6-hydroxy-8-azabicyclo[3.2.1]octane-3-carbonitrile 150b (0.8 g).

Step II: 0.8 g of nitrile 150b was dissolved in 10 ml of DCM. Then 3 eq of Dess-Martin reagent was added to the solution and stirred at room temperature overnight. The mixture was filtered and the filtrate was concentrated to give 8-benzyl-6-oxo-8-azabicyclo[3.2.1]octane-3-carbonitrile 150c as a crude product (0.9 g), which was used in the next step without further purification.

Step III: 0.3 g of ketone 150c was dissolved in 1 ml of DCM. To it was added 0.5 ml of DAST. The resulting mixture was heated at 60° C. overnight, then concentrated. The residue was purified by silica gel chromatography to give 0.2 g of 8-benzyl-6,6-difluoro-8-azabicyclo[3.2.1]octane-3-carbonitrile 150d as an oil. Step IV: 0.2 g of compound 150d was dissolved in 10 ml of 2 M HCl in methanol and heated at 80° C. overnight. After removal of the solvent, the residue was purified by silica gel chromatography to give methyl 8-benzyl-6,6-difluoro-8-azabicyclo[3.2.1]octane-3-carboxylate 150e as an oil, 0.22 g.

Step V: A mixture of compound 150d (0.22 g) and Pd(OH)2 (25 mg) in 20 ml methanol under 1 atm of H₂ was stirred at room temperature overnight. Removal of the solvent afforded methyl 6,6-difluoro-8-azabicyclo[3.2.1]octane-3-carboxylate 150a (200 mg).

234

Examples 151 and 152

(5S)-7-[[(4R)-4-(2-chloro-4-fluoro-phenyl)-5-methoxycarbonyl-2-thiazol-2-yl-1,4-dihydropyrimidin-6-yl]methyl]-2,2-difluoro-7-azabicyclo[2.2.1]heptane-5-carboxylic acid (5R)-7-[[(4R)-4-(2-chloro-4-fluoro-phenyl)-5-methoxycarbonyl-2-thiazol-2-yl-1,4-dihydropyrimidin-6-yl]methyl]-2,2-difluoro-7-azabicyclo[2.2.1]heptane-5-carboxylic acid

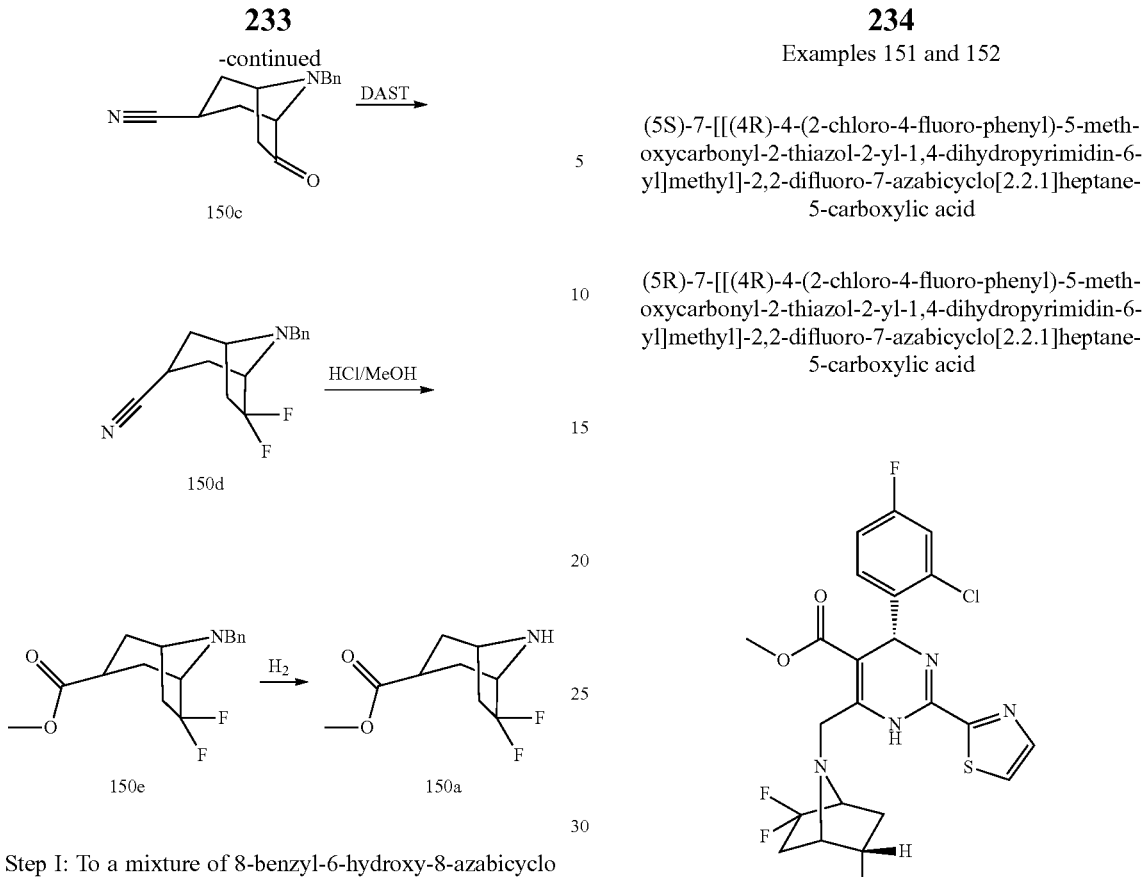

The title compounds were prepared in analogy to Example 1 by using methyl 2,2-difluoro-7-azabicyclo[2.2.1]heptane-5-carboxylate 151a (150 mg) and methyl (4R)-6-(bromomethyl)-4-(2-chloro-4-fluoro-phenyl)-2-thiazol-2-yl-1,4-dihydropyrimidine-5-carboxylate (compound C, 520 mg) in the N-alkylation step. Purification of the final product by preparative HPLC afforded Example 151 (2 mg) and Example 152 (2 mg).

Preparation of methyl 2,2-difluoro-7-azabicyclo[2.2.1]heptane-5-carboxylate 151a

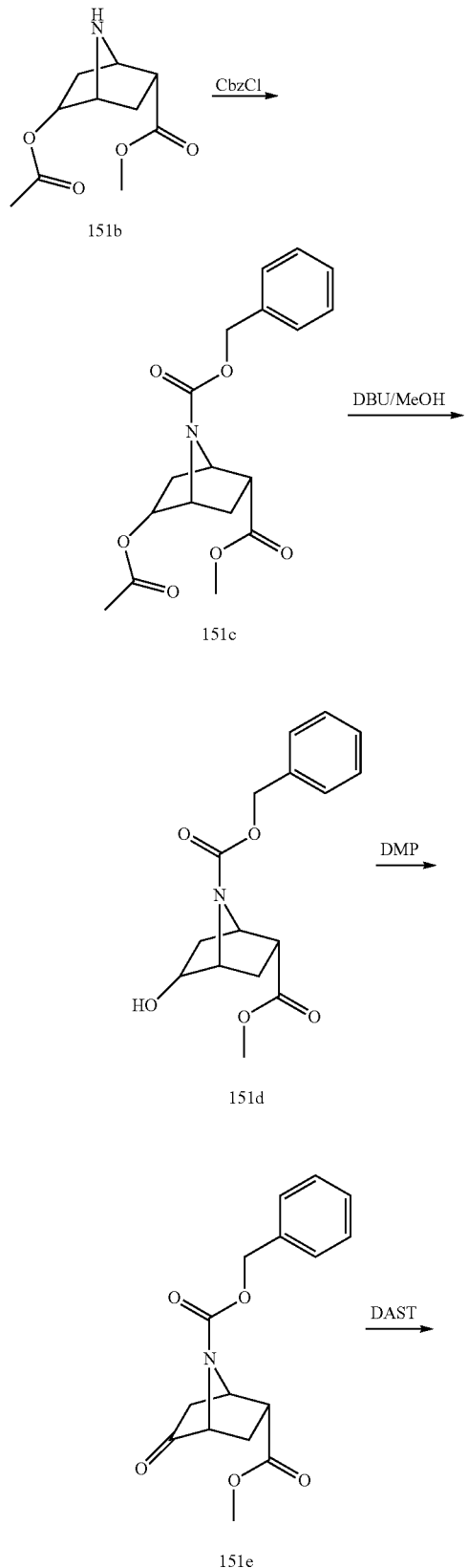

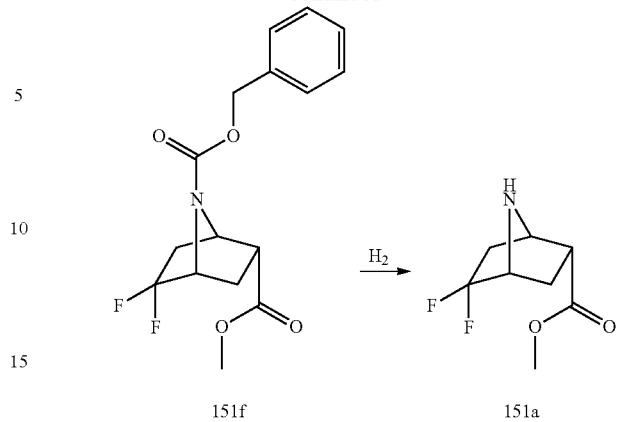

Step I: A mixture of ethyl (5R)-2-acetoxy-7-azabicyclo[2.2.1]heptane-5-carboxylate 151b (prepared in analogy to O7-tert-butyl O4-methyl 2-oxo-7-azabicyclo[2.2.1]heptane-4,7-dicarboxylate starting from methyl trans-6-acetamidocyclohex-3-ene-1-carboxylate with procedures reported in the literature: Org. Lett., Vol. 9, No. 7, 2007 p 1235-p 1238) (0.55 g, 2.4 mmol) in DCM (10 mL) and sodium carbonate (0.76 g, 7.2 mmol) in water (3 mL) was added CbzCl (0.61 g, 3.6 mmol) dropwise. After addition, the mixture was stirred for 2 hours, then extracted with DCM. Removal of solvent afforded O7-benzyl O5-methyl 2-acetoxy-7-azabicyclo[2.2.1]heptane-5,7-dicarboxylate 151c, which was used in next step without purification. Crude yield: 100%. MS: calc'd (MH+) 362, measured (MH +) 362.

Step II: A mixture of O7-benzyl O5-ethyl (5R)-2-acetoxy-7-azabicyclo[2.2.1]heptane-5,7-dicarboxylate (0.87 g, 2.4 mmol) and DBU (0.73 g, 4.8 mmol) in methanol (20 mL) was stirred for 12 hours at room temperature. After removal of solvent, the residue was purified by silica gel chromatography to give O7-benzyl O5-ethyl (5R)-2-hydroxy-7-azabicyclo[2.2.1]heptane-5,7-dicarboxylate 151d. Yield: 45%. MS: calc'd (MH +) 306, measured (MH+) 306.

Step III: A mixture of O7-benzyl O5-ethyl (5R)-2-hydroxy-7-azabicyclo[2.2.1]heptane-5,7-dicarboxylate (0.37 g, 1.1 mmol), Dess-martin reagent (1.38 g, 3.3 mmol) in DCM (50 mL) was stirred for 12 hours. After removal of solvent, the residue was purified by silica gel chromatography to give O7-benzyl O5-ethyl (5R)-2-oxo-7-azabicyclo[2.2.1]heptane-5,7-dicarboxylate 151e. Yield: 90%. MS: calc'd (MH +) 304, measured (MH +) 304.

Step III: A mixture of O7-benzyl O5-ethyl (5R)-2-oxo-7-azabicyclo[2.2.1]heptane-5,7-dicarboxylate (0.4 g, 1.32 mmol), DAST (2.13 g, 13.2 mmol) in DCM (2 mL) was stirred for 12 hours at 50° C., then quenched with water, extracted with DCM. After removal of solvent, the residue was purified by silica gel chromatography to give O7-benzyl O5-ethyl (5R)-2,2-difluoro-7-azabicyclo[2.2.1]heptane-5,7-dicarboxylate 151f. Yield: 38%. MS: calc'd (MH +) 326, measured (MH +) 326.

Step IV: A mixture of O7-benzyl O5-ethyl (5R)-2,2-difluoro-7-azabicyclo[2.2.1]heptane-5,7-dicarboxylate (0.33 g, 1.0 mmol), 10% Pd/C (0.4 g) in methanol (20 mL) was stirred for 24 hours at 1 atm of $H_2$. Removal of catalyst and solvent afforded crude methyl 2,2-difluoro-7-azabicyclo[2.2.1]heptane-5-carboxylate 151a, which was used in next step without purification. Yield: 100%. MS: calc'd (MH +) 192, measured (MH +) 192.

Example 153

HBV Inhibition Assays

Cell Lines and Culture Conditions:

HepG2.2.15 and HepDE19 are stably-transfected cell lines containing the HBV genome. Both cell lines are derived from the hepatoblastoma cell line Hep G2 (American Type Culture Collection, ATCC® HB-8065™) by the published procedures described in references: M A Selles et al. Proc. Natl. Acad. Sci. USA 1987, 84, 1005-1009 and H Guo et al. Journal of Virology 2007, 81, 12472-12484, respectively. Both cell lines were maintained in Dulbecco's modified Eagle's medium (DMEM)-F12 medium supplemented with 10% fetal bovine serum, 100 U/mL penicillin, 100 µg/mL streptomycin, and 0.5 mg/mL of G418.

While HepG2.2.15 cells constitutively support HBV replication and production of virus particles, HepDE19 cells are inducible by tetracycline. Addition of 1 µg/mL tetracycline in culture medium suppresses HBV replication in HepDE19 cells, whereas switching to tetracycline-free medium resumes this process.

Anti-HBV Activity In Vitro:

HepG2.2.15 cells were seeded into 96-well plates ($3 \times 10^4$ cells in 100 µL media per well) and incubated overnight at 37° C. The test compounds were serially half-log diluted in DMSO, then diluted 100 times in culture media. 100 µL diluted compounds were added into the plates to reach 0.5% final concentration of DMSO in every well. Five days after compound treatment, culture supernatant was collected for further analysis.

For quantitative PCR detection of extracellular HBV DNA, 100 µL culture supernatant was collected and processed in MagNA Pure 96 Nucleic Acid Purification System (Roche Applied Science) for viral DNA extraction. The extracted samples were subjected to HBV DNA quantification by qPCR. The effective compound concentration at which HBV replication is inhibited by 50% ($EC_{50}$) was determined.

The Examples were tested in the above assays as described herein and found to have $EC_{50}<1$ µM in HepG2.2.15 assay. Particular compounds of formula I were found to have $EC_{50}<0.1$ µM in HepG2.2.15 assay (See Table 2).

Cytotoxicity and Selectivity Indexes:

In a cell culture model, apparent antiviral activity of a compound can be the result of host cell death after exposure to the compound. To determine whether the anti-HBV effect of a test compound is due to cytotoxicity, HepDE19 cells were seeded into 96-well plates ($5 \times 10^3$ cells per well) and treated with compounds as described above for $EC_{50}$ determination. Five days after treatment, cell viability was measured by addition of 20 µL of CCK-8 reagent. Two hours after incubation at 37° C., the absorbance at wavelengths of 450 nm and 630 nm ($OD_{450}$ and $OD_{630}$) was recorded by a plate reader. The concentration results in the death of 50% of the host cells ($CC_{50}$) of each compound was determined (See Table 5).

Based on $CC_{50}$ and $EC_{50}$ data, selectivity indexes were determined as shown in Table 5.

Example 154

Human Microsomal Clearance Assay

Microsomes were preincubated with test compound for 10 minutes at 37° C. in 100 mM phosphate buffer with pH 7.4. The reactions were initiated by adding NADPH regenerating system to give a final incubation volume of 400 µL. The incubations finally contained 1 µM test compound, 0.5 mg/mL liver microsomal protein, 3.0 mM glucose 6-phosphate, 1.0 mM NADP, 3.0 mM $MgCl_2$ and 0.05 mg/mL glucose 6-phosphate dehydrogenase in 100 mM phosphate buffer with pH 7.4. After incubation times of 0, 3, 6, 9, 15 and 30 minutes, 50 µL, incubation was transferred to the quench solution containing the internal standard which was 2 µM tolbutamide. After precipitation and centrifugation, test compound concentrations in the samples were determined by LC-MS/MS. Controls of no NADPH regenerating system at zero and 30 minutes were also prepared and analyzed.

Results of human microsomal clearance data of particular compounds are given in Table 3.

Example 155

LYSA Description

Samples are prepared in duplicate from 10 mM DMSO stock solutions. After evaporation of DMSO with a centrifugal vacuum evaporator, the residue is solved in 0.05 M phosphate buffer (pH 6.5), stirred for one hour and then shook for two hours. After one night, the solution is filtered using a microtiter filter plate and then the filtrate and its ¹/₁₀ dilution are then analyzed by direct UV measurement or by HPLC-UV. In addition a four-point calibration curve is prepared from the 10 mM stock solutions and used for the solubility determination of the compounds. The results are in µg/ml. In case the percentage of sample measured in solution after evaporation divided by the calculated maximum of sample amount is bigger than 80% the solubility is reported as bigger than this value.

Results of Lysa are given in Table 4.

Example 156

Cytochrome P450 (Cyp450) Induction Screening Assay

Materials

Cell Culture

Human cryopreserved hepatocytes (Life Technologies, Carlsbad, USA) were thawed and cultured in collagen I coated 96-well plates with a density of 52,000 cells/well. After attachment, medium was changed and cells were precultured overnight in hepatocyte maintenance medium (HMM; Lonza, Switzerland).

Test compounds were dosed to the cells next morning at an indicated concentration (up to 10 µM) in HMM culture media containing gentamycin and a constant 0.1% DMSO. Similarly, dilutions of the positive inducer compounds omeprazole (prototypical inducer of human CYP1A2; final concentrations: 1 and 10 µM), phenobarbital (prototypical inducer of human CYP2B6; final concentrations: 100 and 1000 µM) and rifampicin (prototypical inducer of human CYP3A4; final concentrations: 1 and 10 µM) were prepared from 1000 fold DMSO stock solutions in HMM containing gentamycin. Medium change was then performed and cells were exposed for 24 hours to test compounds, positive inducer compounds, or vehicle (0.1% DMSO), respectively.

At the end of the compound exposure period, medium was removed and cells lysed using 100 µL/well MagNA Pure LC RNA isolation tissue lysis buffer (Roche Diagnostics AG, Rotkreuz, Switzerland). Plates were then sealed and frozen at −80° C. until further workup.

mRNA Isolation, Processing and qRT-PCR mRNA isolation was performed using the MagNA Pure 96 system (Roche Diagnostics AG, Rotkreuz, Switzerland) and the respective cellular RNA large volume kit (Roche Diagnostics AG, Rotkreuz, Switzerland) from thawed samples diluted 1:1 with PBS. The volume of the cell lysis and an elution volume of 100 μL were used. 20 μL of the resulting mRNA suspension was then used for reverse transcription using 20 μL of the transcript or first stand cDNA synthesis kit (Roche prime Supply, Mannheim, Germany). The resulting cDNA was diluted with 40 μL of H$_2$O before using for qRT-PCR. qRT-PCR was performed by using the forward and the reverse primer, the corresponding UPL (all from Microsynth, Balgach, Switzerland) and the Taqman Fast advanced master mix (Applied Biosystems), on an ABI 7900 machine (Applied Biosystems).

Calculations qRT-PCR Ct-values for the respective P450s were put into relation to the Ct-value of RN18S1 (microsynth, Balgach, Switzerland) of the same sample. Doing so, a respective Δct-value was calculated. Using the average of all Δct-values for the vehicle control samples, a ΔΔct-value was calculated for each sample (ΔΔct-value(sample)=Δct-value(sample)−average of Δct-value of all vehicle controls). The fold induction of the respective sample was calculated as $2^{(-\Delta\Delta ct)}$. The individual fold induction values were then averaged per treatment condition (usually n=3 biological replicates).

Relative induction values to the respective positive inducer compound condition (10 μM omeprazole for CYP1A2; 1000 μM Phenobarbital for CYP2B6; 10 μM rifampicin for CYP3A4) were then calculated from the fold induction values as follows:

Relative induction(%)=100×(T−V)/(P−V)

T: fold induction of test compound condition
P: fold induction of positive inducer compound
V: fold induction of vehicle controls
Results of CYP3A4 induction are given in Table 6.

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compounds of formula (I)

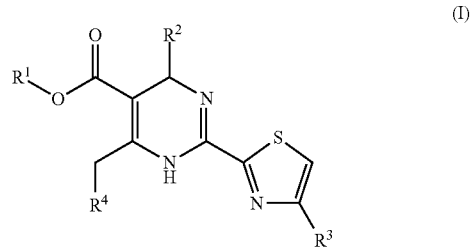

wherein $R^1$ is $C_{1-6}$alkyl;

$R^2$ is phenyl, which is once or twice or three times substituted by halogen or $C_{1-6}$alkyl;

$R^3$ is hydrogen or $C_{1-6}$alkyl;

$R^4$ is

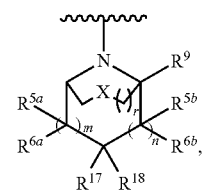

wherein one of $R^{5a}$ and $R^{6a}$ is hydrogen or halogen, and the other one is hydrogen, halogen or hydroxy;

one of $R^{5b}$ and $R^{6b}$ is hydrogen or halogen, and the other one is hydrogen or halogen;

$R^9$ is hydrogen or carboxy;

one of $R^{17}$ and $R^{18}$ is hydrogen, halogen, hydroxy, amino, $C_{1-6}$alkylsulfonylamino or trifluoromethylcarbonylamino, the other one is hydrogen, halogen, hydroxy-$C_yH_{2y}$—, $C_{1-6}$alkylcarbonyl-O—, $C_{1-6}$alkoxycarbonyl-$C_yH_{2y}$—, carboxy-$C_yH_{2y}$—O—, carboxy-$C_yH_{2y}$—, $C_{1-6}$alkylcarbonyl-NH—, $C_{1-6}$alkylsulfonyl-NH—, aminocarbonyl-NH— or aminosulfonyl-NH—;

wherein —$C_yH_{2y}$— is unsubstituted once or more times substituted by hydroxy;

or $R^{6a}$ and $R^{17}$ together with the carbon atoms, to which they are attached, form a ring of isoxazolyl, pyrazolyl or oxo-dihydropyrazolyl, which ring is unsubstituted or once or more times substituted by $C_{1-6}$alkyl;

or $R^{17}$ and $R^{18}$ together with the carbon atom, to which they are attached, form diazirinyl;

X is oxygen; sulfur; —N(carbonyl$C_{1-6}$alkyl)-; or —C($R^{15}R^{16}$)—, wherein one of $R^{15}$ and $R^{16}$ is hydrogen or hydroxy, and the other one is hydrogen or carboxy-$C_yH_{2y}$—;

r is 0 or 1;

m is 0 or 1;

n is 0 or 1;

y is 0-6;

or R$^4$ is

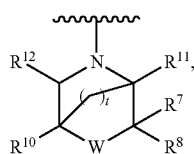

wherein R$^7$ is hydrogen or halogen;
R$^8$ is hydrogen or halogen;
R$^{10}$ is hydrogen, halogen, hydroxy-C$_y$H$_{2y}$— or C$_{1-6}$alkylcarbonylamino-C$_y$H$_{2y}$—;
R$^{11}$ is hydrogen or carboxy;
R$^{12}$ is hydrogen or carboxy;
W is a bond, oxygen, —CH$_2$—, —CF$_2$— or —N(carbonylC$_{1-6}$alkyl)-;
t is 1 or 2;
y is 0-6;
with the proviso that

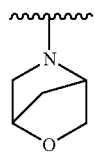 [SMILES: *N1CC2CC1CO2]

is excluded;
or R$^4$ is

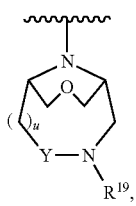

wherein R$^{19}$ is hydrogen; C$_{1-6}$alkyl, which is unsubstituted or once or more times substituted by halogen; C$_{1-6}$alkoxycarbonyl-C$_y$H$_{2y}$—; hydroxy-C$_y$H$_{2y}$-carbonyl; carboxy-C$_y$H$_{2y}$-carbonyl; C$_{1-6}$alkylaminosulfonyl; C$_{1-6}$alkylcarbonyl; C$_{1-6}$alkylsulfonyl; aminocarbonyl; or aminosulfonyl;
Y is carbonyl or —CH$_2$—;
u is 0 or 1;
y is 0-6;
or R$^4$ is

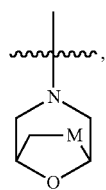

wherein M is a bond, —CH$_2$— or —N(R$^{14}$)—CH$_2$—;
R$^{14}$ is C$_{1-6}$alkoxycarbonyl;
or pharmaceutically acceptable salts, or tautomerism isomers, or enantiomers, or diastereomers thereof.

2. A compound according to claim 1, wherein
R$^1$ is methyl or ethyl;
R$^2$ is phenyl, which is once or twice or three times substituted by fluoro, chloro, bromo or methyl;
R$^3$ is hydrogen or methyl;
R$^4$ is

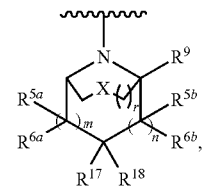

wherein one of R$^{5a}$ and R$^{6a}$ is hydrogen or fluoro, and the other one is hydrogen, fluoro or hydroxy;
one of R$^{5b}$ and R$^{6b}$ is hydrogen or fluoro, and the other one is hydrogen or fluoro;
R$^9$ is hydrogen or carboxy;
one of R$^{17}$ and R$^{18}$ is hydrogen, fluoro, hydroxy, amino, methylsulfonylamino or trifluoromethylcarbonylamino, the other one is hydrogen, fluoro, hydroxy, hydroxymethyl, methylcarbonyl-O—, methoxycarbonyl, methoxycarbonylmethyl, ethoxycarbonylmethyl, methoxycarbonyl(hydroxy)methyl, ethoxycarbonyl(hydroxy)methyl, carboxymethyl-O—, carboxy, carboxymethyl, methylcarbonylamino, aminocarbonylamino, methylsulfonylamino or aminosulfonylamino;
or R$^{6a}$ and R$^{17}$ together with the carbon atoms, to which they are attached, form a ring of isoxazolyl, pyrazolyl or oxo-dihydropyrazolyl, which ring is unsubstituted or once or more times substituted by methyl;
or R$^{17}$ and R$^{18}$ together with the carbon atom, to which they are attached, form diazirinyl;
X is oxygen; sulfur; —N(carbonylmethyl)-; or —C(R$^{15}$R$^{16}$)—, wherein one of R$^{15}$ and R$^{16}$ is hydrogen or hydroxy, and the other one is hydrogen, carboxy or carboxymethyl;
r is 0 or 1;
m is 0 or 1;
n is 0 or 1;
or R$^4$ is

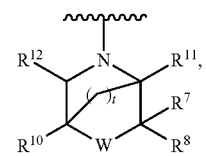

wherein R$^7$ is hydrogen or fluoro;
R$^8$ is hydrogen or fluoro;
R$^{10}$ is hydrogen, fluoro, hydroxymethyl or methylcarbonylaminomethyl;
R$^{11}$ is hydrogen or carboxy;
R$^{12}$ is hydrogen or carboxy;
W is a bond, oxygen, —CH$_2$—, —CF$_2$— or —N(carbonylmethyl)-;
t is 1 or 2;

with the proviso that

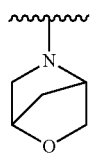

is excluded;
or R⁴ is

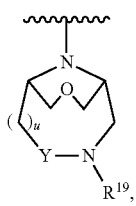

wherein R¹⁹ is hydrogen, methyl, isopropyl, difluoromethylmethyl, methylcarbonyl, methoxycarbonyl, ethoxycarbonylisopropyl, hydroxymethylcarbonyl, carboxyisopropylcarbonyl, aminocarbonyl, methylsulfonyl, aminosulfonyl or methylaminosulfonyl;
Y is carbonyl or —CH₂—;
u is 0 or 1;
or R⁴ is

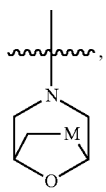

wherein M is a bond, —CH₂— or —N(carbonyltert-butoxy)-CH₂—;
or pharmaceutically acceptable salts, or tautomerism isomers, or enantiomers, or diastereomers thereof.

3. A compound according to claim 1, wherein
R¹ is C₁₋₆alkyl;
R² is phenyl, which is once or twice or three times substituted by halogen or C₁₋₆alkyl;
R³ is hydrogen or C₁₋₆alkyl;
R⁴ is

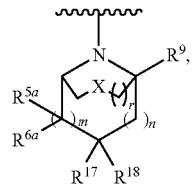

wherein one of R⁵ᵃ and R⁶ᵃ is hydrogen or halogen, and the other one is hydrogen or halogen;
R⁹ is hydrogen or carboxy;
one of R¹⁷ and R¹⁸ is hydrogen or C₁₋₆alkylsulfonylamino, the other one is hydrogen, C₁₋₆alkoxycarbonyl-C_yH_{2y}—, carboxy-C_yH_{2y}—O—, carboxy-C_yH_{2y}—, C₁₋₆alkylcarbonyl-NH—, C₁₋₆alkylsulfonyl-NH— or aminosulfonyl-NH—;
or R⁶ᵃ and R¹⁷ together with the carbon atoms, to which they are attached, form pyrazolyl;
X is oxygen; sulfur; or —C(R¹⁵R¹⁶)—, wherein one of R¹⁵ and R¹⁶ is hydrogen or hydroxy, and the other one is hydrogen or carboxy-C_yH_{2y}—;
r is 0 or 1;
m is 0 or 1;
n is 0 or 1;
y is 0-6;
or pharmaceutically acceptable salts, or tautomerism isomers, or enantiomers, or diastereomers thereof.

4. A compound according to claim 1, wherein
R¹ is methyl or ethyl;
R² is phenyl, which is once or twice or three times substituted by fluoro, chloro, bromo or methyl;
R³ is hydrogen or methyl;
R⁴ is

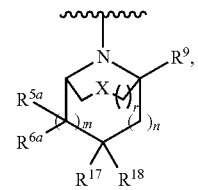

wherein one of R⁵ᵃ and R⁶ᵃ is hydrogen or fluoro, and the other one is hydrogen or fluoro;
R⁹ is hydrogen or carboxy;
one of R¹⁷ and R¹⁸ is hydrogen or methylsulfonylamino, the other one is hydrogen, ethoxycarbonylmethyl, carboxymethyl-O—, carboxy, carboxymethyl, methylcarbonyl-NH—, methylsulfonyl-NH— or aminosulfonyl-NH—;
or R⁶ᵃ and R¹⁷ together with the carbon atoms, to which they are attached, form pyrazolyl;
X is oxygen; sulfur; or —C(R¹⁵R¹⁶)—, wherein one of R¹⁵ and R¹⁶ is hydrogen or hydroxy, and the other one is hydrogen, carboxy or carboxymethyl;
r is 0 or 1;
m is 0 or 1;
n is 0 or 1;
or pharmaceutically acceptable salts, or tautomerism isomers, or enantiomers, or diastereomers thereof.

5. A compound of formula (IA) according to claim 1,

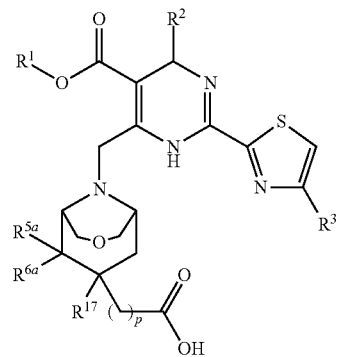

(IA)

wherein
- $R^1$ is $C_{1-6}$alkyl;
- $R^2$ is phenyl, which is once or twice or three times substituted by halogen or $C_{1-6}$alkyl;
- $R^3$ is hydrogen or $C_{1-6}$alkyl;
- one of $R^{5a}$ and $R^{6a}$ is hydrogen or halogen, and the other one is hydrogen, halogen or hydroxy;
- $R^{17}$ is hydrogen or amino;
- p is 0 or 1;

or pharmaceutically acceptable salts, or tautomerism isomers, or enantiomers, or diastereomers thereof.

6. A compound according to claim 1, wherein
- $R^1$ is methyl or ethyl;
- $R^2$ is phenyl, which is once or twice or three times substituted by fluoro, chloro, bromo or methyl;
- $R^3$ is hydrogen or methyl;
- one of $R^{5a}$ and $R^{6a}$ is hydrogen or fluoro, and the other one is hydrogen, fluoro or hydroxy;
- $R^{17}$ is hydrogen or amino;
- p is 0 or 1;

or pharmaceutically acceptable salts, or tautomerism isomers, or enantiomers, or diastereomers thereof.

7. A compound of formula (IB) of claim 1, (IB)

wherein
- $R^1$ is $C_{1-6}$alkyl;
- $R^2$ is phenyl, which is once or twice or three times substituted by halogen or $C_{1-6}$alkyl;
- $R^3$ is hydrogen;
- $R^{15}$ is hydrogen or hydroxy;
- q is 0 or 1;

or pharmaceutically acceptable salts, or tautomerism isomers, or enantiomers, or diastereomers thereof.

8. A compound of claim 1, wherein
- $R^1$ is methyl or ethyl;
- $R^2$ is phenyl, which is once or twice or three times substituted by fluoro, chloro, bromo or methyl;
- $R^3$ is hydrogen;
- $R^{15}$ is hydrogen or hydroxy;
- q is 0 or 1;

or pharmaceutically acceptable salts, or tautomerism isomers, or enantiomers, or diastereomers thereof.

9. A compound of claim 1, wherein
- $R^1$ is $C_{1-6}$alkyl;
- $R^2$ is phenyl, which is once or twice or three times substituted by halogen;
- $R^3$ is hydrogen;
- $R^4$ is wherein $R^{19}$ is hydrogen, aminocarbonyl, aminosulfonyl or hydroxy-$C_yH_{2y}$-carbonyl;
- Y is —$CH_2$— or carbonyl;
- j is 0 or 1;
- y is 0-6;

or pharmaceutically acceptable salts, or tautomerism isomers, or enantiomers, or diastereomers thereof.

10. A compound of claim 1, wherein
- $R^1$ is methyl;
- $R^2$ is phenyl, which is once or twice or three times substituted by fluoro or chloro;
- $R^3$ is hydrogen;
- $R^4$ is wherein $R^{19}$ is hydrogen, aminocarbonyl, aminosulfonyl or hydroxymethylcarbonyl;
- Y is —$CH_2$— or carbonyl;
- j is 0 or 1;

or pharmaceutically acceptable salts, or tautomerism isomers, or enantiomers, or diastereomers thereof.

11. A compound of formula I, wherein
- $R^1$ is $C_{1-6}$alkyl;
- $R^2$ is phenyl, which is once or twice or three times substituted by halogen;
- $R^3$ is hydrogen;
- $R^4$ is wherein one of $R^{5a}$ and $R^{6a}$ is hydrogen or halogen, and the other one is hydrogen or halogen;
- $R^9$ is hydrogen or carboxy;
- one of $R^{17}$ and $R^{18}$ is hydrogen, the other one is hydrogen or carboxy-$C_yH_{2y}$—;
- X is oxygen; or —$C(R^{15}R^{16})$—, wherein one of $R^{15}$ and $R^{16}$ is hydrogen or hydroxy, and the other one is hydrogen or carboxy-$C_yH_{2y}$—;
- r is 0 or 1;
- m is 1;
- n is 0 or 1;
- y is 0-6;

or a pharmaceutically acceptable salt or tautomerism isomers or enantiomers or diastereomers thereof.

12. A compound of formula I, wherein $R^1$ is methyl or ethyl;

$R^2$ is phenyl, which is once or twice or three times substituted by fluoro or chloro;

$R^3$ is hydrogen;

$R^4$ is

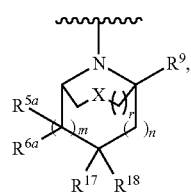

wherein one of $R^{5a}$ and $R^{6a}$ is hydrogen or fluoro, and the other one is hydrogen or fluoro;

$R^9$ is hydrogen or carboxy;

one of $R^{17}$ and $R^{18}$ is hydrogen, the other one is hydrogen or carboxymethyl;

X is oxygen; or —C($R^{15}R^{16}$)—, wherein one of $R^{15}$ and $R^{16}$ is hydrogen or hydroxy, and the other one is hydrogen or carboxymethyl;

r is 0 or 1;

m is 1;

n is 0 or 1;

or a pharmaceutically acceptable salt or tautomerism isomers or enantiomers or diastereomers thereof.

13. A compound of formula (IC) of claim 1,

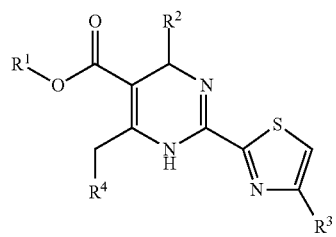

(IC)

wherein $R^1$ is $C_{1-6}$alkyl;

$R^2$ is phenyl, which is once or twice or three times substituted by halogen;

$R^3$ is hydrogen or $C_{1-6}$alkyl;

$R^4$ is selected from

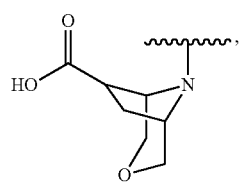 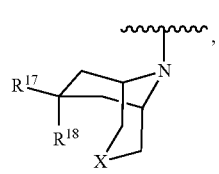

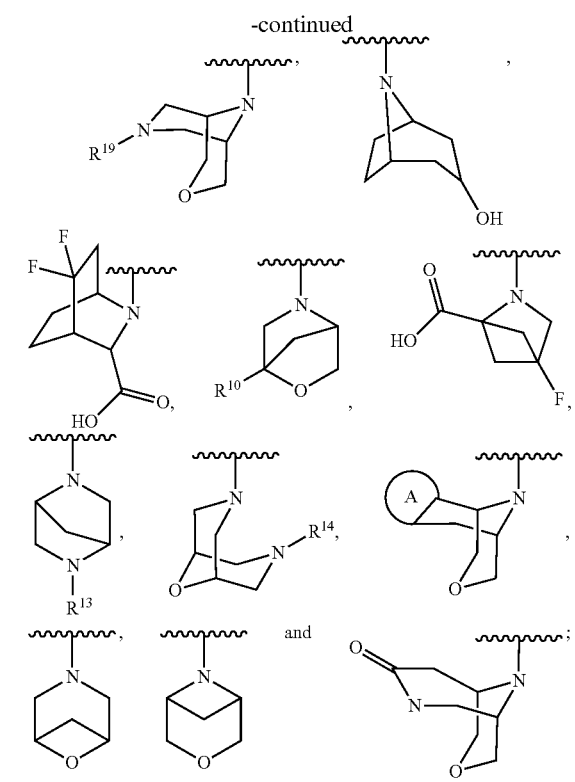

wherein $R^{10}$ is hydroxy-$C_yH_{2y}$—;

$R^{13}$ is $C_{1-6}$alkylcarbonyl;

$R^{14}$ is $C_{1-6}$alkoxycarbonyl;

X is —O— or —S—; provided that when X is —O—, $R^{17}$ is hydrogen or hydroxy, $R^{18}$ is $C_{1-6}$alkoxycarbonyl-$C_yH_{2y}$—, carboxy-$C_yH_{2y}$—, hydroxy-$C_yH_{2y}$—, $C_{1-6}$alkylcarbonyl-O—, $C_{1-6}$alkylcarbonylamino, $C_{1-6}$alkylsulfonylamino or

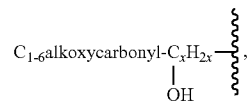

or $R^{17}$ and $R^{18}$, together with the carbon atom, to which they are attached, form

when X is —S—, $R^{17}$ is hydrogen, $R^{18}$ is carboxy-$C_yH_{2y}$—;

$R^{19}$ is selected from aminocarbonyl; aminosulfonyl; $C_{1-6}$alkoxycarbonyl-$C_yH_{2y}$—; $C_{1-6}$alkyl, which is unsubstituted or substituted by fluoro; $C_{1-6}$alkylaminosulfonyl; $C_{1-6}$alkylcarbonyl; $C_{1-6}$alkylsulfonyl and hydroxy-$C_xH_{2x}$-carbonyl;

A is pyrazolyl or oxopyrazolyl, which is unsubstituted or substituted by $C_{1-6}$alkyl;

x is 1-6;

y is 0-6;

or pharmaceutically acceptable salts, or tautomerism isomers, or enantiomers, or diastereomers thereof.

14. A compound of claim 1, wherein $R^1$ is methyl or ethyl;

$R^2$ is phenyl, which is once or twice or three times substituted by fluoro, chloro or bromo;

$R^3$ is hydrogen or methyl;

$R^4$ is selected from

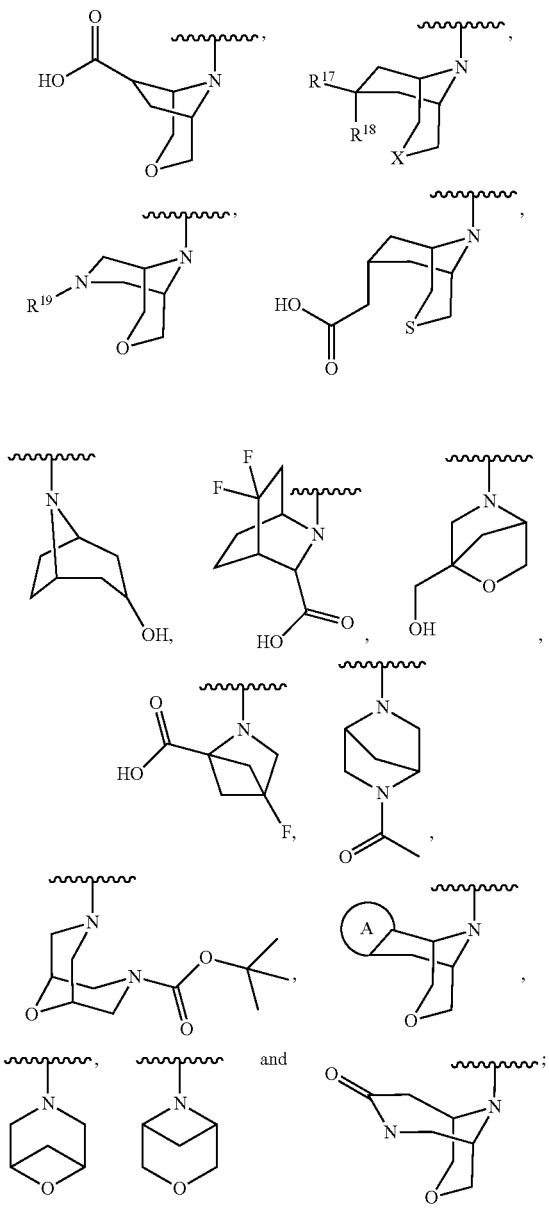

wherein $R^{17}$ is hydrogen or hydroxy;

$R^{18}$ is methoxycarbonyl, methoxycarbonylmethyl, methoxycarbonylmethyl(hydroxy), carboxy, carboxymethyl, hydroxy, hydroxymethyl, methylcarbonyl-O—, methylcarbonylamino or methylsulfonylamino;

or $R^{17}$ and $R^{18}$, together with the carbon atom, to which they are attached, form

$R^{19}$ is aminocarbonyl, aminosulfonyl, methoxycarbonyl, ethoxycarbonylisopropyl, methyl, isopropyl, difluoroethyl, methylaminosulfonyl, methylcarbonyl, methylsulfonyl or hydroxymethylcarbonyl;

A is pyrazolyl or oxopyrazolyl, which is unsubstituted or substituted by methyl;

or pharmaceutically acceptable salts, or tautomerism isomers, or enantiomers, or diastereomers thereof.

15. A compound of claim 1 or pharmaceutically acceptable salts, or tautomerism isomers, or enantiomers, or diastereomers thereof, wherein $R^1$ is $C_{1-6}$alkyl;

$R^2$ is phenyl, which is once or twice or three times substituted by halogen;

$R^3$ is hydrogen or $C_{1-6}$alkyl;

$R^4$ is selected from

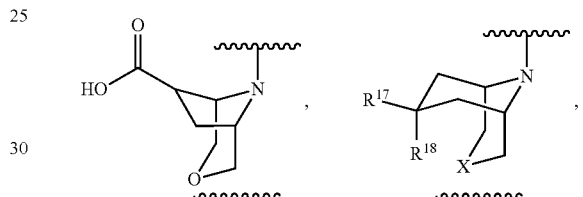

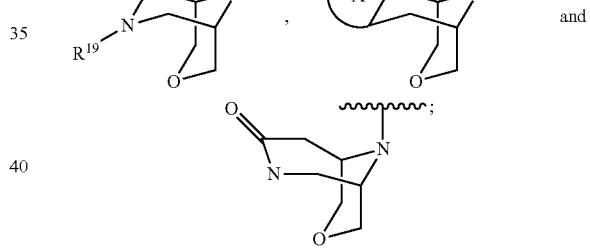

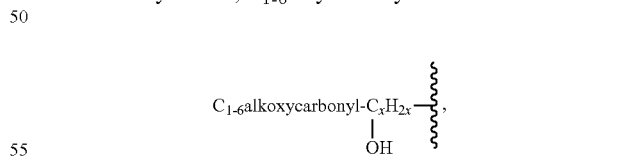

X is —O— or —S—; provided that when X is —O—, $R^{17}$ is hydrogen or hydroxy, $R^{18}$ is $C_{1-6}$alkoxycarbonyl-$C_yH_{2y}$—, carboxy-$C_yH_{2y}$—, hydroxy-$C_yH_{2y}$—, $C_{1-6}$alkylcarbonyl-O—, $C_{1-6}$alkylcarbonylamino, $C_{1-6}$alkylsulfonylamino or $$C_{1-6}\text{alkoxycarbonyl-}C_xH_{2x}\underset{OH}{-}\xi,$$

or $R^{17}$ and $R^{18}$, together with the carbon atom, to which they are attached, form

when X is —S—, $R^{17}$ is hydrogen, $R^{18}$ is carboxy-$C_yH_{2y}$—;

$R^{19}$ is selected from aminocarbonyl; aminosulfonyl; $C_{1-6}$alkoxycarbonyl-$C_yH_{2y}$—; $C_{1-6}$alkyl, which is unsubstituted or substituted by fluoro; $C_{1-6}$alkylaminosulfonyl; $C_{1-6}$alkylcarbonyl; $C_{1-6}$alkylsulfonyl and hydroxy-$C_xH_{2x}$-carbonyl;

A is pyrazolyl or oxopyrazolyl, which is unsubstituted or substituted by $C_{1-6}$alkyl;

x is 1-6;

y is 0-6.

16. A compound of claim 1, or pharmaceutically acceptable salts, or tautomerism isomers, or enantiomers, or diastereomers thereof, wherein $R^1$ is methyl or ethyl;

$R^2$ is phenyl, which is once or twice or three times substituted by fluoro, chloro or bromo;

$R^3$ is hydrogen or methyl;

$R^4$ is selected from

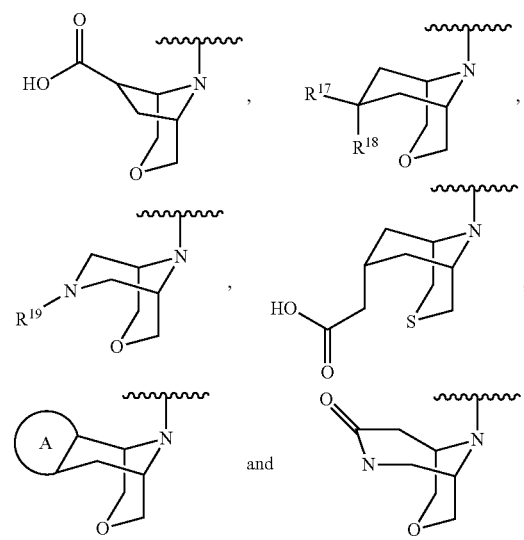

$R^{17}$ is hydrogen or hydroxy;

$R^{18}$ is methoxycarbonyl, methoxycarbonylmethyl, methoxycarbonylmethyl(hydroxy), carboxy, carboxymethyl, hydroxy, hydroxymethyl, methylcarbonyl-O—, methylcarbonylamino or methylsulfonylamino;

or $R^{17}$ and $R^{18}$, together with the carbon atom, to which they are attached, form

$R^{19}$ is aminocarbonyl, aminosulfonyl, methoxycarbonyl, ethoxycarbonylisopropyl, methyl, isopropyl, difluoroethyl, methylaminosulfonyl, methylcarbonyl, methylsulfonyl or hydroxymethylcarbonyl;

A is pyrazolyl or oxopyrazolyl, which is unsubstituted or substituted by methyl.

17. A compound of claim 1 or pharmaceutically acceptable salts, or tautomerism isomers, or enantiomers, or diastereomers thereof, wherein $R^1$ is $C_{1-6}$alkyl;

$R^2$ is phenyl, which is once or twice or three times substituted by halogen;

$R^3$ is hydrogen;

$R^4$ is

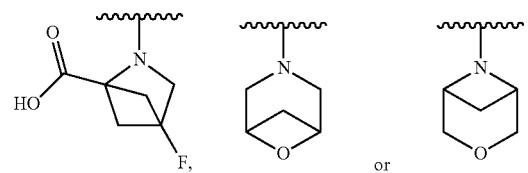 [SMILES: *N1CC2(F)CC1(C(=O)O)C2 ; *N1CC2CC(C1)O2 ; *N1C2COCC1C2]

18. A compound of claim 1, or pharmaceutically acceptable salts, or tautomerism isomers, or enantiomers, or diastereomers thereof, wherein $R^1$ is methyl;

$R^2$ is phenyl, which is once or twice or three times substituted by fluoro, chloro or bromo;

$R^3$ is hydrogen;

$R^4$ is

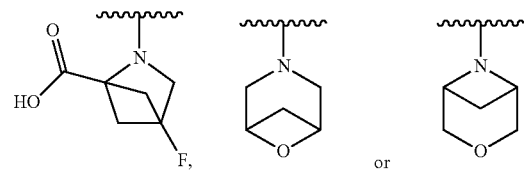 [SMILES: *N1CC2(F)CC1(C(=O)O)C2 ; *N1CC2CC(C1)O2 ; *N1C2COCC1C2]

19. A compound of claim 1 to selected from

9-[[(4R)-4-(2-chloro-4-fluoro-phenyl)-5-methoxycarbonyl-2-thiazol-2-yl-1,4-dihydropyrimidin-6-yl]methyl]-3-oxa-9-azabicyclo[3.3.1]nonane-7-carboxylic acid;

9-[(R)-6-(2-Chloro-4-fluoro-phenyl)-5-methoxycarbonyl-2-(4-methyl-thiazol-2-yl)-3,6-dihydro-pyrimidin-4-ylmethyl]-3-oxa-9-aza-bicyclo[3.3.1]nonane-7-carboxylic acid;

9-[6-(3,4-Difluoro-phenyl)-5-methoxycarbonyl-2-thiazol-2-yl-3,6-dihydro-pyrimidin-4-ylmethyl]-3-oxa-9-aza-bicyclo[3.3.1]nonane-7-carboxylic acid;

9-[(R)-6-(2-Bromo-4-fluoro-phenyl)-5-methoxycarbonyl-2-thiazol-2-yl-3,6-dihydro-pyrimidin-4-ylmethyl]-3-oxa-9-aza-bicyclo[3.3.1]nonane-7-carboxylic acid methyl ester;

9-[(R)-6-(2-Bromo-4-fluoro-phenyl)-5-methoxycarbonyl-2-thiazol-2-yl-3,6-dihydro-pyrimidin-4-ylmethyl]-3-oxa-9-aza-bicyclo[3.3.1]nonane-7-carboxylic acid;

8-[(R)-6-(2-Chloro-4-fluoro-phenyl)-5-methoxycarbonyl-2-thiazol-2-yl-3,6-dihydro-pyrimidin-4-ylmethyl]-3-oxa-8-aza-bicyclo[3.2.1]octane-6-carboxylic acid;

(R)-4-(2-Chloro-4-fluoro-phenyl)-6-(7-hydroxy-3-oxa-9-aza-bicyclo[3.3.1]non-9-ylmethyl)-2-thiazol-2-yl-1,4-dihydro-pyrimidine-5-carboxylic acid methyl ester;

(R)-6-(7-Acetoxy-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-4-(2-Chloro-4-fluoro-phenyl)-6-(7-hydroxy-3-oxa-9-aza-bicyclo[3.3.1]non-9-ylmethyl)-2-thiazol-2-yl-1,4-dihydro-pyrimidine-5-carboxylic acid methyl ester;

(R)-4-(2-Chloro-4-fluoro-phenyl)-6-(7-hydroxy-7-hydroxymethyl-3-oxa-9-aza-bicyclo[3.3.1]non-9-ylmethyl)-2-thiazol-2-yl-1,4-dihydro-pyrimidine-5-carboxylic acid methyl ester;

(R)-4-(2-Chloro-4-fluoro-phenyl)-6-(7-methanesulfonyl-3-oxa-7,9-diaza-bicyclo[3.3.1]non-9-ylmethyl)-2-thiazol-2-yl-1,4-dihydro-pyrimidine-5-carboxylic acid methyl ester;

(R)-4-(2-Chloro-4-fluoro-phenyl)-6-(7-methyl-3-oxa-7, 9-diaza-bicyclo[3.3.1]non-9-ylmethyl)-2-thiazol-2-yl-1,4-dihydro-pyrimidine-5-carboxylic acid methyl ester;

(R)-4-(2-Chloro-4-fluoro-phenyl)-6-(7-isopropyl-3-oxa-7,9-diaza-bicyclo[3.3.1]non-9-ylmethyl)-2-thiazol-2-yl-1,4-dihydro-pyrimidine-5-carboxylic acid methyl ester;

(R)-4-(2-Chloro-4-fluoro-phenyl)-6-[7-(2,2-difluoro-ethyl)-3-oxa-7,9-diaza-bicyclo[3.3.1]non-9-ylmethyl]-2-thiazol-2-yl-1,4-dihydro-pyrimidine-5-carboxylic acid methyl ester;

(R)-6-(7-Acetyl-3-oxa-7,9-diaza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-4-(2-Chloro-4-fluoro-phenyl)-6-(7-methylsulfamoyl-3-oxa-7,9-diaza-bicyclo[3.3.1]non-9-ylmethyl)-2-thiazol-2-yl-1,4-dihydro-pyrimidine-5-carboxylic acid methyl ester;

9-[(R)-6-(2-Chloro-4-fluoro-phenyl)-5-methoxycarbonyl-2-thiazol-2-yl-3,6-dihydro-pyrimidin-4-ylmethyl]-3-oxa-7,9-diaza-bicyclo[3.3.1]nonane-7-carboxylic acid methyl ester;

(R)-6-(7-Carbamoyl-3-oxa-7,9-diaza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-4-(2-Chloro-4-fluoro-phenyl)-6-(7-sulfamoyl-3-oxa-7,9-diaza-bicyclo[3.3.1]non-9-ylmethyl)-2-thiazol-2-yl-1,4-dihydro-pyrimidine-5-carboxylic acid methyl ester;

(R)-4-(2-Chloro-4-fluoro-phenyl)-6-[7-(1-ethoxycarbonyl-1-methyl-ethyl)-3-oxa-7,9-diaza-bicyclo[3.3.1]non-9-ylmethyl]-2-thiazol-2-yl-1,4-dihydro-pyrimidine-5-carboxylic acid methyl ester;

(R)-4-(2-Chloro-4-fluoro-phenyl)-6-[7-(2-hydroxy-acetyl)-3-oxa-7,9-diaza-bicyclo[3.3.1]non-9-ylmethyl]-2-thiazol-2-yl-1,4-dihydro-pyrimidine-5-carboxylic acid methyl ester;

7-[(R)-6-(2-Chloro-4-fluoro-phenyl)-5-methoxycarbonyl-2-thiazol-2-yl-3,6-dihydro-pyrimidin-4-ylmethyl]-9-oxa-3,7-diaza-bicyclo[3.3.1]nonane-3-carboxylic acid tert-butyl ester;

(S)-2-[(R)-6-(2-Chloro-4-fluoro-phenyl)-5-methoxycarbonyl-2-thiazol-2-yl-3,6-dihydro-pyrimidin-4-ylmethyl]-5,5-difluoro-2-aza-bicyclo[2.2.2]octane-3-carboxylic acid;

(R)-6-(7-Carboxymethyl-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-4-(2-Chloro-4-fluoro-phenyl)-6-(7-methoxycarbonylmethyl-3-oxa-9-aza-bicyclo[3.3.1]non-9-ylmethyl)-2-thiazol-2-yl-1,4-dihydro-pyrimidine-5-carboxylic acid methyl ester;

(R)-6-(7-Carboxymethyl-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid ethyl ester;

6-(7-Carboxymethyl-3-oxa-9-aza-bicyclo[3.3.1]non-9-ylmethyl)-4-(3,4-difluoro-phenyl)-2-thiazol-2-yl-1,4-dihydro-pyrimidine-5-carboxylic acid methyl ester;

(R)-4-(2-Bromo-4-fluoro-phenyl)-6-(7-carboxymethyl-3-oxa-9-aza-bicyclo[3.3.1]non-9-ylmethyl)-2-thiazol-2-yl-1,4-dihydro-pyrimidine-5-carboxylic acid methyl ester;

(S)-6-(7-Carboxymethyl-3-oxa-9-aza-bicyclo[3.3.1]non-9-ylmethyl)-4-(3,4-difluoro-phenyl)-2-thiazol-2-yl-1,4-dihydro-pyrimidine-5-carboxylic acid ethyl ester;

(R)-4-(2-Chloro-4-fluoro-phenyl)-6-[7-(hydroxy-methoxycarbonyl-methyl)-3-oxa-9-aza-bicyclo[3.3.1]non-9-ylmethyl]-2-thiazol-2-yl-1,4-dihydro-pyrimidine-5-carboxylic acid methyl ester;

(R)-4-(2-Chloro-4-fluoro-phenyl)-6-(10-oxa-4,5,12-triaza-tricyclo[6.3.1.0*2,6*]dodeca-2(6),3-dien-12-ylmethyl)-2-thiazol-2-yl-1,4-dihydro-pyrimidine-5-carboxylic acid methyl ester;

(R)-4-(2-Chloro-4-fluoro-phenyl)-6-(3-methyl-10-oxa-4,5,12-triaza-tricyclo[6.3.1.0*2,6*]dodeca-2(6),3-dien-12-ylmethyl)-2-thiazol-2-yl-1,4-dihydro-pyrimidine-5-carboxylic acid methyl ester;

(R)-4-(2-Chloro-4-fluoro-phenyl)-6-(5-methyl-3-oxo-10-oxa-4,5,12-triaza-tricyclo[6.3.1.0*2,6*]dodec-2(6)-en-12-ylmethyl)-2-thiazol-2-yl-1,4-dihydro-pyrimidine-5-carboxylic acid methyl ester;

(R)-4-(2-Chloro-4-fluoro-phenyl)-6-(4-oxo-8-oxa-3,10-diaza-bicyclo[4.3.1]dec-10-ylmethyl)-2-thiazol-2-yl-1,4-dihydro-pyrimidine-5-carboxylic acid methyl ester;

(R)-6-(7-Acetylamino-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-4-(2-Chloro-4-fluoro-phenyl)-6-(7-methanesulfonylamino-3-oxa-9-aza-bicyclo[3.3.1]non-9-ylmethyl)-2-thiazol-2-yl-1,4-dihydro-pyrimidine-5-carboxylic acid methyl ester;

(R)-4-(2-Chloro-4-fluoro-phenyl)-6-(2-methoxymethyl-azetidin-1-ylmethyl)-2-thiazol-2-yl-1,4-dihydro-pyrimidine-5-carboxylic acid methyl ester;

(R)-4-(2-Chloro-4-fluoro-phenyl)-6-(6-oxa-3-aza-bicyclo[3.1.1]hept-3-ylmethyl)-2-thiazol-2-yl-1,4-dihydro-pyrimidine-5-carboxylic acid methyl ester;

(S)-3-[(R)-6-(2-Chloro-4-fluoro-phenyl)-5-methoxycarbonyl-2-thiazol-2-yl-3,6-dihydro-pyrimidin-4-ylmethyl]-3,6-diaza-bicyclo[3.2.1]octane-7-carboxylic acid;

2-[(R)-6-(2-Chloro-4-fluoro-phenyl)-5-methoxycarbonyl-2-thiazol-2-yl-3,6-dihydro-pyrimidin-4-ylmethyl]-4-fluoro-2-aza-bicyclo[2.1.1]hexane-1-carboxylic acid;

(R)-6-(5-Acetyl-2,5-diaza-bicyclo[2.2.1]hept-2-ylmethyl)-4-(2-chloro-4-fluoro-phenyl)-2-thiazol-2-yl-1,4-dihydro-pyrimidine-5-carboxylic acid methyl ester;

6-(7-Carboxymethyl-3-thia-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-6-(7-Diazirine-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-4-(2-Chloro-4-fluoro-phenyl)-6-((1R,3R,5S)-3-hydroxy-8-aza-bicyclo[3.2.1]oct-8-ylmethyl)-2-thiazol-2-yl-1,4-dihydro-pyrimidine-5-carboxylic acid methyl ester;

(R)-4-(2-Chloro-4-fluoro-phenyl)-6-(9-oxa-3,4,11-triaza-tricyclo[5.3.1.0*2,6*]undeca-2(6),4-dien-11-ylmethyl)-2-thiazol-2-yl-1,4-dihydro-pyrimidine-5-carboxylic acid methyl ester;

2-[[(1R,5S)-9-[[(4R)-4-(2-chloro-4-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]oxy]acetic acid;

2-[[(1R,5S)-9-[[(4S)-4-(3,4-difluorophenyl)-5-methoxycarbonyl-2-thiazol-2-yl-1,4-dihydropyrimidin-6-yl]methyl]-3-oxa-9-azabicyclo[3.3.1]nonan-7-yl]oxy]acetic acid;

Methyl (4R)-6-[(6-acetamido-3-oxa-8-azabicyclo[3.2.1]octan-8-yl)methyl]-4-(2-chloro-4-fluoro-phenyl)-2-thiazol-2-yl-1,4-dihydropyrimidine-5-carboxylate;

Methyl (4R)-4-(2-chloro-4-fluoro-phenyl)-6-[(6-hydroxy-3-oxa-8-azabicyclo[3.2.1]octan-8-yl)methyl]-2-thiazol-2-yl-1,4-dihydropyrimidine-5-carboxylate;

2-[[8-[[(4R)-4-(2-bromo-4-fluoro-phenyl)-5-ethoxycarbonyl-2-thiazol-2-yl-1,4-dihydropyrimidin-6-yl]methyl]-3-oxa-8-azabicyclo[3.2.1]octan-6-yl]oxy]acetic acid;

Methyl (4R)-4-(2-chloro-4-fluoro-phenyl)-6-[(6-fluoro-3-oxa-8-azabicyclo[3.2.1]octan-8-yl)methyl]-2-thiazol-2-yl-1,4-dihydropyrimidine-5-carboxylate;

8-[[(4R)-4-(2-bromo-4-fluoro-phenyl)-5-ethoxycarbonyl-2-thiazol-2-yl-1,4-dihydropyrimidin-6-yl]methyl]-3-oxa-8-azabicyclo[3.2.1]octane-6-carboxylic acid;

Methyl (4R)-4-(2-bromo-4-fluoro-phenyl)-6-[[7-(2-hydroxyacetyl)-3-oxa-7,9-diazabicyclo[3.3.1]nonan-9-yl]methyl]-2-thiazol-2-yl-1,4-dihydropyrimidine-5-carboxylate;

Methyl (4R)-4-(2-bromo-4-fluoro-phenyl)-6-[(7-carbamoyl-3-oxa-7,9-diazabicyclo[3.3.1]nonan-9-yl)methyl]-2-thiazol-2-yl-1,4-dihydropyrimidine-5-carboxylate;

2-[(1R,5S)-9-[[(4R)-4-(2-chloro-3-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Methyl (4R)-4-(2-chloro-4-fluoro-phenyl)-6-[[(1R,5S)-7-endo-(sulfamoylamino)-3-oxa-9-azabicyclo[3.3.1]nonan-9-yl]methyl]-2-thiazol-2-yl-1,4-dihydropyrimidine-5-carboxylate;

Methyl (4R)-4-(2-chloro-4-fluoro-phenyl)-2-thiazol-2-yl-6-[[(1S,5R)-7-endo-ureido-3-oxa-9-azabicyclo[3.3.1]nonan-9-yl]methyl]-1,4-dihydropyrimidine-5-carboxylate;

2-[(1S,5R)-9-[[(4R)-4-(2-bromo-4-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-chloro-3-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Methyl (4R)-4-(2-chloro-4-fluoro-phenyl)-6-[[(1R,5S)-7-exo-(methanesulfonamido)-3-oxa-9-azabicyclo[3.3.1]nonan-9-yl]methyl]-2-thiazol-2-yl-1,4-dihydropyrimidine-5-carboxylate;

Methyl (4R)-6-[[(1S,5R)-7-exo-acetamido-3-oxa-9-azabicyclo[3.3.1]nonan-9-yl]methyl]-4-(2-chloro-4-fluoro-phenyl)-2-thiazol-2-yl-1,4-dihydropyrimidine-5-carboxylate;

Methyl (4R)-4-(2-chloro-4-fluoro-phenyl)-2-thiazol-2-yl-6-[[(1S,5R)-7-exo-ureido-3-oxa-9-azabicyclo[3.3.1]nonan-9-yl]methyl]-1,4-dihydropyrimidine-5-carboxylate;

Methyl (4R)-4-(2-chloro-4-fluoro-phenyl)-6-[[(1R,5S)-7-exo-(sulfamoylamino)-3-oxa-9-azabicyclo[3.3.1]nonan-9-yl]methyl]-2-thiazol-2-yl-1,4-dihydropyrimidine-5-carboxylate;

2-[(1R,5S,6S)-8-[[(4R)-4-(2-bromo-4-fluoro-phenyl)-5-methoxycarbonyl-2-thiazol-2-yl-1,4-dihydropyrimidin-6-yl]methyl]-3-oxa-8-azabicyclo[3.2.1]octan-6-yl]acetic acid;

Endo-2-[(1S,5R)-9-[[(4R)-4-(2-chloro-3-fluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-chloro-3-fluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-bromo-4-fluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-bromo-3-fluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-chloro-3,4-difluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Ethyl (4R)-6-[[(1S,5R)-7-endo-acetamido-3-oxa-9-azabicyclo[3.3.1]nonan-9-yl]methyl]-4-(2-bromo-4-fluoro-phenyl)-2-thiazol-2-yl-1,4-dihydropyrimidine-5-carboxylate;

Ethyl (4R)-6-[[(1S,5R)-7-exo-acetamido-3-oxa-9-azabicyclo[3.3.1]nonan-9-yl]methyl]-4-(2-bromo-4-fluoro-phenyl)-2-thiazol-2-yl-1,4-dihydropyrimidine-5-carboxylate;

Exo-2-[(1S,5R)-9-[[(4R)-4-(2-chlorophenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-chloro-3,4-difluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-bromo-3-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2,3-difluorophenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-bromophenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4R)-4-(2-bromophenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4S)-4-(3,4-difluoro-2-methyl-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

3-[(1S,5R)-9-[[(4R)-4-(2-chloro-4-fluoro-phenyl)-5-methoxycarbonyl-2-thiazol-2-yl-1,4-dihydropyrimidin-6-yl]methyl]-3-oxa-7,9-diazabicyclo[3.3.1]nonan-7-yl]-2,2-dimethyl-3-oxo-propanoic acid;

Exo-2-[(1S,5R)-9-[[(4R)-4-(2-bromo-3,4-difluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

(1S,5R)-8-[[(4R)-4-(2-chloro-4-fluoro-phenyl)-5-methoxycarbonyl-2-thiazol-2-yl-1,4-dihydropyrimidin-6-yl]methyl]-3-oxa-8-azabicyclo[3.2.1]octane-5-carboxylic acid;

(1R,5S)-8-[[(4R)-4-(2-chloro-4-fluoro-phenyl)-5-methoxycarbonyl-2-thiazol-2-yl-1,4-dihydropyrimidin-6-yl]methyl]-3-oxa-8-azabicyclo[3.2.1]octane-5-carboxylic acid;

8-[[(4R)-4-(2-chloro-3-fluoro-phenyl)-5-ethoxycarbonyl-2-thiazol-2-yl-1,4-dihydropyrimidin-6-yl]methyl]-3-oxa-8-azabicyclo[3.2.1]octane-5-carboxylic acid;

(1S,5R)-8-[[(4S)-4-(3,4-difluoro-2-methyl-phenyl)-5-methoxycarbonyl-2-thiazol-2-yl-1,4-dihydropyrimidin-6-yl]methyl]-3-oxa-8-azabicyclo[3.2.1]octane-5-carboxylic acid;

(1R,5S)-8-[[(4S)-4-(3,4-difluoro-2-methyl-phenyl)-5-methoxycarbonyl-2-thiazol-2-yl-1,4-dihydropyrimidin-6-yl]methyl]-3-oxa-8-azabicyclo[3.2.1]octane-5-carboxylic acid;

2-[(1R,3S,5S)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4R)-4-(2-chlorophenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-chlorophenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4R)-4-(2-bromophenyl)-5-ethoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-bromophenyl)-5-ethoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4R)-4-(2-bromo-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-bromo-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4S)-4-(4-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4S)-4-(4-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4R)-4-(2-chloro-3-fluoro-phenyl)-5-ethoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-chloro-3-fluoro-phenyl)-5-ethoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,5S,6R,7R)-9-[[(4R)-4-(2-chloro-3-fluoro-phenyl)-5-methoxycarbonyl-2-thiazol-2-yl-1,4-dihydropyrimidin-6-yl]methyl]-6-fluoro-3-oxa-9-azabicyclo[3.3.1]nonan-7-yl]acetic acid;

2-[(1R,5R,6S,7S)-9-[[(4R)-4-(2-chloro-3-fluoro-phenyl)-5-methoxycarbonyl-2-thiazol-2-yl-1,4-dihydropyrimidin-6-yl]methyl]-6-fluoro-3-oxa-9-azabicyclo[3.3.1]nonan-7-yl]acetic acid;

2-[(1S,5S,6R,7R)-9-[[(4R)-4-(2-chlorophenyl)-5-ethoxycarbonyl-2-thiazol-2-yl-1,4-dihydropyrimidin-6-yl]methyl]-6-fluoro-3-oxa-9-azabicyclo[3.3.1]nonan-7-yl]acetic acid;

2-[(1R,5R,6S,7S)-9-[[(4R)-4-(2-chlorophenyl)-5-ethoxycarbonyl-2-thiazol-2-yl-1,4-dihydropyrimidin-6-yl]methyl]-6-fluoro-3-oxa-9-azabicyclo[3.3.1]nonan-7-yl]acetic acid;

(4R)-4-(2-Chloro-4-fluoro-phenyl)-6-(4,10-dioxa-5,12-diaza-tricyclo[6.3.1.0*2,6*]dodeca-2,5-dien-12-ylmethyl)-2-thiazol-2-yl-1,4-dihydro-pyrimidine-5-carboxylic acid methyl ester;

(4R)-4-(2-Chloro-4-fluoro-phenyl)-6-(5,10-dioxa-4,12-diaza-tricyclo[6.3.1.0*2,6*]dodeca-2(6),3-dien-12-ylmethyl)-2-thiazol-2-yl-1,4-dihydro-pyrimidine-5-carboxylic acid methyl ester;

(4R)-4-(2-Chloro-4-fluoro-phenyl)-6-(7-fluoro-5,10-dioxa-4,12-diaza-tricyclo[6.3.1.0*2,6*]dodeca-2(6),3-dien-12-ylmethyl)-2-thiazol-2-yl-1,4-dihydropyrimidine-5-carrboxylic acid methyl ester;

(R)-4-(2-Chloro-4-fluoro-phenyl)-6-(7,7-difluoro-10-oxa-4,5,12-triaza-tricyclo[6.3.1.0*2,6*]dodeca-2(6),3-dien-12-ylmethyl)-2-thiazol-2-yl-1,4-dihydro-pyrimidine-5-arboxylic acid methyl ester;

Methyl (4R)-4-(2-chloro-4-fluorophenyl)-6-[(6,6-difluoro-3-oxa-8-azabicyclo[3.2.1]octan-8-yl)methyl]-2-(1,3-thiazol-2-yl)-1,4-dihydropyrimidine-5-carboxylate;

2-[(1R,3R,5S)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3S,5R)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3R,5S)-8-[[(4S)-4-(3,4-difluoro-2-methyl-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3S,5R)-8-[[(4S)-4-(3,4-difluoro-2-methyl-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3R,5S)-8-[[(4S)-4-(4-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid or 2-[(1 S,3 S,5R)-8-[[(4S)-4-(4-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4S)-4-(3,4-difluorophenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4S)-4-(3,4-difluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(3R)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3S)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3R)-8-[[(4R)-4-(3,4-difluoro-2-methyl-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3S)-8-[[(4S)-4-(3,4-difluoro-2-methyl-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

Methyl (4R)-6-[(3-acetyl-3,8-diazabicyclo[3.2.1]octan-8-yl)methyl]-4-(2-chloro-4-fluoro-phenyl)-2-thiazol-2-yl-1,4-dihydropyrimidine-5-carboxylate;

2-[(7S)-9-[[(4R)-4-(2-chloro-4-fluoro-phenyl)-5-methoxycarbonyl-2-thiazol-2-yl-1,4-dihydropyrimidin-6-yl]methyl]-6-hydroxy-3-oxa-9-azabicyclo[3.3.1]nonan-7-yl]acetic acid;

2-[(7R)-9-[[(4R)-4-(2-chloro-4-fluoro-phenyl)-5-methoxycarbonyl-2-thiazol-2-yl-1,4-dihydropyrimidin-6-yl]methyl]-6-hydroxy-3-oxa-9-azabicyclo[3.3.1]nonan-7-yl]acetic acid;

2-[(7R)-9-[[(4R)-4-(2-chloro-4-fluoro-phenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

2-[(7S)-9-[[(4R)-4-(2-chloro-4-fluoro-phenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

2-[(7R)-9-[[(4S)-4-(3,4-difluoro-2-methyl-phenyl)-5-ethoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

2-[(7S)-9-[[(4S)-4-(3,4-difluoro-2-methyl-phenyl)-5-ethoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

2-[(7R)-9-[[(4R)-4-(2-chloro-3-fluoro-phenyl)-5-ethoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

2-[(7S)-9-[[(4R)-4-(2-chloro-3-fluoro-phenyl)-5-ethoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

2-[(1R,5S,7S)-9-[[(4R)-4-(2-chloro-3,4-difluoro-phenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid or 2-[(1S,5S,7R)-9-[[(4R)-4-(2-chloro-3,4-difluoro-phenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

2-[(1R,5R,7S)-9-[[(4S)-4-(3,4-difluoro-2-methyl-phenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid or 2-[(1S,5S,7R)-9-[[(4S)-4-(3,4-difluoro-2-methyl-phenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

Methyl (4R)-4-(2-chloro-4-fluoro-phenyl)-6-[(6-oxo-3-oxa-7,9-diazabicyclo[3.3.1]nonan-9-yl)methyl]-2-thiazol-2-yl-1,4-dihydropyrimidine-5-carboxylate;

Endo-2-[9-[[(4R)-4-(2-bromophenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Endo-2-[9-[[(4R)-4-(2-chloro-3,4-difluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Endo-2-[9-[[(4S)-4-(4-chloro-3-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]acetic acid;

Methyl (4R)-4-(2-chloro-4-fluoro-phenyl)-6-[[7-(2-ethoxy-1-hydroxy-2-oxo-ethyl)-7-hydroxy-3-oxa-9-azabicyclo[3.3.1]nonan-9-yl]methyl]-2-thiazol-2-yl-1,4-dihydropyrimidine-5-carboxylate;

Methyl (4R)-4-(2-chloro-4-fluoro-phenyl)-6-[[7-(2-ethoxy-2-oxo-ethyl)-6,7-dihydroxy-3-oxa-9-azabicyclo[3.3.1]nonan-9-yl]methyl]-2-thiazol-2-yl-1,4-dihydropyrimidine-5-carboxylate;

7-amino-9-[[(4R)-4-(2-chloro-4-fluoro-phenyl)-5-methoxycarbonyl-2-thiazol-2-yl-1,4-dihydropyrimidin-6-yl]methyl]-3-oxa-9-azabicyclo[3.3.1]nonane-7-carboxylic acid;

7-amino-9-[[(4R)-4-(2,3-difluorophenyl)-5-ethoxycarbonyl-2-thiazol-2-yl-1,4-dihydropyrimidin-6-yl]methyl]-3-oxa-9-azabicyclo[3.3.1]nonane-7-carboxylic acid;

7-amino-9-[[(4R)-4-(2-bromo-4-fluoro-phenyl)-5-ethoxycarbonyl-2-thiazol-2-yl-1,4-dihydropyrimidin-6-yl]methyl]-3-oxa-9-azabicyclo[3.3.1]nonane-7-carboxylic acid;

Methyl (4R)-4-(2-chloro-4-fluoro-phenyl)-6-(8-oxa-3-azabicyclo[3.2.1]octan-3-ylmethyl)-2-thiazol-2-yl-1,4-dihydropyrimidine-5-carboxylate;

Methyl (4R)-4-(2-chloro-4-fluoro-phenyl)-6-[(5,5-difluoro-2-azabicyclo[2.2.1]heptan-2-yl)methyl]-2-thiazol-2-yl-1,4-dihydropyrimidine-5-carboxylate;

Methyl (4R)-4-(2-chloro-4-fluoro-phenyl)-6-[(5,5-difluoro-3-azabicyclo[2.2.1]heptan-3-yl)methyl]-2-thiazol-2-yl-1,4-dihydropyrimidine-5-carboxylate;

Methyl (4R)-6-[[4-(acetamidomethyl)-5-oxa-2-azabicyclo[2.2.1]heptan-2-yl]methyl]-4-(2-chloro-4-fluoro-phenyl)-2-thiazol-2-yl-1,4-dihydropyrimidine-5-carboxylate;

Methyl (4R)-4-(2-chloro-4-fluoro-phenyl)-6-[[7-(2-ethoxy-2-oxo-ethyl)-7-(methanesulfonamido)-3-oxa-9-azabicyclo[3.3.1]nonan-9-yl]methyl]-2-thiazol-2-yl-1,4-dihydropyrimidine-5-carboxylate;

Methyl (4R)-4-(2-chloro-4-fluoro-phenyl)-6-[[7-(2-ethoxy-2-oxo-ethyl)-7-[(2,2,2-trifluoroacetyl)amino]-3-oxa-9-azabicyclo[3.3.1]nonan-9-yl]methyl]-2-thiazol-2-yl-1,4-dihydropyrimidine-5-carboxylate;

(1S,4R)-7-[[(4R)-4-(2-chloro-4-fluoro-phenyl)-5-methoxycarbonyl-2-thiazol-2-yl-1,4-dihydropyrimidin-6-yl]methyl]-2,2-difluoro-7-azabicyclo[2.2.1]heptane-4-carboxylic acid;

(1R,4S)-7-[[(4R)-4-(2-chloro-4-fluoro-phenyl)-5-methoxycarbonyl-2-thiazol-2-yl-1,4-dihydropyrimidin-6-yl]methyl]-2,2-difluoro-7-azabicyclo[2.2.1]heptane-4-carboxylic acid;

8-[[(4R)-4-(2-chloro-3-fluoro-phenyl)-5-ethoxycarbonyl-2-thiazol-2-yl-1,4-dihydropyrimidin-6-yl]methyl]-6,6-difluoro-8-azabicyclo[3.2.1]octane-3-carboxylic acid;

(5S)-7-[[(4R)-4-(2-chloro-4-fluoro-phenyl)-5-methoxycarbonyl-2-thiazol-2-yl-1,4-dihydropyrimidin-6-yl]methyl]-2,2-difluoro-7-azabicyclo[2.2.1]heptane-5-carboxylic acid; and (5R)-7-[[(4R)-4-(2-chloro-4-fluoro-phenyl)-5-methoxycarbonyl-2-thiazol-2-yl-1,4-dihydropyrimidin-6-yl]methyl]-2,2-difluoro-7-azabicyclo[2.2.1]heptane-5-carboxylic acid.

20. A compound of claim 1, selected from

9-[[(4R)-4-(2-chloro-4-fluoro-phenyl)-5-methoxycarbonyl-2-thiazol-2-yl-1,4-dihydropyrimidin-6-yl]methyl]-3-oxa-9-azabicyclo[3.3.1]nonane-7-carboxylic acid;

8-[(R)-6-(2-Chloro-4-fluoro-phenyl)-5-methoxycarbonyl-2-thiazol-2-yl-3,6-dihydro-pyrimidin-4-ylmethyl]-3-oxa-8-aza-bicyclo[3.2.1]octane-6-carboxylic acid;

(R)-6-(7-Carbamoyl-3-oxa-7,9-diaza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-4-(2-Chloro-4-fluoro-phenyl)-6-(7-sulfamoyl-3-oxa-7,9-diaza-bicyclo[3.3.1]non-9-ylmethyl)-2-thiazol-2-yl-1,4-dihydro-pyrimidine-5-carboxylic acid methyl ester;

(R)-4-(2-Chloro-4-fluoro-phenyl)-6-[7-(2-hydroxy-acetyl)-3-oxa-7,9-diaza-bicyclo[3.3.1]non-9-ylmethyl]-2-thiazol-2-yl-1,4-dihydro-pyrimidine-5-carboxylic acid methyl ester;

(R)-6-(7-Carboxymethyl-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-6-(7-Carboxymethyl-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid ethyl ester;

(R)-4-(2-Bromo-4-fluoro-phenyl)-6-(7-carboxymethyl-3-oxa-9-aza-bicyclo[3.3.1]non-9-ylmethyl)-2-thiazol-2-yl-1,4-dihydro-pyrimidine-5-carboxylic acid methyl ester;

(R)-4-(2-Chloro-4-fluoro-phenyl)-6-(10-oxa-4,5,12-triaza-tricyclo[6.3.1.0*2,6*]dodeca-2(6),3-dien-12-ylmethyl)-2-thiazol-2-yl-1,4-dihydro-pyrimidine-5-carboxylic acid methyl ester;

(R)-4-(2-Chloro-4-fluoro-phenyl)-6-(4-oxo-8-oxa-3,10-diaza-bicyclo[4.3.1]dec-10-ylmethyl)-2-thiazol-2-yl-1,4-dihydro-pyrimidine-5-carboxylic acid methyl ester;

(R)-6-(7-Acetylamino-3-oxa-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-4-(2-Chloro-4-fluoro-phenyl)-6-(7-methanesulfonylamino-3-oxa-9-aza-bicyclo[3.3.1]non-9-ylmethyl)-2-thiazol-2-yl-1,4-dihydro-pyrimidine-5-carboxylic acid methyl ester;

2-[(R)-6-(2-Chloro-4-fluoro-phenyl)-5-methoxycarbonyl-2-thiazol-2-yl-3,6-dihydro-pyrimidin-4-ylmethyl]-4-fluoro-2-aza-bicyclo[2.1.1]hexane-1-carboxylic acid;

6-(7-Carboxymethyl-3-thia-9-aza-bicyclo[3.3.1]non-9-ylmethyl)-4-(2-chloro-4-fluoro-phenyl)-2-thiazol-2-yl-1,4-dihydro-pyrimidine-5-carboxylic acid methyl ester;

(R)-4-(2-Chloro-4-fluoro-phenyl)-6-(9-oxa-3,4,11-triaza-tricyclo[5.3.1.0*2,6*]undeca-2(6),4-dien-11-ylmethyl)-2-thiazol-2-yl-1,4-dihydro-pyrimidine-5-carboxylic acid methyl ester;

2-[[(1R,5S)-9-[[(4R)-4-(2-chloro-4-fluoro-phenyl)-5-methoxycarbonyl-2-thiazol-2-yl-1,4-dihydropyrimidin-6-yl]methyl]-3-oxa-9-azabicyclo[3.3.1]nonan-7-yl]oxy]acetic acid;

2-[[8-[[(4R)-4-(2-bromo-4-fluoro-phenyl)-5-ethoxycarbonyl-2-thiazol-2-yl-1,4-dihydropyrimidin-6-yl]methyl]-3-oxa-8-azabicyclo[3.2.1]octan-6-yl]oxy]acetic acid;

8-[[(4R)-4-(2-bromo-4-fluoro-phenyl)-5-ethoxycarbonyl-2-thiazol-2-yl-1,4-dihydropyrimidin-6-yl]methyl]-3-oxa-8-azabicyclo[3.2.1]octane-6-carboxylic acid;

Methyl (4R)-4-(2-bromo-4-fluoro-phenyl)-6-[(7-carbamoyl-3-oxa-7,9-diazabicyclo[3.3.1]nonan-9-yl)methyl]-2-thiazol-2-yl-1,4-dihydropyrimidine-5-carboxylate;

Methyl (4R)-4-(2-chloro-4-fluoro-phenyl)-6-[[(1R,5S)-7-endo-(sulfamoylamino)-3-oxa-9-azabicyclo[3.3.1]nonan-9-yl]methyl]-2-thiazol-2-yl-1,4-dihydropyrimidine-5-carboxylate;

Methyl (4R)-4-(2-chloro-4-fluoro-phenyl)-6-[[(1R,5S)-7-exo-(methanesulfonamido)-3-oxa-9-azabicyclo[3.3.1]nonan-9-yl]methyl]-2-thiazol-2-yl-1,4-dihydropyrimidine-5-carboxylate;

2-[(1R,5S,6S)-8-[[(4R)-4-(2-bromo-4-fluoro-phenyl)-5-methoxycarbonyl-2-thiazol-2-yl-1,4-dihydropyrimidin-6-yl]methyl]-3-oxa-8-azabicyclo[3.2.1]octan-6-yl]acetic acid;

Exo-2-[(1S,5R)-9-[[(4R)-4-(2-chloro-3-fluoro-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

Exo-2-[(1S,5R)-9-[[(4S)-4-(3,4-difluoro-2-methyl-phenyl)-5-ethoxycarbonyl-2-thiazol-2-yl-1,4-dihydropyrimidin-6-yl]methyl]-3-oxa-9-azabicyclo[3.3.1]nonan-7-yl]acetic acid;

(1S,5R)-8-[[(4R)-4-(2-chloro-4-fluoro-phenyl)-5-methoxycarbonyl-2-thiazol-2-yl-1,4-dihydropyrimidin-6-yl]methyl]-3-oxa-8-azabicyclo[3.2.1]octane-5-carboxylic acid;

(1R,5S)-8-[[(4R)-4-(2-chloro-4-fluoro-phenyl)-5-methoxycarbonyl-2-thiazol-2-yl-1,4-dihydropyrimidin-6-yl]methyl]-3-oxa-8-azabicyclo[3.2.1]octane-5-carboxylic acid;

2-[(1R,3S,5S)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4R)-4-(2-chloro-3-fluoro-phenyl)-5-ethoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3R,5R)-8-[[(4R)-4-(2-chloro-3-fluoro-phenyl)-5-ethoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3R,5S)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1S,3S,5R)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-8-azabicyclo[3.2.1]octan-3-yl]acetic acid;

2-[(1R,3S,5S)-8-[[(4S)-4-(3,4-difluorophenyl)-5-methoxycarbonyl-2-thiazol-2-yl-1,4-dihydropyrimidin-6-yl]methyl]-6,6-difluoro-8-azabicyclo[3.2.1]octan-3-yl] acetic acid;

2-[(1S,3R,5R)-8-[[(4S)-4-(3,4-difluoro-phenyl)-5-methoxycarbonyl-2-thiazol-2-yl-1,4-dihydropyrimidin-6-yl]methyl]-6,6-difluoro-8-azabicyclo[3.2.1]octan-3-yl] acetic acid;

2-[(3R)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3S)-8-[[(4R)-4-(2-chloro-4-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3R)-8-[[(4R)-4-(3,4-difluoro-2-methyl-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3S)-8-[[(4S)-4-(3,4-difluoro-2-methyl-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3R)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(3S)-8-[[(4R)-4-(2-chloro-3-fluoro-phenyl)-5-methoxycarbonyl-2-thiazol-2-yl-1,4-dihydropyrimidin-6-yl]methyl]-6,6-difluoro-3-hydroxy-8-azabicyclo[3.2.1]octan-3-yl]acetic acid;

2-[(7R)-9-[[(4R)-4-(2-chloro-4-fluoro-phenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

2-[(7S)-9-[[(4R)-4-(2-chloro-4-fluoro-phenyl)-5-methoxycarbonyl-2-thiazol-2-yl-1,4-dihydropyrimidin-6-yl]methyl]-6,6-difluoro-3-oxa-9-azabicyclo[3.3.1]nonan-7-yl]acetic acid;

Methyl (4R)-4-(2-chloro-4-fluoro-phenyl)-6-[[7-(2-ethoxy-2-oxo-ethyl)-7-(methanesulfonamido)-3-oxa-9-azabicyclo[3.3.1]nonan-9-yl]methyl]-2-thiazol-2-yl-1,4-dihydropyrimidine-5-carboxylate;

(1S,4R)-7-[[(4R)-4-(2-chloro-4-fluoro-phenyl)-5-methoxycarbonyl-2-thiazol-2-yl-1,4-dihydropyrimidin-6-yl]methyl]-2,2-difluoro-7-azabicyclo[2.2.1]heptane-4-carboxylic acid;

(1R,4S)-7-[[(4R)-4-(2-chloro-4-fluoro-phenyl)-5-methoxycarbonyl-2-thiazol-2-yl-1,4-dihydropyrimidin-6-yl]methyl]-2,2-difluoro-7-azabicyclo[2.2.1]heptane-4-carboxylic acid;

8-[[(4R)-4-(2-chloro-3-fluoro-phenyl)-5-ethoxycarbonyl-2-thiazol-2-yl-1,4-dihydropyrimidin-6-yl]methyl]-6,6-difluoro-8-azabicyclo[3.2.1]octane-3-carboxylic acid;

2-[(7R)-9-[[(4R)-4-(2-chloro-3-fluoro-phenyl)-5-ethoxycarbonyl-2-thiazol-2-yl-1,4-dihydropyrimidin-6-yl]methyl]-6,6-difluoro-3-oxa-9-azabicyclo[3.3.1]nonan-7-yl]acetic acid; and 2-[(7S)-9-[[(4R)-4-(2-chloro-3-fluoro-phenyl)-5-ethoxycarbonyl-2-thiazol-2-yl-1,4-dihydropyrimidin-6-yl]methyl]-6,6-difluoro-3-oxa-9-azabicyclo[3.3.1]nonan-7-yl]acetic acid.

21. A process for the preparation of a compound of claim 1 comprising the reaction of (a) a compound of formula (A)

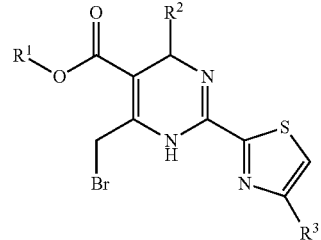

(A)

with bridged amine in the presence of a base;

(b) a compound of formula (B)

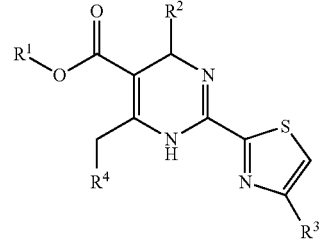

(B)

under chiral separation condition;

wherein $R^1$ to $R^4$ are defined as in claim 1.

22. A pharmaceutical composition comprising a compound of claim 1 and a therapeutically inert carrier.

23. A method for the treatment of hepatitis B virus infection, which method comprises administering an effective amount of a compound of claim 1.

* * * * *